United States Patent
Hida et al.

(10) Patent No.: US 11,613,702 B2
(45) Date of Patent: Mar. 28, 2023

(54) LIQUID CRYSTAL COMPOSITION

(71) Applicant: Sumitomo Chemical Company, Limited, Tokyo (JP)

(72) Inventors: Noriyuki Hida, Osaka (JP); Haruki Okawa, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 869 days.

(21) Appl. No.: 16/423,730

(22) Filed: May 28, 2019

(65) Prior Publication Data

US 2019/0276744 A1 Sep. 12, 2019

Related U.S. Application Data

(62) Division of application No. 15/358,732, filed on Nov. 22, 2016, now abandoned.

(30) Foreign Application Priority Data

Nov. 25, 2015 (JP) ................. 2015-230054

(51) Int. Cl.
| | | |
|---|---|---|
| C09K 19/34 | (2006.01) | |
| C09K 19/38 | (2006.01) | |
| C09D 133/14 | (2006.01) | |
| H01L 51/00 | (2006.01) | |
| C08F 20/18 | (2006.01) | |
| C07C 67/08 | (2006.01) | |
| C07C 69/74 | (2006.01) | |
| C09K 19/20 | (2006.01) | |
| H01L 27/32 | (2006.01) | |
| H01L 51/52 | (2006.01) | |
| C09K 19/04 | (2006.01) | |
| G02B 5/30 | (2006.01) | |

(52) U.S. Cl.
CPC .......... C09K 19/3861 (2013.01); C07C 67/08 (2013.01); C07C 69/74 (2013.01); C08F 20/18 (2013.01); C09D 133/14 (2013.01); C09K 19/2007 (2013.01); C09K 19/34 (2013.01); C09K 19/3497 (2013.01); H01L 27/3232 (2013.01); H01L 51/004 (2013.01); H01L 51/0076 (2013.01); H01L 51/5281 (2013.01); C09K 2019/0448 (2013.01); C09K 2219/03 (2013.01); G02B 5/3016 (2013.01); H01L 51/0071 (2013.01); H01L 51/0073 (2013.01)

(58) Field of Classification Search
CPC C09K 19/3861; C09K 19/34; C09K 19/3497; C09K 2019/0448; C09K 2219/03; C07C 67/08; C07C 67/74; H01L 51/0076; H01L 51/0071; G02B 5/3016
USPC ...................................................... 560/127
See application file for complete search history.

(56) References Cited

U.S. PATENT DOCUMENTS

| | | | |
|---|---|---|---|
| 9,442,232 B2 | 9/2016 | Hatanaka et al. | |
| 9,529,130 B2 | 12/2016 | Hatanaka et al. | |
| 9,664,833 B2 | 5/2017 | Kobayashi et al. | |
| 9,784,894 B2 | 10/2017 | Kobayashi | |
| 2015/0175564 A1* | 6/2015 | Sakamoto | C08F 20/36 548/161 |
| 2015/0218453 A1 | 8/2015 | Kobayashi et al. | |
| 2015/0218454 A1 | 8/2015 | Kobayashi et al. | |
| 2018/0037817 A1 | 2/2018 | Kuwana et al. | |

FOREIGN PATENT DOCUMENTS

| | | |
|---|---|---|
| JP | 2010024438 A | 2/2010 |
| JP | 2010031223 A | 2/2010 |
| JP | 2010241919 A | 10/2010 |
| TW | 201509683 A | 3/2015 |

OTHER PUBLICATIONS

English Translation of Office Action dated Apr. 28, 2020 in TW Application No. 105138380.
Mock-Knoblauch et al, "L-7: Late-News Paper: Novel Polymerisable Liquid Crystalline Acrylates for the Manufacturing of Ultrathin Optical Films," SID Symposium Digest of Technical Papers, vol. 37, No. 1 pp. 1673-1676 (2006).
Office Action dated Nov. 29, 2018 in U.S. Appl. No. 15/358,732, by Hida.

* cited by examiner

Primary Examiner — Ruiyun Zhang
(74) Attorney, Agent, or Firm — Panitch Schwarze Belisario & Nadel LLP

(57) ABSTRACT

A liquid crystal composition is provided containing a first liquid crystal compound represented by formula (1):

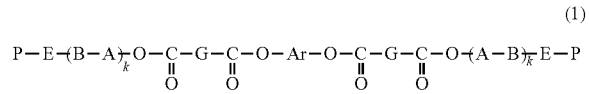

and a second liquid crystal compound represented by formula (2):

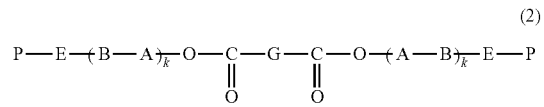

Also provided is a method for producing the liquid crystal composition having a desired wavelength dispersion characteristic.

3 Claims, No Drawings

LIQUID CRYSTAL COMPOSITION

CROSS-REFERENCE TO RELATED APPLICATIONS

This application is a Divisional of U.S. patent application Ser. No. 15/358,732 filed Nov. 22, 2016, which claims priority under 35 U.S.C. § 119(b) to Japanese Patent Application No. 2015-230054, filed Nov. 25, 2015, and the disclosures of which are incorporated herein by reference.

BACKGROUND OF THE INVENTION

Field of the Invention

The present invention relates to a liquid crystal composition, an optical film, and a method for producing the optical film.

Description of the Related Art

A flat panel display device (FPD) includes a member using an optical film such as a polarizing plate and a retardation plate. Examples of the optical film include an optical film obtained by applying to a supporting substrate a solution which is prepared by dissolving a polymerizable compound in a solvent, followed by polymerization. It is known that the retardation (Re($\lambda$)) of the optical film which light having a wavelength of nm generates is determined by the product of a birefringence index $\Delta n$ and a film thickness d (Re($\lambda$)=$\Delta n \times d$). Furthermore, it is known that the wavelength dispersion characteristic is usually expressed as the value (Re($\lambda$)/Re(550)) obtained by dividing the retardation value Re($\lambda$) at a wavelength $\lambda$ by the retardation value Re(550) at 550 nm, and that uniform conversion of polarized light is possible over the wavelength band where the quotient of (Re($\lambda$)/Re(550)) is near 1 or over the wavelength band which exhibits a reverse wavelength dispersion characteristic satisfying the following relations: [Re 450)/Re (550)]<1 and [Re(650)/Re(550)]>1. For example, LC242 (manufactured by BASF A.G.) is commercially available as the polymerizable compound (Non Patent Literature

PRIOR ART DOCUMENTS

Non Patent Literature

Non Patent Literature 1: Cordula Mock-Knoblauch, Olivier S. Enger, Ulrich D. Schalkowsky, "L-7 Novel Polymerisable Liquid Crystalline Acrylates for the Manufacturing of Ultrathin Optical Films", SID Symposium Digest of Technical Papers, 2006, vol. 37, p. 1673

SUMMARY OF THE INVENTION

Problems To Be Solved

The wavelength dispersion characteristic of the optical film varies depending on the compounds which compose the film. Therefore, in order to produce an optical film having a desired wavelength dispersion characteristic, it is necessary to synthesize a compound which yields the desired wavelength dispersion characteristic. However, synthesis of a compound often involves too much labor and requires repeated experiments. Furthermore, even if the synthesis is repeatedly conducted, such desirable compound may not be obtained in some cases. Therefore, it is not economically or technically easy to produce a film having a desired wavelength dispersion characteristic.

An object of the present invention is to provide a liquid crystal composition which yields a desired wavelength dispersion characteristic. Another object of the present invention is to provide a production method capable of easily producing such liquid crystal composition.

Means for Solving the Problem

The present invention provides the following preferred embodiments [1] to [18].

[1] A liquid crystal compound containing a liquid crystal compound (1) represented by formula (1) and a liquid crystal compound (2) represented by formula (2).

[Chem. 1]

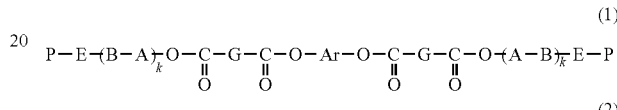

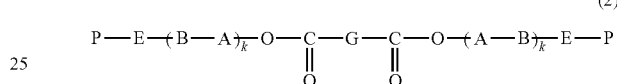

[wherein Ar is a divalent aromatic group, and at least one atom selected from the group consisting of a nitrogen atom, an oxygen atom and a sulfur atom may be contained in the aromatic group;

G represents a divalent alicyclic hydrocarbon group, where a hydrogen atom contained in the alicyclic hydrocarbon group is optionally substituted with a halogen atom, an alkyl group having 1 to 4 carbon atoms, a fluoro alkyl group having 1 to 4 carbon atoms, an alkoxy group having 1 to 4 carbon atoms, a cyano group or a nitro group, and —CH$_2$— contained in the alicyclic hydrocarbon group is optionally substituted with —O—, —S— or —NH—;

B represents a single bond or a divalent linking group;

A represents a divalent alicyclic hydrocarbon group having 3 to 20 carbon atoms or a divalent aromatic hydrocarbon group having 6 to 20 carbon atoms, the hydrogen atom contained in the alicyclic hydrocarbon group and the aromatic hydrocarbon group is optionally substituted with an alkyl group having 1 to 4 carbon atoms optionally substituted with a halogen atom, an alkoxy group having 1 to 4 carbon atoms optionally substituted with a fluorine atom, a cyano group or a nitro group, —CH$_2$— contained in the alicyclic hydrocarbon group is optionally substituted with —O—, —S—, or —NR$^1$—, and —CH (-)-contained in the alicyclic hydrocarbon group may be substituted with —N(-)—;

R$^1$ represents a hydrogen atom or an alkyl group having 1 to 4 carbon atoms;

k represents an integer of 0 to 3, where when k is an integer of 2 or more, a plurality of As and Bs maybe the same or different from each other;

E represents an alkanediyl group having 1 to 17 carbon atoms, where the hydrogen atom contained in an alkanediyl group is optionally substituted with a halogen atom, and —CH$_2$— contained in the alkanediyl group is optionally substituted with —O— or —CO—; and P represents a polymerizable group.]

[2] The liquid crystal composition according to [1], in which G, A, B, E, P and k in the formula (1) are the same as G, A, B, E, P and k in the formula (2), respectively.

[3] The liquid crystal composition according to [1] or [2], in which the optical film obtained by orienting the liquid crystal compound (1) exhibits a reverse wavelength dispersion characteristic.

[4] The liquid crystal composition according to any of [1] to [3], in which the optical film obtained by orienting the liquid crystal compound (2) exhibits a positive wavelength dispersion characteristic.

[5] The liquid crystal composition according to any of [1] to [4], in which the aromatic group in Ar has 10 to 30n electrons.

[6] The liquid crystal composition according to any of [1] to [5], in which the maximum absorption wavelength ($\lambda_{max}$) of the liquid crystal compound (1) is from 300 to 400 nm.

[7] The liquid crystal composition according to any of [1] to [6], in which the optical film obtained by orienting the liquid crystal composition has a degree of wavelength dispersion Re(450 nm)/Re(550 nm) of 0.65 or more and less than 1.

[8] The liquid crystal composition according to any of [1] to [7], in which Ar is an aromatic group having a heterocyclic ring.

[9] The liquid crystal composition according to [8], in which the aromatic group having a heterocyclic ring is an aromatic group having a benzothiazole ring.

[10] The liquid crystal composition according to any of [1] to [9], in which the content of the liquid crystal compound (2) in the liquid crystal composition is in the range of 0.1 to 70 parts by mass relative to 100 parts by mass of the liquid crystal compound (1).

[11] An optical film comprising a polymer of the liquid crystal composition as defined in any of [1] to [10].

[12] The optical film according to [11], in which the retardation value (Re(550)) at a wavelength of 550 nm is from 113 to 163 nm.

[13] A circularly polarizing plate comprising the optical film as defined in [11] or [12] and a polarizing film.

[14] An organic electro-luminescence (EL) display device comprising an organic electro-luminescence panel containing the circularly polarizing plate as defined in [13].

[15] A method for producing a liquid crystal composition comprising a liquid crystal compound (1) represented by formula (1):

[Chem. 2]

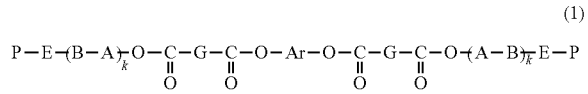
(1)

and a liquid crystal compound (2) represented by formula (2):

[Chem. 3]

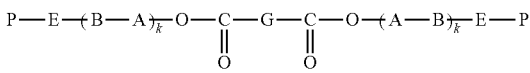
(2)

including a step of allowing an alcohol compound (3) represented by formula (3):

[Chem. 4]

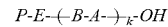
(3)

and a dicarboxylic acid compound (4) represented by formula (4):

[Chem. 5]

(4)

to react each other to thereby obtain a mixture containing a carboxylic acid compound (5) represented by formula (5):

[Chem. 6]

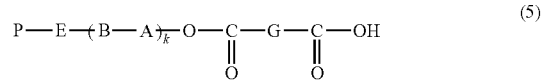
(5)

and the liquid crystal compound (2).

[16] The method according to [15], including a step of allowing the mixture containing the carboxylic acid compound (5) and the liquid crystal compound (2) to react with an alcohol compound (6) represented by formula (6):

[Chem. 7]

(6)

to thereby obtain a liquid crystal composition containing liquid crystal compounds (1) and (2).

[17] The method according to [15] or [16], in which the amount of dicarboxylic acid compound (4) used is from 1 to 50 moles, relative to 1 mole of the alcohol compound (3).

[18] The method according to any of [15] to [17], in which a reaction of the alcohol compound (3) and the dicarboxylic acid compound (4), and/or a reaction of the mixture containing the carboxylic acid compound (5) and the liquid crystal compound (2) with the alcohol compound (6) is/are conducted in the presence of a condensing agent.

Effect of the Invention

According to the present invention, it is possible to provide a liquid crystal composition which yields a desired wavelength dispersion characteristic. Further, according to the present invention, it is possible to provide a production method capable of easily producing such liquid crystal composition.

DETAILED DESCRIPTION OF THE PREFERRED EMBODIMENTS

<Liquid Crystal Compound>

The liquid crystal composition of the present invention contains a liquid crystal compound (1) represented by formula (1):

[Chem. 8]

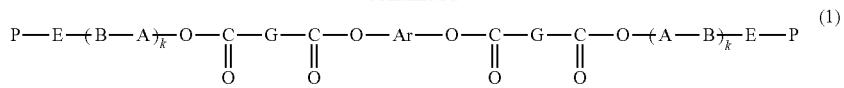

(1)

and a liquid crystal compound (2) represented by formula (2):

[Chem. 9]

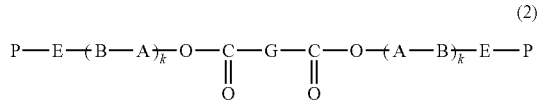

(2)

In formulae (1) and (2), Ar is a divalent aromatic group, and at least one atom selected from the group consisting of a nitrogen atom, an oxygen atom and a sulfur atom can be contained in the aromatic group.

G represents a divalent alicyclic hydrocarbon group, where a hydrogen atom contained in the alicyclic hydrocarbon group is optionally substituted with a halogen atom, an alkyl group having 1 to 4 carbon atoms, a fluoro alkyl group having 1 to 4 carbon atoms, an alkoxy group having 1 to 4 carbon atoms, a cyano group, or a nitro group, and —$CH_2$— (methylene group) contained in the alicyclic hydrocarbon group is optionally substituted with —O—, —S—, or —NH—.

B represents a single bond or a divalent linking group.

A represents a divalent alicyclic hydrocarbon group having 3 to 20 carbon atoms or a divalent aromatic hydrocarbon group having 6 to 20 carbon atoms; the hydrogen atom contained in the alicyclic hydrocarbon group and the aromatic hydrocarbon group is optionally substituted with an alkyl group having 1 to 4 carbon atoms optionally substituted with a halogen atom, an alkoxy group having 1 to 4 carbon atoms optionally substituted with a fluorine atom, a cyano group or a nitro group; and —$CH_2$— contained in the alicyclic hydrocarbon group is optionally substituted with —O—, —S—, or —$NR^1$—. The group —CH (-)-contained in the alicyclic hydrocarbon group may be substituted with —N (-)-(amino group).

$R^1$ represents a hydrogen atom or an alkyl group having 1 to 4 carbon atoms.

k represents an integer of 0 to 3, where when k is an integer of 2 or more, a plurality of As and Bs may be the same or different from each other.

E represents an alkanediyl group having 1 to 17 carbon atoms, where the hydrogen atom contained in an alkanediyl group is optionally substituted with a halogen atom, and —$CH_2$— contained in the alkanediyl group is optionally substituted with —O— or —CO—.

P represents a polymerizable group.

The divalent aromatic group represented by Ar herein refers to a divalent group which has at least one aromatic ring like the example to be described later. Examples of the divalent group may has a substituent. Examples of the substituent include the groups or atoms to be described later.

In formula (1), the divalent aromatic group represented by Ar preferably contains at least one atom selected from the group consisting of a nitrogen atom, an oxygen atom, and a sulfur atom. This means that these hetero atoms are contained in Ar, and Ar may or may not have a heterocyclic ring. The divalent aromatic group represented by Ar is preferably an aromatic group having a heterocyclic ring, from the viewpoint of exhibiting a reverse wavelength dispersion characteristic. The aromatic group having a heterocyclic ring implies that the divalent group to be bonded to two oxygen atom (—O—) bonding to Ar of the liquid crystal compound may be a heterocyclic ring and the substituent of the divalent group may be a heterocyclic ring. Examples of the heterocyclic ring include a furan ring, a benzofuran ring, a pyrrole ring, a thiophene ring, a pyridine ring, a thiazole ring, a benzothiazole ring, and a phenanthroline ring. That is, examples of the aromatic group having a heterocyclic ring include a compound in which the divalent group to be bonded to two oxygen atom (—O—) bonding to Ar of the liquid crystal compound is the above-mentioned heterocyclic ring, and a compound in which the substituent of the divalent group is the above-mentioned heterocyclic ring. Of these compounds, the aromatic group having a heterocyclic ring is more preferably an aromatic group having a thiazole ring and a benzothiazole ring, and even more preferably an aromatic group having a benzothiazole ring. Further, of these compounds, the divalent group to be bonded to two oxygen atom (—O—) bonding to Ar of the liquid crystal compound is more preferably a thiazole ring and a benzothiazole ring, and even more preferably a benzothiazole ring.

When the aromatic ring in Ar has a nitrogen atom, the nitrogen atom contained in the aromatic ring in Ar preferably has a π electron.

When Ar is a divalent aromatic group having a heterocyclic ring as an aromatic ring, Ar may bond to the one of or both two oxygen atoms (—O—) bonding to Ar via the heterocyclic ring or may bond to the one of or both two oxygen atoms (—O—) bonding to Ar via an atom other than the atom comprising the heterocyclic ring.

A total number $N_\pi$ of the π electron contained in the aromatic ring in Ar is preferably 10 or more, more preferably 12 or more, and even more preferably 14 or more; preferably 30 or less, and more preferably 25 or less, from the viewpoint of exhibiting a reverse wavelength dispersion characteristic.

Examples of the divalent group in Ar to be bonded to two oxygen atom (—O—) bonding to Ar of the liquid crystal compound include the following groups represented by formulae (Ar-1) to (Ar-22).

[Chem. 10]

(Ar-1)

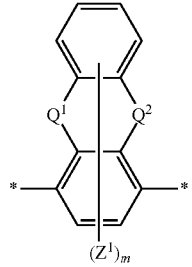

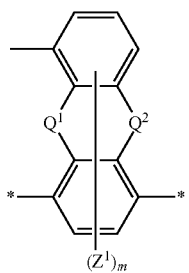
(Ar-2)
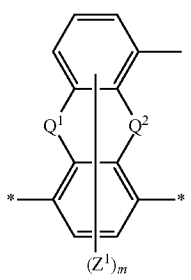
(Ar-3)
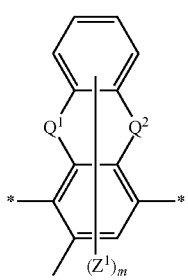
(Ar-4)
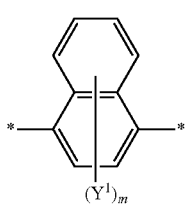
(Ar-5)
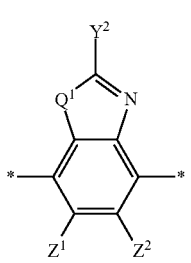
(Ar-6)
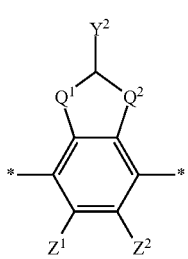
(Ar-7)
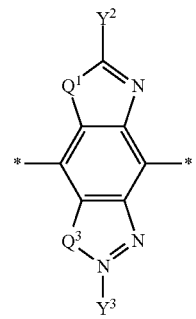
(Ar-8)
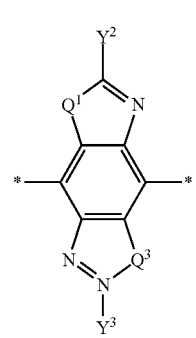
(Ar-9)
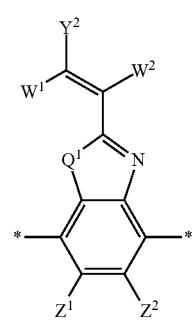
(Ar-10)
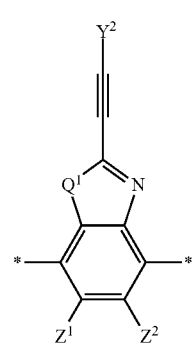
(Ar-11)
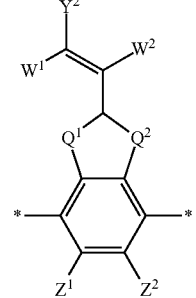
(Ar-12)

-continued

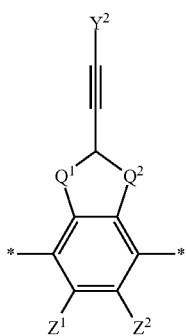
(Ar-13)

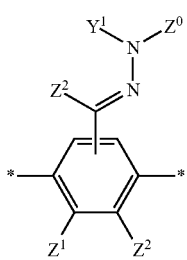
(Ar-14)

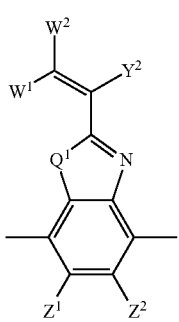
(Ar-15)

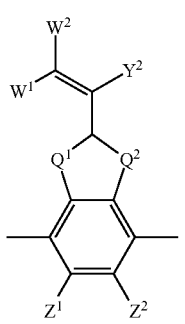
(Ar-16)

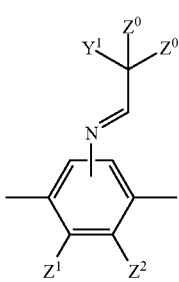
(Ar-17)

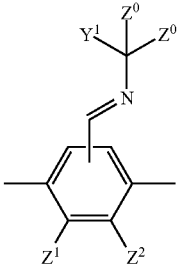
(Ar-18)

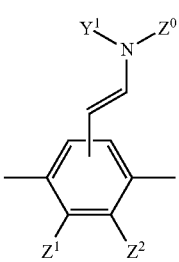
(Ar-19)

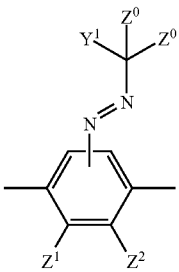
(Ar-20)

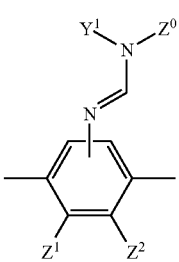
(Ar-21)

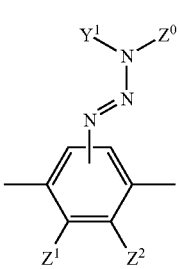
(Ar-22)

[In formulae (Ar-1) to (Ar-22), * represents a linking unit, $Z^0$, $Z^1$, and $Z^2$ each independently represent a hydrogen atom, a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a carboxyl group, a fluoroalkyl group having 1 to 6 carbon atoms, an alkoxy group having 1 to 6 carbon atoms, a fluoroalkyl group having 1 to 6 carbon atoms, an alkoxy group having 1 to 6 carbon atoms, an alkylthio group having 1 to 6 carbon atoms, an N-alkylamino group having 1 to 6 carbon atoms, an N,N-dialkylamino group having 2 to 12 carbon atoms, an N-alkylsulfamoyl group having 1 to 6 carbon atoms, or an N,N-dialkylsulfamoyl group having 2 to 12 carbon atoms.

$Q^1$, $Q^2$, and $Q^3$ each independently represent —$CR^2R^3$—, —S—, —$NR^2$—, —CO—, or —O—.

$R^2$ and $R^3$ each independently represent a hydrogen atom or an alkyl group having 1 to 4 carbon atoms.

$Y^1$, $Y^2$, and $Y^3$ each independently represent an aromatic hydrocarbon group or an aromatic heterocyclic group, which is optionally substituted.

$W^1$ and $W^2$ each independently represent a hydrogen atom, a cyano group, a methyl group, or a halogen atom.

m represents an integer of 0 to 6.]

Examples of the halogen atom include a fluorine atom, a chlorine atom, a bromine atom, and an iodine atom. Of these, a fluorine atom, a chlorine atom, or a bromine atom is preferable.

Examples of the alkyl group having 1 to 6 carbon atoms include a methyl group, an ethyl group, a propyl group, an isopropyl group, a butyl group, an isobutyl group, sec-butyl group, tert-butyl group, a pentyl group, and a hexyl group. Of these, an alkyl group having 1 to 4 carbon atoms is preferable, an alkyl group having 1 to 2 carbon atoms is more preferable, and a methyl group is especially preferable.

Examples of the alkylsulfinyl group having 1 to 6 carbon atoms include a methyl sulfinyl group, an ethyl sulfinyl group, a propyl sulfinyl group, an isopropyl sulfinyl group, a butyl sulfinyl group, an iso-butyl sulfinyl group, a sec-butyl sulfinyl group, a tert-butyl sulfinyl group, a pentyl sulfinyl group, and a hexyl sulfinyl group. Of these, an alkylsulfinyl group having 1 to 4 carbon atoms is preferable, an alkylsulfinyl group having 1 or 2 carbon atoms is more preferable, and a methylsulfinyl group is especially preferable.

Examples of the alkylsulfonyl group having 1 to 6 carbon atoms include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentyl sulfonyl group, and a hexyl sulfonyl group. Of these, an alkylsulfonyl group having 1 to 4 carbon atoms is preferable, an alkylsulfonyl group having 1 to 2 carbon atoms is more preferable, and a methylsulfonyl group is especially preferable.

Examples of the fluoroalkyl group having 1 to 6 carbon atoms include a fluoromethyl group, a trifluoromethyl group, a fluoroethyl group, a pentafluoroethyl group, a heptafluoropropyl group, and a nonafluorobutyl group. Of these, a fluoroalkyl group having 1 to 4 carbon atoms is preferable, a fluoroalkyl group having 1 to 2 carbon atoms is more preferable, and a trifluoromethyl group is especially preferable.

Examples of the alkoxy group having 1 to 6 carbon atoms include a methoxy group, an ethoxy group, a propoxy group, an isopropoxy group, a butoxy group, an isobutoxy group, a sec-butoxy group, a tert-butoxy group, a pentyloxy group, and a hexyloxy group. Of these, an alkoxy group having 1 to 4 carbon atoms is preferable, an alkoxy group having 1 to 2 carbon atoms is more preferable, and a methoxy group is especially preferable.

Examples of the alkylthio group having 1 to 6 carbon atoms include a methylthio group, an ethylthio group, a propylthio group, anisopropylthiogroup, abutylthiogroup, anisobutylthio group, a sec-butylthio group, a tert-butylthio group, a pentylthio group, and a hexylthio group. Of these, an alkylthio group having 1 to 4 carbon atoms is preferable, an alkylthio group having 1 to 2 carbon atoms is more preferable, and a methylthio group is especially preferable.

Examples of the N-alkylamino group having 1 to 6 carbon atoms include an N-methylamino group, an N-ethylamino group, an N-propylamino group, an N-isopropylamino group, an N-butylamino group, an N-isobutylamino group, an N-sec-butylamino group, an N-tert-butylamino group, an N-pentylamino group, and an N-hexylamino group. Of these, an N-alkylamino group having 1 to 4 carbon atoms is preferable, N-alkylamino group having 1 to 2 carbon atoms is more preferable, and an N-methylamino group is especially preferable.

Examples of the N,N-dialkylamino group having 2 to 12 carbon atoms include an N,N-dimethylamino group, an N-methyl-N-ethylamino group, an N,N-diethylamino group, an N,N-dipropylamino group, an N,N-diisopropylamino group, an N,N-dibutylamino group, an N,N-diisobutylamino group, an N,N-dipentylamino group, and an N,N-dihexylamino group. Of these, an N,N-dialkylamino group having 2 to 8 carbon atoms is preferable, an N,N-dialkylamino group having 2 to 4 carbon atoms is more preferable, and an N,N-dimethylamino group is especially preferable.

Examples of the N-alkylsulfamoyl group having 1 to 6 carbon atoms include an N-methylsulfamoyl group, an N-ethylsulfamoyl group, an N-propylsulfamoyl group, an N-isopropylsulfamoyl group, an N-butylsulfamoyl group, an N-isobutyl sulfamoyl group, an N-sec-butylsulfamoyl group, an N-tert-butylsulfamoyl group, an N-pentylsulfamoyl group, and N-hexylsulfamoyl group. Of these, an N-alkylsulfamoyl group having 1 to 4 carbon atoms is preferable, an N-alkylsulfamoyl group having 1 to 2 carbon atoms is more preferable, and an N-methylsulfamoyl group is especially preferable.

Examples of the N,N-dialkylsulfamoyl group having 2 to 12 carbon atoms include an N,N-dimethylsulfamoyl group, an N-methyl-N-ethylsulfamoyl group, an N,N-diethylsulfamoyl group, an N,N-dipropylsulfamoyl group, an N,N-diisopropylsulfamoyl group, an N,N-dibutylsulfamoyl group, an N,N-diisobutylsulfamoyl group, an N,N-dipentylsulfamoyl group, and an N,N-dihexylsulfamoyl group. Of these, an N,N-dialkylsulfamoyl group having 2 to 8 carbon atoms is preferable, an N,N-dialkylsulfamoyl group having 2 to 4 carbon atoms is more preferable, and an N,N-dimethylsulfamoyl group is especially preferable.

It is preferable that $Z^0$, $Z^1$, and $Z^2$ are each independently a hydrogen atom, a halogen atom, a methyl group, a cyano group, a nitro group, a carboxyl group, a methylsulfonyl group, a trifluoromethyl group, a methoxy group, a methylthio group, an N-methylamino group, an N,N-dimethylamino group, an N-methylsulfamoyl group, or a N,N-dimethylsulfamoyl group.

Examples of the alkyl group having 1 to 4 carbon atoms in $R^2$ and $R^3$ include a methyl group, an ethyl group, a propyl group, an isopropyl group, a butyl group, an isobutyl group, and a tert-butyl group. Of these, an alkyl group having 1 to 2 carbon atoms is preferable, and a methyl group is more preferable.

$Q^1$ and $Q^2$ are each independently preferably —S—, —CO—, —NH—, or —N(CH$_3$)—, and $Q^3$ is preferably —S— or —CO—.

Examples of the aromatic hydrocarbon group in $Y^1$, $Y^2$, and $Y^3$ include an aromatic hydrocarbon group having 6 to 20 carbon atoms such as a phenyl group, a naphthyl group, an anthryl group, a phenanthryl group, and a biphenyl group. Of these, a phenyl group and a naphthyl group are preferable, and a phenyl group is more preferable. The aromatic heterocyclic group contains at least one of hetero atoms such as nitrogen atom, oxygen atom, and sulfur atom, including a furyl group, a pyrrolyl group, a thienyl group, a pyridinyl group, a thiazolyl group, and a benzothiazolyl group. Examples thereof include aromatic heterocyclic group having 4 to 20 carbon atoms, and a furyl group, a pyrrolyl group, a thienyl group, a pyridinyl group, and a thiazolyl group are preferable.

The aromatic hydrocarbon group and the aromatic heterocyclic group optionally have at least one substituent, and examples of the substituent include a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a carboxyl group, a fluoroalkyl group having 1 to 6 carbon atoms, an alkoxy group having 1 to 6 carbon atoms, an alkylthio group having 1 to 6 carbon atoms, an N-alkylamino group having 1 to 6 carbon atoms, an N,N-dialkylamino group having 2 to 12 carbon atoms, an N-alkylsulfamoyl group having 1 to 6 carbon atoms, and an N,N-dialkylsulfamoyl group having 2 to 12 carbon atoms. Of these, a halogen atom, an alkyl group having 1 to 2 carbon atoms, a cyano group, a nitro group, an alkylsulfinyl group having 1 to 2 carbon atoms, a fluoroalkyl group having 1 to 2 carbon atoms, an alkoxy group having 1 to 2 carbon atoms, an alkylthio group having 1 to 2 carbon atoms, an N-alkylamino group having 1 to 2 carbon atoms, an N,N-dialkylamino group having 2 to 4 carbon atoms, and an N-alkylsulfamoyl group having 1 to 2 carbon atoms are preferable.

Examples of the halogen atom, alkyl group having 1 to 6 carbon atoms, cyano group, nitro group, alkylsulfinyl group having 1 to 6 carbon atoms, alkylsulfonyl group having 1 to 6 carbon atoms, carboxyl group, fluoroalkyl group having 1 to 6 carbon atoms, alkoxy group having 1 to 6 carbon atoms, alkylthio group having 1 to 6 carbon atoms, N-alkylamino group having 1 to 6 carbon atoms, N,N-dialkylamino group having 2 to 12 carbon atoms, N-alkylsulfamoyl group having 1 to 6 carbon atoms, and N,N-dialkylsulfamoyl group having 2 to 12 carbon atoms include the same groups as those described above.

In formula (Ar-14), $Y^1$ may form an aromatic heterocyclic group together with the nitrogen atom to which $Y^1$ bonds and $Z^0$. Examples of the aromatic heterocyclic group include a pyrrole ring, an imidazole ring, a pyridine ring, a pyrimidine ring, an indole ring, a quinoline ring, an isoquinoline ring, a purine ring, a pyrrolidine ring, and a piperidine ring. Such aromatic heterocyclic group optionally has a substituent. Further, $Y^1$ may be a polycyclic aromatic hydrocarbon group or a polycyclic aromatic heterocyclic group which is optionally substituted, to be described later, together with the nitrogen atom to which $Y^1$ bonds, and $Z^0$.

$Y^1$, $Y^2$, and $Y^3$ may be each independently a polycyclic aromatic hydrocarbon group or a polycyclic aromatic heterocyclic group which is optionally substituted. The polycyclic aromatic hydrocarbon group refers to a group derived from a fused polycyclic aromatic hydrocarbon group or an aromatic ring assembly. The polycyclic aromatic heterocyclic group refers to a group derived from a fused polycyclic aromatic heterocyclic group or an aromatic ring assembly. For example, $Y^1$, $Y^2$ and $Y^3$ are each independently preferably any of the groups represented by formulae ($Y^1$-1) to ($Y^1$-7), and more preferably any of the groups represented by formulae ($Y^1$-1) to ($Y^1$-4).

[Chem. 11]

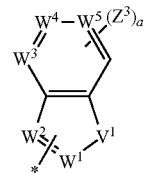

($Y^1$-1)

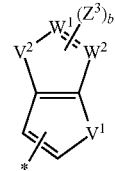

($Y^1$-2)

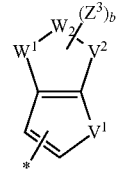

($Y^1$-3)

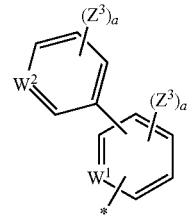

($Y^1$-4)

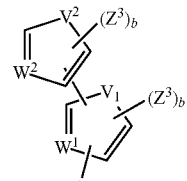

($Y^1$-5)

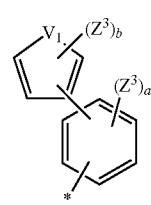

($Y^1$-6)

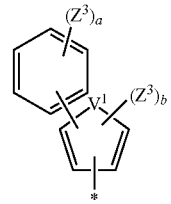

($Y^1$-7)

[In formulae ($Y^1$-1) to ($Y^1$-7), * represents a linking unit, and $Z^3$ independently represents a halogen atom, an alkyl group having 1 to 6 carbon atoms, a cyano group, a nitro group, a nitroxide group, a sulfone group, a sulfoxide group, a carboxyl group, a fluoroalkyl group having 1 to 6 carbon atoms, an alkoxy group having 1 to 6 carbon atoms, a thioalkyl group having 1 to 6 carbon atoms, an N,N- dialkylamino group having 2 to 8 carbon atoms, or an N-alkylamino group having 1 to 4 carbon atoms.

$V^1$ and $V^2$ each independently represent —CO—, —S—, —NR$^4$—, —O—, —Se— or —SO$_2$—.

$W^1$ to $W^5$ each independently represent —C= or —N=, where at least one of $V^1$, $V^2$, and $W^1$ to $W^5$ represents a group containing S, N, O or Se.

$R^4$ represents a hydrogen atom or an alkyl group having 1 to 4 carbon atoms.

a independently represents an integer of 0 to 3.

b independently represents an integer of 0 to 2.

Any of the groups represented by formulae ($Y^1$-1) to ($Y^1$-7) is preferably any of the groups represented by formulae ($Y^2$-1) to ($Y^2$-16), and more preferably any of the groups represented by formulae ($Y^3$-1) to ($Y^3$-6), and especially preferably the group represented by formula ($Y^3$-1) or formula ($Y^3$-3).

[Chem. 12]

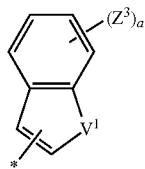
($Y^2$-1)

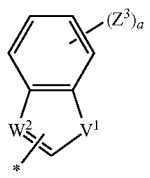
($Y^2$-2)

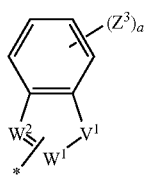
($Y^2$-3)

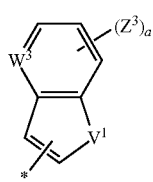
($Y^2$-4)

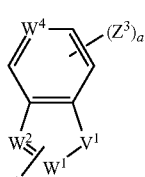
($Y^2$-5)

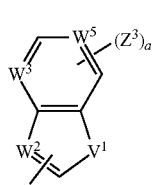
($Y^2$-6)

-continued

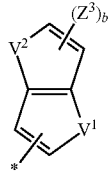
($Y^2$-7)

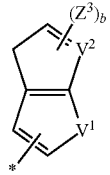
($Y^2$-8)

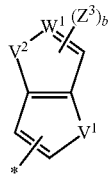
($Y^2$-9)

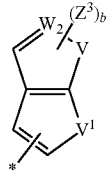
($Y^2$-10)

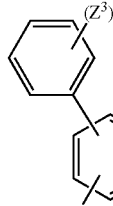
($Y^2$-11)

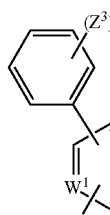
($Y^2$-12)

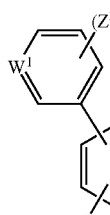
($Y^2$-13)

-continued

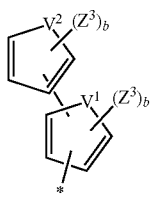
(Y²-14)

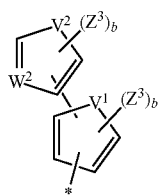
(Y²-15)

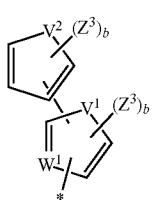
(Y²-16)

[In formulae (Y²-1) to (Y²-16), $Z^3$, a, b, $V^1$, $V^2$ and $W^1$ to $W^5$ are the same as defined above.]

[Chem. 13]

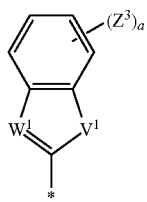
(Y³-1)

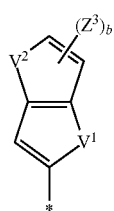
(Y³-2)

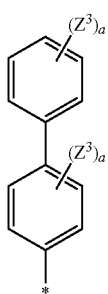
(Y³-3)

-continued

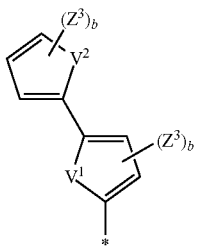
(Y³-4)

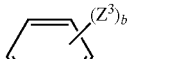
(Y³-5)

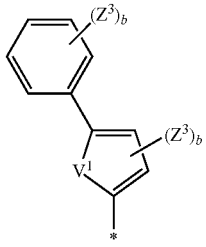

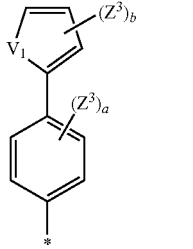
(Y³-6)

[In formulae (Y³-1) to (Y³-6), $Z^3$, a, b, $V^1$, $V^2$ and $W^1$ are the same as defined above.]

Examples of $Z^3$ include a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a carboxyl group, a fluoroalkyl group having 1 to 6 carbon atoms, an alkoxy group having 1 to 6 carbon atoms, an alkylthio group having 1 to 6 carbon atoms, an N-alkylamino group having 1 to 6 carbon atoms, an N, N-dialkylamino group having 2 to 12 carbon atoms, an N-alkylsulfamoyl group having 1 to 6 carbon atoms, and an N,N-dialkylsulfamoyl group having 2 to 12 carbon atoms. Of these, a halogen atom, a methyl group, an ethyl group, an isopropyl group, a sec-butyl group, a cyano group, a nitro group, a sulfone group, a nitroxide group, a carboxyl group, a trifluoromethyl group, a methoxy group, a thiomethyl group, an N,N-dimethylamino group, and an N-methylamino group are preferable; a halogen atom, a methyl group, an ethyl group, an isopropyl group, a sec-butyl group, a cyano group, a nitro group, a trifluoromethyl group are more preferable; and a methyl group, an ethyl group, an isopropyl group, a sec-butyl group, a pentyl group, and a hexyl group are especially preferable.

Examples of the halogen atom, alkyl group having 1 to 6 carbon atoms, alkylsulfinyl group having 1 to 6 carbon atoms, alkylsulfonyl group having 1 to 6 carbon atoms, fluoroalkyl group having 1 to 6 carbon atoms, alkoxy group having 1 to 6 carbon atoms, alkylthio group having 1 to 6 carbon atoms, N-alkylamino group having 1 to 6 carbon atoms, N,N-dialkylamino group having 2 to 12 carbon atoms, N-alkylsulfamoyl group having 1 to 6 carbon atoms, and N,N-dialkylsulfamoyl group having 2 to 12 carbon atoms include the same groups as those described above.

It is preferable that $V^1$ and $V^2$ are each independently —S—, —NR$^4$— or —O—.

It is preferable that $W^1$ to $W^5$ are each independently —C= or —N=.

It is preferable that at least one of $V^1$, $V^2$, and $W^1$ to $W^5$ represents a group containing S, N or O.

It is preferable that a is 0 or 1. It is preferable that b is 0.

Specific examples of $Y^1$ to $Y^3$ include the groups represented by formulae (ar-1) to (ar-840).

[Chem. 14]

(ar-001)
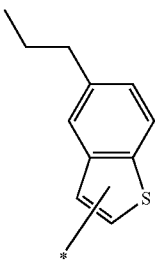

(ar-002)
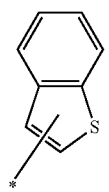

(ar-003)
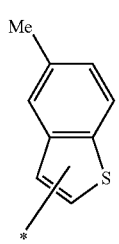

(ar-004)
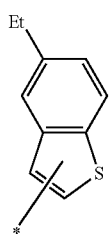

(ar-005)
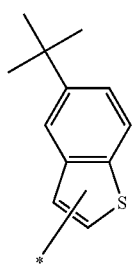

(ar-006)
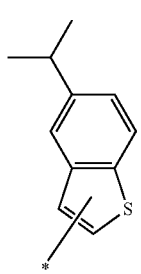

-continued (ar-006)
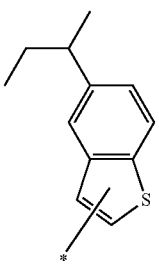

(ar-007)
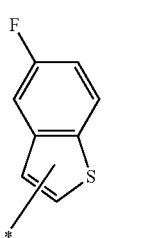

(ar-008)
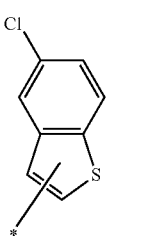

(ar-009)

(ar-010)
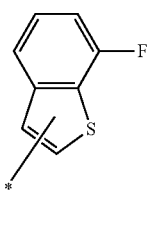

(ar-011)

(ar-012)
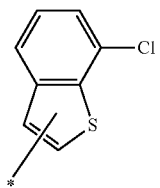
(ar-013)
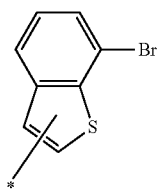
(ar-014)
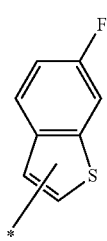
(ar-015)
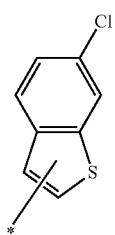
(ar-016)
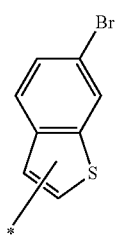
(ar-017)
(ar-018)
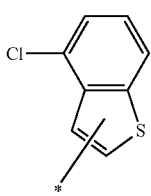
(ar-019)
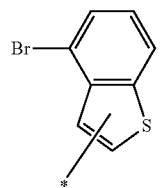
(ar-020)
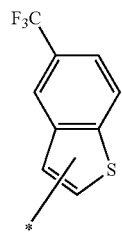
(ar-021)
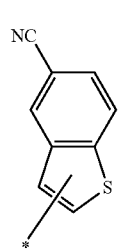
[Chem. 15]
(ar-022)
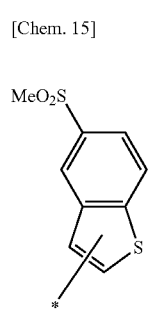
(ar-023)
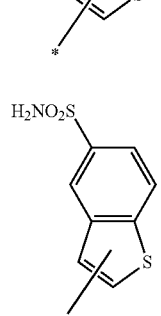
(ar-024)
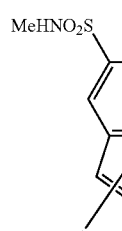

(ar-025)
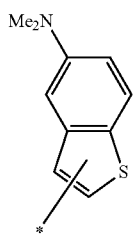
(ar-026)
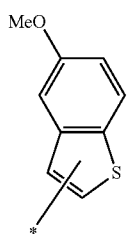
(ar-027)
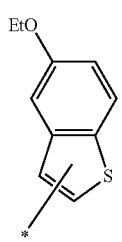
(ar-028)
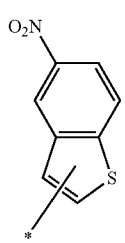
[Chem. 16]
(ar-029)
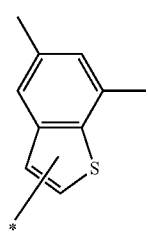
(ar-030)
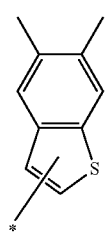
(ar-031)
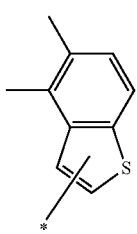
(ar-032)
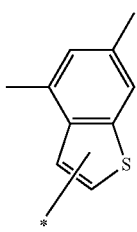
(ar-033)
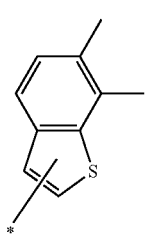
(ar-34)
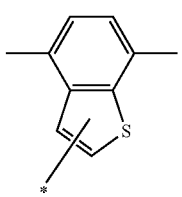
(ar-35)
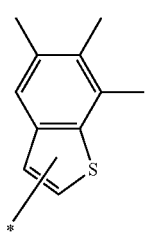
[Chem. 17]
(ar-36)
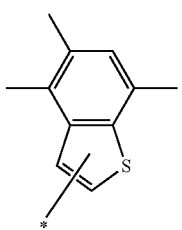

-continued
(ar-37)
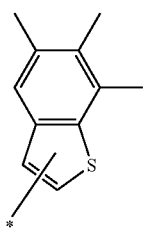
(ar-38)
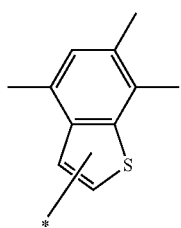
(ar-39)
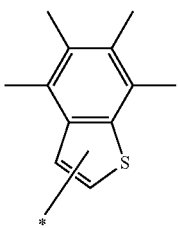
(ar-040)
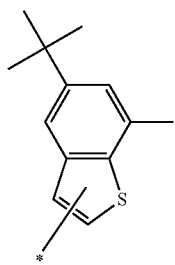
(ar-041)
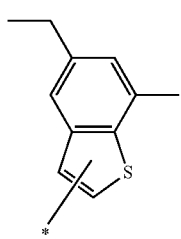
(ar-042)
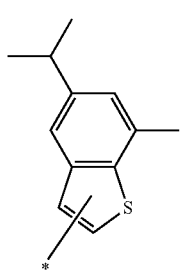
[Chem. 18]
-continued
(ar-043)
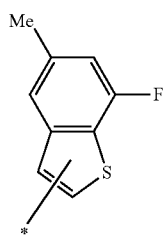
(ar-044)
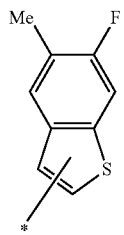
(ar-045)
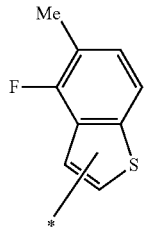
(ar-046)
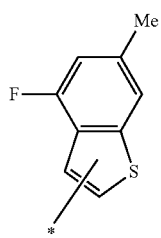
(ar-047)
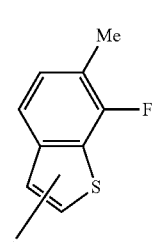
(ar-048)
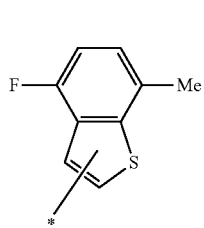

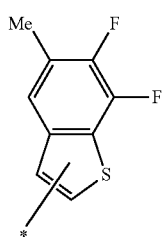 (ar-049)
[Chem. 19]
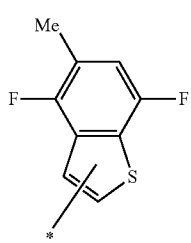 (ar-050)
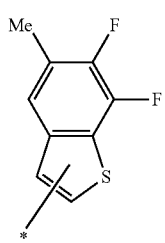 (ar-051)
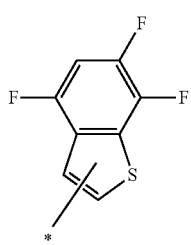 (ar-052)
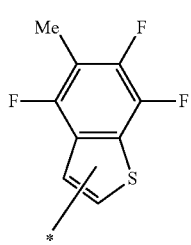 (ar-053)
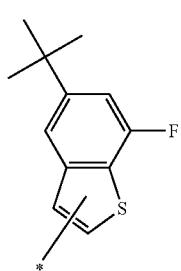 (ar-054)
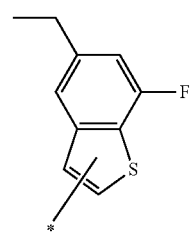 (ar-055)
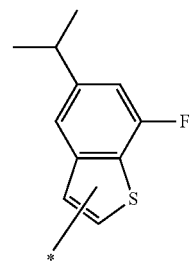 (ar-056)
[Chem. 20]
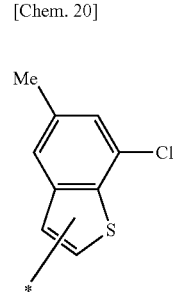 (ar-057)
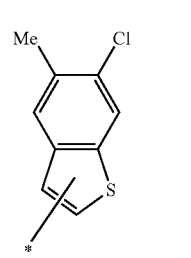 (ar-058)
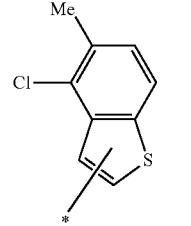 (ar-059)
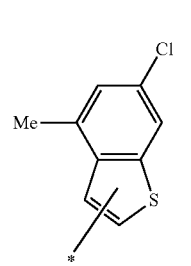 (ar-060)

(ar-061)
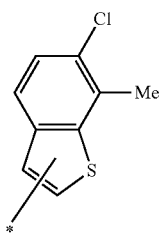
(ar-062)
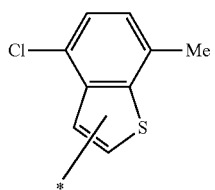
(ar-063)
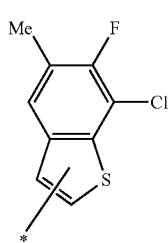
[Chem. 21]
(ar-064)
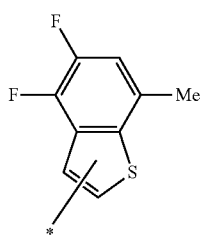
(ar-065)
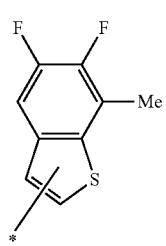
(ar-066)
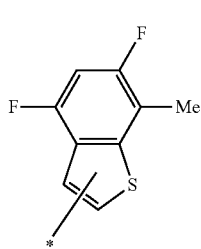
(ar-067)
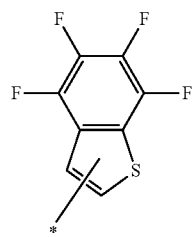
(ar-068)
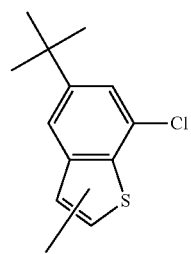
(ar-069)
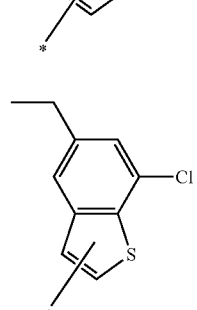
(ar-070)
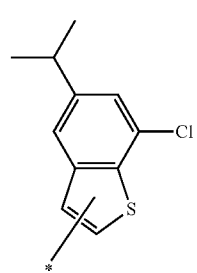
[Chem. 22]
(ar-071)
(ar-072)
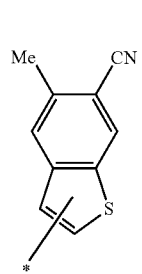

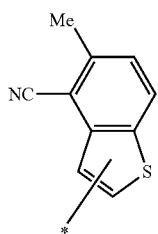 (ar-073)
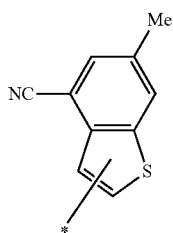 (ar-074)
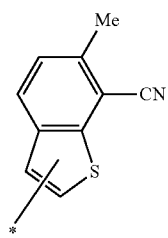 (ar-075)
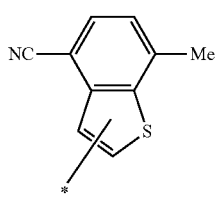 (ar-076)
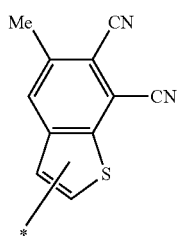 (ar-077)
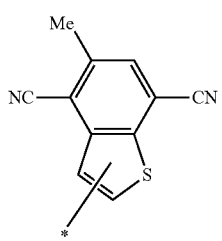 (ar-078)
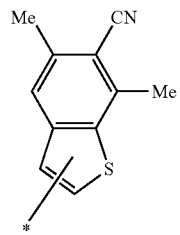 (ar-079)
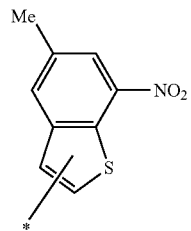 (ar-080)
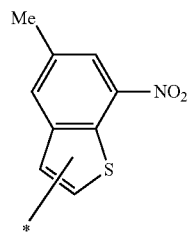 (ar-081)
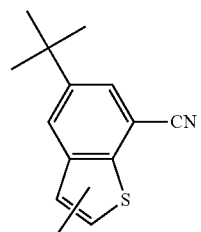 (ar-082)
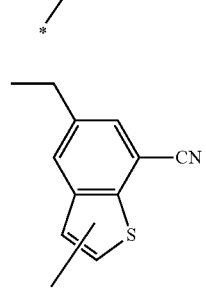 (ar-083)
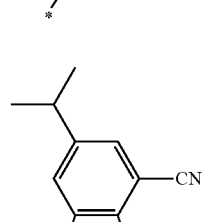 (ar-084)
[Chem. 23]

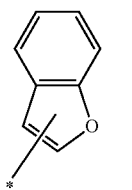 (ar-085)
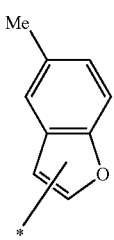 (ar-086)
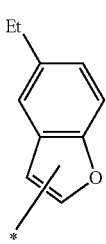 (ar-087)
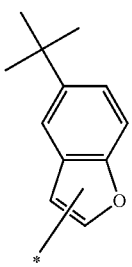 (ar-088)
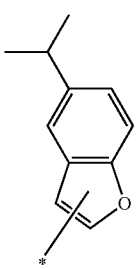 (ar-089)
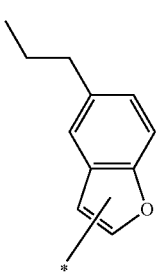 (ar-090)
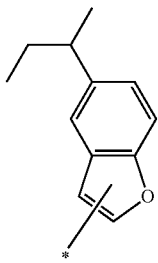 (ar-091)
[Chem. 24]
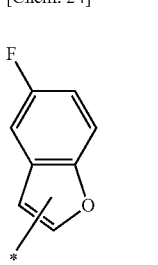 (ar-092)
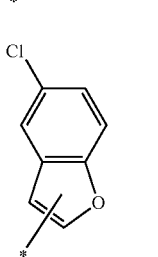 (ar-093)
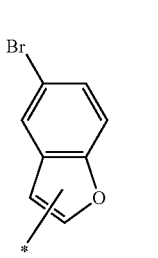 (ar-094)
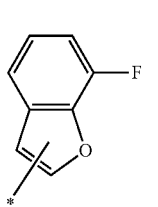 (ar-095)
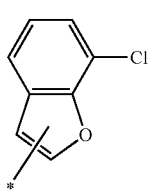 (ar-096)
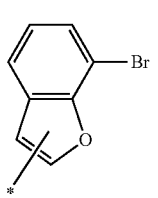 (ar-097)

(ar-098) 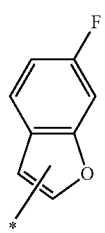
[Chem. 25]
(ar-099) 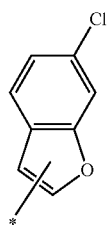
(ar-100) 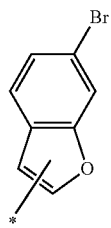
(ar-101) 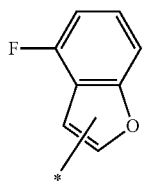
(ar-102) 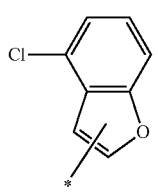
(ar-103) 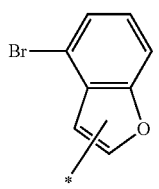
(ar-104) 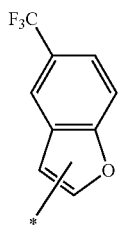
(ar-105) 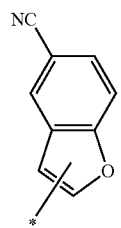
[Chem. 26]
(ar-106) 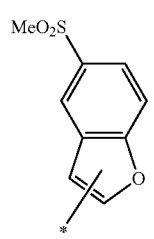
(ar-107) 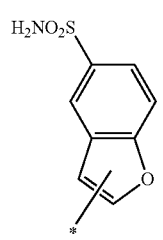
(ar-108) 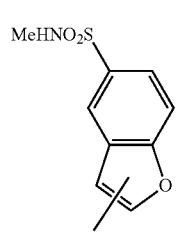
(ar-109) 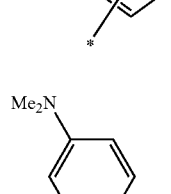
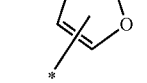
(ar-110) 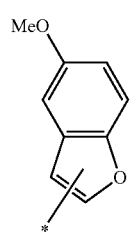

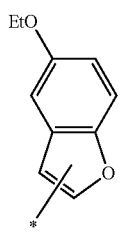 (ar-111)
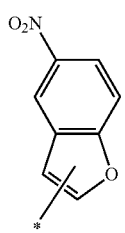 (ar-112)
[Chem. 27]
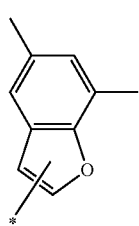 (ar-113)
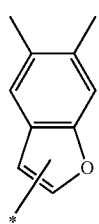 (ar-114)
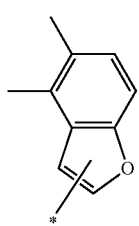 (ar-115)
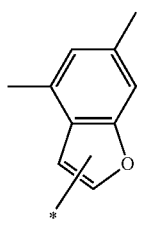 (ar-116)
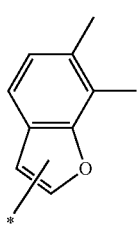 (ar-117)
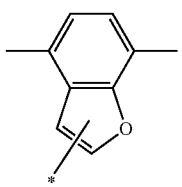 (ar-118)
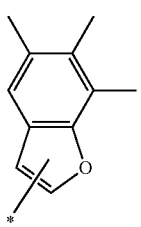 (ar-119)
[Chem. 28]
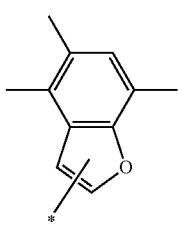 (ar-120)
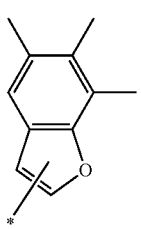 (ar-121)
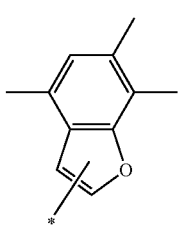 (ar-122)

(ar-123) 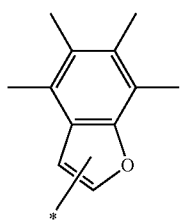
(ar-124) 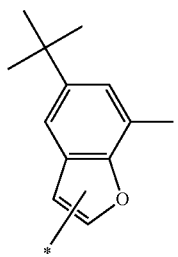
(ar-125) 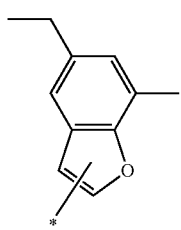
(ar-126) 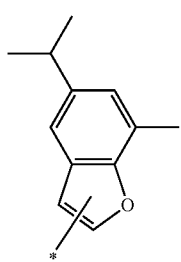
[Chem. 29]
(ar-127) 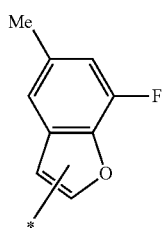
(ar-128) 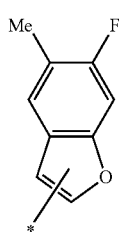
(ar-129) 
(ar-130) 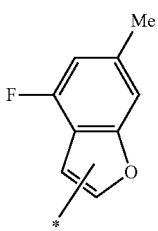
(ar-131) 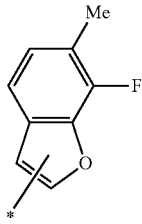
(ar-132) 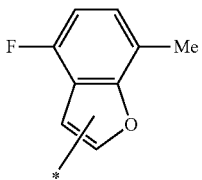
(ar-133) 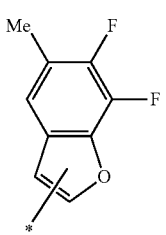
[Chem. 30]
(ar-134) 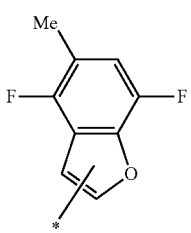

-continued
(ar-135)
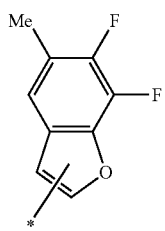
(ar-136)
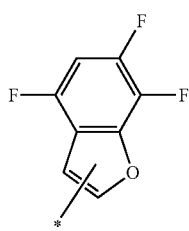
(ar-137)
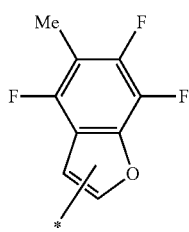
(ar-138)
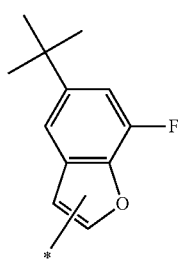
(ar-139)
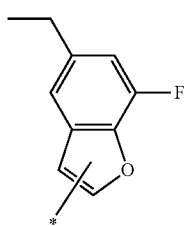
(ar-140)
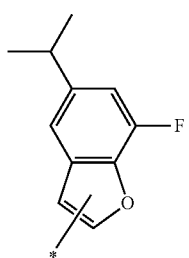
[Chem. 31]
-continued
(ar-141)
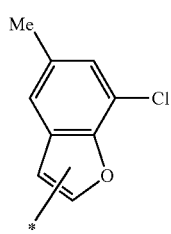
(ar-142)
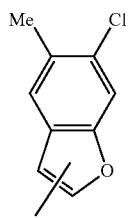
(ar-143)
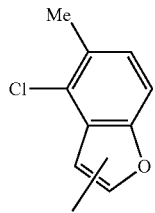
(ar-144)
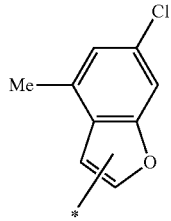
(ar-145)
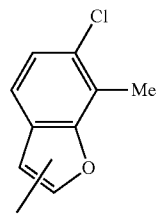
(ar-146)
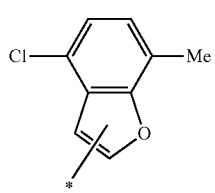
(ar-147)
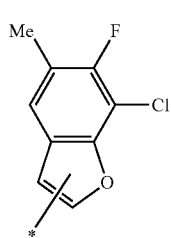

[Chem. 32]
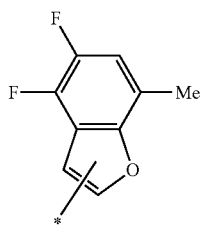
(ar-148)
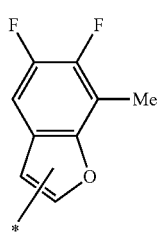
(ar-149)
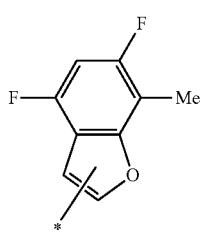
(ar-150)
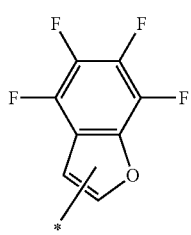
(ar-151)
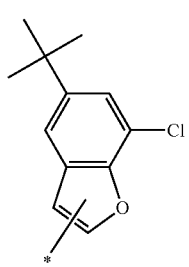
(ar-152)
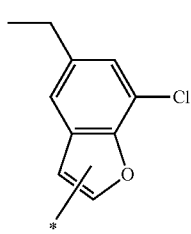
(ar-153)
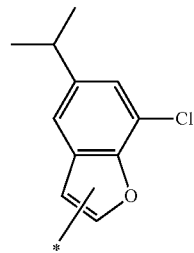
(ar-154)
[Chem. 33]
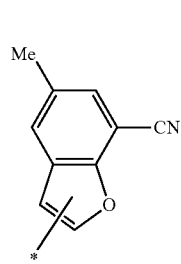
(ar-155)
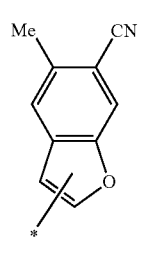
(ar-156)
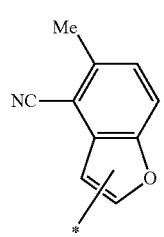
(ar-157)
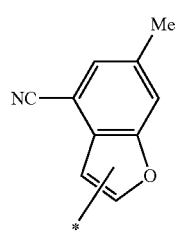
(ar-158)
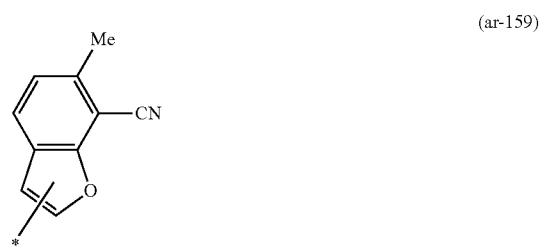
(ar-159)

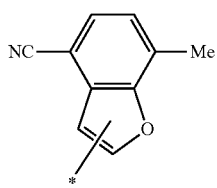
(ar-160)
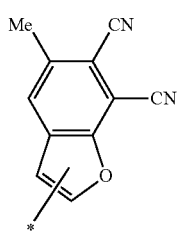
(ar-161)
[Chem. 34]
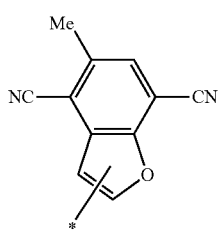
(ar-162)
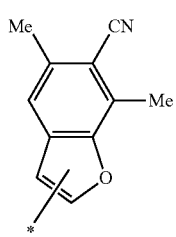
(ar-163)
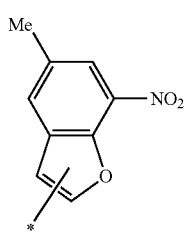
(ar-164)
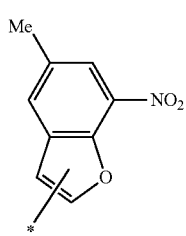
(ar-165)
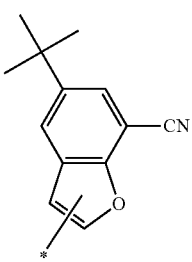
(ar-166)
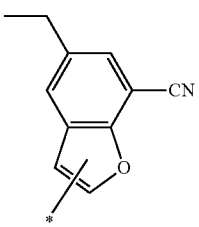
(ar-167)
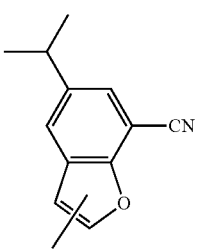
(ar-168)
[Chem. 35]
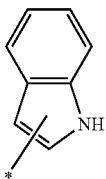
(ar-169)
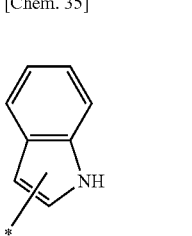
(ar-170)
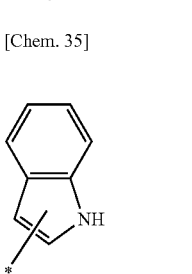
(ar-171)

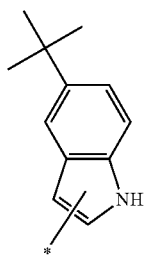 (ar-172)
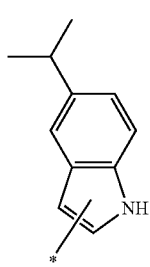 (ar-173)
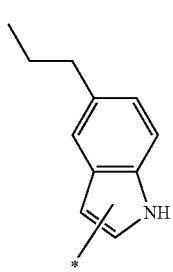 (ar-174)
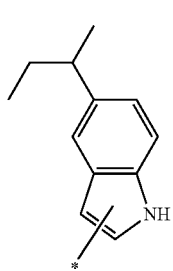 (ar-175)
[Chem. 36]
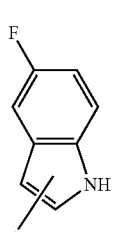 (ar-176)
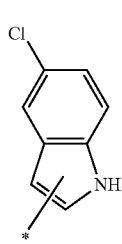 (ar-177)
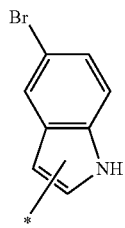 (ar-178)
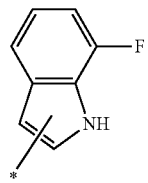 (ar-179)
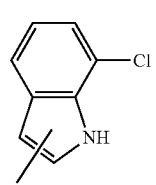 (ar-180)
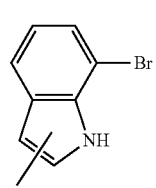 (ar-181)
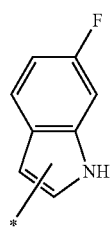 (ar-182)
[Chem. 37]
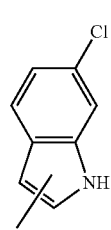 (ar-183)
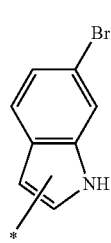 (ar-184)

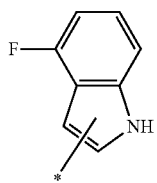 (ar-185)
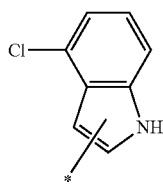 (ar-186)
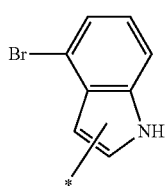 (ar-187)
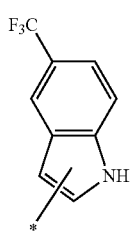 (ar-188)
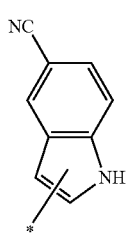 (ar-189)
[Chem. 38]
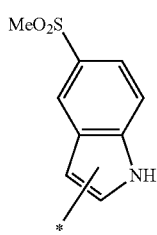 (ar-190)
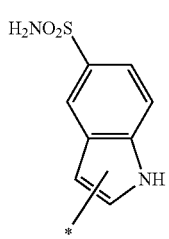 (ar-191)
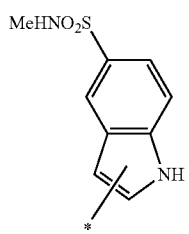 (ar-192)
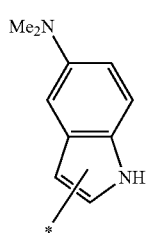 (ar-193)
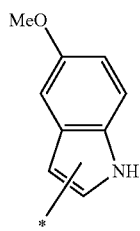 (ar-194)
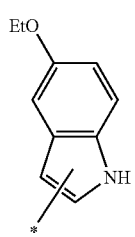 (ar-195)
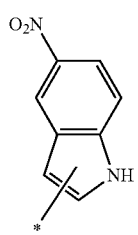 (ar-196)
[Chem. 39]
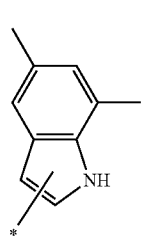 (ar-197)

(ar-198)
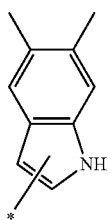
(ar-199)
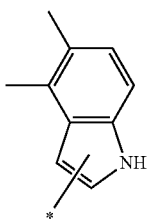
(ar-200)
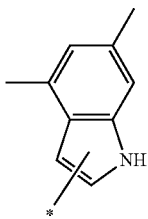
(ar-201)
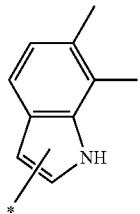
(ar-202)
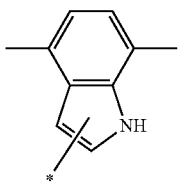
(ar-203)
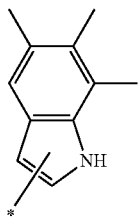
[Chem. 40]
(ar-204)
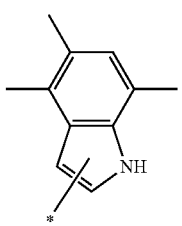
(ar-205)
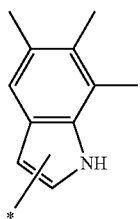
(ar-206)
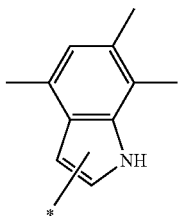
(ar-207)
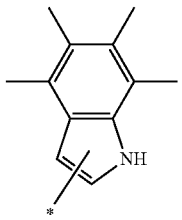
(ar-208)
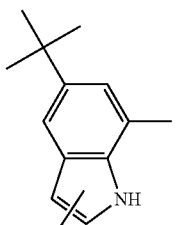
(ar-209)
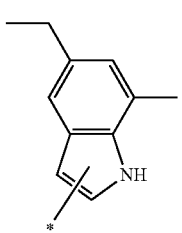

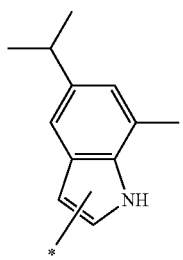
(ar-210)
[Chem. 41]
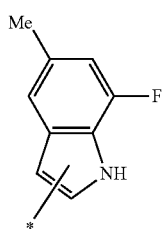
(ar-211)
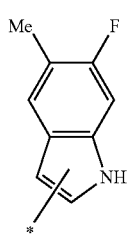
(ar-212)
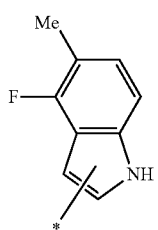
(ar-213)
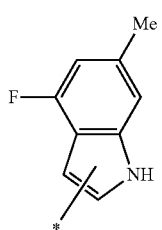
(ar-214)
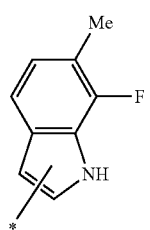
(ar-215)
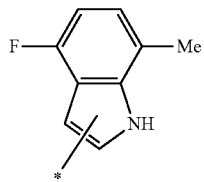
(ar-216)
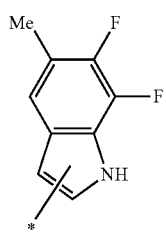
(ar-217)
[Chem. 42]
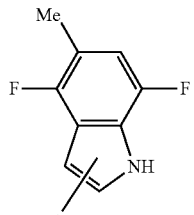
(ar-218)
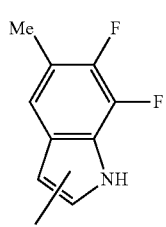
(ar-219)
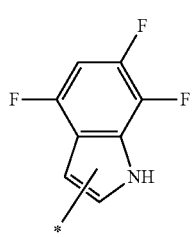
(ar-220)
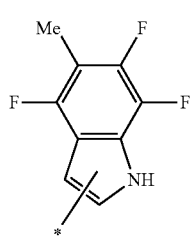
(ar-221)

(ar-222) 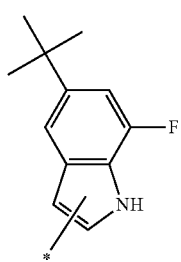
(ar-223) 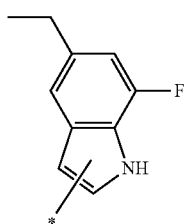
(ar-224) 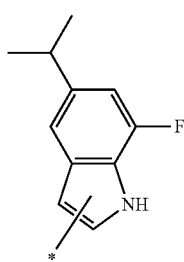
[Chem. 43]
(ar-225) 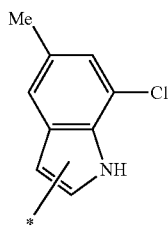
(ar-226) 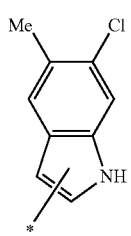
(ar-227) 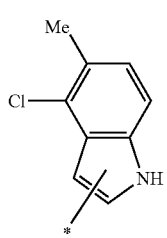
(ar-228) 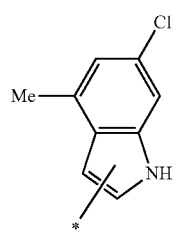
(ar-229) 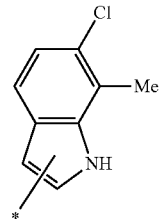
(ar-230) 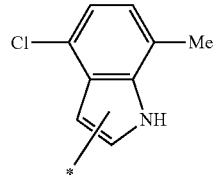
(ar-231) 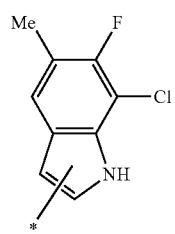
[Chem. 44]
(ar-232) 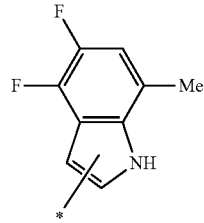
(ar-233) 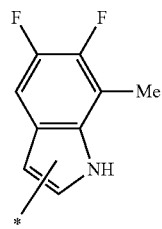

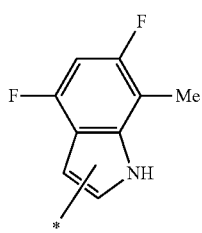 (ar-234)
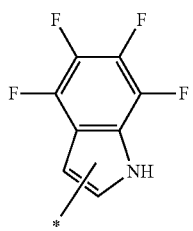 (ar-235)
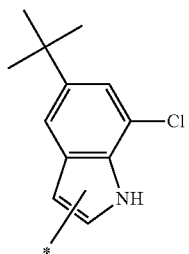 (ar-236)
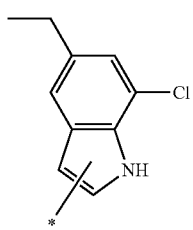 (ar-237)
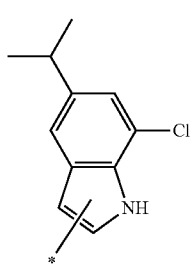 (ar-238)
[Chem. 45]
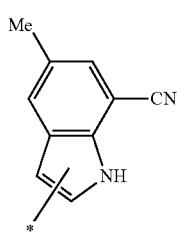 (ar-239)
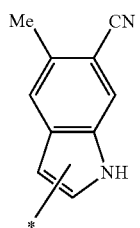 (ar-240)
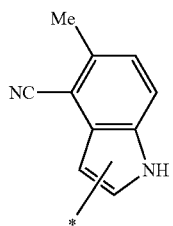 (ar-241)
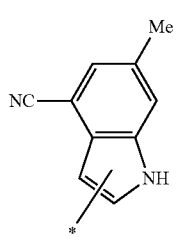 (ar-242)
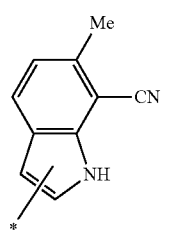 (ar-243)
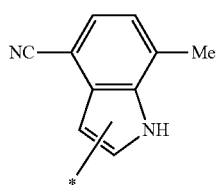 (ar-244)
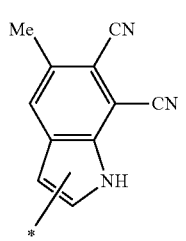 (ar-245)
[Chem. 46]

(ar-246)
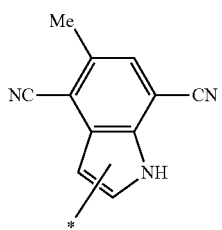
(ar-247)
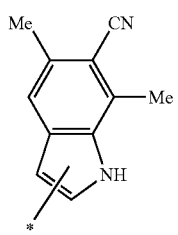
(ar-248)
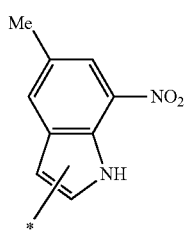
(ar-249)
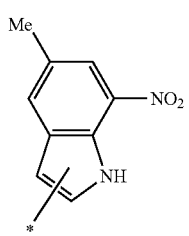
(ar-250)
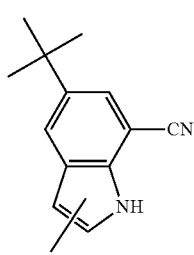
(ar-251)
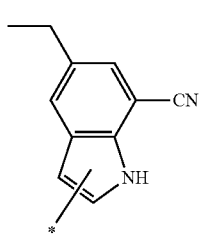
(ar-252)
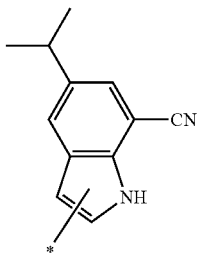
[Chem. 47]
(ar-253)
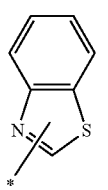
(ar-254)
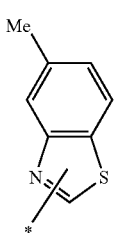
(ar-255)
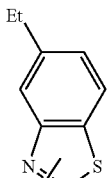
(ar-256)
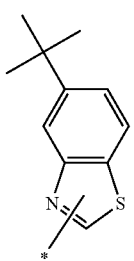
(ar-257)
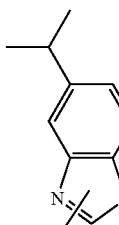

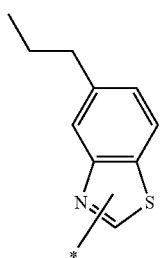
(ar-258)
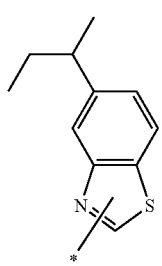
(ar-259)
[Chem. 48]
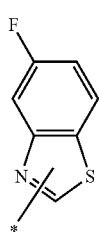
(ar-260)
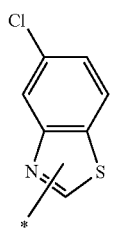
(ar-261)
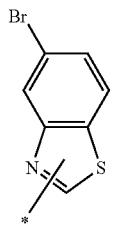
(ar-262)
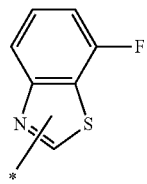
(ar-263)
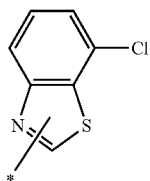
(ar-264)
(ar-265)
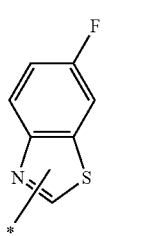
(ar-266)
[Chem. 49]
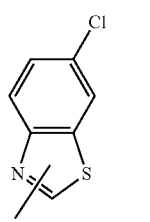
(ar-267)
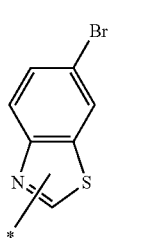
(ar-268)
(ar-269)
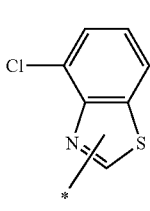
(ar-270)

(ar-271) 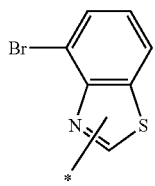
(ar-272) 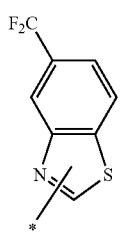
(ar-273) 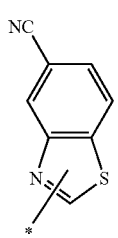
[Chem. 50]
(ar-274) 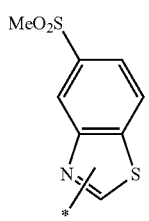
(ar-275) 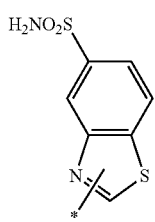
(ar-276) 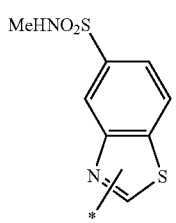
(ar-277) 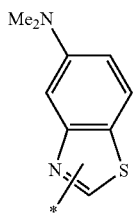
(ar-278) 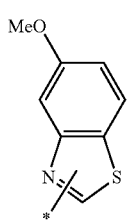
(ar-279) 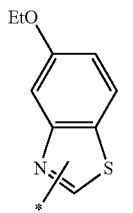
(ar-280) 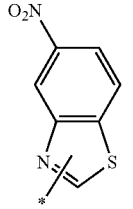
[Chem. 51]
(ar-281) 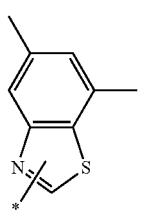
(ar-282) 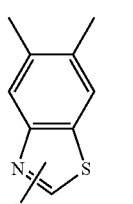
(ar-283) 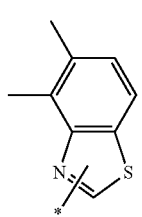

(ar-284) 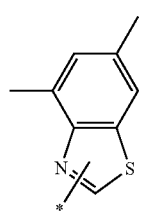
(ar-285) 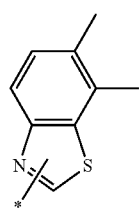
(ar-286) 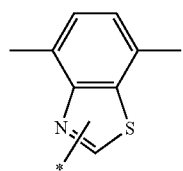
(ar-287) 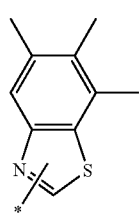
[Chem. 52]
(ar-288) 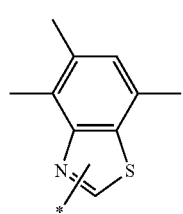
(ar-289) 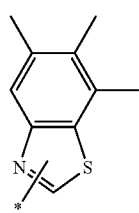
(ar-290) 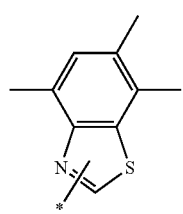
(ar-291) 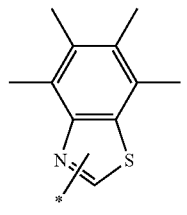
(ar-292) 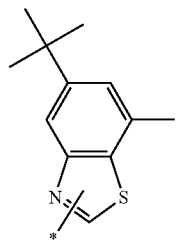
(ar-293) 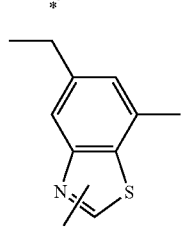
(ar-294) 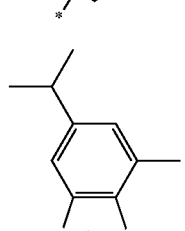
[Chem. 53]
(ar-295) 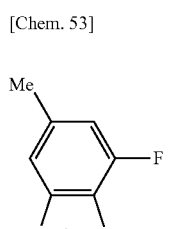
(ar-296) 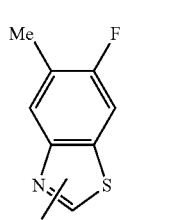
(ar-297) 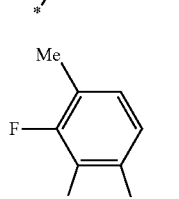

(ar-298) 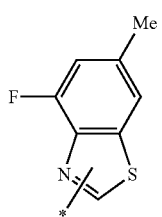
(ar-299) 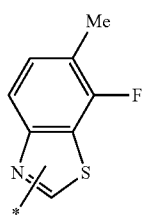
(ar-300) 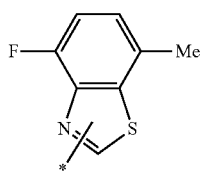
(ar-301) 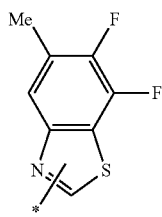
[Chem. 54]
(ar-302) 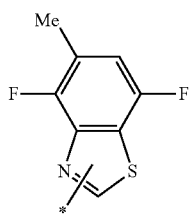
(ar-303) 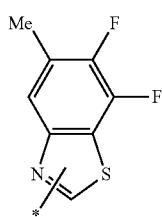
(ar-304) 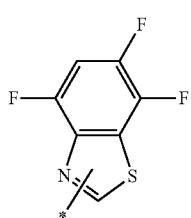
(ar-305) 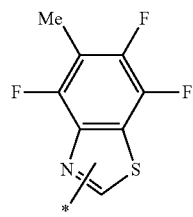
(ar-306) 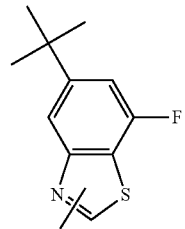
(ar-307) 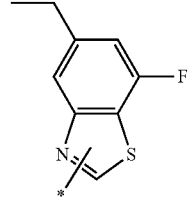
(ar-308) 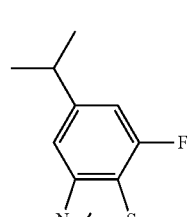
[Chem. 55]
(ar-309) 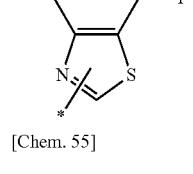
(ar-310) 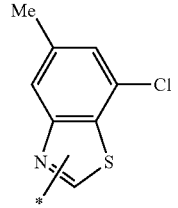
(ar-311) 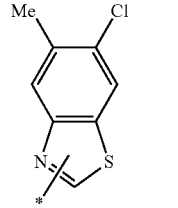
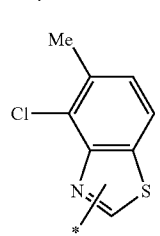

(ar-312) 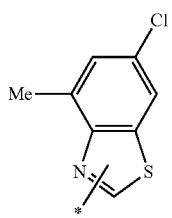
(ar-313) 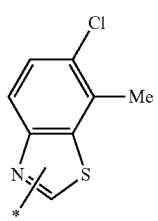
(ar-314) 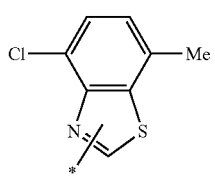
(ar-315) 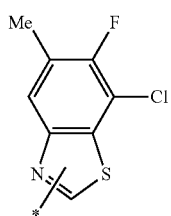
[Chem. 56]
(ar-316) 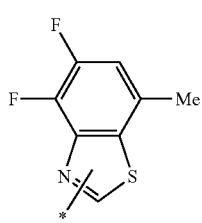
(ar-317) 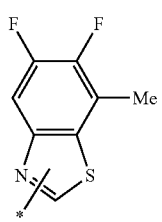
(ar-318) 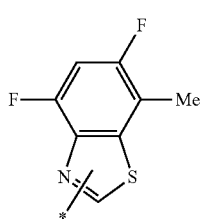
(ar-319) 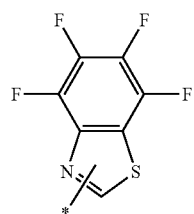
(ar-320) 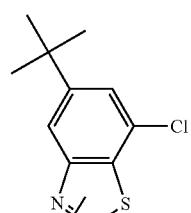
(ar-321) 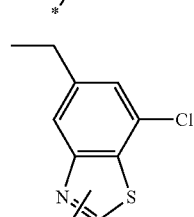
(ar-322) 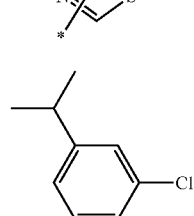
[Chem. 57]
(ar-323) 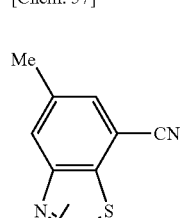
(ar-324) 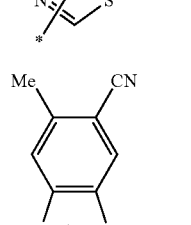
(ar-325) 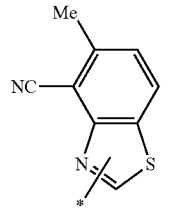

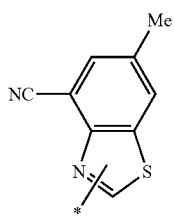 (ar-326)
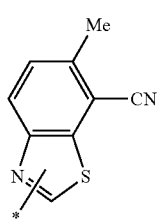 (ar-327)
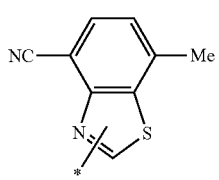 (ar-328)
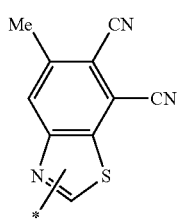 (ar-329)
[Chem. 58]
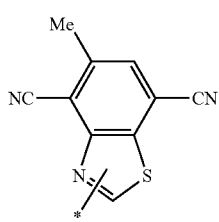 (ar-330)
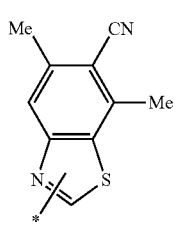 (ar-331)
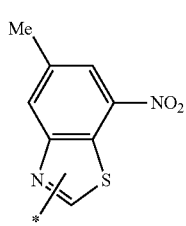 (ar-332)
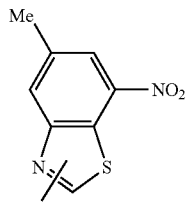 (ar-333)
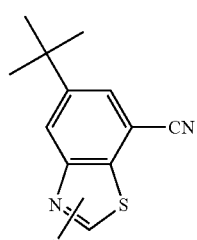 (ar-334)
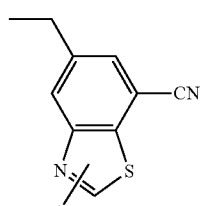 (ar-335)
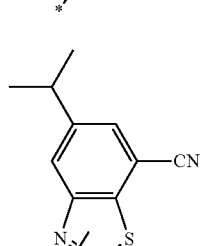 (ar-336)
[Chem. 59]
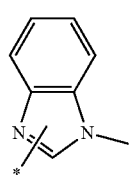 (ar-337)
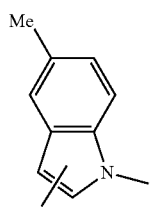 (ar-338)
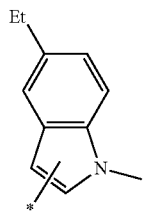 (ar-339)

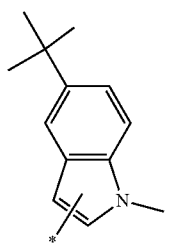 (ar-340)
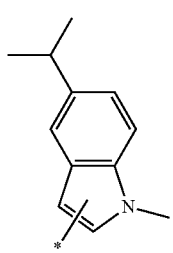 (ar-341)
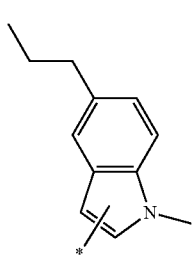 (ar-342)
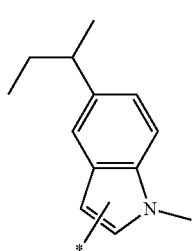 (ar-343)
[Chem. 60]
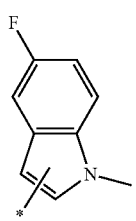 (ar-344)
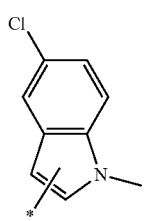 (ar-345)
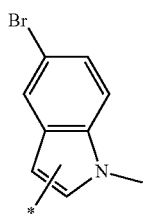 (ar-346)
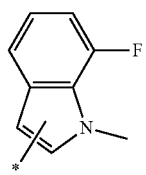 (ar-347)
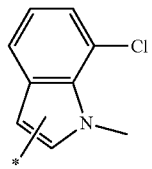 (ar-348)
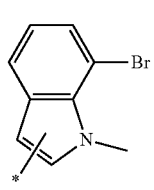 (ar-349)
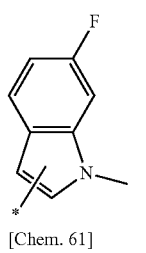 (ar-350)
[Chem. 61]
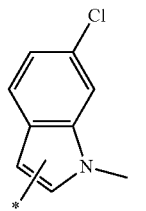 (ar-351)
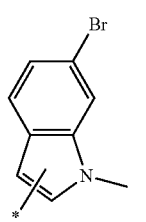 (ar-352)
 (ar-353)

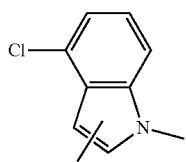 (ar-354)
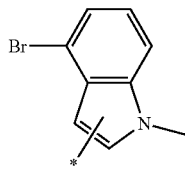 (ar-355)
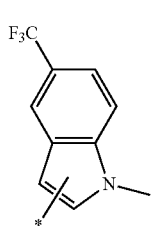 (ar-356)
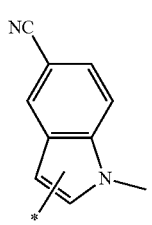 (ar-357)
[Chem. 62]
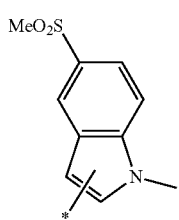 (ar-358)
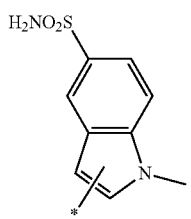 (ar-359)
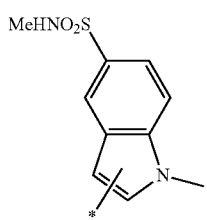 (ar-360)
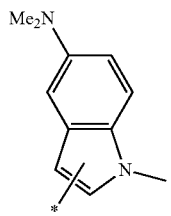 (ar-361)
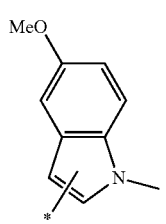 (ar-362)
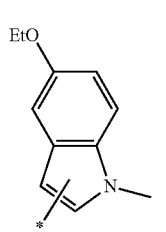 (ar-363)
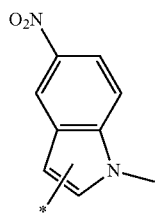 (ar-364)
[Chem. 63]
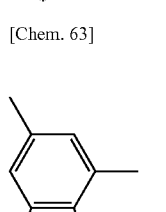 (ar-365)
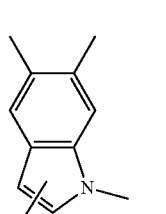 (ar-366)
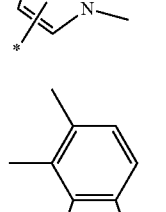 (ar-367)

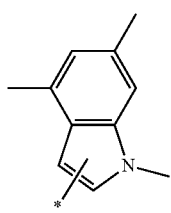 (ar-367)
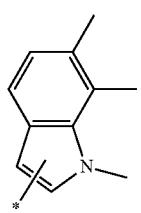 (ar-368)
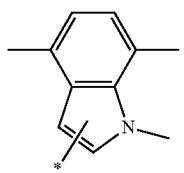 (ar-369)
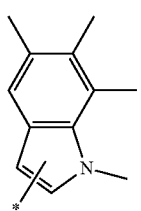 (ar-370)
[Chem. 64]
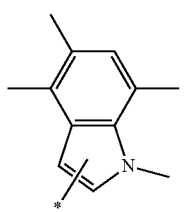 (ar-371)
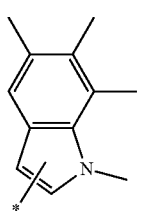 (ar-372)
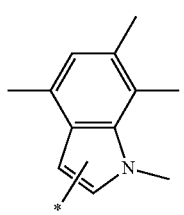 (ar-373)
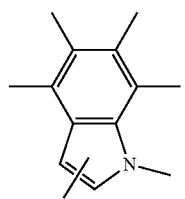 (ar-374)
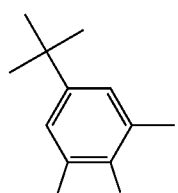 (ar-375)
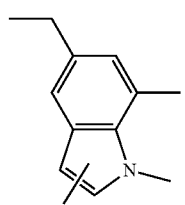 (ar-376)
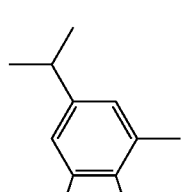 (ar-377)
[Chem. 65]
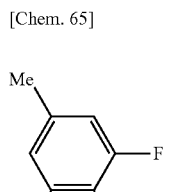 (ar-378)
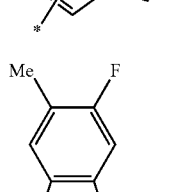 (ar-379)
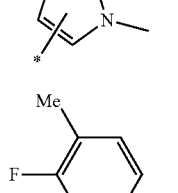 (ar-380)

(ar-382)
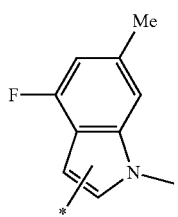
(ar-383)
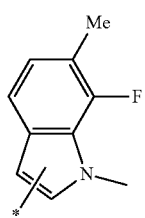
(ar-384)
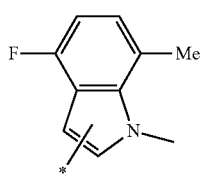
(ar-385)
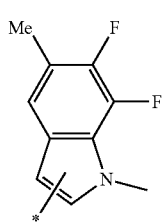
[Chem. 66]
(ar-386)
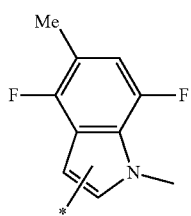
(ar-387)
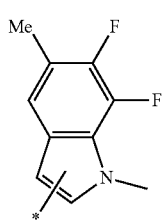
(ar-388)
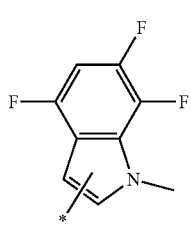
(ar-389)
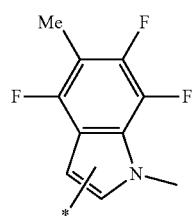
(ar-390)
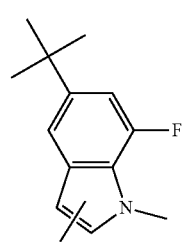
(ar-391)
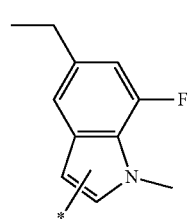
(ar-392)
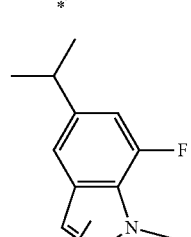
[Chem. 67]
(ar-393)
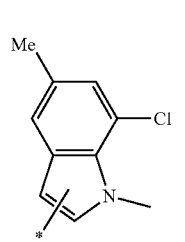
(ar-394)
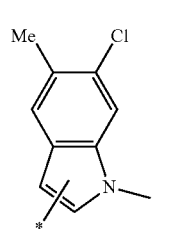
(ar-395)
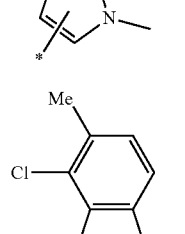

(ar-396) 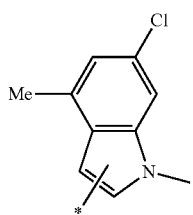
(ar-397) 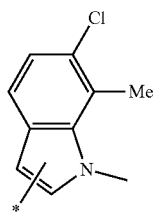
(ar-398) 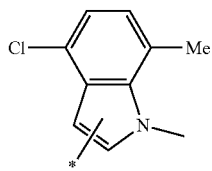
(ar-399) 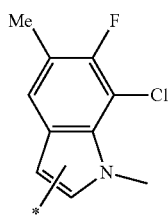
[Chem. 68]
(ar-400) 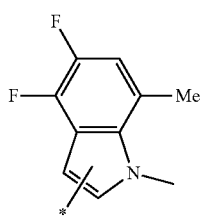
(ar-401) 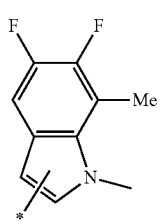
(ar-402) 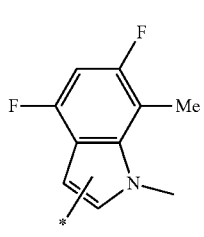
(ar-403) 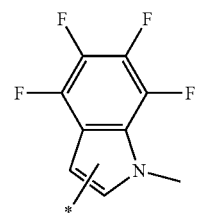
(ar-404) 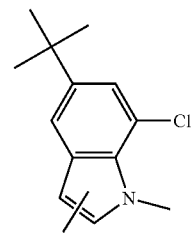
(ar-405) 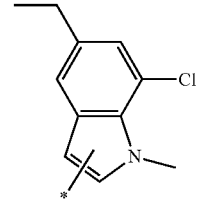
(ar-406) 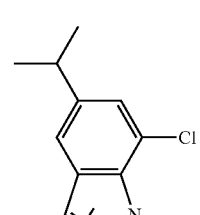
[Chem. 69]
(ar-407) 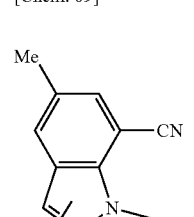
(ar-408) 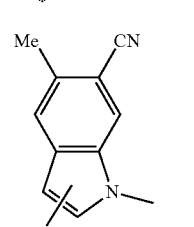
(ar-409) 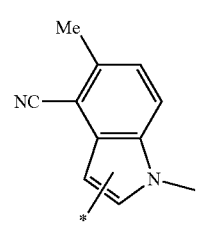

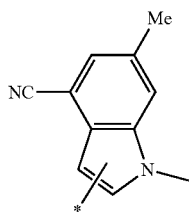 (ar-410)
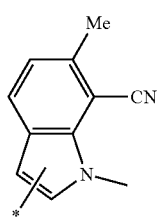 (ar-411)
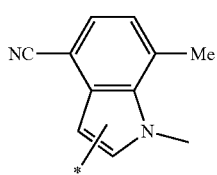 (ar-412)
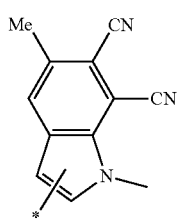 (ar-413)
[Chem. 70]
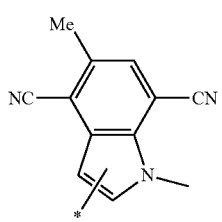 (ar-414)
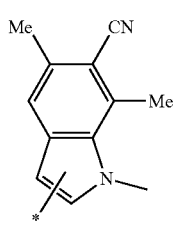 (ar-415)
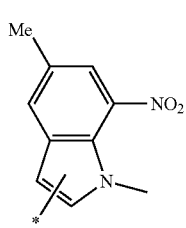 (ar-416)
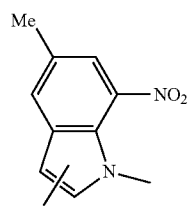 (ar-417)
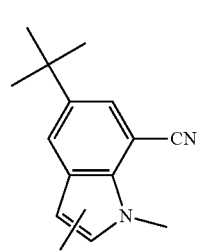 (ar-418)
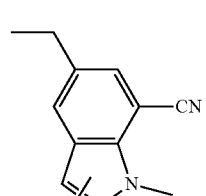 (ar-419)
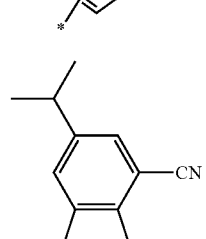 (ar-420)
[Chem. 71]
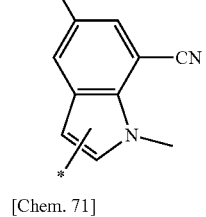 (ar-421)
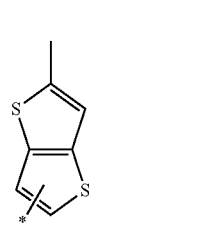 (ar-422)
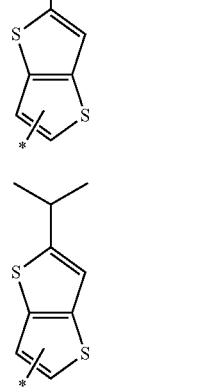 (ar-423)

(ar-424)
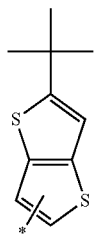
(ar-425)
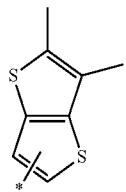
(ar-426)
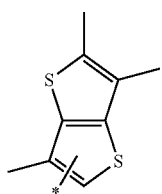
[Chem. 72]
(ar-427)
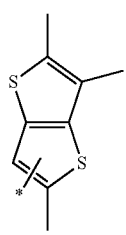
(ar-428)
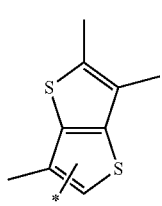
(ar-429)
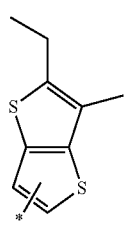
(ar-430)
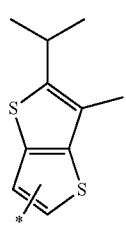
(ar-431)
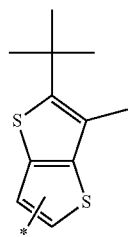
(ar-432)
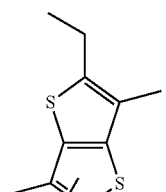
(ar-433)
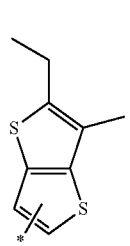
(ar-434)
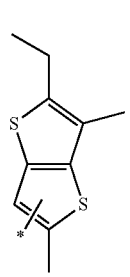
[Chem. 73]
(ar-435)
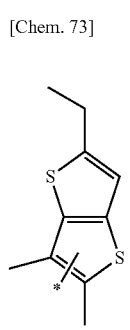
(ar-436)
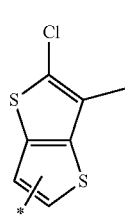

(ar-437) 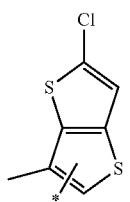
(ar-438) 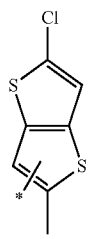
(ar-439) 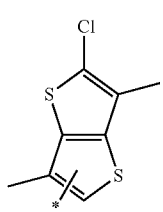
(ar-440) 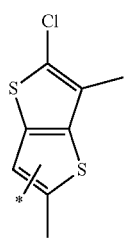
(ar-441) 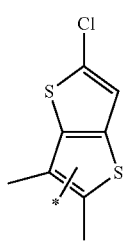
[Chem. 74]
(ar-442) 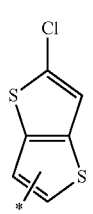
(ar-443) 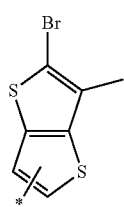
(ar-444) 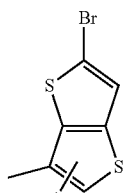
(ar-445) 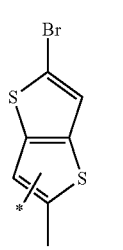
(ar-446) 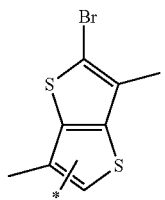
(ar-447) 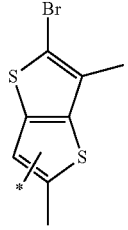
(ar-448) 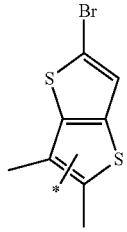
[Chem. 75]
(ar-449) 
(ar-450) 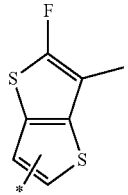

(ar-451) 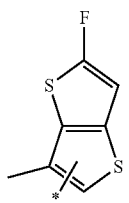
(ar-452) 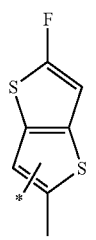
(ar-453) 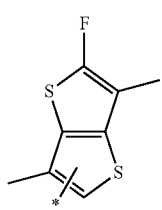
(ar-454) 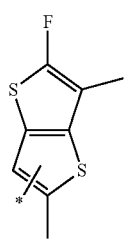
(ar-455)
[Chem. 76]
(ar-456) 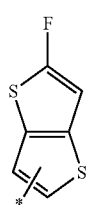
(ar-457) 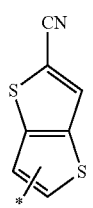
(ar-458) 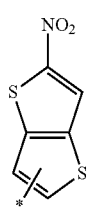
(ar-459) 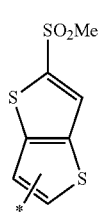
(ar-460) 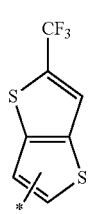
(ar-461) 
(ar-462) 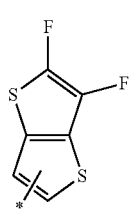
[Chem. 77]
(ar-463) 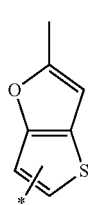
(ar-464) 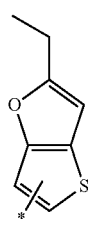

-continued
(ar-465) 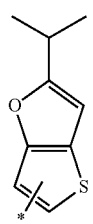
(ar-466) 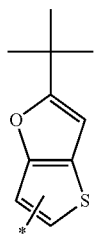
(ar-467) 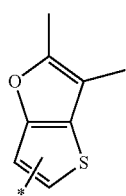
(ar-468) 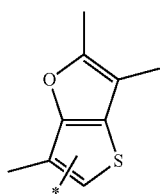
(ar-469) 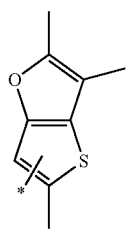
[Chem. 78]
(ar-470) 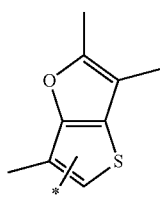
(ar-471) 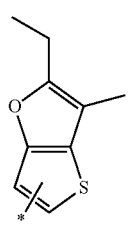
-continued
(ar-472) 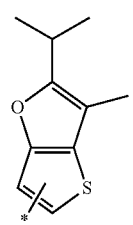
(ar-473) 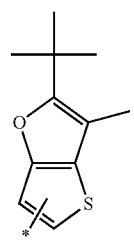
(ar-474) 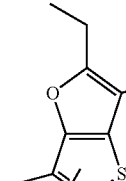
(ar-475) 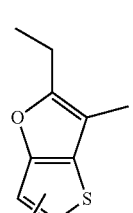
(ar-476) 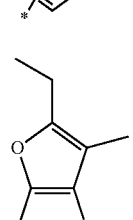
[Chem. 79]
(ar-477) 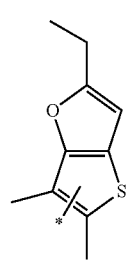

(ar-478) 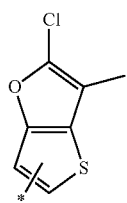
(ar-479) 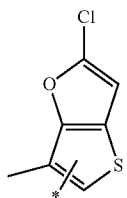
(ar-480) 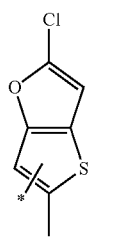
(ar-481) 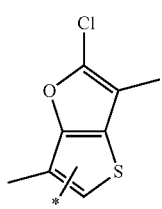
(ar-482) 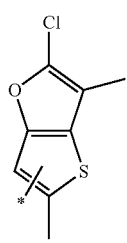
(ar-483) 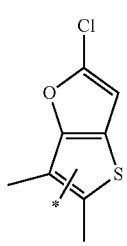
[Chem. 80]
(ar-484) 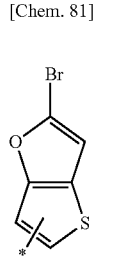
(ar-485) 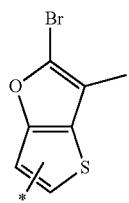
(ar-486) 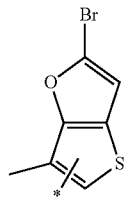
(ar-487) 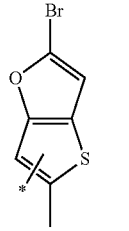
(ar-488) 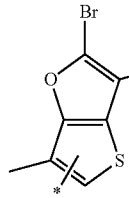
(ar-489) 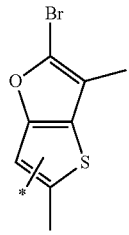
(ar-490) 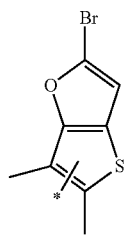
[Chem. 81]
(ar-491)

(ar-492) 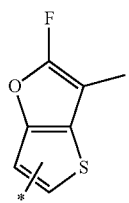
(ar-493) 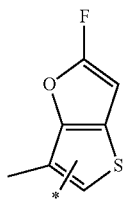
(ar-494) 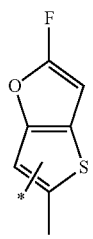
(ar-495) 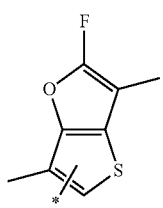
(ar-496) 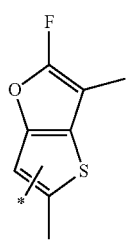
(ar-497) 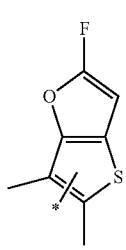
[Chem. 82]
(ar-498) 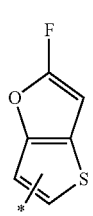
(ar-499) 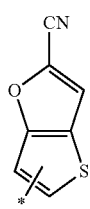
(ar-500) 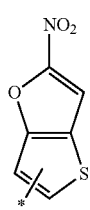
(ar-501) 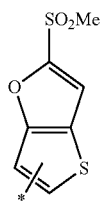
(ar-502) 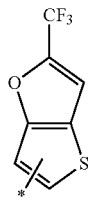
(ar-503) 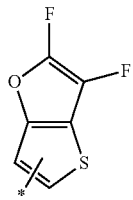
(ar-504) 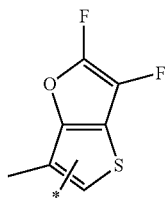
[Chem. 83]
(ar-505) 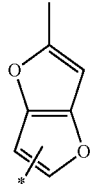

(ar-506) 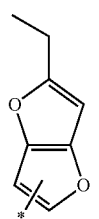
(ar-507) 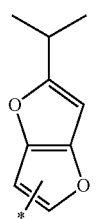
(ar-508) 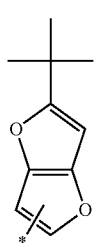
(ar-509) 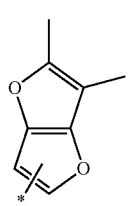
(ar-510) 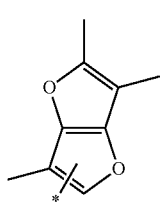
(ar-511) 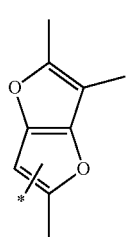
[Chem. 84]
(ar-512) 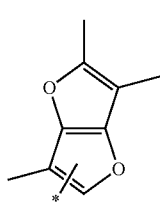
(ar-513) 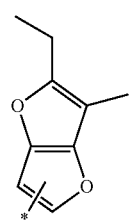
(ar-514) 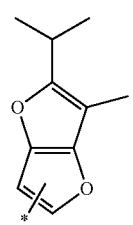
(ar-515) 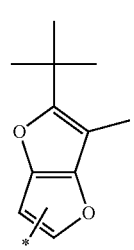
(ar-516) 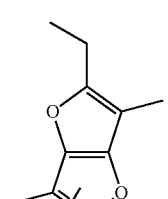
(ar-517) 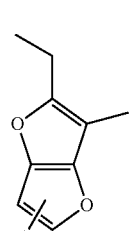
(ar-518) 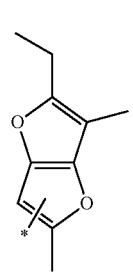
[Chem. 85]

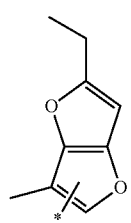
(ar-519)
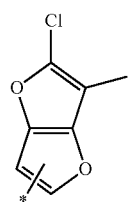
(ar-520)
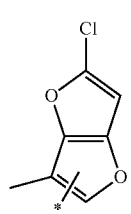
(ar-521)
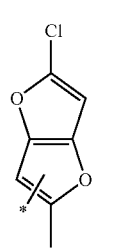
(ar-522)
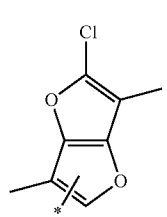
(ar-523)
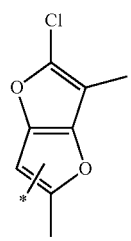
(ar-524)
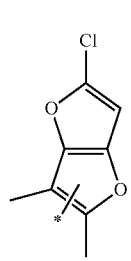
(ar-525)
[Chem. 86]
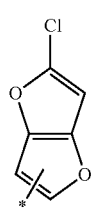
(ar-526)
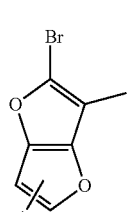
(ar-527)
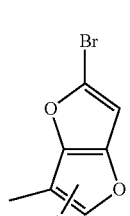
(ar-528)
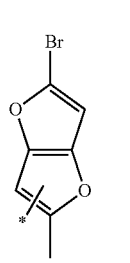
(ar-529)
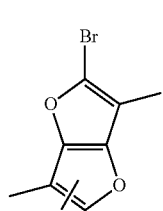
(ar-530)
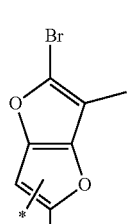
(ar-531)
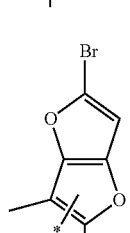
(ar-532)
[Chem. 87]

(ar-533) (ar-534) (ar-535) (ar-536) (ar-537) (ar-538) (ar-539)

(ar-540) (ar-541) (ar-542) (ar-543) (ar-544) (ar-545) (ar-546)

[Chem. 88]

[Chem. 89]

-continued
(ar-547) 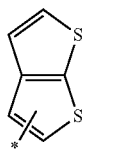
(ar-548) 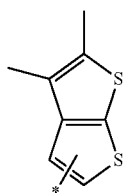
(ar-549) 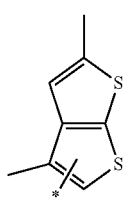
(ar-550) 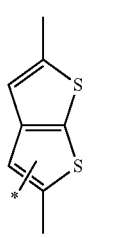
(ar-551) 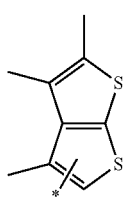
(ar-552) 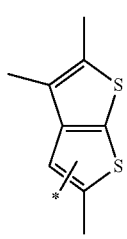
(ar-553) 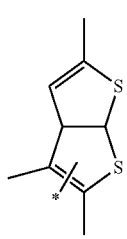
[Chem. 90]
-continued
(ar-554) 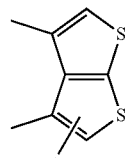
(ar-555) 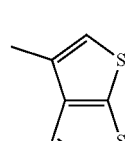
(ar-556) 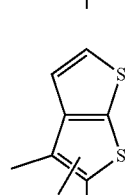
(ar-557) 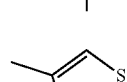
(ar-558) 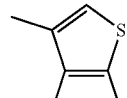
(ar-559) 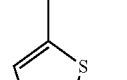
(ar-560) 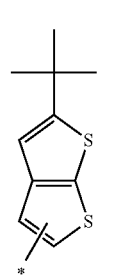
[Chem. 91]

(ar-561) 
(ar-562) 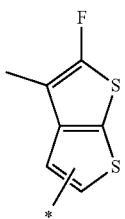
(ar-563) 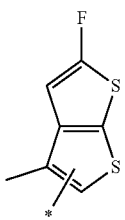
(ar-564) 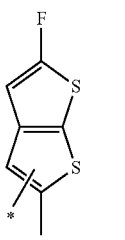
(ar-565) 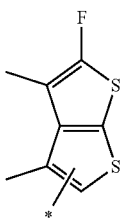
(ar-566) 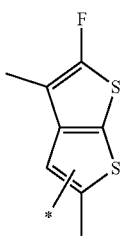
(ar-567) 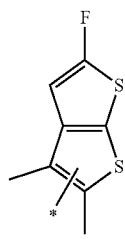
[Chem. 92]
(ar-568) 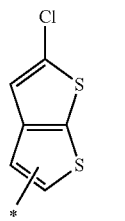
(ar-569) 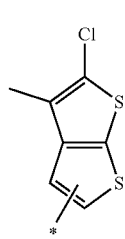
(ar-570) 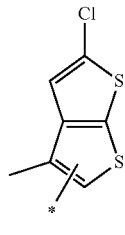
(ar-571) 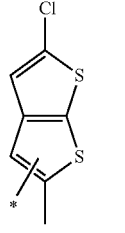
(ar-572) 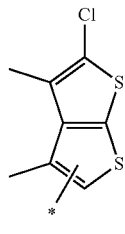

107
-continued
(ar-573)
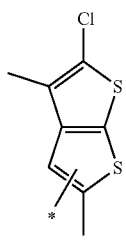
(ar-574)
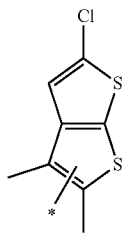
[Chem. 93]
(ar-575)
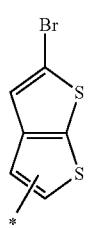
(ar-576)
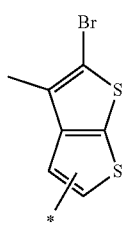
(ar-577)
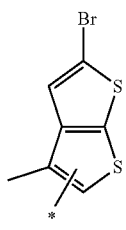
(ar-578)
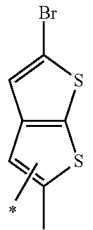
108
-continued
(ar-579)
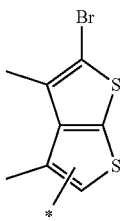
(ar-580)
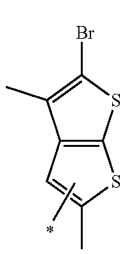
(ar-581)
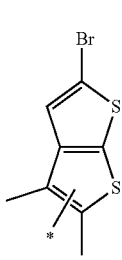
[Chem. 94]
(ar-582)
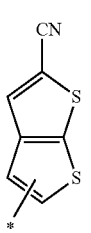
(ar-583)
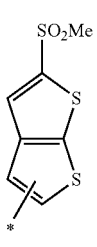
(ar-584)
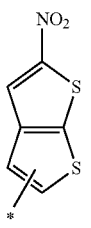

(ar-585) 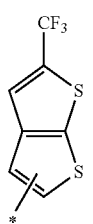
(ar-586) 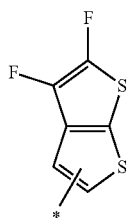
(ar-587) 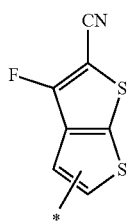
(ar-588) 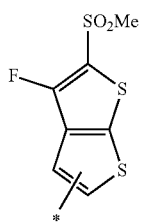
[Chem. 95]
(ar-589) 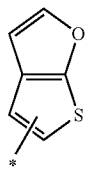
(ar-590) 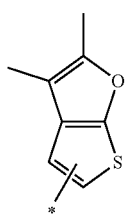
(ar-591) 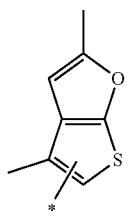
(ar-592) 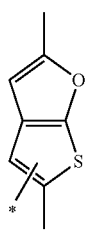
(ar-593) 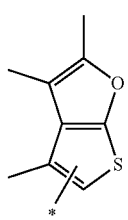
(ar-594) 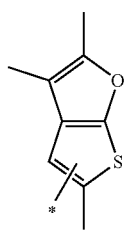
(ar-595) 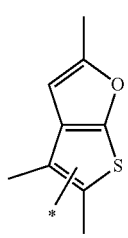
[Chem. 96]
(ar-596) 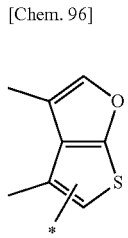
(ar-597) 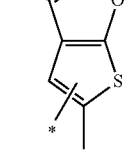
(ar-598) 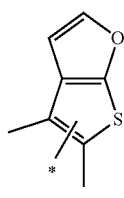

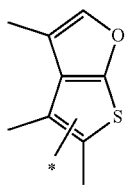 (ar-599)
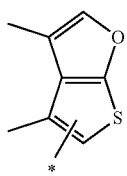 (ar-600)
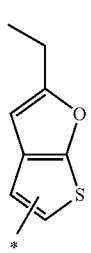 (ar-601)
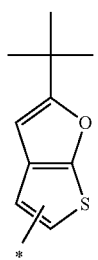 (ar-602)
[Chem. 97]
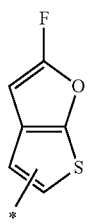 (ar-603)
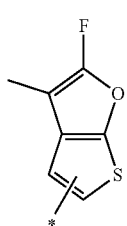 (ar-604)
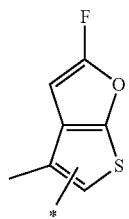 (ar-605)
(ar-606)
(ar-607)
(ar-608)
(ar-609)
[Chem. 98]
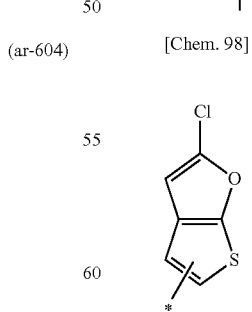 (ar-610)

(ar-611) 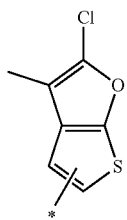
(ar-612) 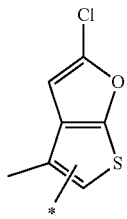
(ar-613) 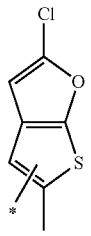
(ar-614) 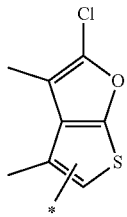
(ar-615) 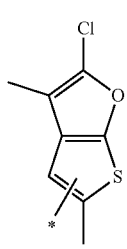
(ar-616) 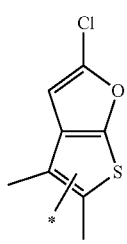
[Chem. 99]
(ar-617) 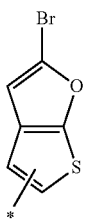
(ar-618) 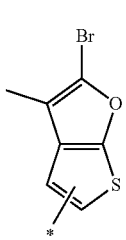
(ar-619) 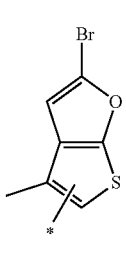
(ar-620) 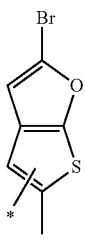
(ar-621) 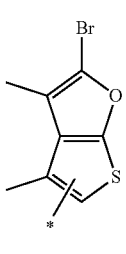
(ar-622) 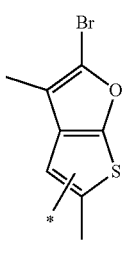

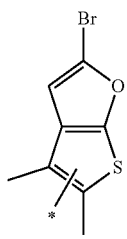
[Chem. 100]
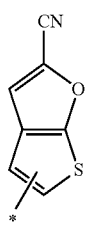
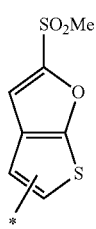
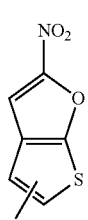
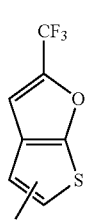
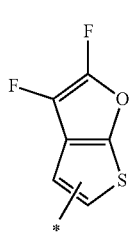
(ar-623)
(ar-624)
(ar-625)
(ar-626)
(ar-627)
(ar-628)
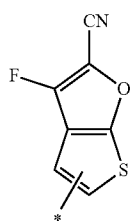
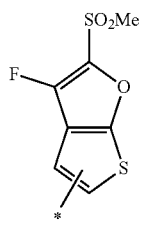
[Chem. 101]
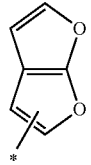
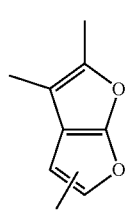
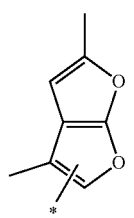
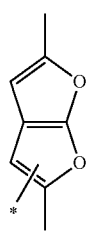
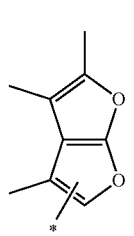
(ar-629)
(ar-630)
(ar-631)
(ar-632)
(ar-633)
(ar-634)
(ar-635)

(ar-636)
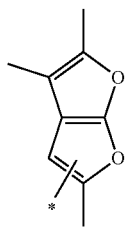
(ar-637)
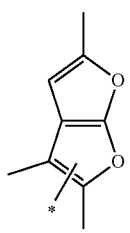
[Chem. 102]
(ar-638)
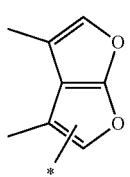
(ar-639)
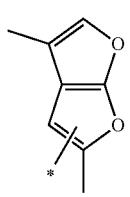
(ar-640)
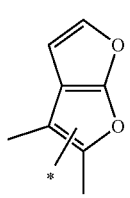
(ar-641)
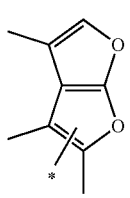
(ar-642)
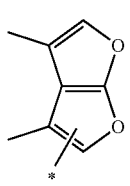
(ar-643)
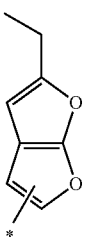
(ar-644)
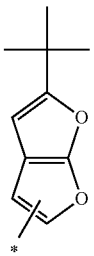
[Chem. 103]
(ar-645)
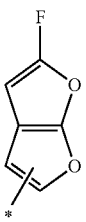
(ar-646)
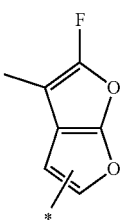
(ar-647)
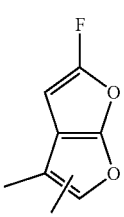
(ar-648)
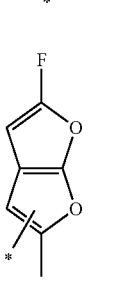

(ar-649) 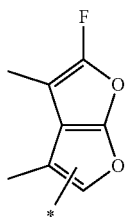
(ar-650) 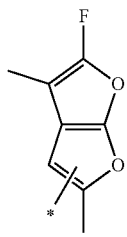
(ar-651) 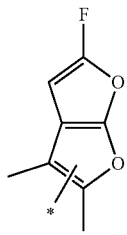
[Chem. 104]
(ar-652) 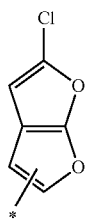
(ar-653) 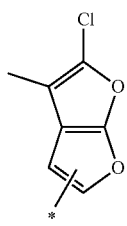
(ar-654) 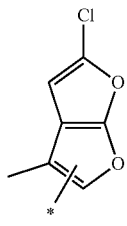
(ar-655) 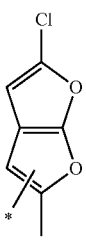
(ar-656) 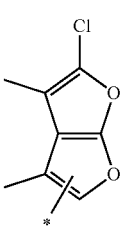
(ar-657) 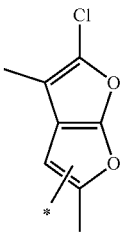
(ar-658) 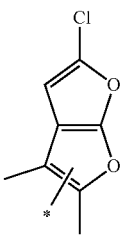
[Chem. 105]
(ar-659) 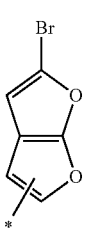
(ar-660) 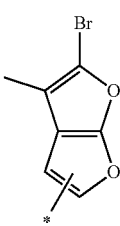

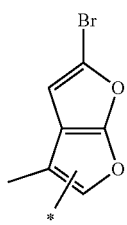 (ar-661)
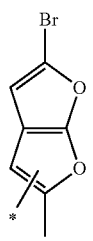 (ar-662)
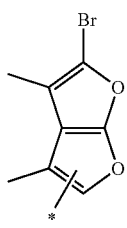 (ar-663)
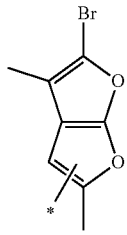 (ar-664)
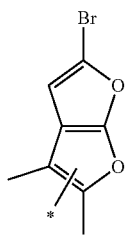 (ar-665)
[Chem. 106]
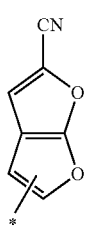 (ar-666)
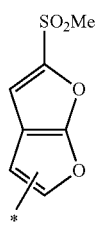 (ar-667)
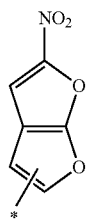 (ar-668)
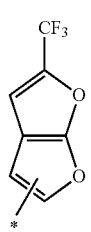 (ar-669)
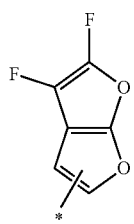 (ar-670)
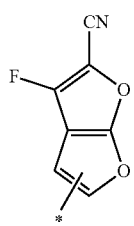 (ar-671)
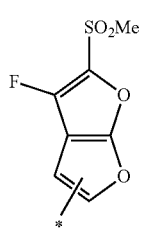 (ar-672)
[Chem. 107]

(ar-673) 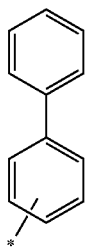
(ar-674) 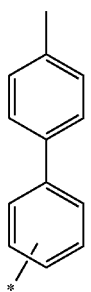
(ar-675) 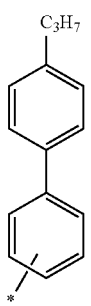
(ar-676) 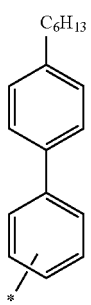
(ar-677) 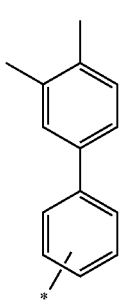
(ar-678) 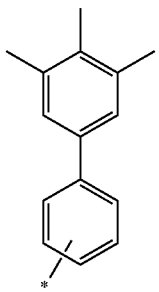
(ar-679) 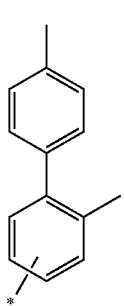
[Chem. 108]
(ar-680) 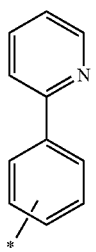
(ar-681) 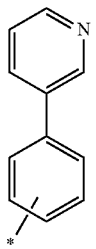
(ar-682) 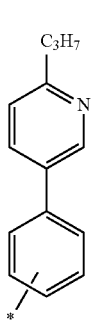

(ar-683) 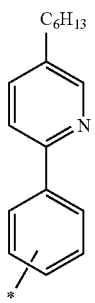
(ar-684) 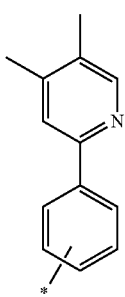
(ar-685) 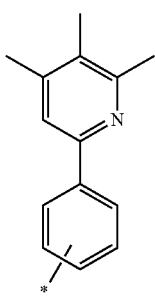
(ar-686) 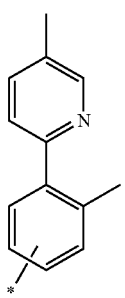
[Chem. 109]
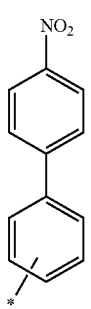
(ar-688) 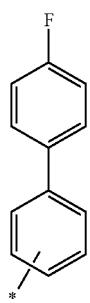
(ar-689) 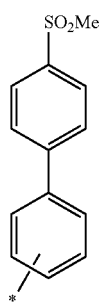
(ar-690) 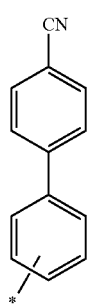
(ar-691) 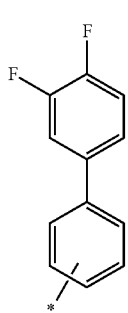
(ar-692) 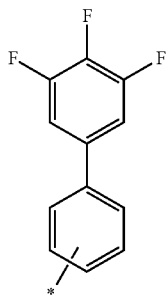
(ar-687)

-continued
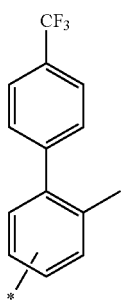 (ar-693)
[Chem. 110]
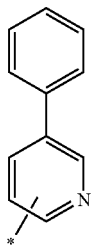 (ar-694)
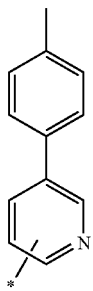 (ar-695)
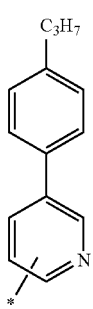 (ar-696)
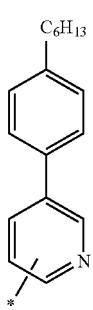 (ar-697)
-continued
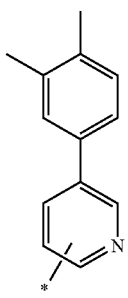 (ar-698)
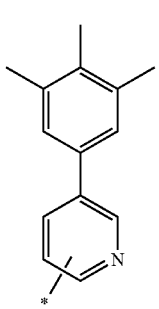 (ar-699)
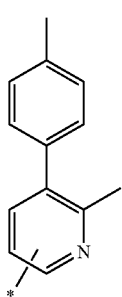 (ar-700)
[Chem. 111]
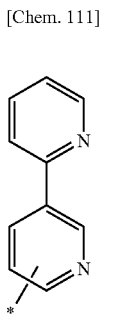 (ar-701)
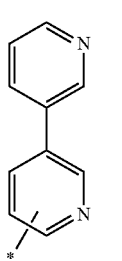 (ar-702)

(ar-703) 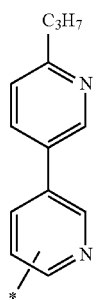
(ar-704) 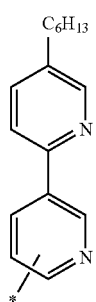
(ar-705) 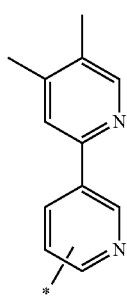
(ar-706) 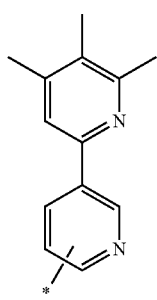
(ar-707) 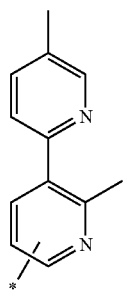
[Chem. 112]
(ar-708) 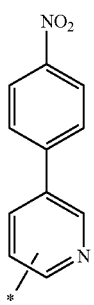
(ar-709) 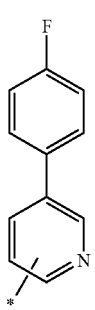
(ar-710) 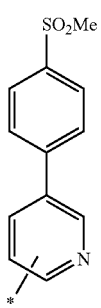
(ar-711) 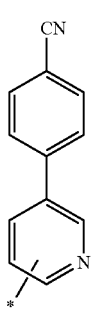
(ar-712) 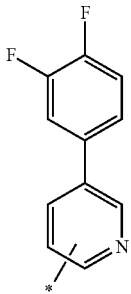

-continued
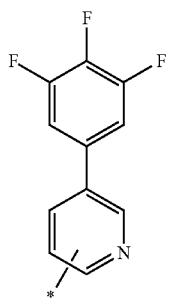
(ar-713)
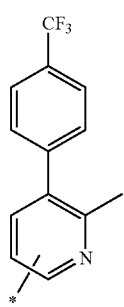
(ar-714)
[Chem. 113]
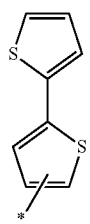
(ar-715)
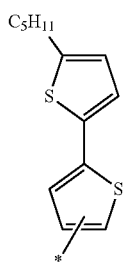
(ar-716)
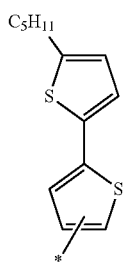
(ar-717)
-continued
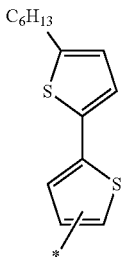
(ar-718)
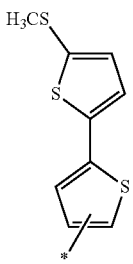
(ar-719)
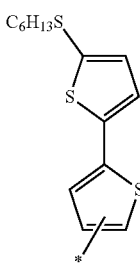
(ar-720)
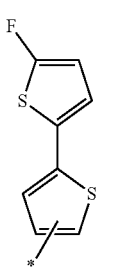
(ar-721)
[Chem. 114]
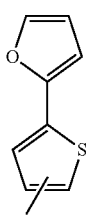
(ar-722)
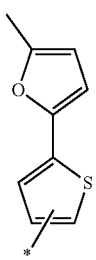
(ar-723)

(ar-724) 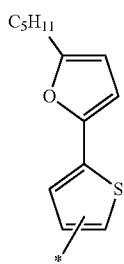
(ar-725) 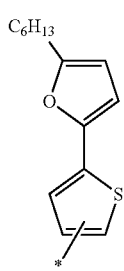
(ar-726) 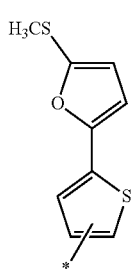
(ar-727) 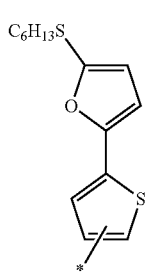
(ar-728) 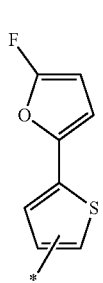
[Chem. 115]
(ar-729) 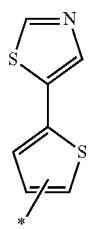
(ar-730) 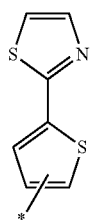
(ar-731) 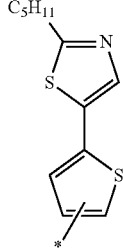
(ar-732) 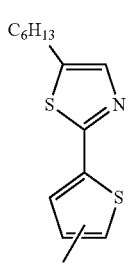
(ar-733) 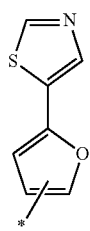
(ar-734) 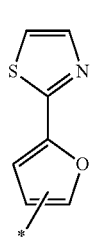

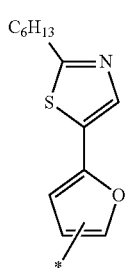 (ar-735)
[Chem. 116]
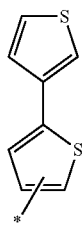 (ar-736)
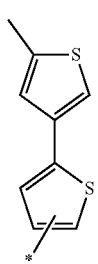 (ar-737)
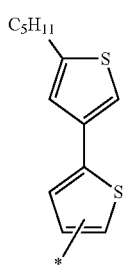 (ar-738)
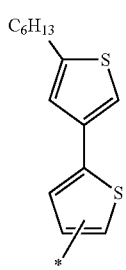 (ar-739)
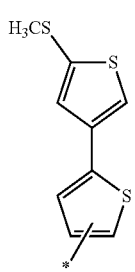 (ar-740)
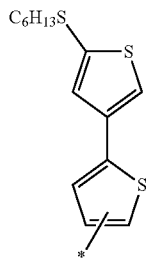 (ar-741)
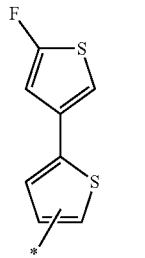 (ar-742)
[Chem. 117]
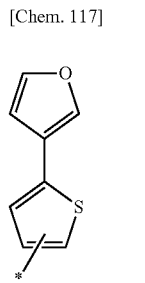 (ar-743)
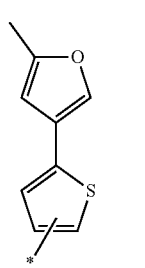 (ar-744)
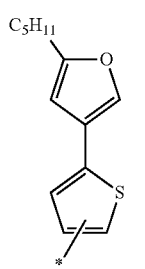 (ar-745)
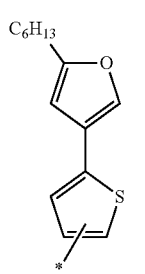 (ar-746)

(ar-747) 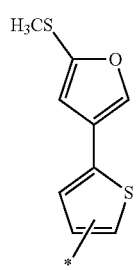
(ar-748) 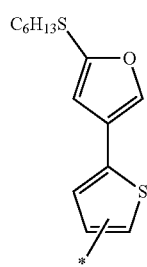
(ar-749) 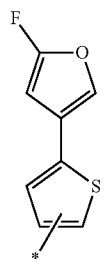
[Chem. 118]
(ar-750) 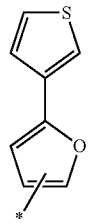
(ar-751) 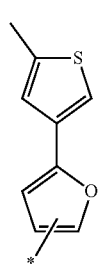
(ar-752) 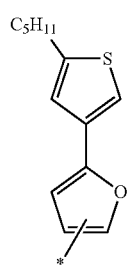
(ar-753) 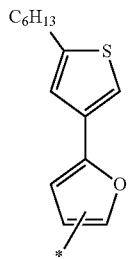
(ar-754) 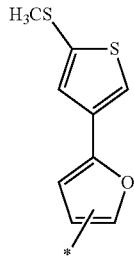
(ar-755) 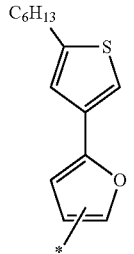
(ar-756) 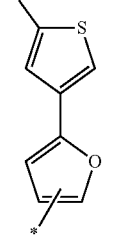
[Chem. 119]
(ar-757) 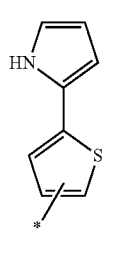
(ar-758) 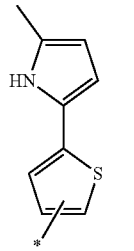

(ar-759) 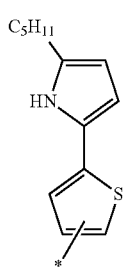
(ar-760) 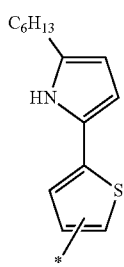
(ar-761) 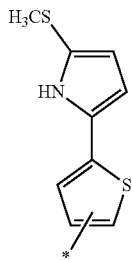
(ar-762) 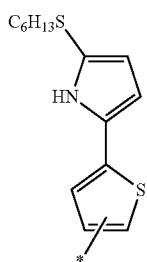
(ar-763) 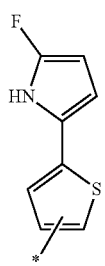
[Chem. 120]
(ar-764) 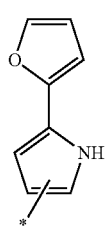
(ar-765) 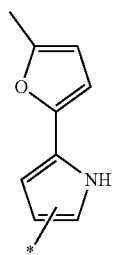
(ar-766) 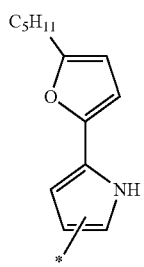
(ar-767) 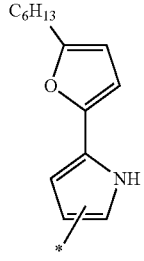
(ar-768) 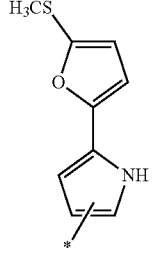
(ar-769) 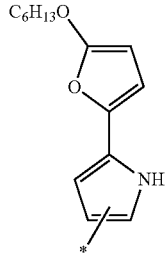
(ar-770) 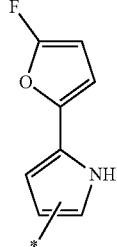

[Chem. 121]
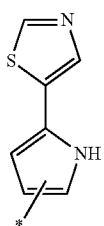 (ar-771)
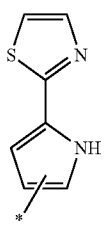 (ar-772)
C₅H₁₁
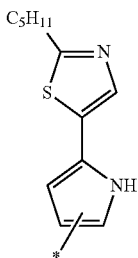 (ar-773)
C₆H₁₃
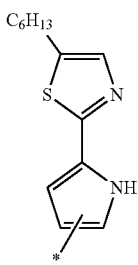 (ar-774)
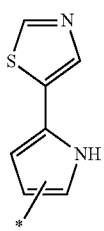 (ar-775)
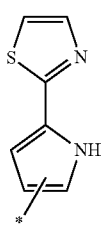 (ar-776)
C₆H₁₃
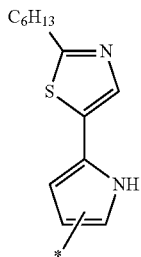 (ar-777)
[Chem. 122]
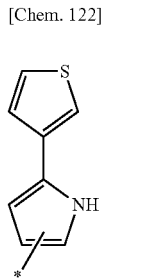 (ar-778)
(ar-779)
C₅H₁₁ (ar-780)
C₆H₁₃ (ar-781)
H₃CS (ar-782)

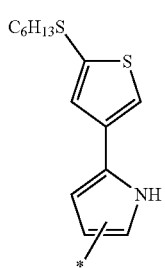 (ar-783)
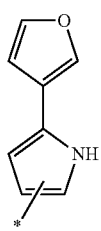 (ar-784)
[Chem. 123]
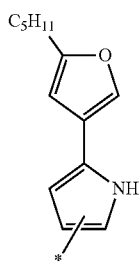 (ar-785)
(ar-786)
(ar-787)
(ar-788)
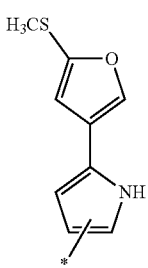 (ar-789)
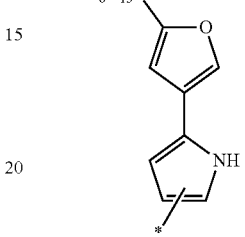 (ar-790)
(ar-791)
[Chem. 124]
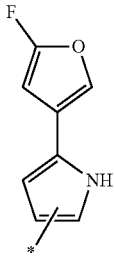 (ar-792)
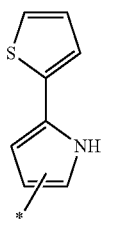 (ar-793)
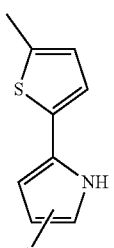 (ar-794)
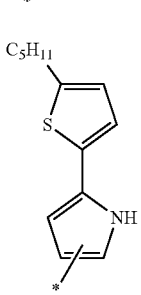

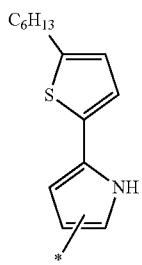 (ar-795)
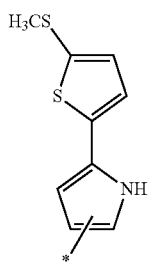 (ar-796)
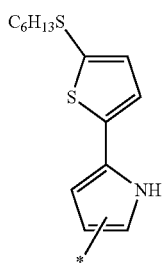 (ar-797)
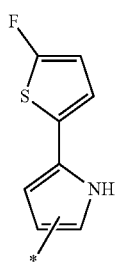 (ar-798)
[Chem. 125]
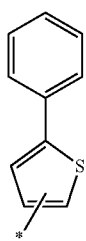 (ar-799)
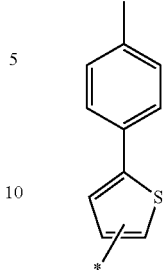 (ar-800)
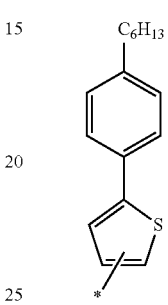 (ar-801)
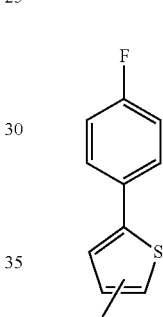 (ar-802)
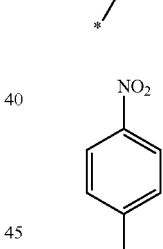 (ar-803)
(ar-804)

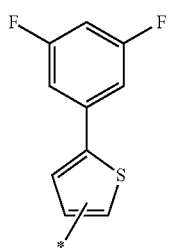
(ar-805)
[Chem. 126]
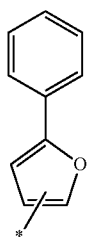
(ar-806)
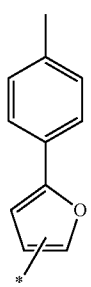
(ar-807)
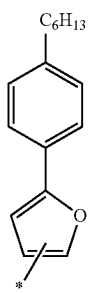
(ar-808)
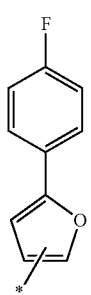
(ar-809)
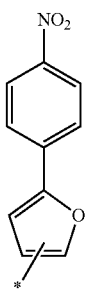
(ar-810)
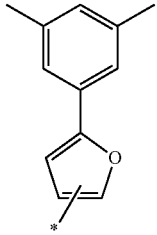
(ar-811)
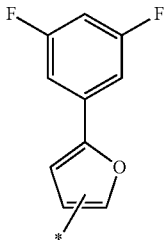
(ar-812)
[Chem. 127]
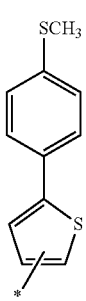
(ar-813)
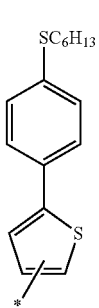
(ar-814)

(ar-815) 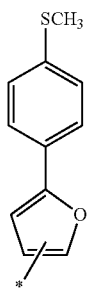
(ar-816) 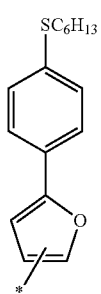
(ar-817) 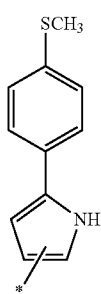
(ar-818) 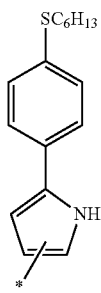
(ar-819) 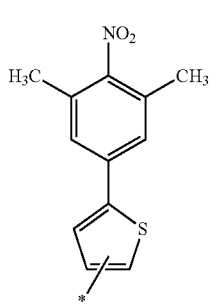
[Chem. 128]
(ar-820) 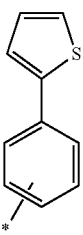
(ar-821) 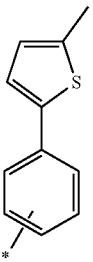
(ar-822) 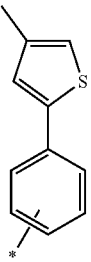
(ar-823) 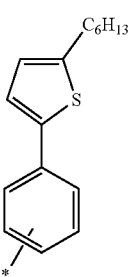
(ar-824) 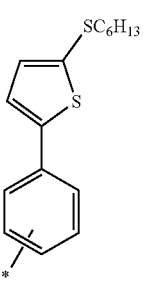

(ar-825) 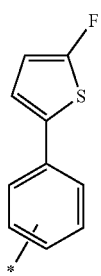
(ar-826) 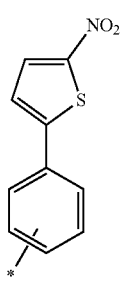
[Chem. 129]
(ar-827) 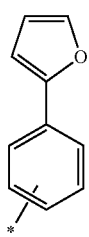
(ar-828) 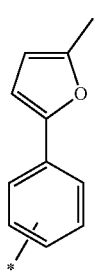
(ar-829) 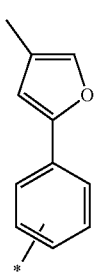
(ar-830) 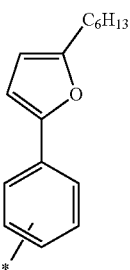
(ar-831) 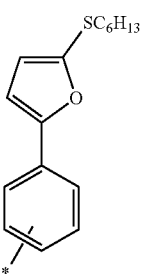
(ar-832) 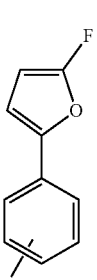
(ar-833) 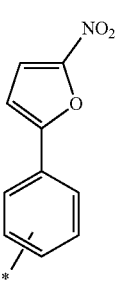
[Chem. 130]
(ar-834) 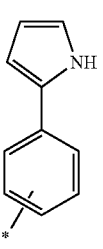

(ar-835) 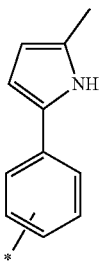

(ar-836) 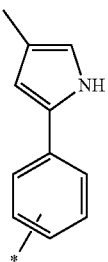

(ar-837) 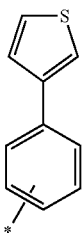

(ar-838) 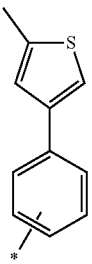

(ar-839) 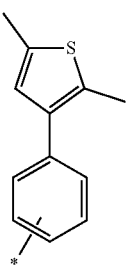

(ar-840) 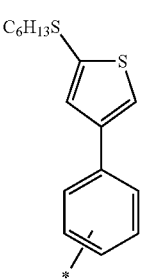

In formulae (1) and (2), G is a divalent alicyclic hydrocarbon group, and the number of carbon atoms thereof is, for example, from 3 to 30, preferably from 3 to 20, more preferably from 4 to 15, and even more preferably from 5 to 10. Examples of the divalent alicyclic hydrocarbon group include a cycloalkanediyl group. The hydrogen atom contained in the alicyclic hydrocarbon group is optionally substituted with a halogen atom, an alkyl group having 1 to 4 carbon atoms, a fluoro alkyl group having 1 to 4 carbon atoms, an alkoxy group, a cyano group, or a nitro group having 1 to 4 carbon atoms, and —CH$_2$— (methylene group) contained in the alicyclic hydrocarbon group is optionally substituted with —O—, —S—, or —NH—.

Examples of the alkyl group having 1 to 4 carbon atoms include a methyl group, an ethyl group, a propyl group, an isopropyl group, a butyl group, an isobutyl group, a sec-butyl group, and a tert-butyl group. Of these, an alkyl group having 1 to 3 carbon atoms is preferable, an alkyl group having 1 to 2 carbon atoms is more preferable, and a methyl group is especially preferable.

Examples of the fluoroalkyl group having 1 to 4 carbon atoms include a fluoromethyl group, a trifluoromethyl group, a fluoroethyl group, a pentafluoroethyl group, a heptafluoropropyl group, and a nonafluorobutyl group. Of these, a fluoroalkyl group having 1 to 3 carbon atoms is preferable, a fluoroalkyl group having 1 to 2 carbon atoms is more preferable, and a trifluoromethyl group is especially preferable.

Examples of the alkoxy group having 1 to 4 carbon atoms include a methoxy group, an ethoxy group, a propoxy group, an isopropoxy group, a butoxy group, an isobutoxy group, a sec-butoxy group, and a tert-butoxy group. Of these, an alkoxy group having 1 to 3 carbon atoms is preferable, an alkoxy group having 1 to 2 carbon atoms, and a methoxy group is especially preferable.

Examples of the divalent alicyclic hydrocarbon group include the groups represented by formulae (g-1) to (g-4). Examples of the divalent alicyclic hydrocarbon group in which —CH$_2$— contained in the alicyclic hydrocarbon group is replaced by —O—, —S—, or —N (R$^5$)— include the groups represented by formulae (g-5) to (g-8). R$^5$ represents a hydrogen atom or an alkyl group having 1 to 4 carbon atoms. Examples of the divalent alicyclic hydrocarbon group in which the the methine group (—CH(-)-) contained in the alicyclic hydrocarbon group is replaced by an amino group include the groups represented by formulae (g-9) to (g-10). Of these, a 5- or 6-membered alicyclic hydrocarbon group is preferable.

[Chem. 131]

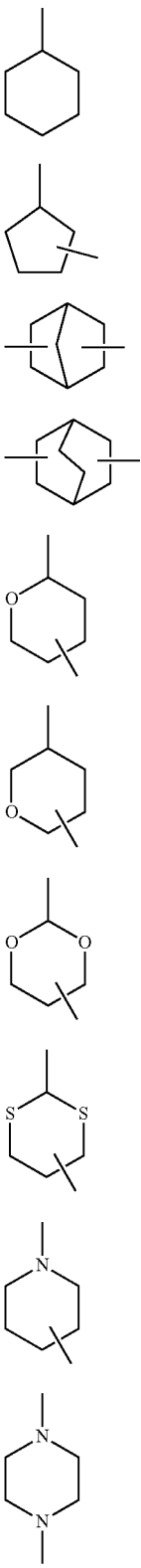

(g-1)
(g-2)
(g-3)
(g-4)
(g-5)
(g-6)
(g-7)
(g-8)
(g-9)
(g-10)

The divalent alicyclic hydrocarbon group is preferably a group represented by formula (g-1), more preferably a 1,4-cyclohexanediyl group, and especially preferably a trans-1,4-cyclohexanediyl group.

In formulae (1) and (2), B is a single bond or a divalent linking group. Examples of the divalent linking group include —O—, —S—, —CO—O, —O—CO—, —C(=S)—O—, —O—C(=S)—, —CR$^6$R$^7$—, —CR$^6$R$^7$—CR$^8$R$^9$—, —O—CR$^6$R$^7$—, —CR$^6$R$^7$—O—, —CR$^6$R$^7$—O—CR$^8$R$^9$—, —CR$^6$R$^7$—O—CO—, —O—CO—CR$^6$R$^7$—, —CR$^6$R$^7$—O—CO—CR$^8$R$^9$—, —CR$^6$R$^7$—CO—O—CR$^8$R$^9$—, —NR$^{10}$—CR$^6$R$^7$—, —CR$^6$R$^7$—NR$^{10}$—, —CO—NR$^{10}$—, —NR$^{10}$—CO—, —O—, —S—, —NR$^{10}$—, and —CR$^6$=CR$^7$—. R$^6$, R$^7$, R$^8$ and R$^9$ each independently represent a hydrogen atom, a fluorine atom, or an alkyl group having 1 to 4 carbon atoms. R$^{10}$ represents a hydrogen atom or an alkyl group having 1 to 4 carbon atoms.

B is preferably —O—, —S—, —O—CO—, —O—C(=S)—, —O—CR$^6$R$^7$—, —NR$^{10}$—CR$^6$R$^7$—, or —NR$^{10}$—CO—. D$^1$ and D$^2$ are each more preferably —O—, —S—, —O—CO—, —O—C(=S)— or —NR$^{10}$—CO—. R$^6$, R$^7$, R$^8$ and R$^9$ are each independently preferably a hydrogen atom or an alkyl group having 1 to 4 carbon atoms, and more preferably a hydrogen atom, a methyl group or an ethyl group. R$^{10}$ is preferably a hydrogen atom, a methyl group or an ethyl group.

In formulae (1) and (2), A represents a divalent alicyclic hydrocarbon group having 3 to 20 carbon atoms or a divalent aromatic hydrocarbon group having 6 to 20 carbon atoms, preferably a divalent alicyclic hydrocarbon group having 4 to 15 carbon atoms or a divalent aromatic hydrocarbon group having 6 to 15 carbon atoms, more preferably a divalent alicyclic hydrocarbon group having 5 to 12 carbon atoms or a divalent aromatic hydrocarbon group having 6 to 12 carbon atoms, and even more preferably a divalent alicyclic hydrocarbon group having 6 to 10 carbon atoms or a divalent aromatic hydrocarbon group having 6 to 10 carbon atoms. Of these, a 5- or 6-membered alicyclic hydrocarbon group is preferable.

The hydrogen atom contained in the alicyclic hydrocarbon group and the aromatic hydrocarbon group is optionally substituted with a halogen atom such as a fluorine atom, a chlorine atom, a bromine atom, and an iodine atom; an alkyl group having 1 to 4 carbon atoms such as a methyl group, an ethyl group, an isopropyl group, and a tert-butyl group; a fluoroalkyl group having 1 to 4 carbon atoms such as a trifluoromethyl group; a cyano group; or a nitro group. —CH$_2$— contained in the alicyclic hydrocarbon group is optionally substituted with —O—, —S—, or —NR$^{11}$—, and the methine group (—CH (-) -) contained in the alicyclic hydrocarbon group is optionally replaced by —N(-)-, where R$^{11}$ represents a hydrogen atom or an alkyl group having 1 to 4 carbon atoms.

Examples of the divalent alicyclic hydrocarbon group include the groups represented by the above formulae (g-1) to (g-10).

The divalent alicyclic hydrocarbon group is preferably a group represented by formula (g-1), more preferably 1,4-cyclohexanediyl group, and especially preferably trans-1,4-cyclohexanediyl group.

Examples of the divalent aromatic hydrocarbon group include the groups represented by formulae (a-1) to (a-8).

[Chem. 132]

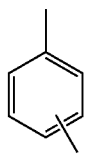

(a-1)

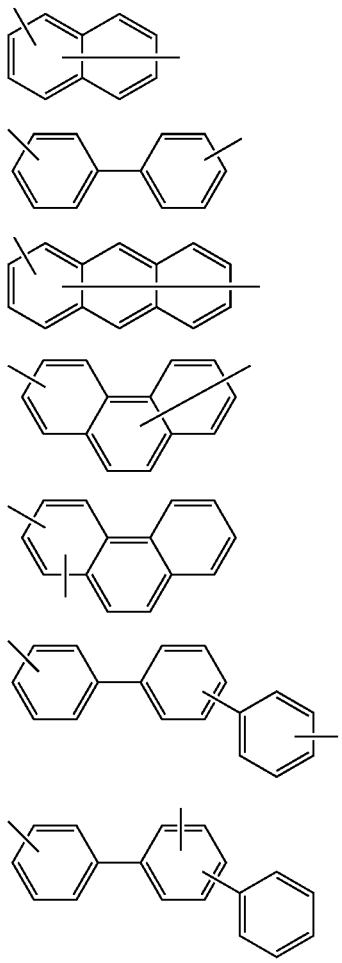

(a-2)
(a-3)
(a-4)
(a-5)
(a-6)
(a-7)
(a-8)

The divalent aromatic hydrocarbon group is preferably 1,4-phenylene group.

In formulae (1) and (2), k represents an integer of 0 to 3, preferably 1 or 2, and more preferably 1. When k is an integer of 2 or more, a plurality of As and Bs may be the same or different from each other. From the viewpoint of industrially easily producing liquid compounds (1) and (2), it is preferable that a plurality of As and Bs are the same as each other.

In formulae (1) and (2), E represents an alkanediyl group having 1 to 17 carbon atoms, preferably 2 to 15 carbon atoms, more preferably 3 to 12 carbon atoms, and even more preferably 4 to 10 carbon atoms. The hydrogen atom contained in the alkanediyl group is optionally substituted with a halogen atom, and —$CH_2$— contained in the alkanediyl group is optionally substituted with —O— or —CO—.

In formulae (1) and (2), Pisa polymerizable group. The polymerizable group contains a group capable of being involved in polymerization reaction. Examples thereof include a vinyl group, a p-(2-phenylethenyl) phenyl group, an acryloyl group, an acryloyloxy group, a methacryloyl group, a methacryloyloxy group, a carboxy group, a methylcarboxy group, a hydroxyl group, a carbamoyl group, an alkylamino group having 1 to 4 carbon atoms, an amino group, a formyl group, —N═C═O, —N═C═S, an oxiranyl group, and an oxetanyl group.

Of these, the polymerizable group is preferably a radical polymerizable group or a cationic polymerizable group from the viewpoint of suitability for photo polymerization; preferably an acryloyl group, an acryloyloxy group, a methacryloyl group, and a methacryloyloxy group, from the viewpoint of easy handling and easy production; and more preferably an acryloyl group and an acryloyloxy group from the viewpoint of high polymerizing ability.

<Liquid Crystal Composition and Method for Producing the Same>

The liquid crystal composition of the present invention contains the liquid crystal compounds (1) and (2). G, A, B, E, P and k in formula (1) representing liquid crystal compound (1) may be different from or the same as G, A, B, E, P and k in the formula (2) representing liquid crystal compound (2), respectively. In the preferred embodiment of the present invention, G, A, B, E, P and k in the formula (1) are the same as G, A, B, E, P and k in the formula (2), respectively. In this case, it is possible to simultaneously prepare liquid crystal compounds (1) and (2) contained in the liquid crystal composition of the present invention in one pot. Therefore, it is possible to prepare the liquid crystal composition of the present invention very conveniently, which is economically advantageous.

The optical film obtained by orienting the liquid crystal compound (1) preferably exhibits a reverse wavelength dispersion characteristic. When it exhibits such characteristic, uniform conversion of polarized light is possible over a wide range of wavelength region, which is preferable. In the case of satisfying the relation: [Re(450)/Re(550)]<1, a reverse wavelength dispersion characteristic is exhibited while in the case of satisfying the relation: [Re(450)/Re(550))9 ≥1, a positive wavelength dispersion characteristic is exhibited. The optical film obtained by orienting the liquid crystal compound refers to an optical film formed from oriented liquid crystal compounds.

The maximum absorption wavelength ($\lambda_{max}$) of the liquid crystal compound (1) is preferably from 300 to 400 nm, more preferably from 315 to 385 nm, and even more preferably from 330 to 360 nm. When the maximum absorption wavelength ($\lambda_{max}$) of the liquid crystal compound (1) is not less than the lower limit, the optical film obtained by orienting liquid crystal compound (1) tends to exhibit a reverse wavelength dispersion characteristic. When it is not more than the upper limit, light absorption in the visible light region is suppressed and coloring of the film can be avoided, which is preferable.

Examples of the liquid crystal compound (1) include the following compounds.

[Chem. 133]

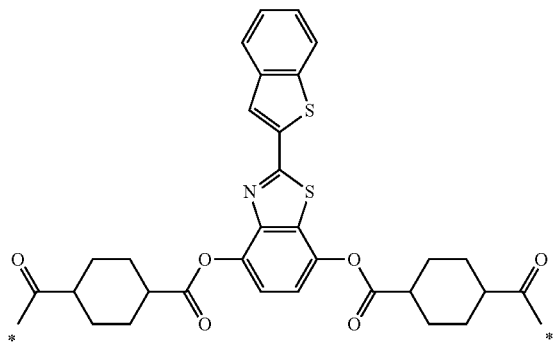

(A1-1)
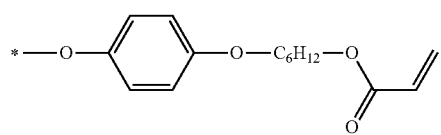
(A1-2)
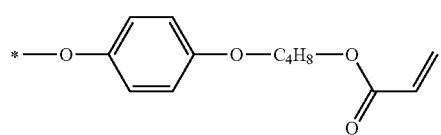
(A1-3)
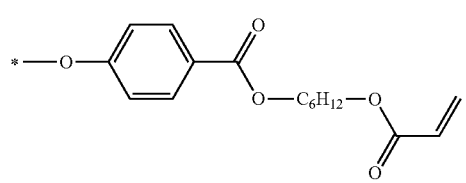
(A1-4)
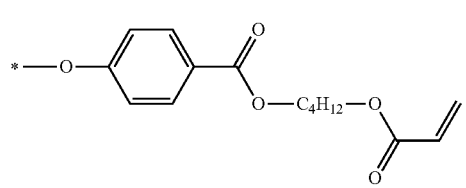
(A1-5)
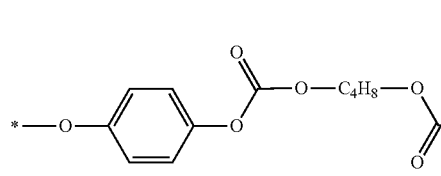
(A1-6)
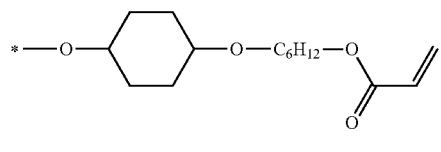
(A1-7)
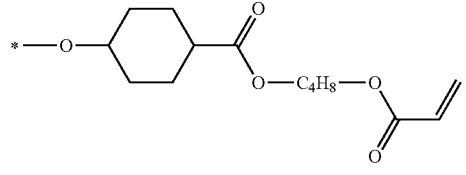
(A1-8)
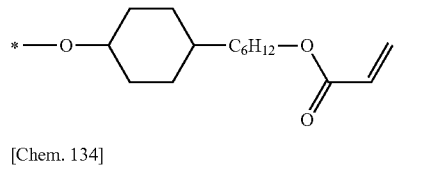
[Chem. 134]
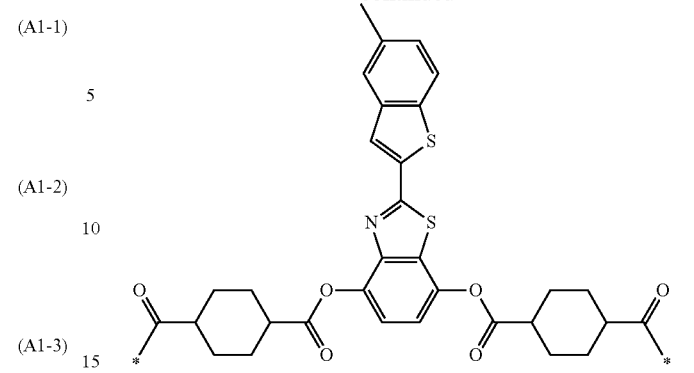
(A2-1)
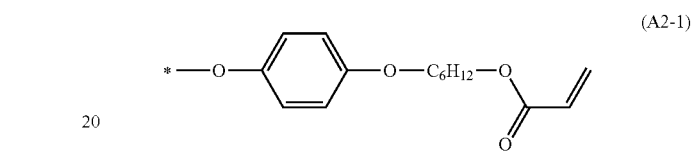
(A2-2)
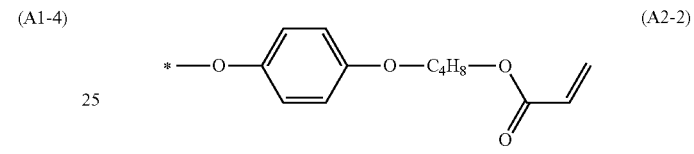
(A2-3)
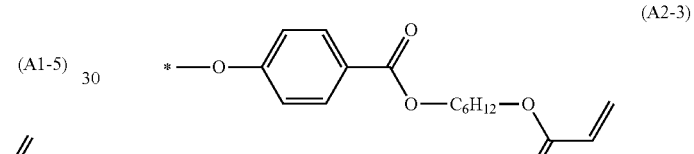
(A2-4)
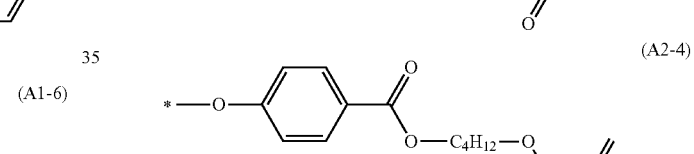
(A2-5)
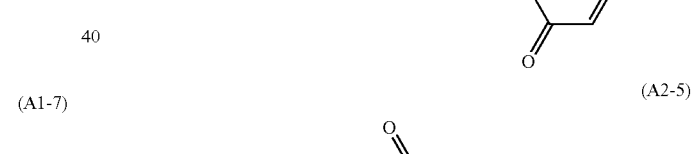
(A2-6)
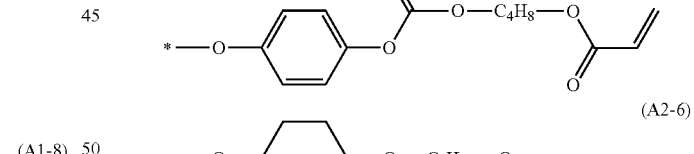
(A2-7)
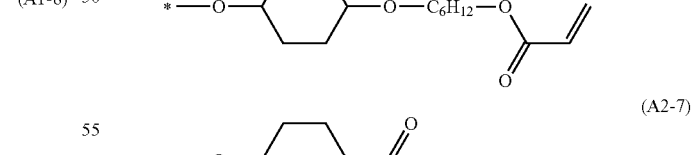
(A2-8)
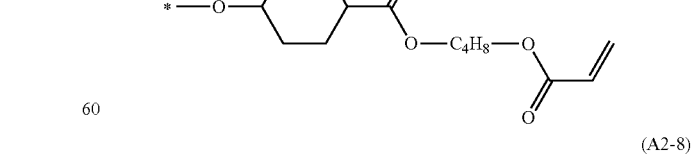

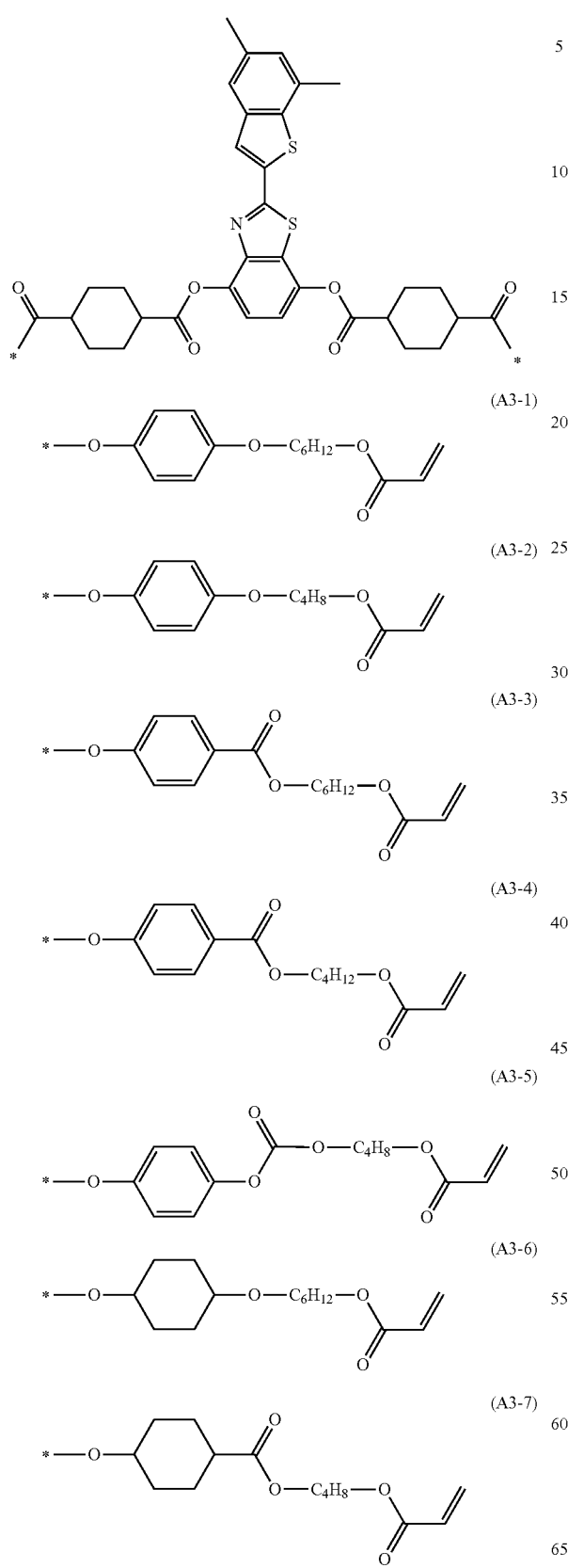
(A3-1)
(A3-2)
(A3-3)
(A3-4)
(A3-5)
(A3-6)
(A3-7)
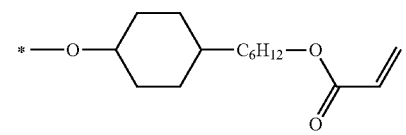
(A3-8)
[Chem. 136]
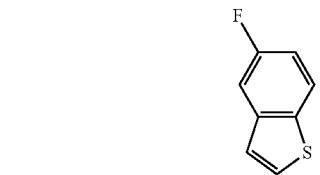
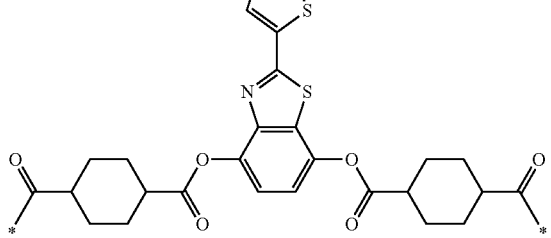
(A4-1)
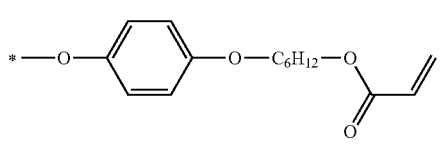
(A4-2)
(A4-3)
(A4-4)
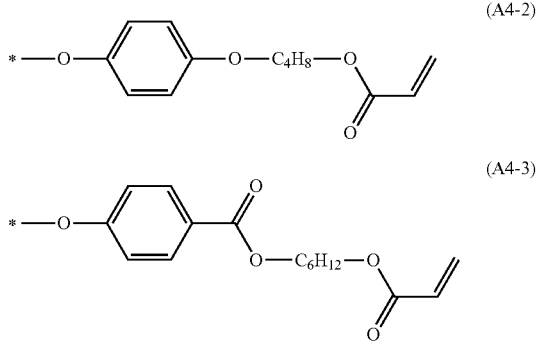
(A4-5)
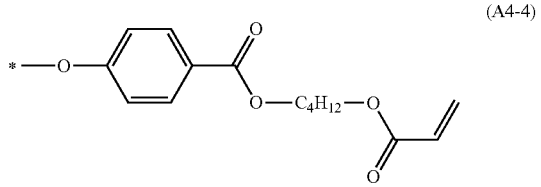
(A4-6)
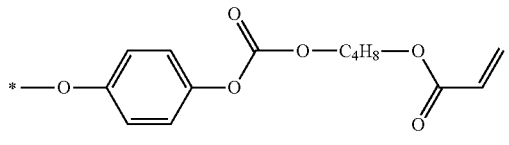
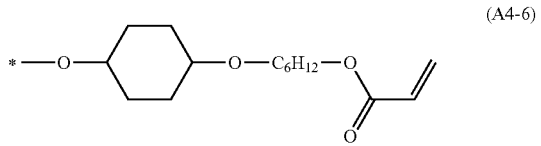

(A4-7)
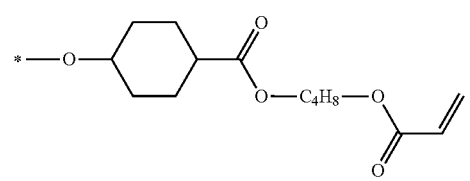
(A4-8)
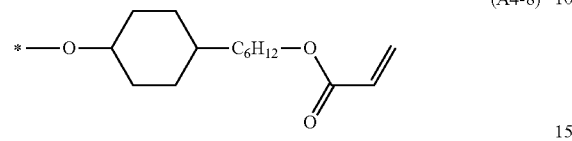
[Chem. 137]
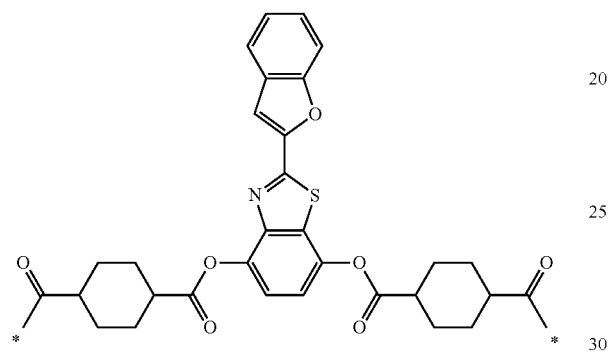
(A5-1)
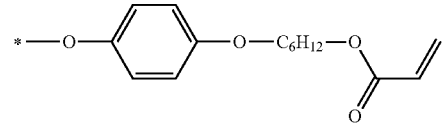
(A5-2)
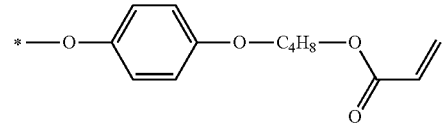
(A5-3)
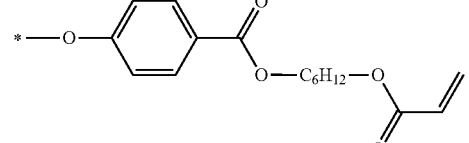
(A5-4)
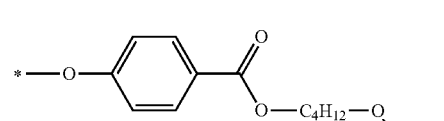
(A5-5)
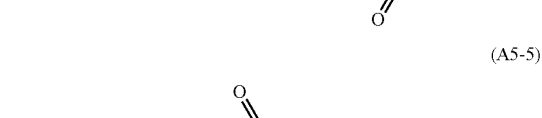
(A5-6)
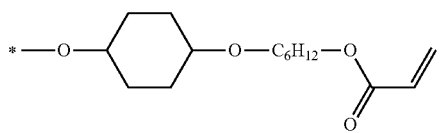
(A5-7)
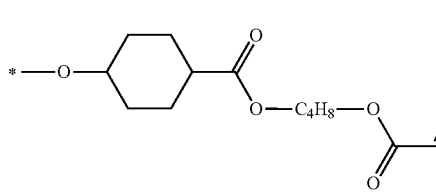
(A5-8)
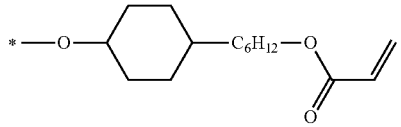
[Chem. 138]
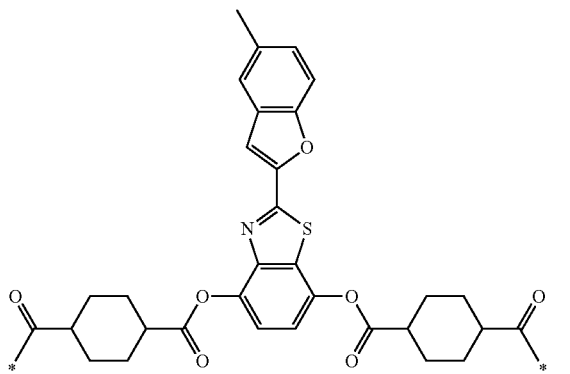
(A6-1)
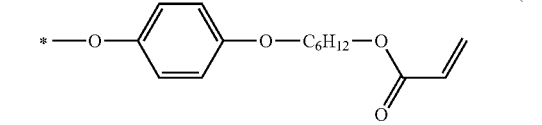
(A6-2)
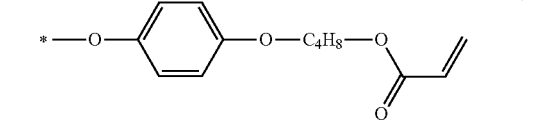
(A6-3)
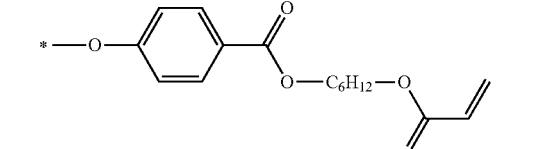
(A6-4)

-continued
(A6-5)
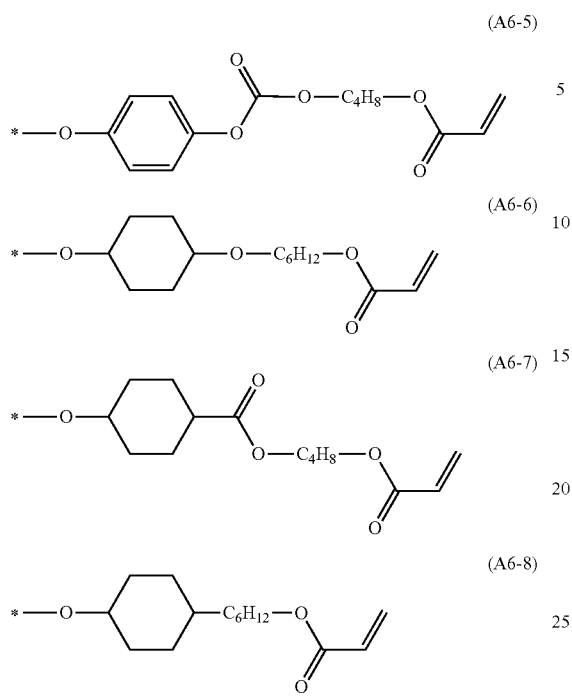
(A6-6)
(A6-7)
(A6-8)
[Chem. 139]
(A7-1)
(A7-2)
(A7-3)
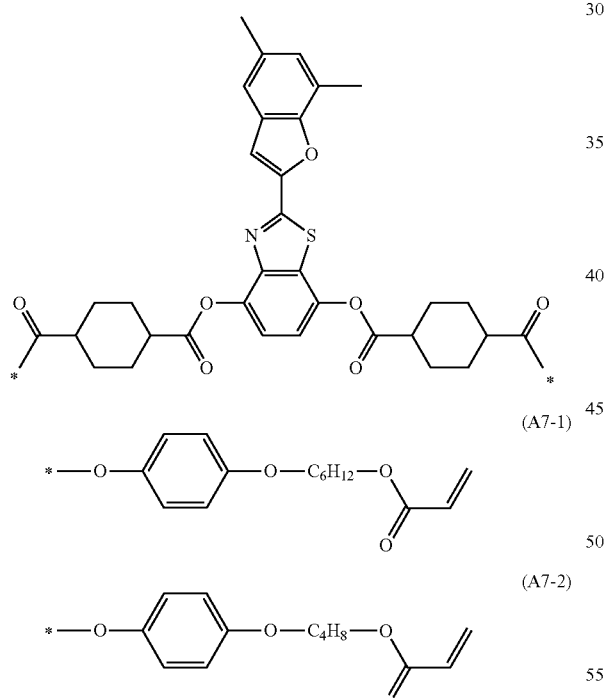
-continued
(A7-4)
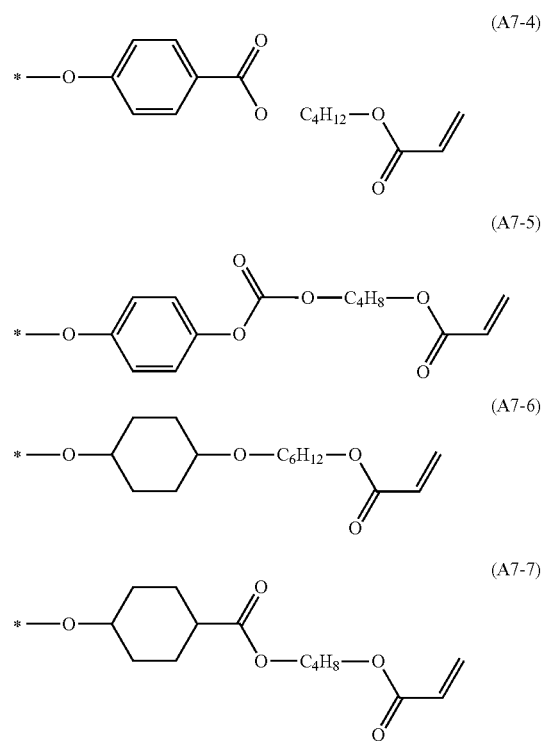
(A7-5)
(A7-6)
(A7-7)
(A7-8)
[Chem. 140]
(A8-1)
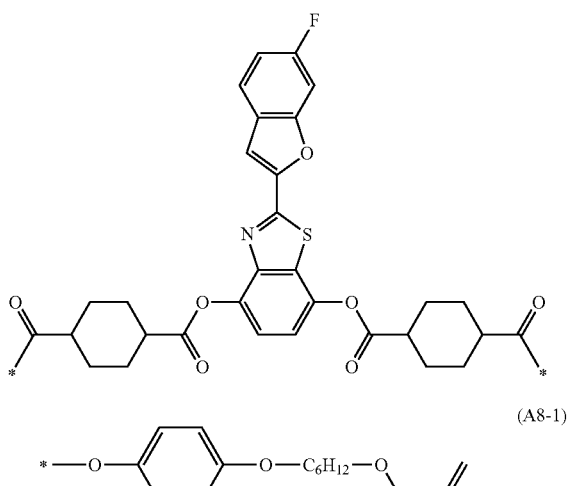
(A8-2)

(A8-3)
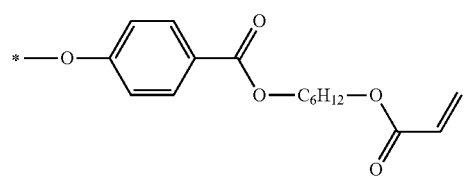
(A8-4)
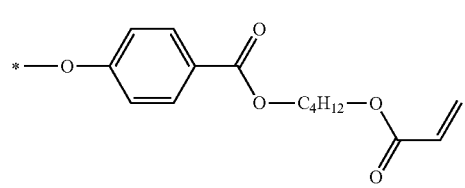
(A8-5)
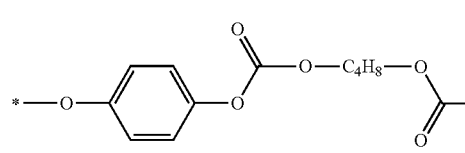
(A8-6)
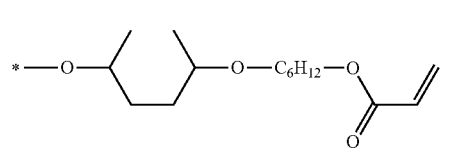
(A8-7)
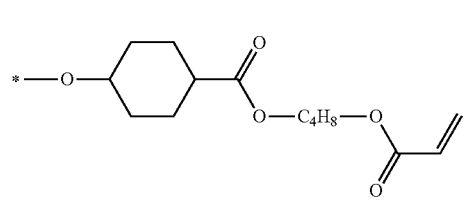
(A8-8)
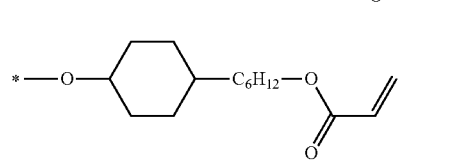
[Chem. 141]
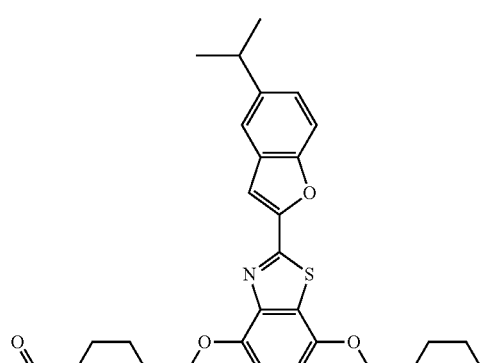
(A9-1)
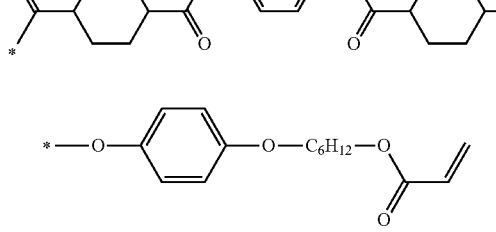
(A9-2)
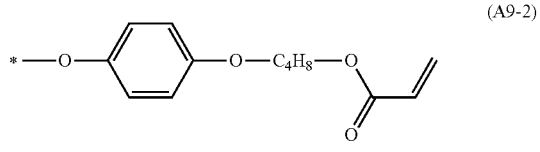
(A9-3)
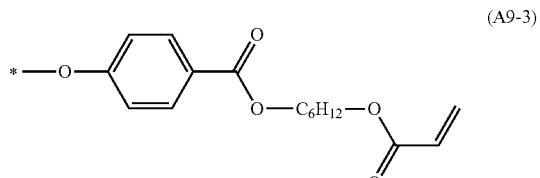
(A9-4)
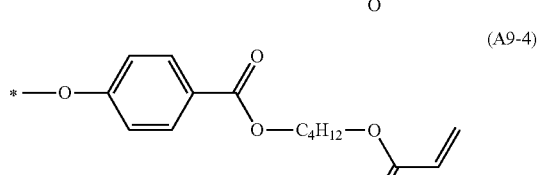
(A9-5)
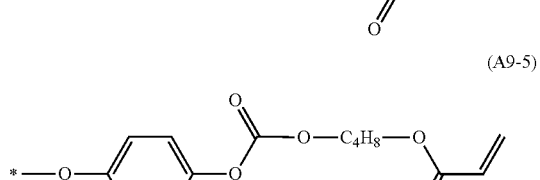
(A9-6)
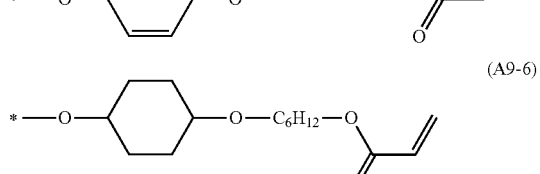
(A9-7)
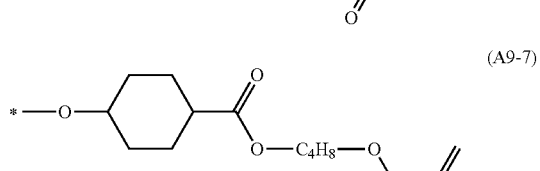
(A9-8)
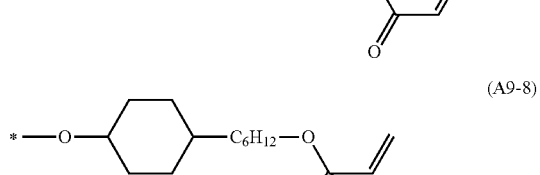
[Chem. 142]
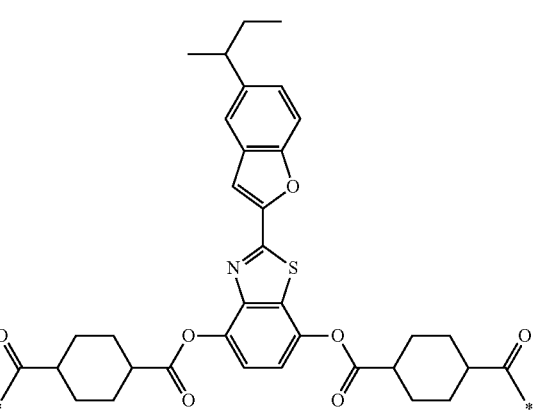

(A10-1)
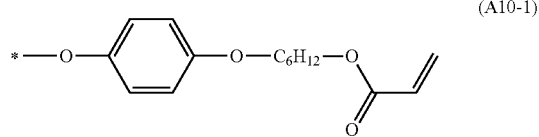
(A10-2)
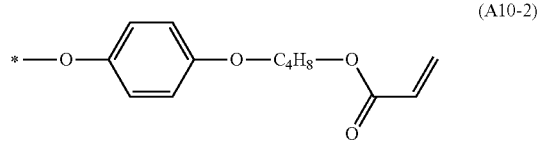
(A10-3)
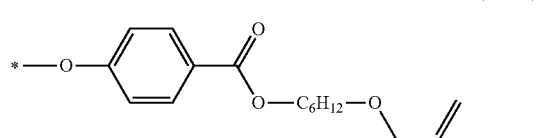
(A10-4)
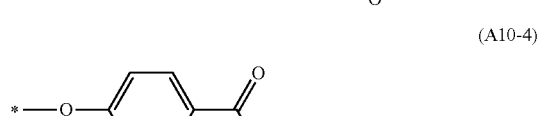
(A10-5)
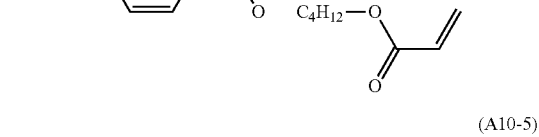
(A10-6)
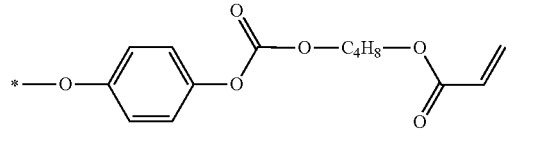
(A10-7)
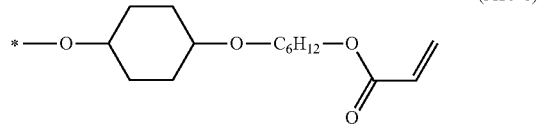
(A10-8)
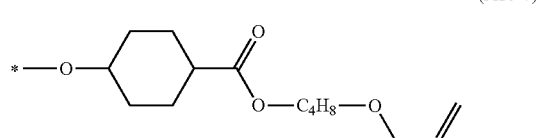
[Chem. 143]
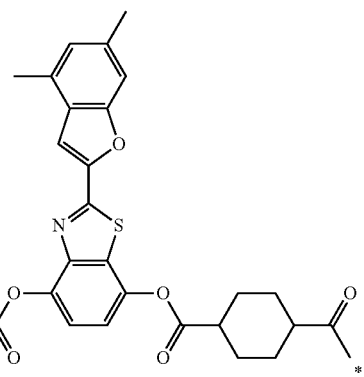
(A11-1)
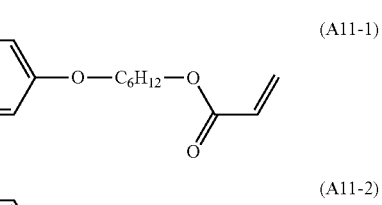
(A11-2)
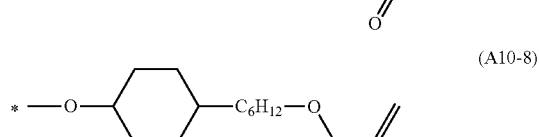
(A11-3)
(A11-4)
(A11-5)
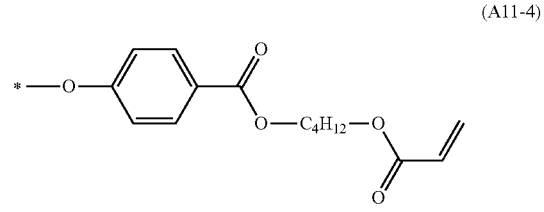
(A11-6)
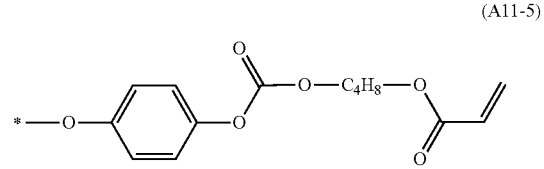
(A11-7)
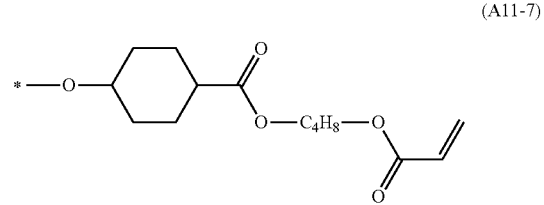

(A11-8)
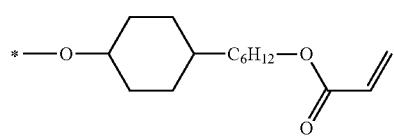
[Chem. 144]
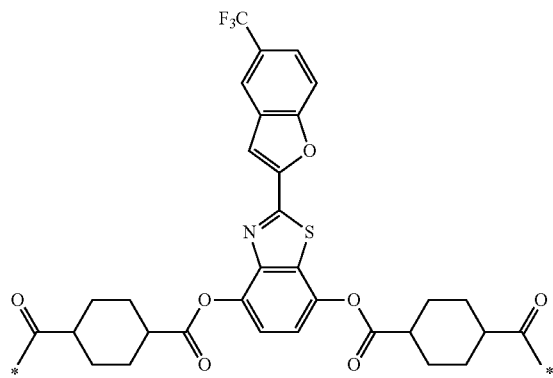
(A12-1)
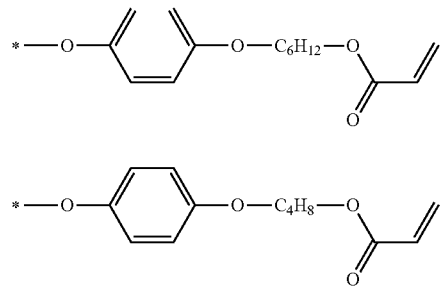
(A12-2)
(A12-3)
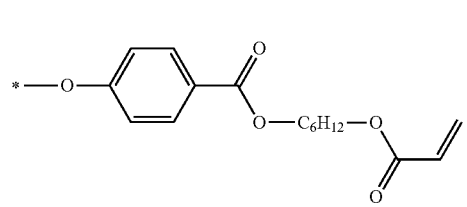
(A12-4)
(A12-5)
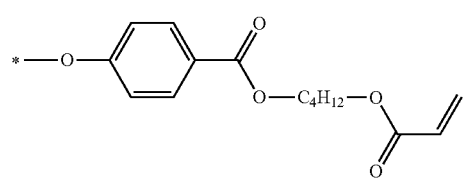
(A12-6)
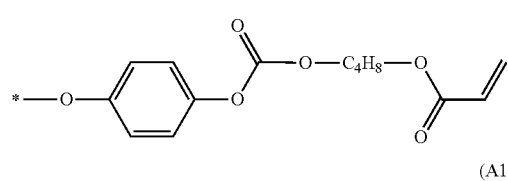
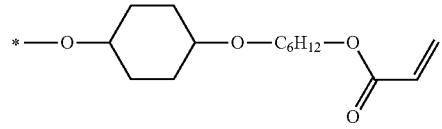
(A12-7)
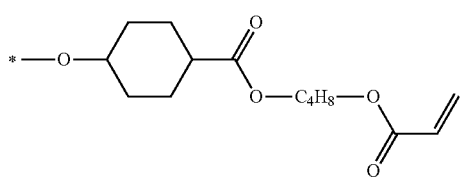
(A12-8)
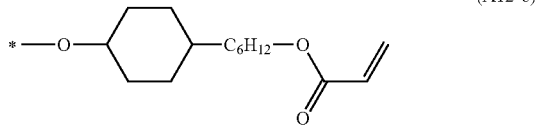
[Chem. 145]
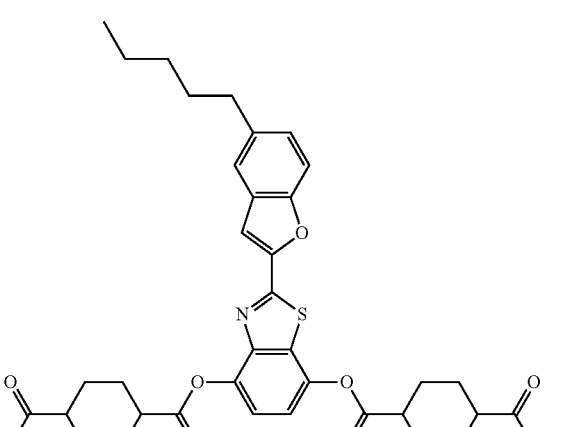
(A13-1)
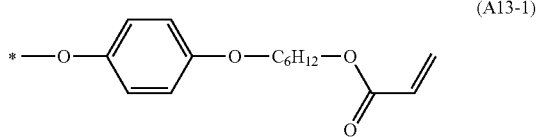
(A13-2)
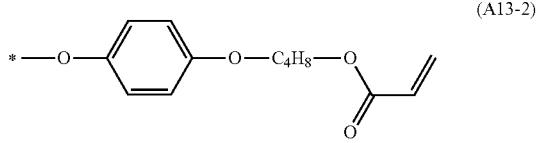
(A13-3)
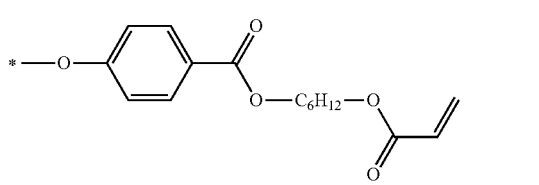
(A13-4)
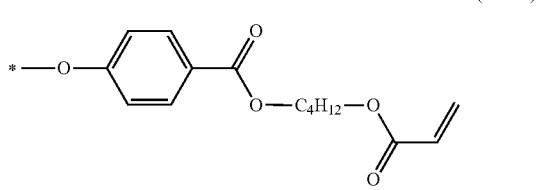

(A13-5)
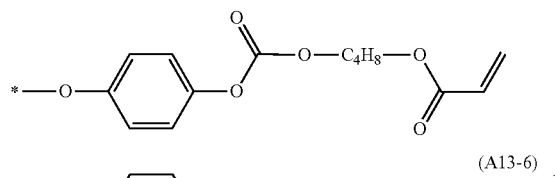
(A13-6)
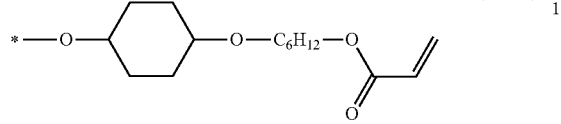
(A13-7)
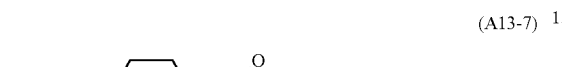
(A13-8)
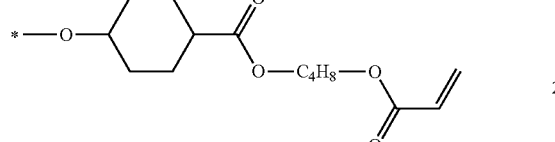
[Chem. 146]
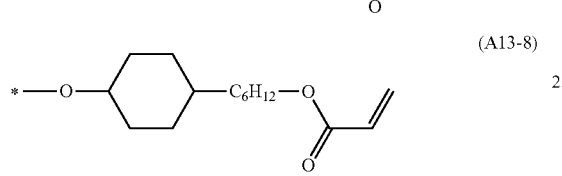
(A14-1)
(A14-2)
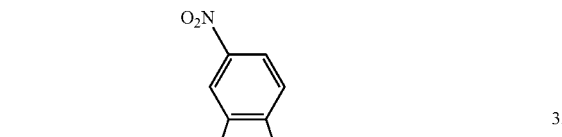
(A14-3)
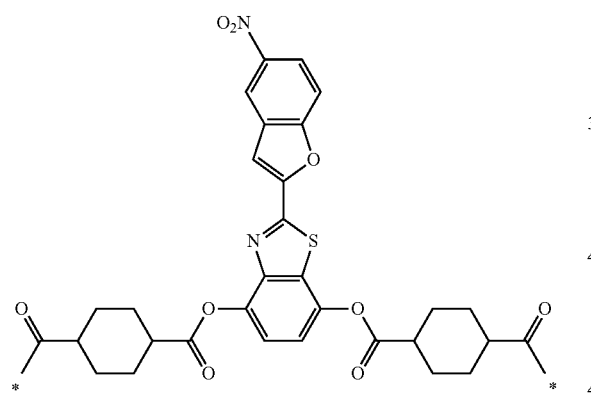
(A14-4)
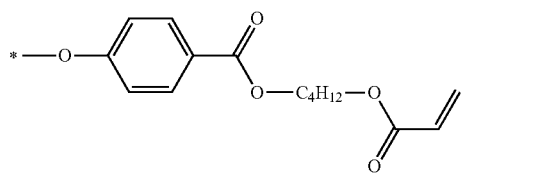
(A14-5)
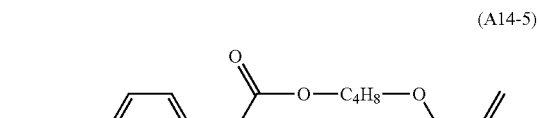
(A14-6)
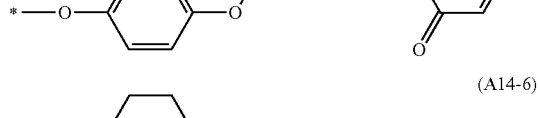
(A14-7)
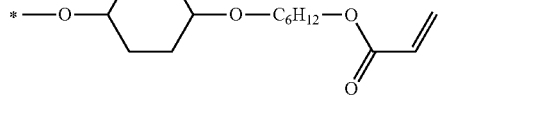
(A14-8)
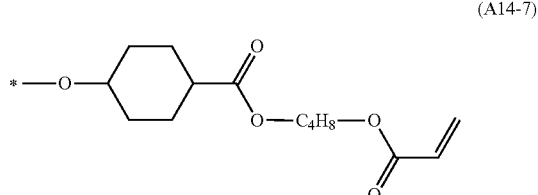
[Chem. 147]
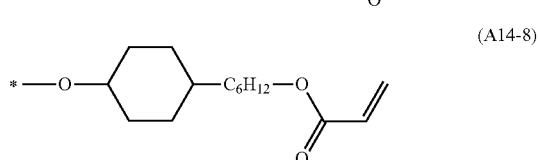
(A15-1)
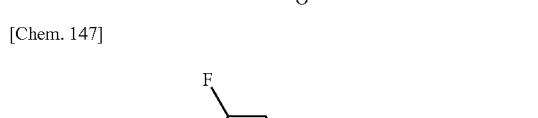
(A15-2)
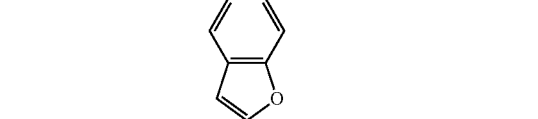

(A15-3)
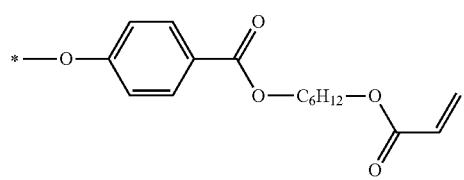
(A15-4)
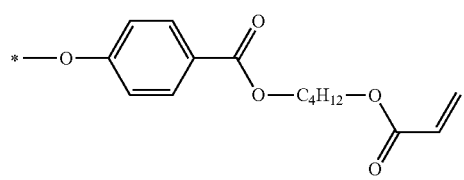
(A15-5)
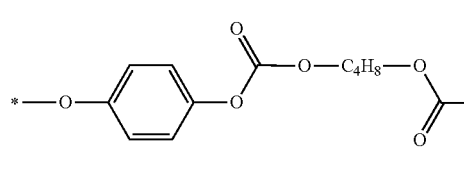
(A15-6)
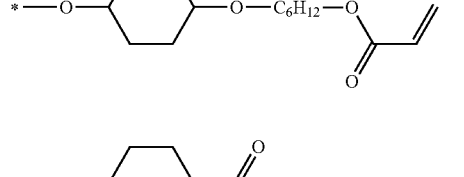
(A15-7)
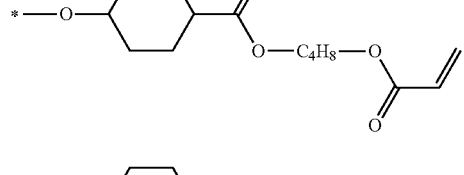
(A15-8)
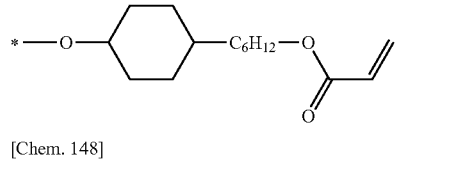
[Chem. 148]
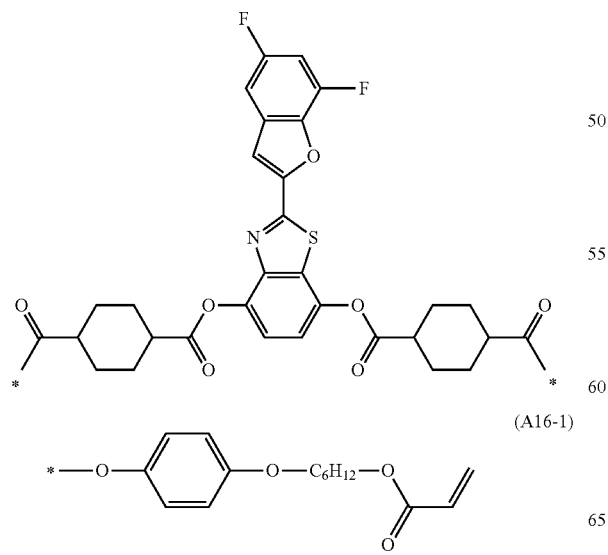
(A16-1)
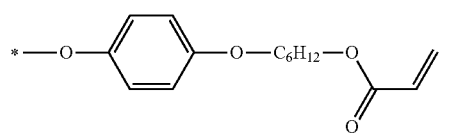
(A16-2)
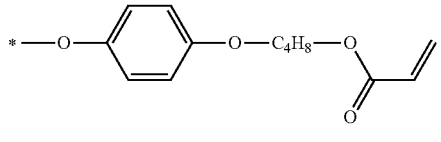
(A16-3)
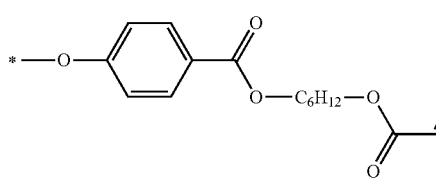
(A16-4)
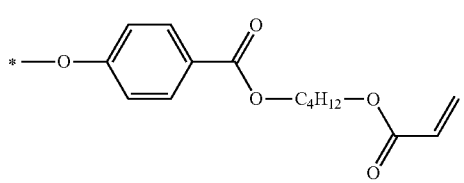
(A16-5)
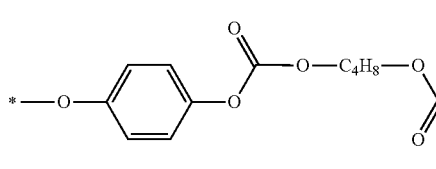
(A16-6)
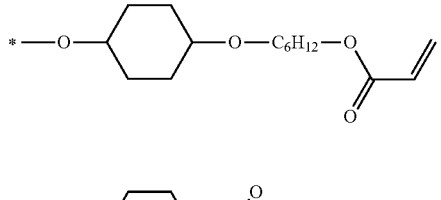
(A16-7)
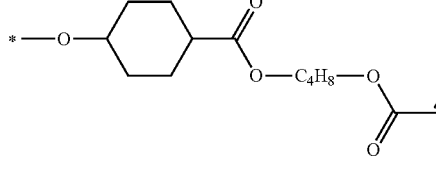
(A16-8)
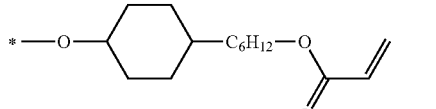
[Chem. 149]
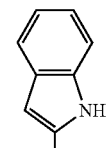
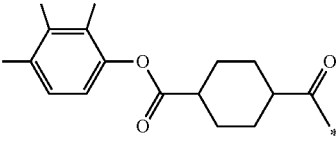

(A17-1)
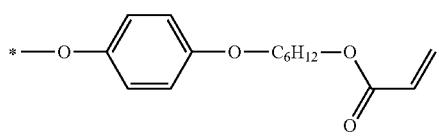
(A17-2)
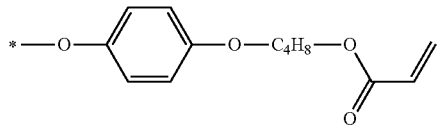
(A17-3)
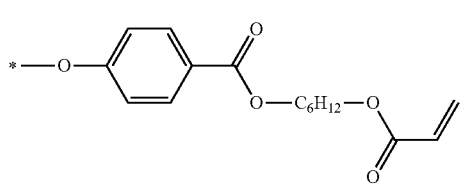
(A17-4)
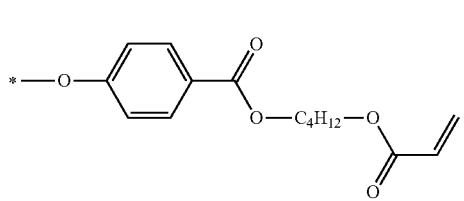
(A17-5)
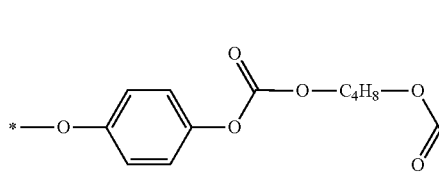
(A17-6)
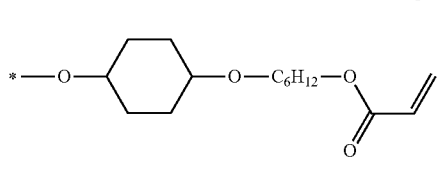
(A17-7)
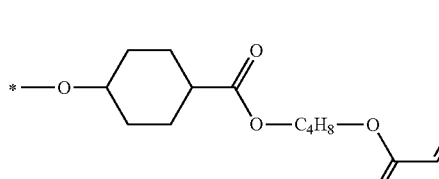
(A17-8)
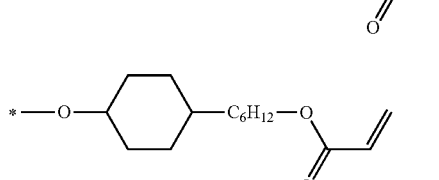
[Chem. 150]
-continued
(A18-1)

(A18-8) 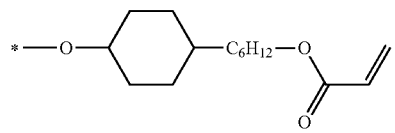
[Chem. 151]
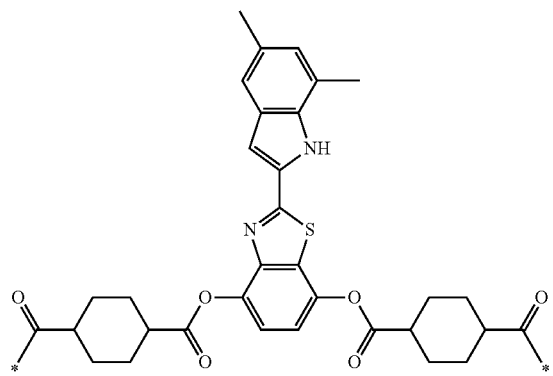
(A19-1) 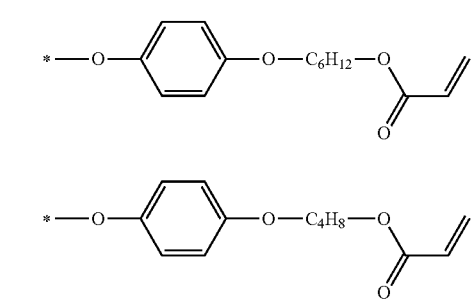
(A19-2)
(A19-3) 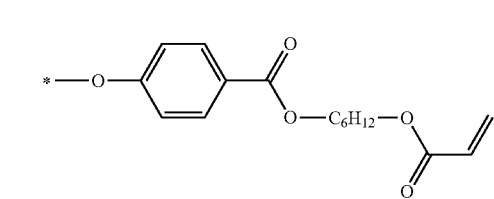
(A19-4) 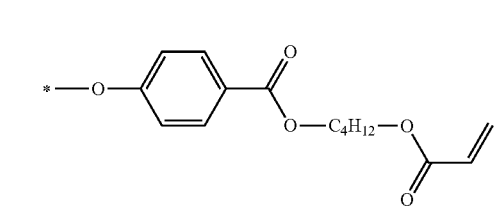
(A19-5) 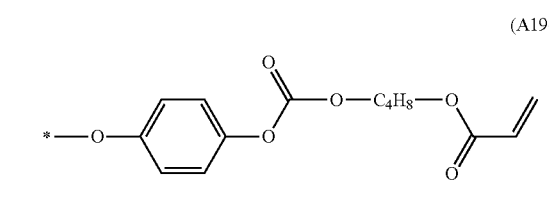
(A19-6) 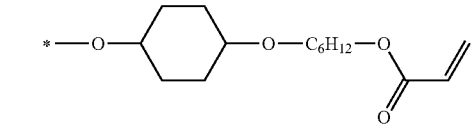
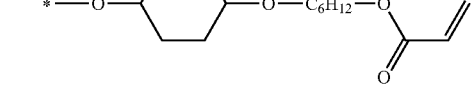
(A19-7) 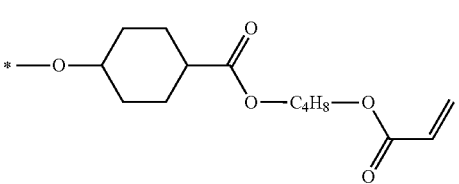
(A19-8) 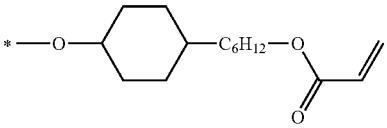
[Chem. 152]
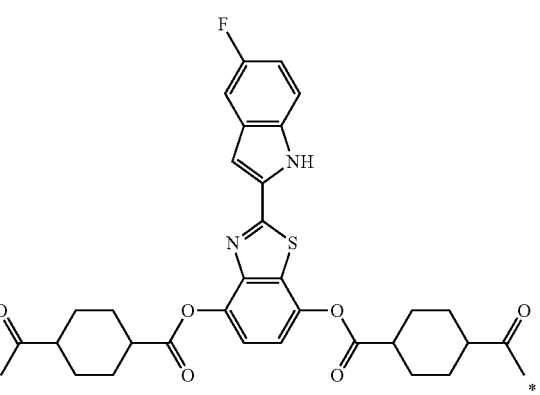
(A20-1) 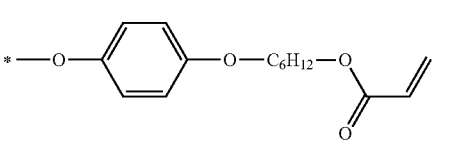
(A20-2) 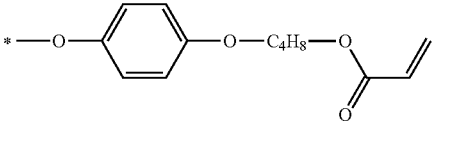
(A20-3) 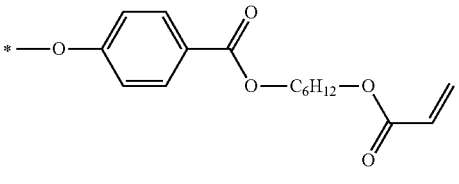
(A20-4) 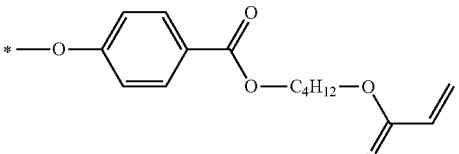
(A20-5) 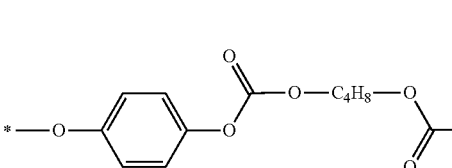

(A20-6)
(A20-7)
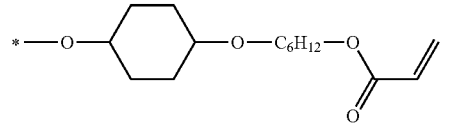
(A20-8)
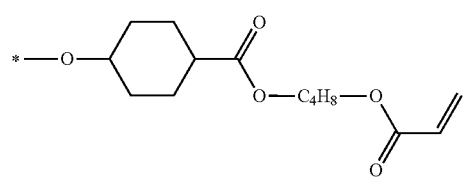
[Chem. 153]
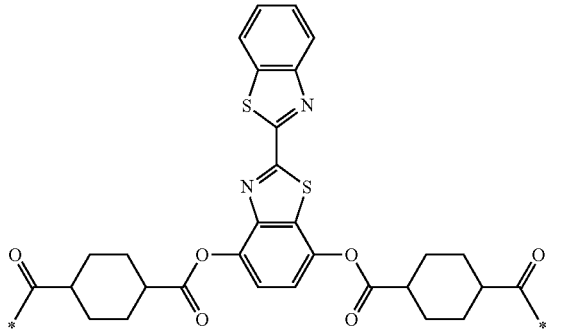
(A21-1)
(A21-2)
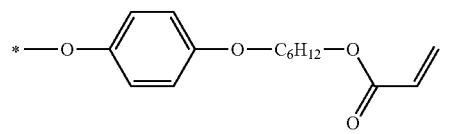
(A21-3)
(A21-4)
(A21-5)
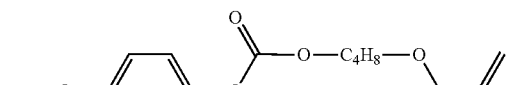
(A21-6)
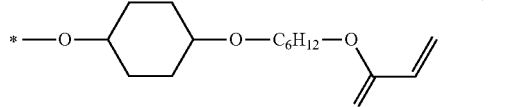
(A21-7)
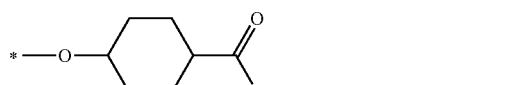
(A21-8)
[Chem. 154]
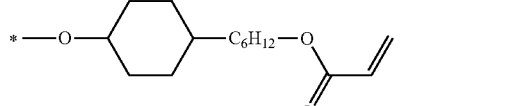
(A22-1)
(A22-2)
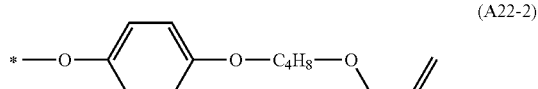
(A22-3)
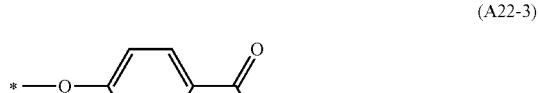

(A22-4) 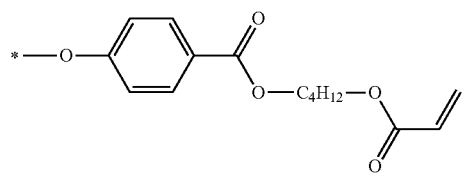
(A22-5) 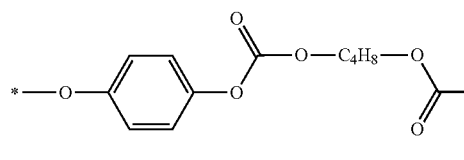
(A22-6) 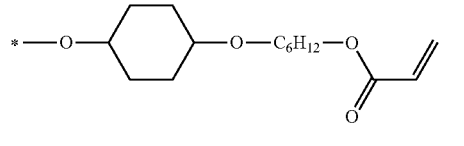
(A22-7) 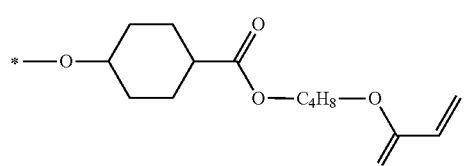
(A22-8) 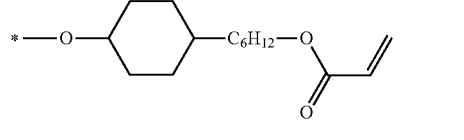
[Chem. 155]
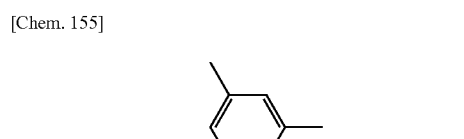
(A23-1) 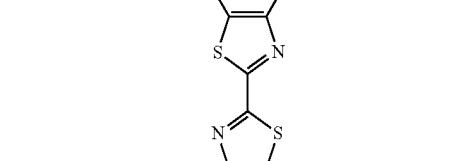
(A23-2) 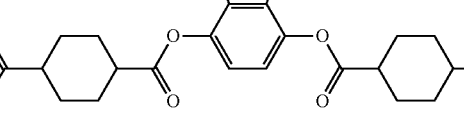
(A23-3) 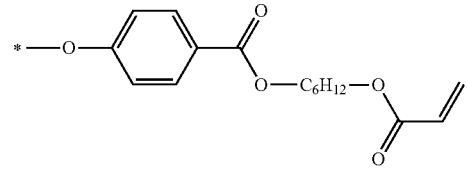
(A23-4) 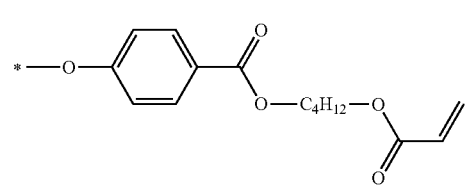
(A23-5) 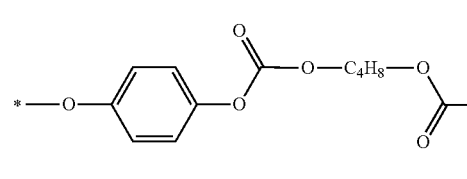
(A23-6) 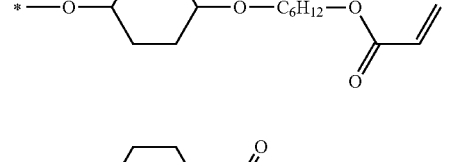
(A23-7) 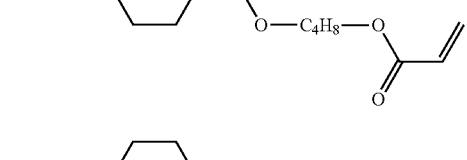
(A23-8) 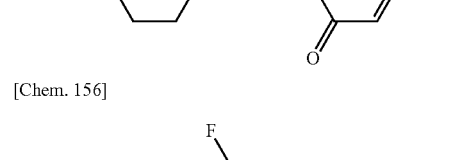
[Chem. 156]
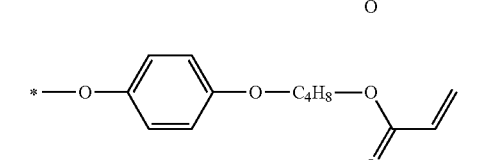
(A24-1) 

(A24-2)
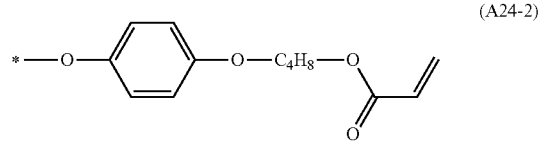
(A24-3)
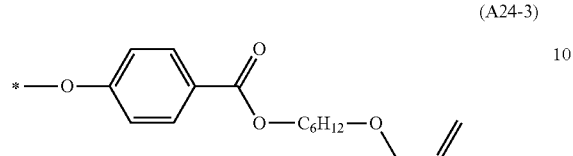
(A24-4)
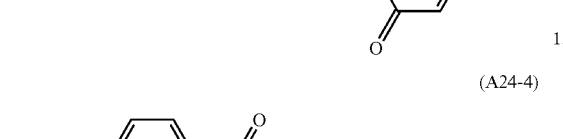
(A24-5)
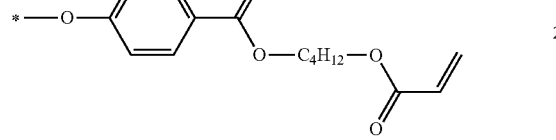
(A24-6)
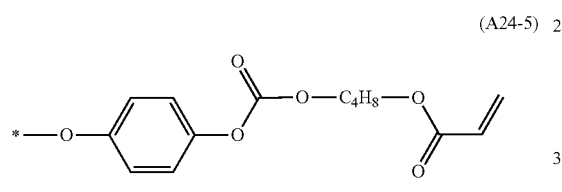
(A24-7)
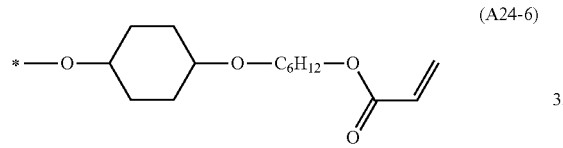
(A24-8)
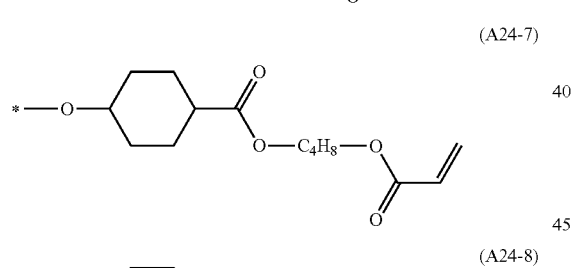
[Chem. 157]
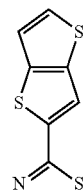
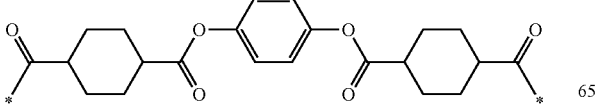
(A25-1)
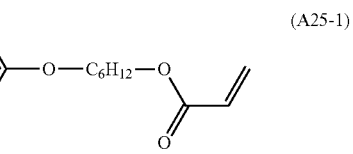
(A25-2)
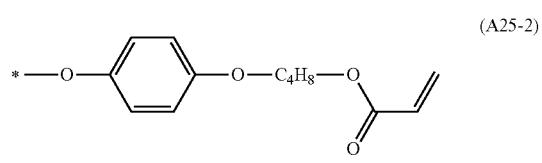
(A25-3)
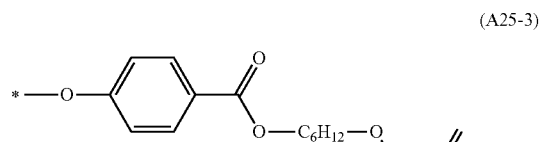
(A25-4)
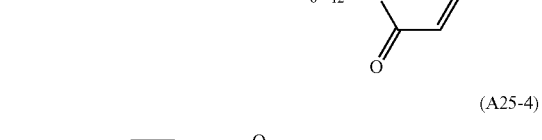
(A25-5)
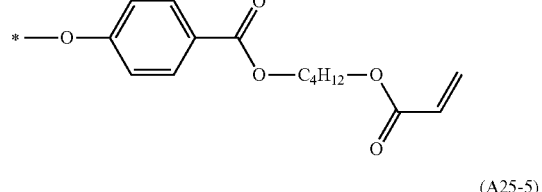
(A25-6)
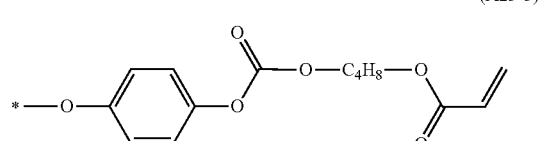
(A25-7)
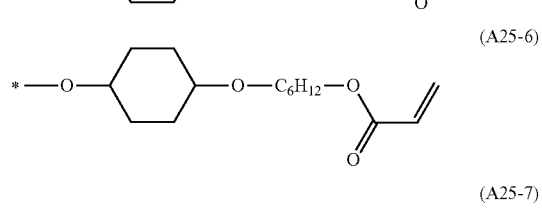
(A25-8)
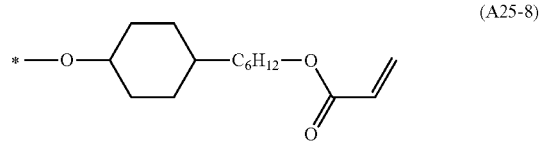
[Chem. 158]

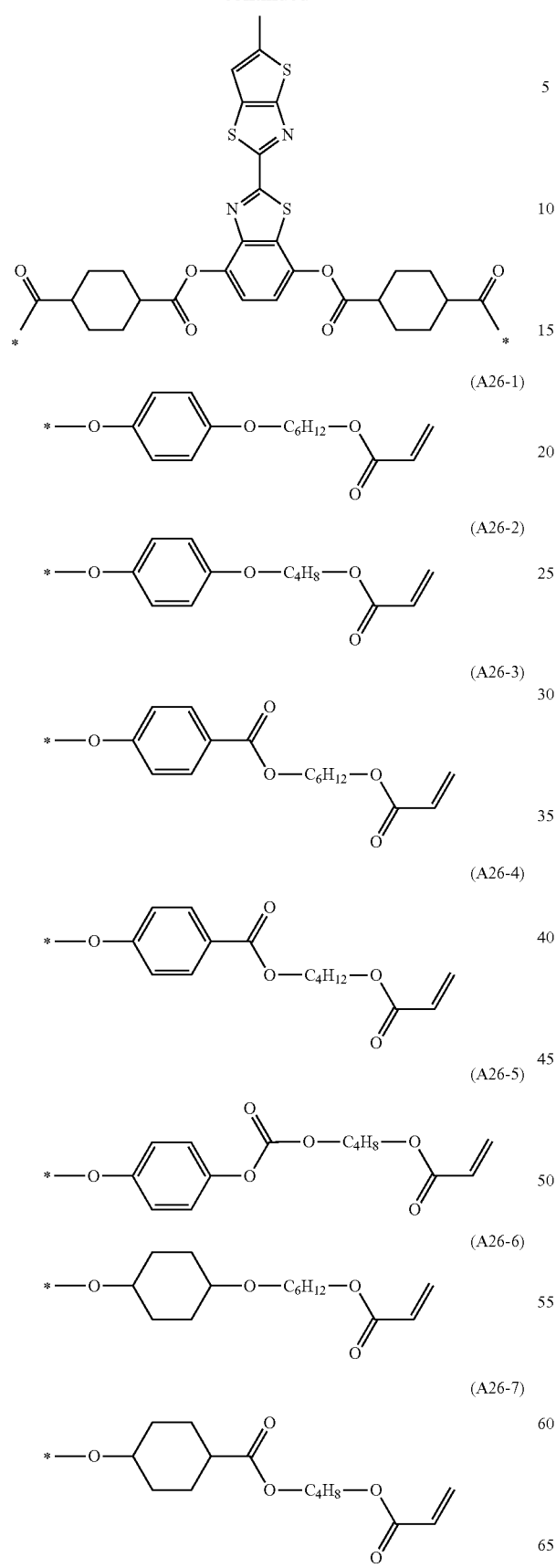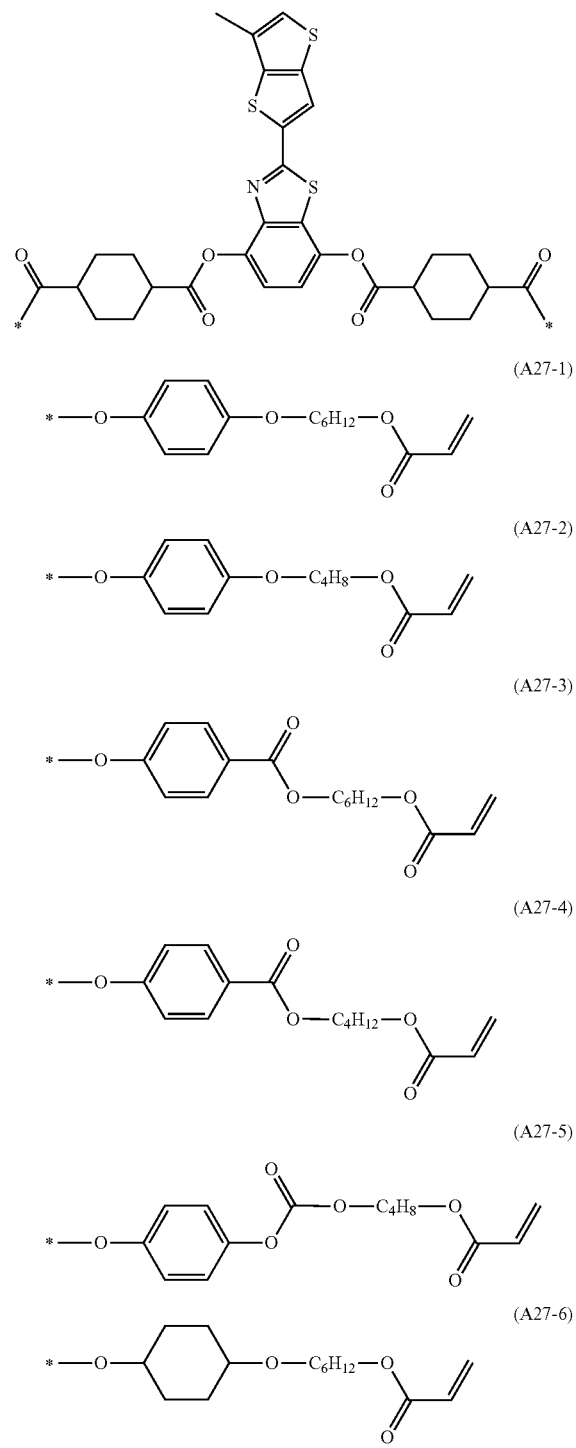

(A27-7)
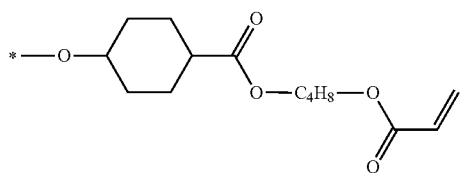
(A27-8)
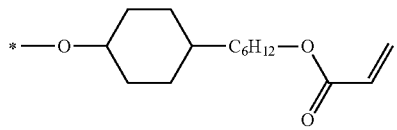
[Chem. 160]
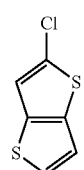
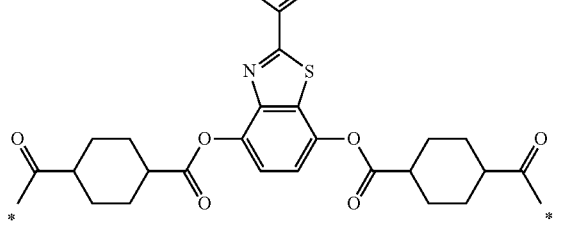
(A28-1)
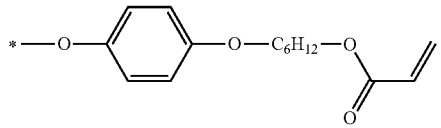
(A28-2)
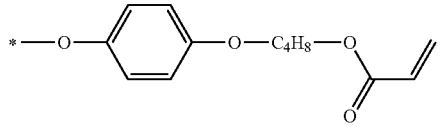
(A28-3)
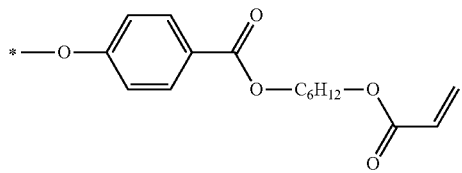
(A28-4)
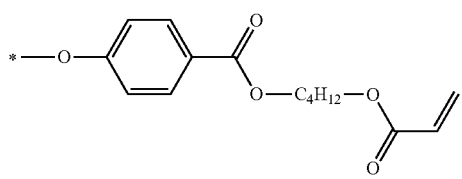
(A28-5)
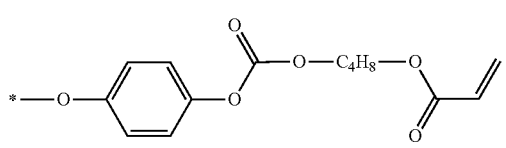
(A28-6)
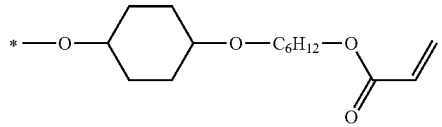
(A28-7)
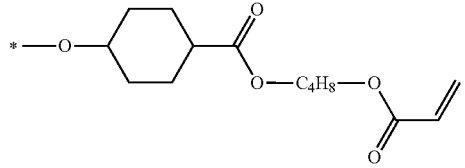
(A28-8)
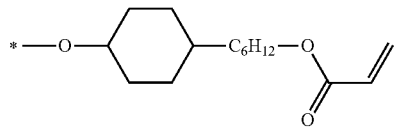
[Chem. 161]
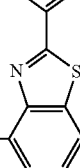
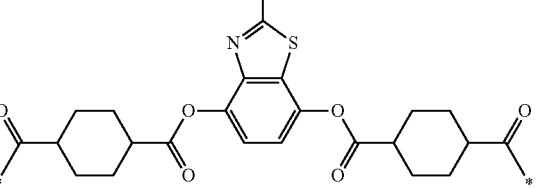
(A29-1)
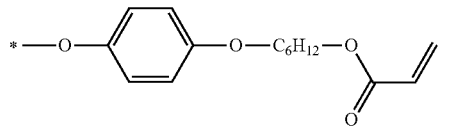
(A29-2)
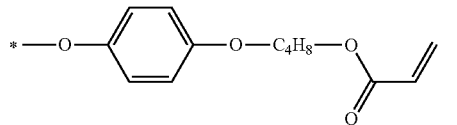
(A29-3)
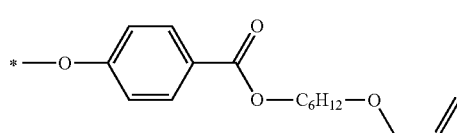
(A29-4)
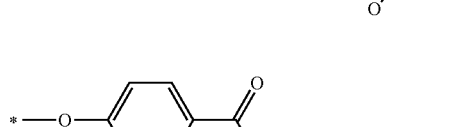

(A29-5)
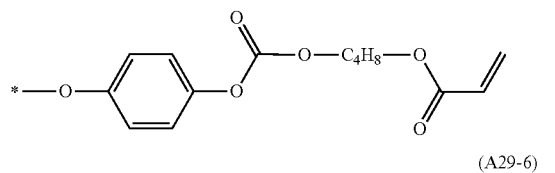
(A29-6)
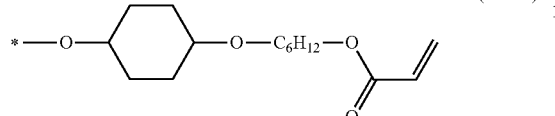
(A29-7)
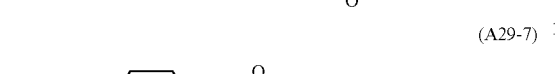
(A29-8)
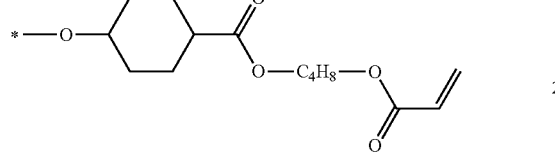
[Chem. 162]
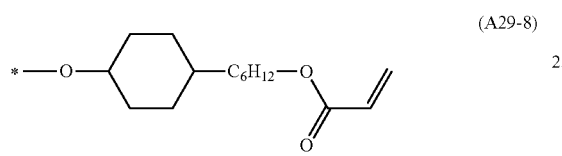
(A30-1)
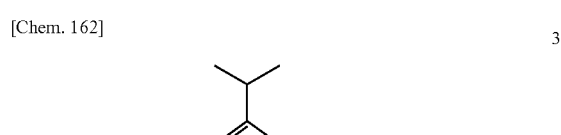
(A30-2)
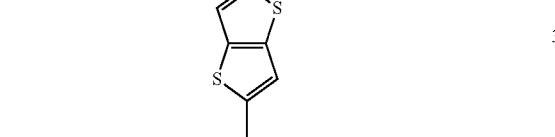
(A30-3)
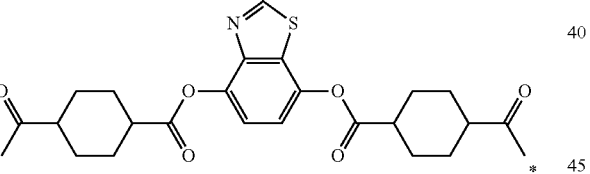
(A30-4)
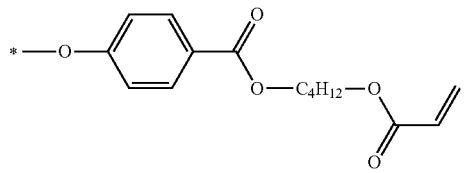
(A30-5)
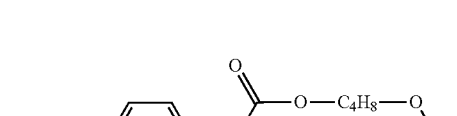
(A30-6)
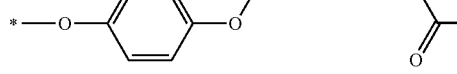
(A30-7)
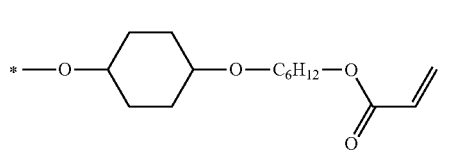
(A30-8)
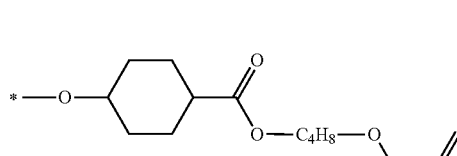
[Chem. 163]
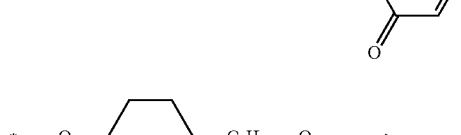
(A31-1)
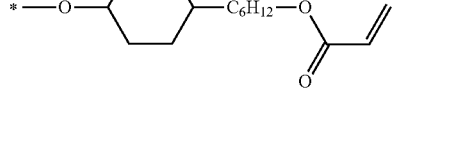

-continued
(A31-2)
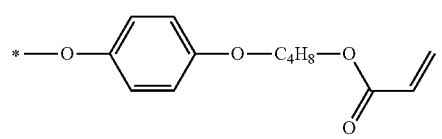
(A31-3)
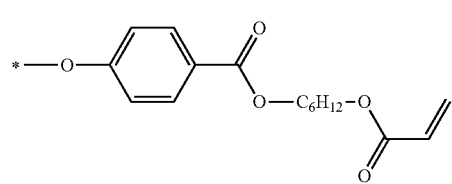
(A31-4)
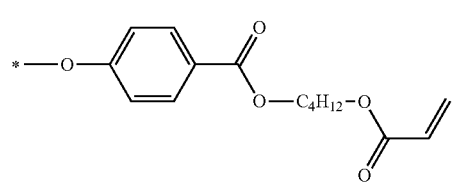
(A31-5)
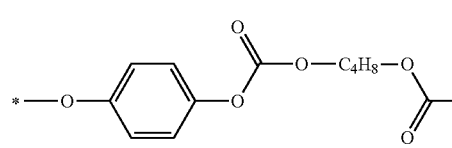
(A31-6)
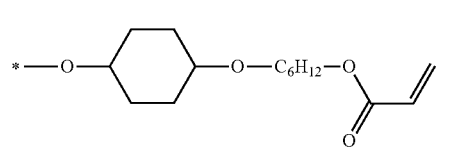
(A31-7)
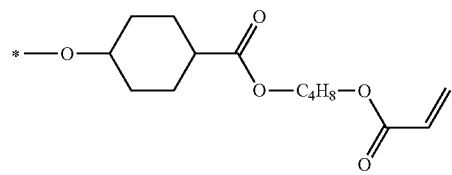
(A31-8)
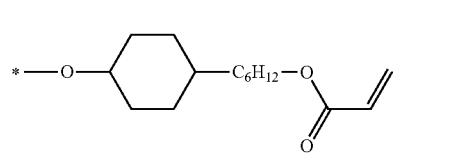
[Chem. 164]
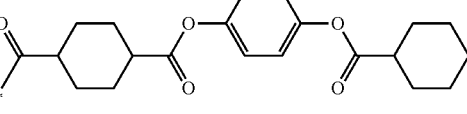
-continued
(A32-1)
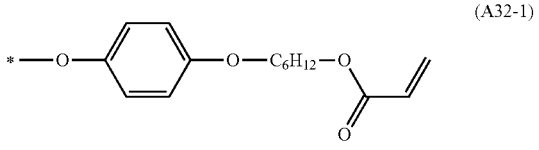
(A32-2)
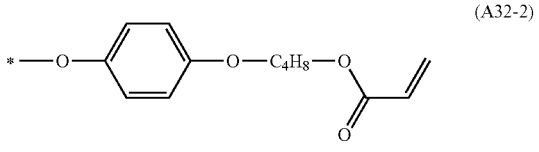
(A32-3)
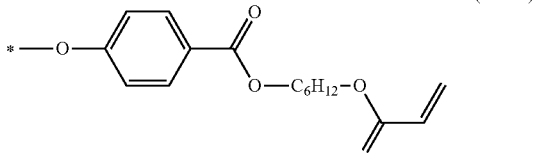
(A32-4)
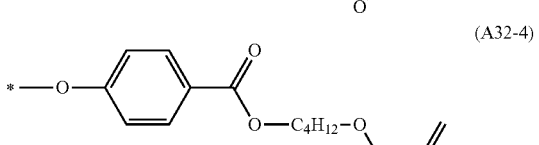
(A32-5)
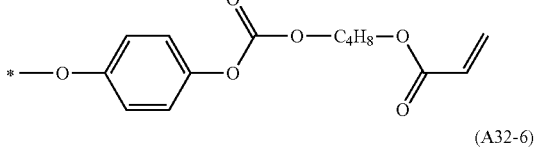
(A32-6)
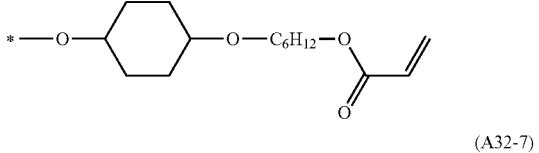
(A32-7)
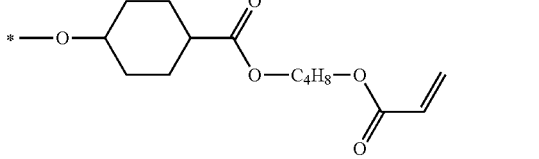
(A32-8)
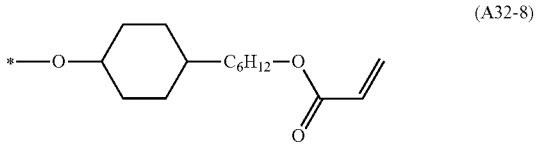
[Chem. 165]
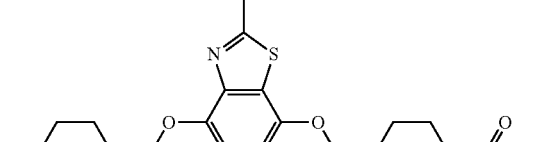

-continued
(A33-1)
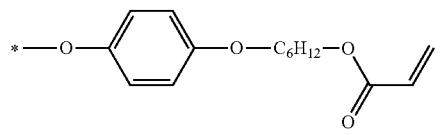
(A33-2)
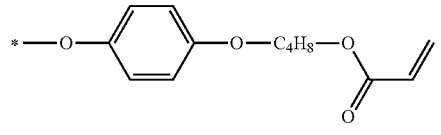
(A33-3)
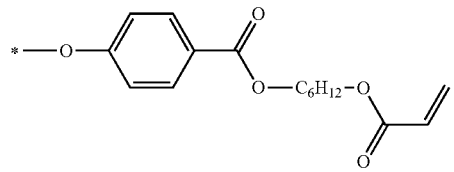
(A33-4)
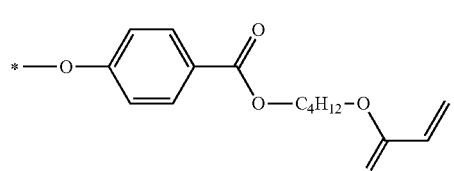
(A33-5)
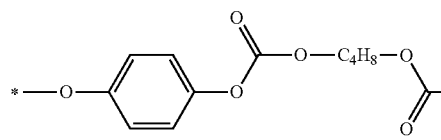
(A33-6)
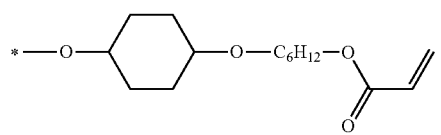
(A33-7)
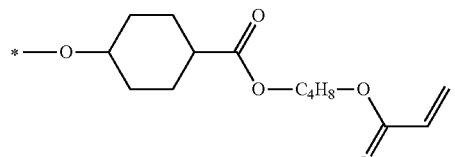
(A33-8)
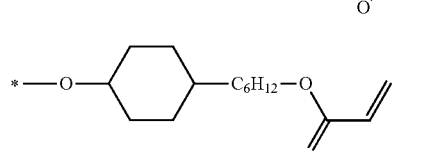
[Chem. 166]
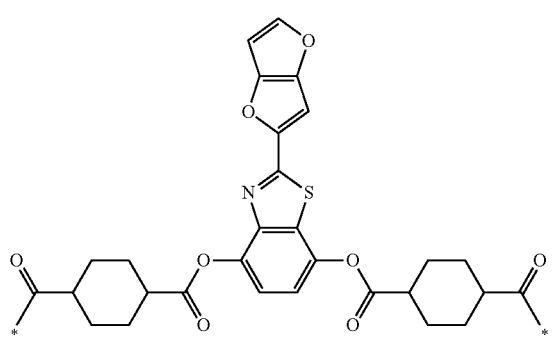
-continued
(A34-1)
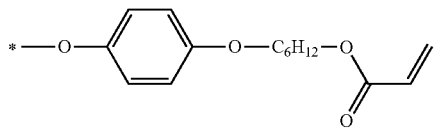
(A34-2)
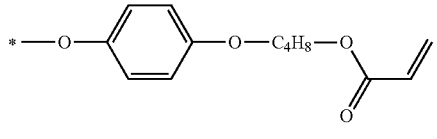
(A34-3)
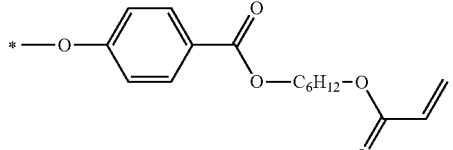
(A34-4)
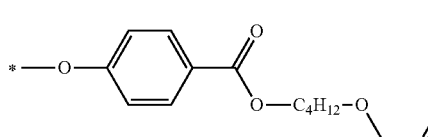
(A34-5)
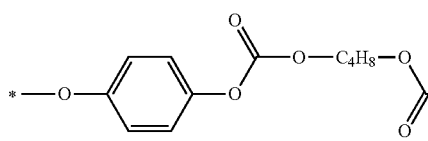
(A34-6)
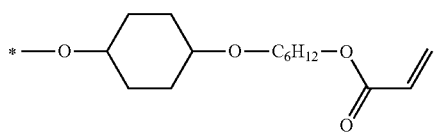
(A34-7)
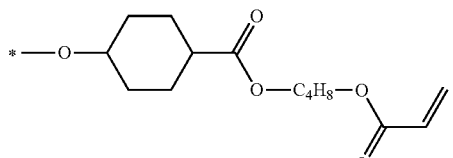
(A34-8)
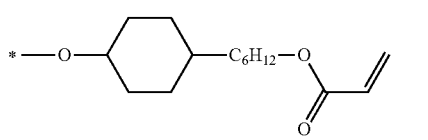
[Chem. 167]
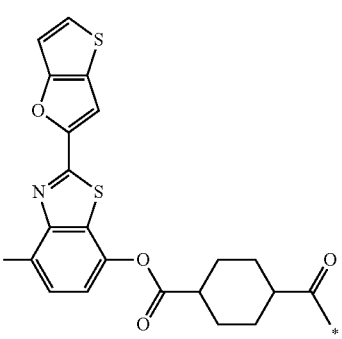

(A35-1)
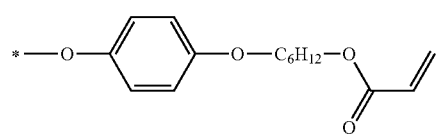
(A35-2)
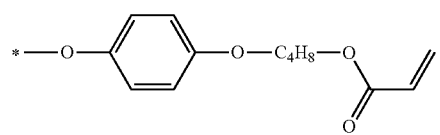
(A35-3)
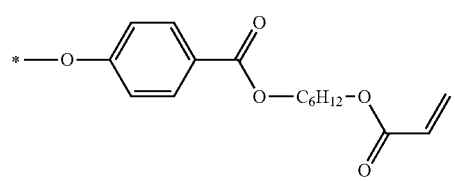
(A35-4)
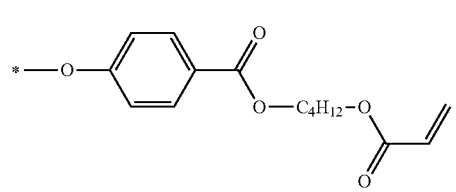
(A35-5)
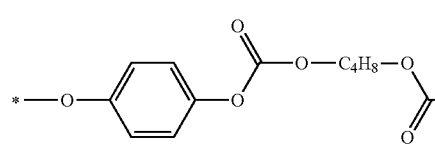
(A35-6)
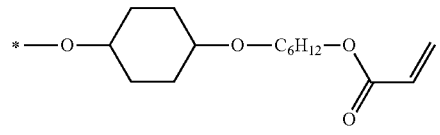
(A35-7)
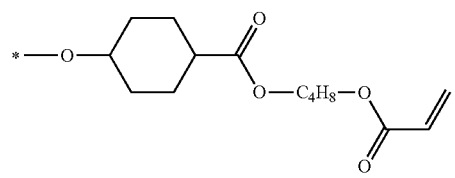
(A35-8)
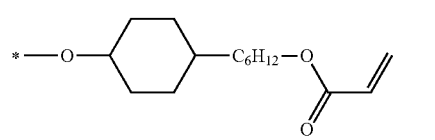
[Chem. 168]
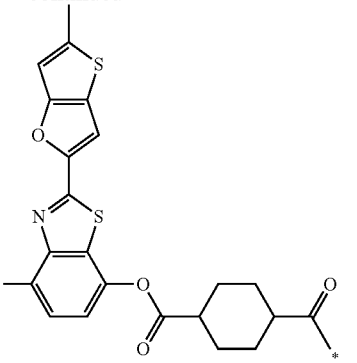
(A36-1)
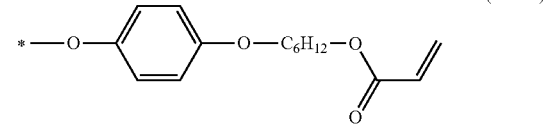
(A36-2)
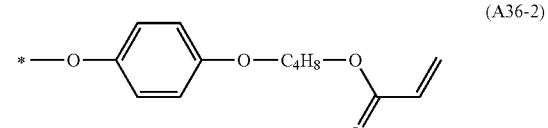
(A36-3)
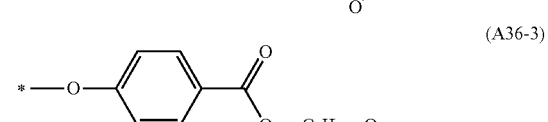
(A36-4)
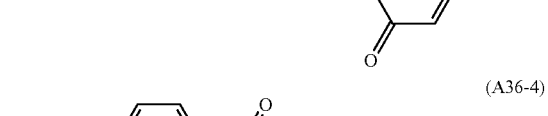
(A36-5)
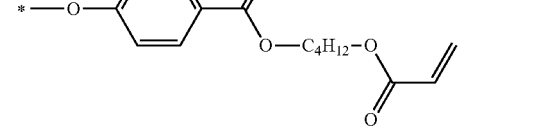
(A36-6)
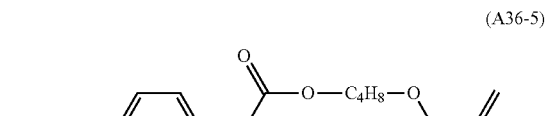
(A36-7)
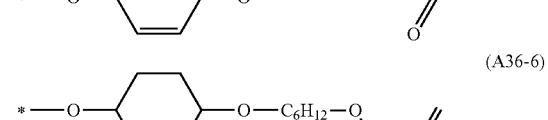
(A36-8)
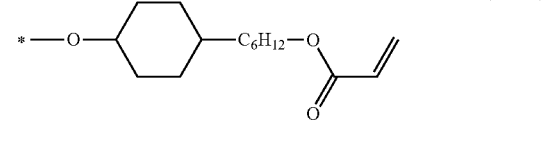

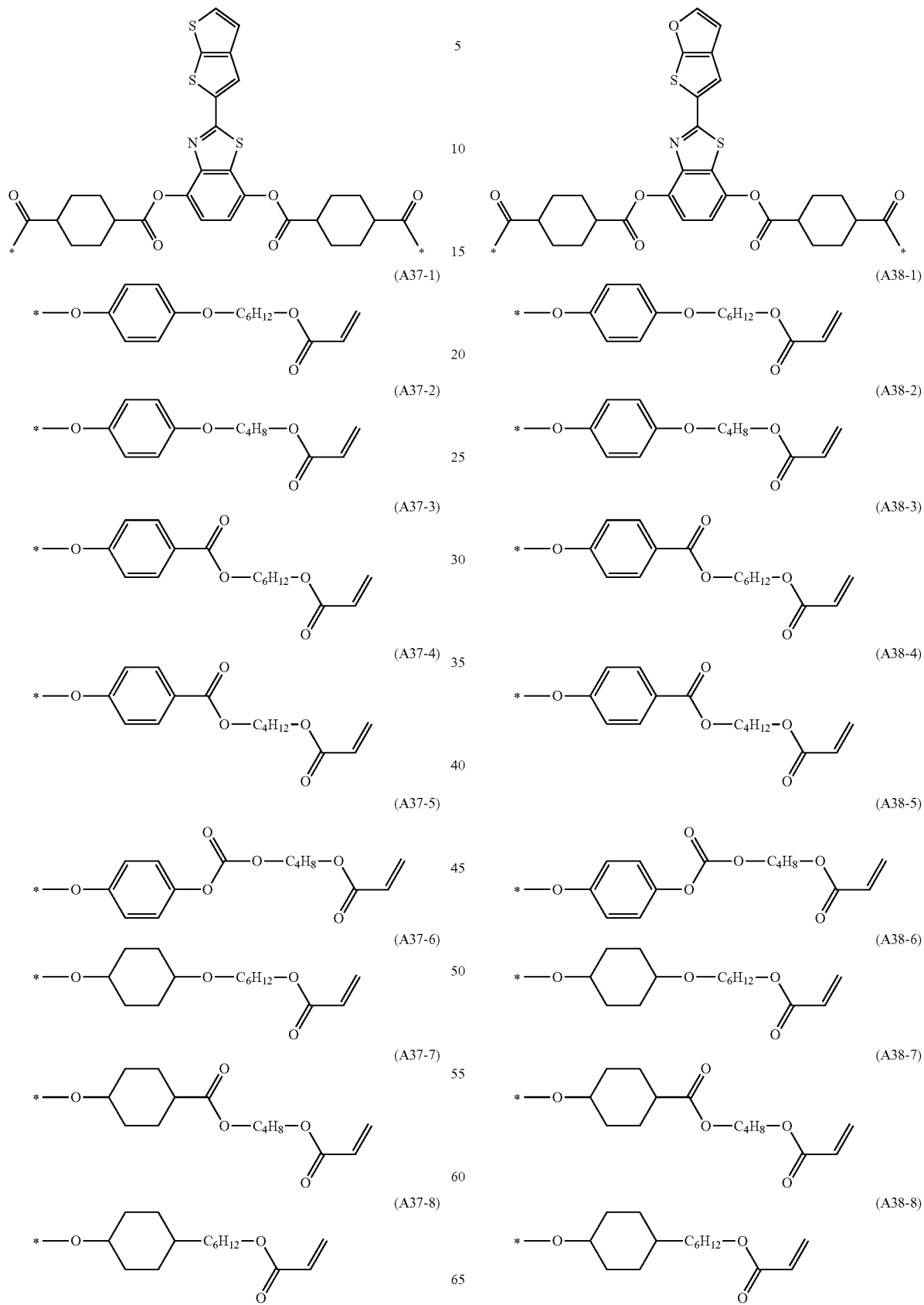

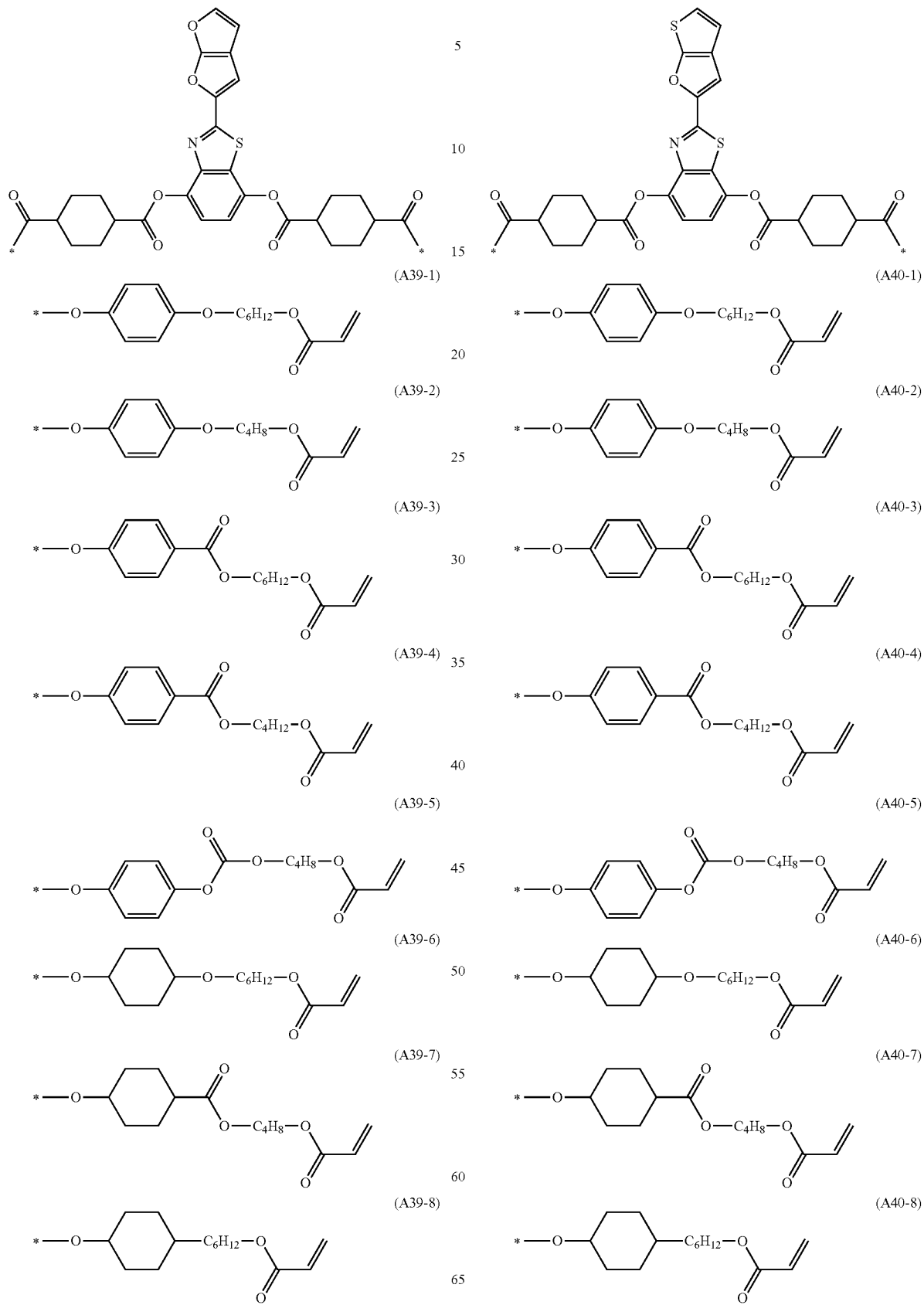

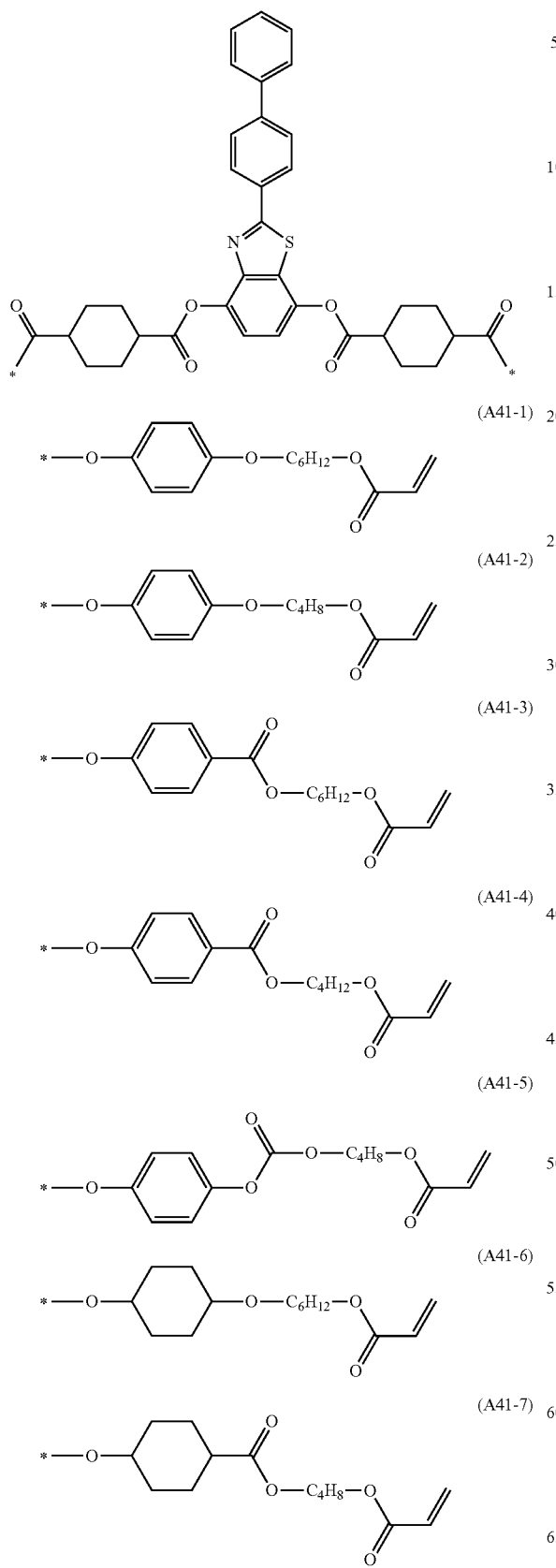
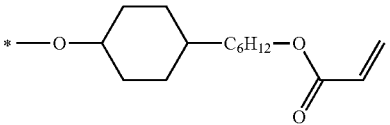
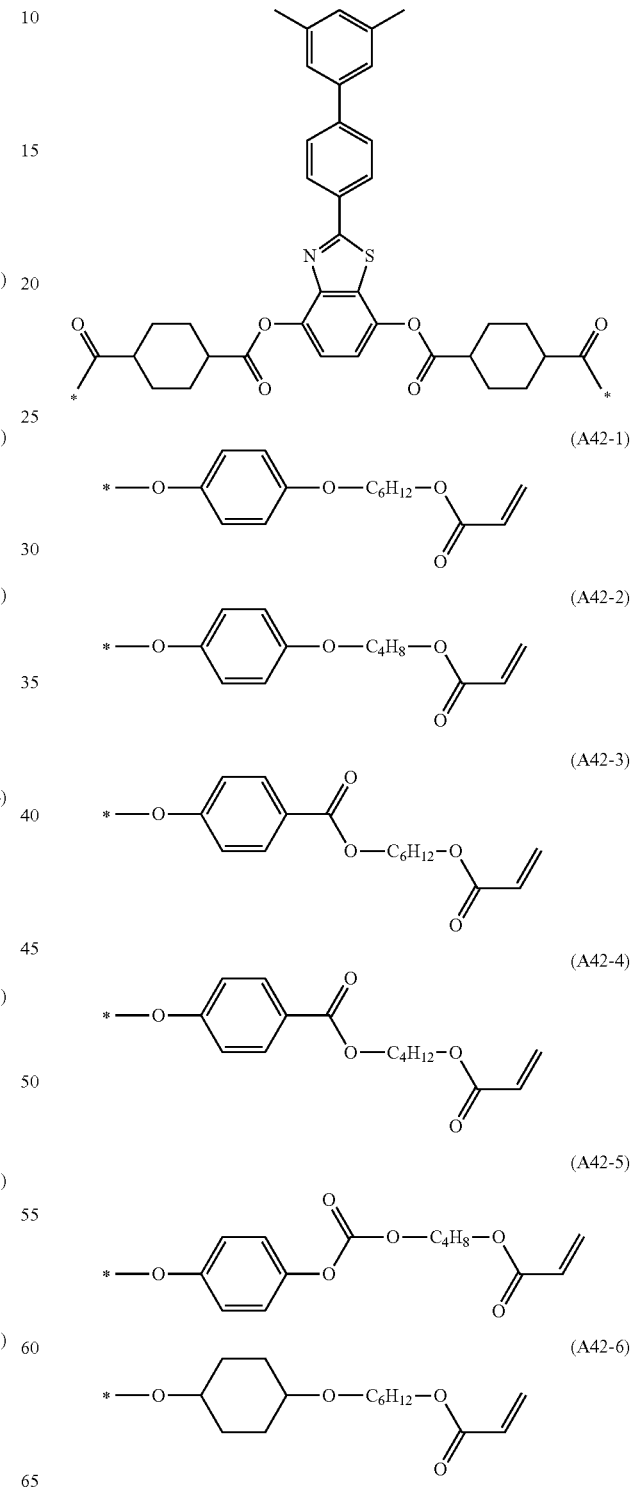

(A42-7)
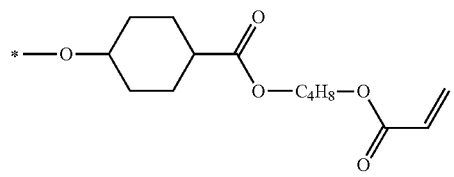
(A42-8)
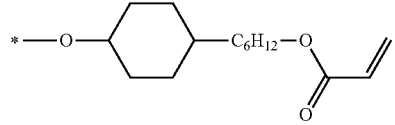
[Chem. 175]
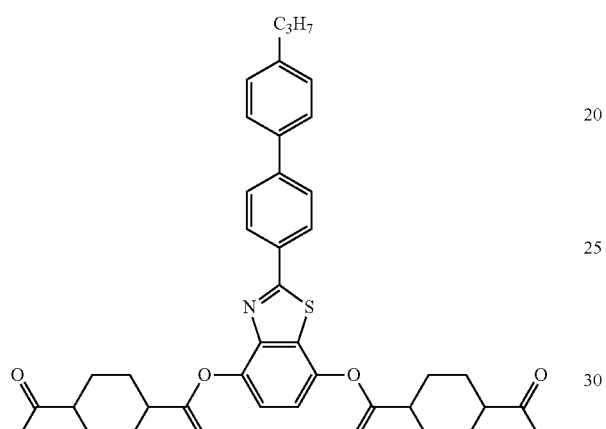
(A43-1)
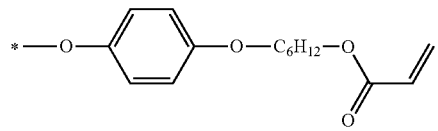
(A43-2)
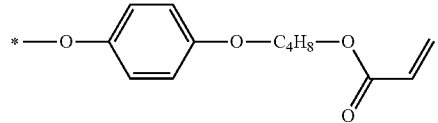
(A43-3)
(A43-4)
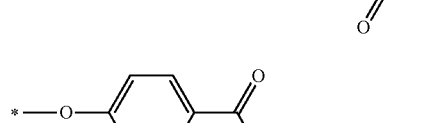
(A43-5)
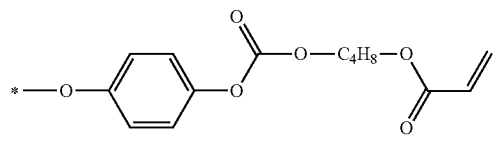
(A43-6)
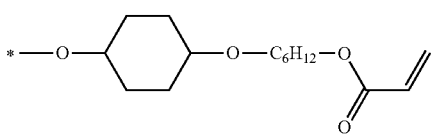
(A43-7)
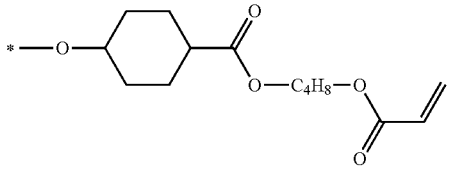
(A43-8)
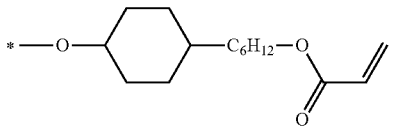
[Chem. 176]
(A44-1)
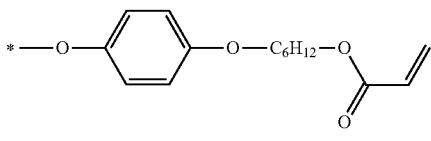
(A44-2)
(A44-3)
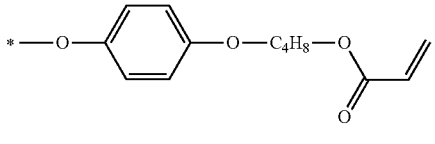
(A44-4)
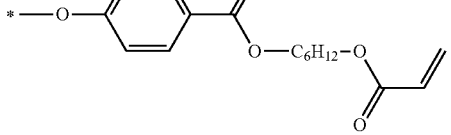

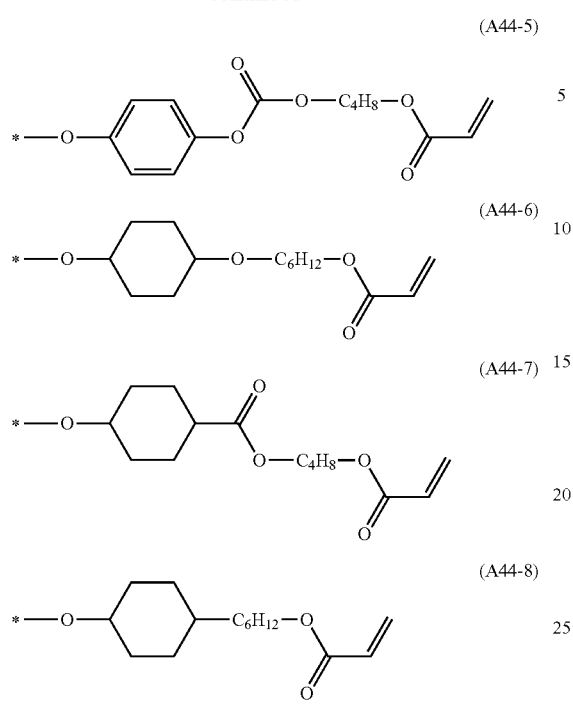
(A44-5)
(A44-6)
(A44-7)
(A44-8)
[Chem. 177]
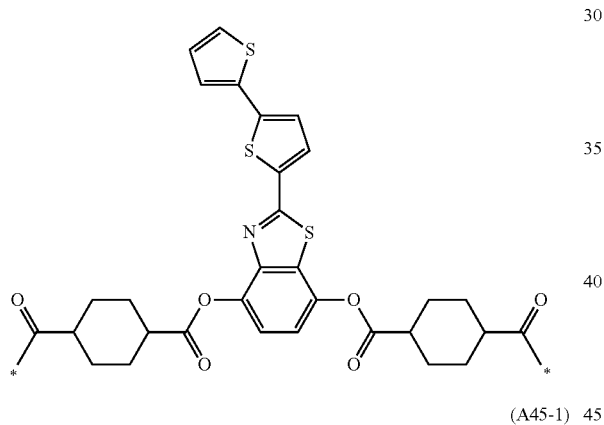
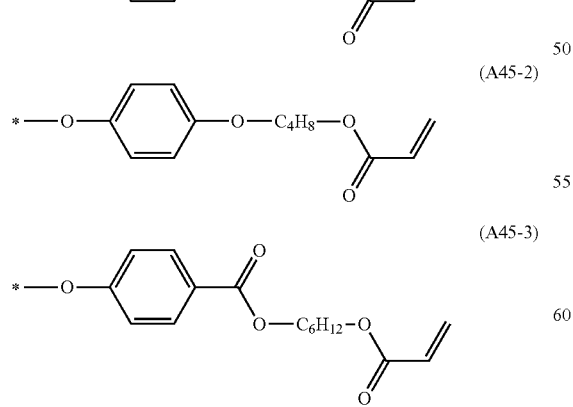
(A45-1)
(A45-2)
(A45-3)
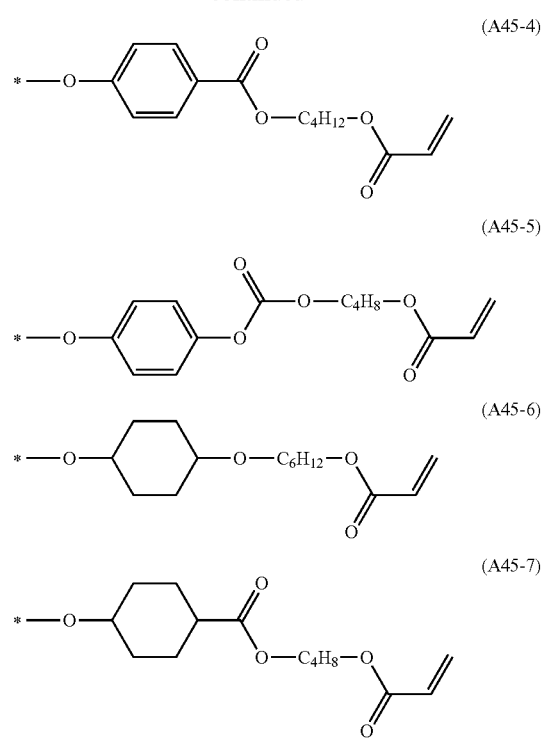
(A45-4)
(A45-5)
(A45-6)
(A45-7)
(A45-8)
[Chem. 178]
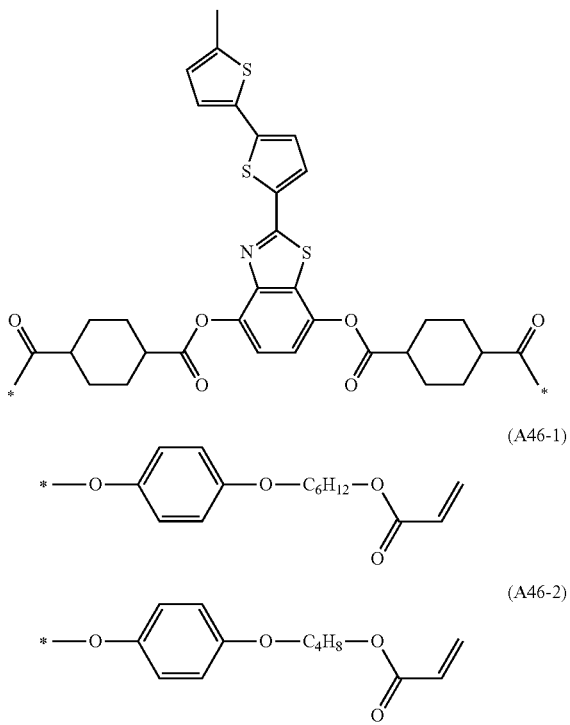
(A46-1)
(A46-2)

(A46-3)
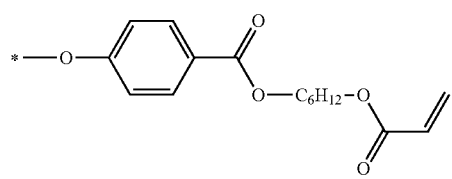
(A46-4)
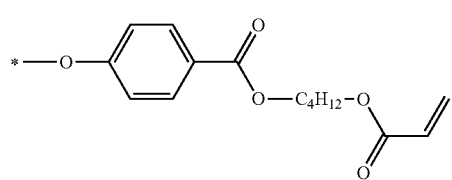
(A46-5)
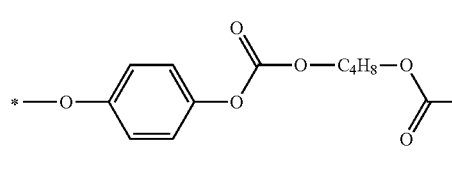
(A46-6)
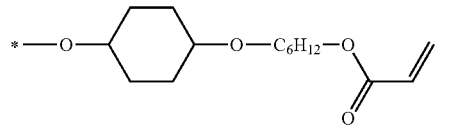
(A46-7)
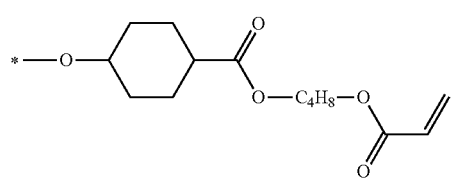
(A46-8)
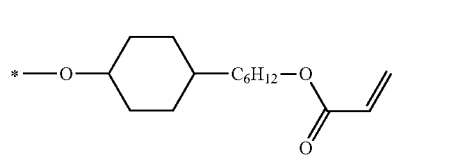
[Chem. 179]
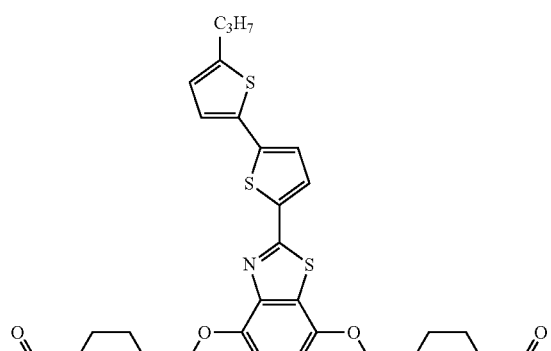
(A47-1)
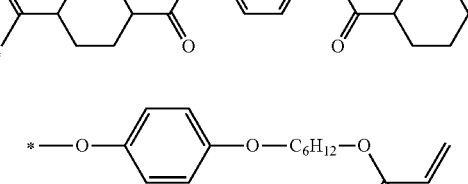
(A47-2)
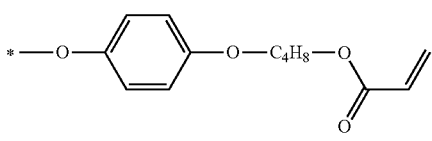
(A47-3)
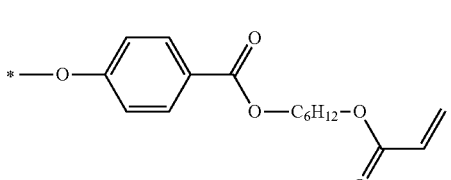
(A47-4)
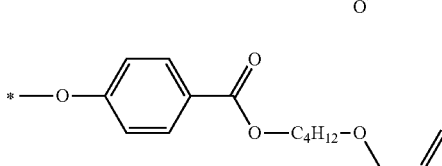
(A47-5)
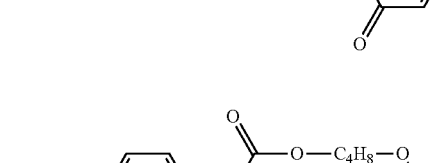
(A47-6)
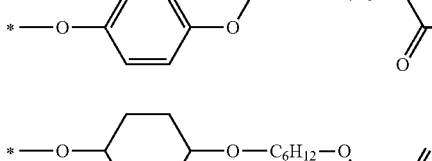
(A47-7)
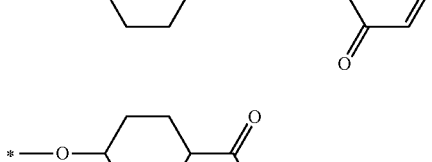
(A47-8)
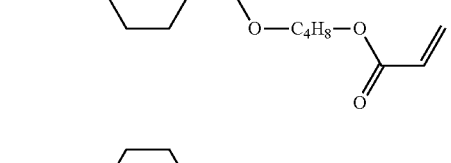
[Chem. 180]
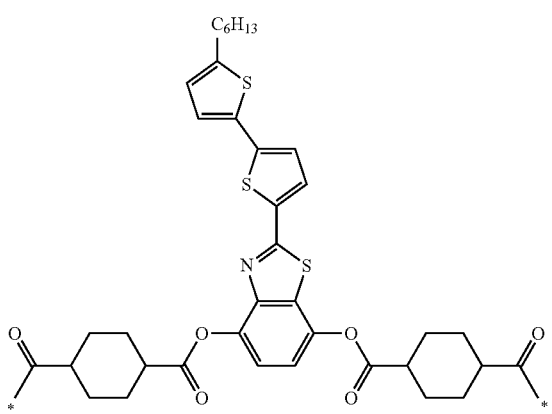

(A48-1)
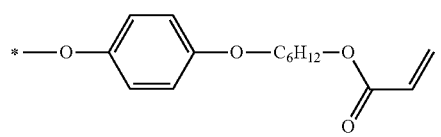
(A48-2)
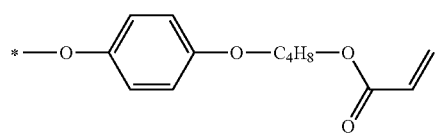
(A48-3)
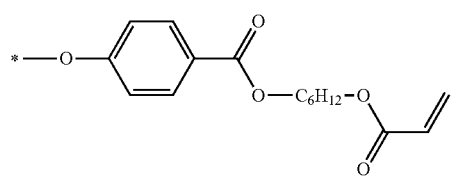
(A48-4)
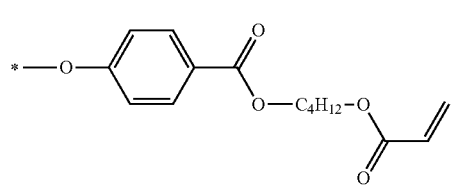
(A48-5)
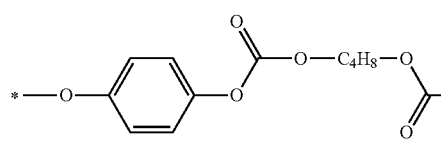
(A48-6)
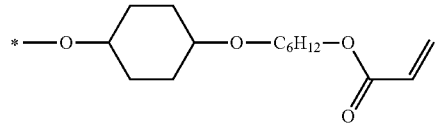
(A48-7)
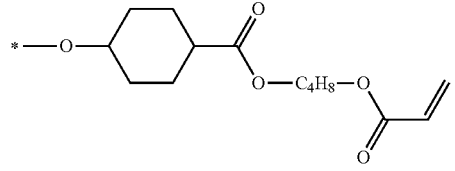
(A48-8)
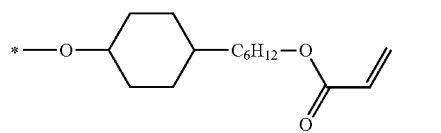
[Chem. 181]
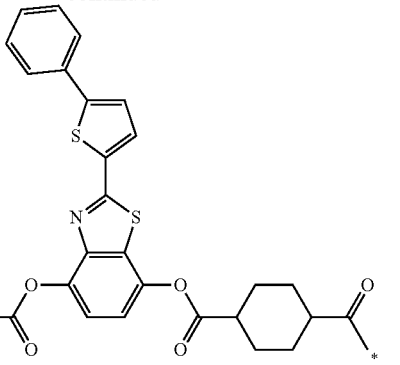
(A49-1)
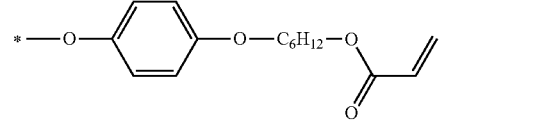
(A49-2)
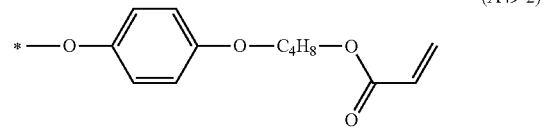
(A49-3)
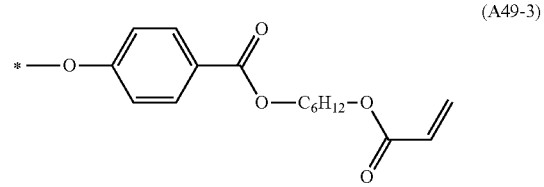
(A49-4)
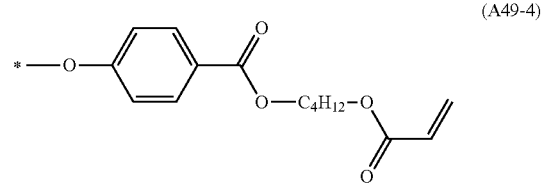
(A49-5)
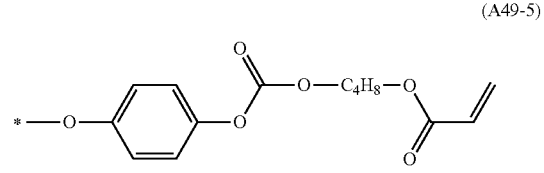
(A49-6)
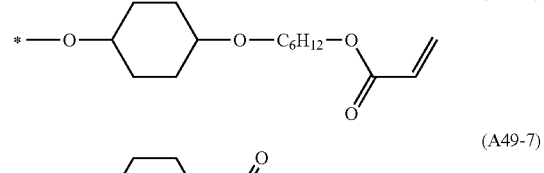
(A49-7)
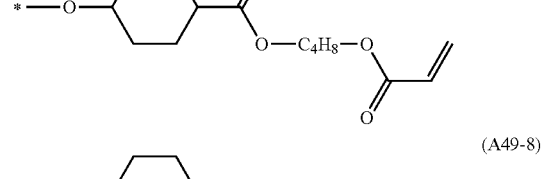
(A49-8)
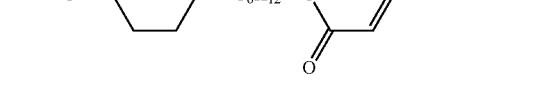

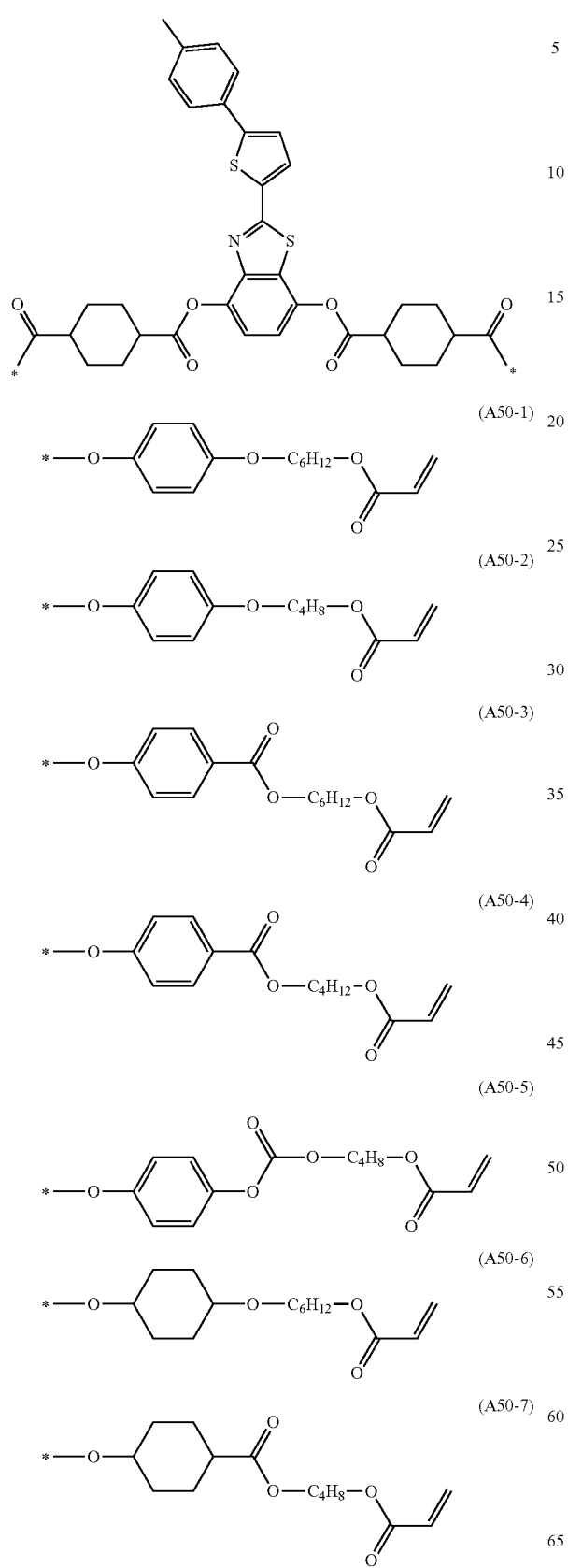

-continued
(A51-7)
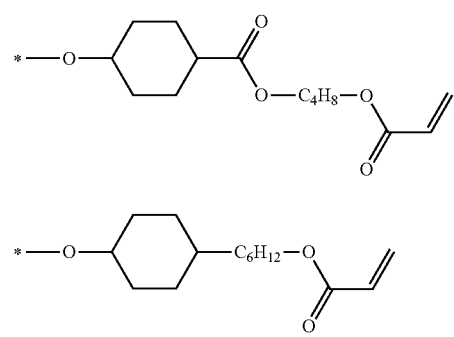
(A51-8)
[Chem. 184]
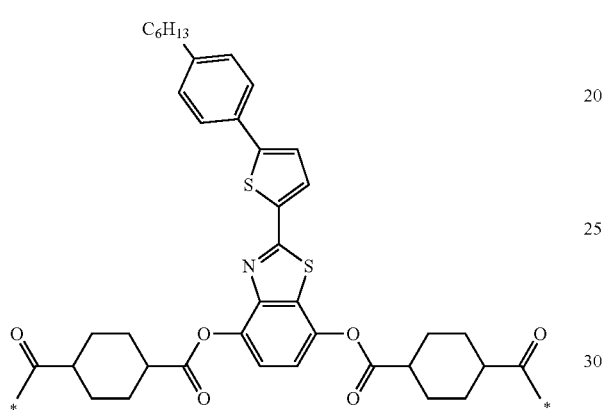
(A52-1)
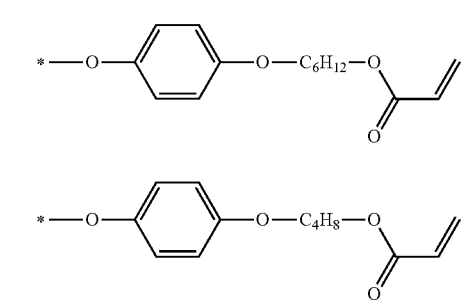
(A52-2)
(A52-3)
(A52-4)
(A52-5)
(A52-6)
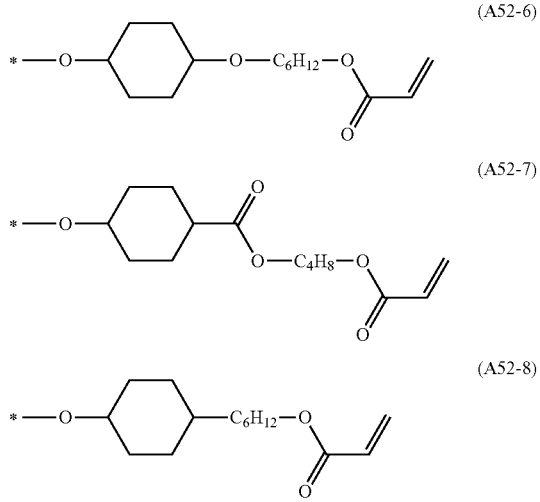
(A52-7)
(A52-8)
[Chem. 185]
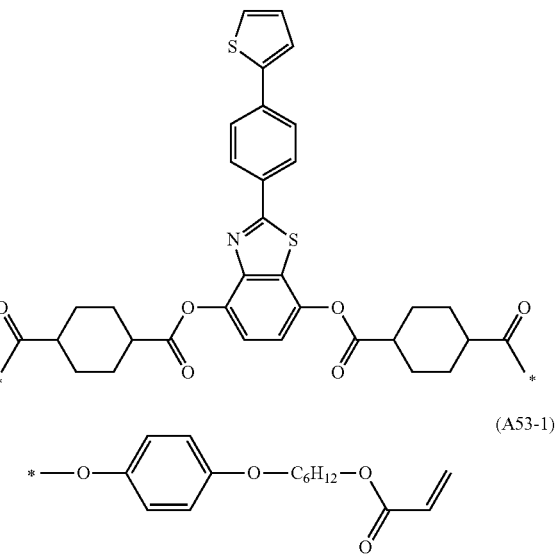
(A53-1)
(A53-2)
(A53-3)
(A53-4)

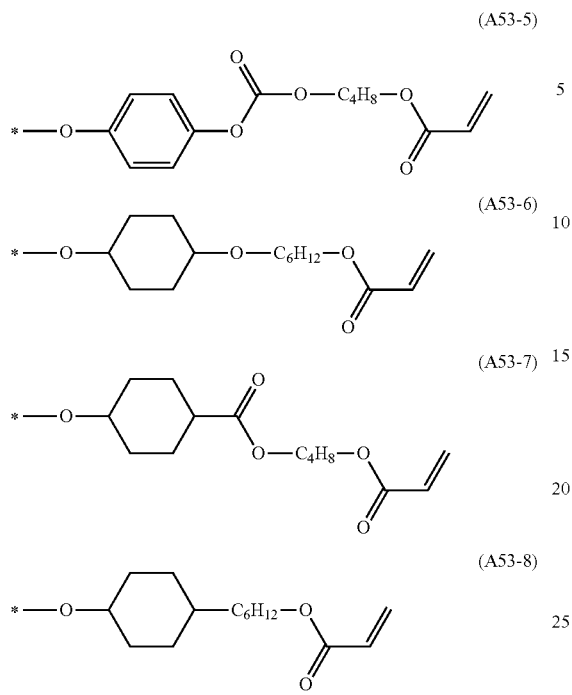
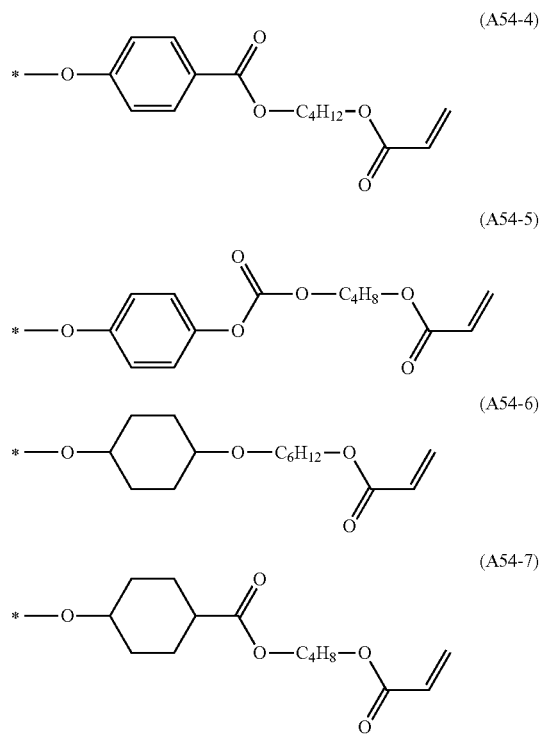
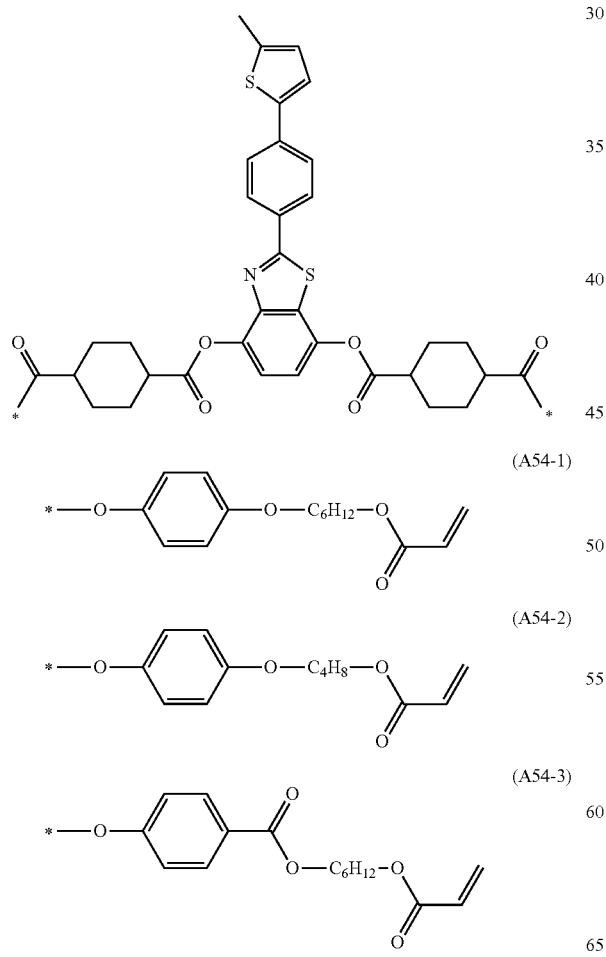
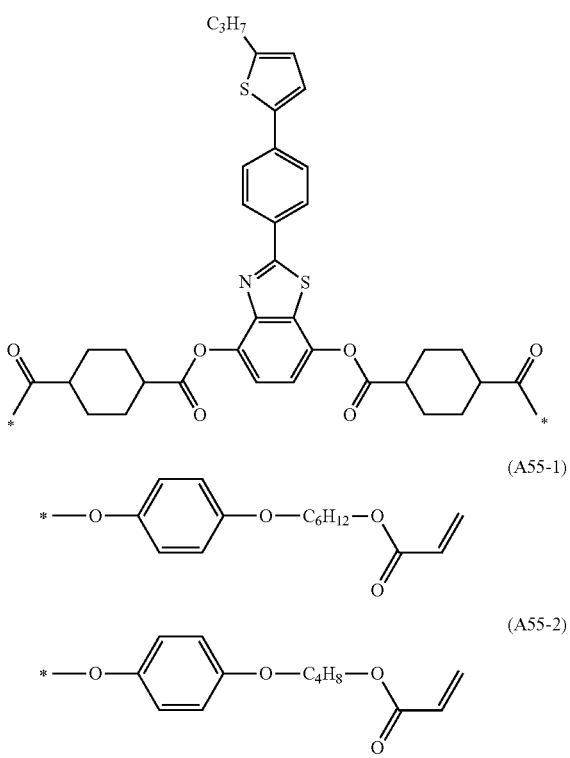

(A55-3)
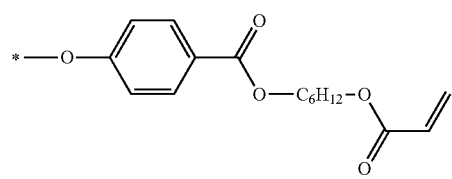
(A55-4)
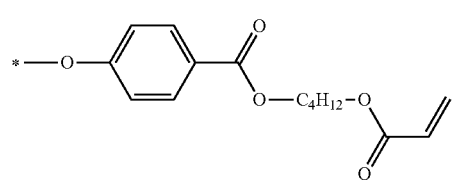
(A55-5)
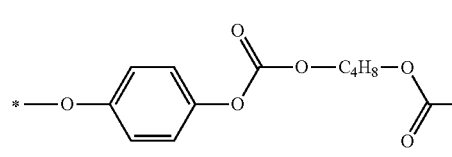
(A55-6)
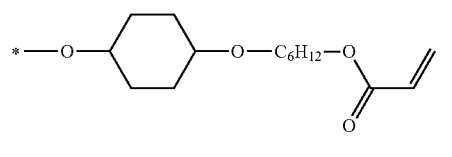
(A55-7)
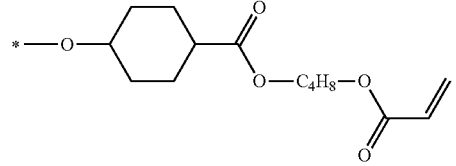
(A55-8)
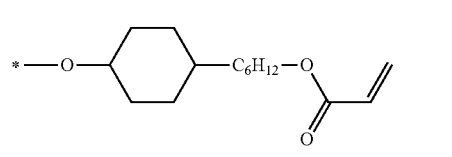
[Chem. 188]
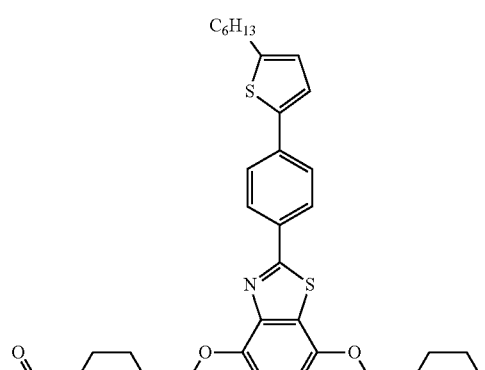
(A56-1)
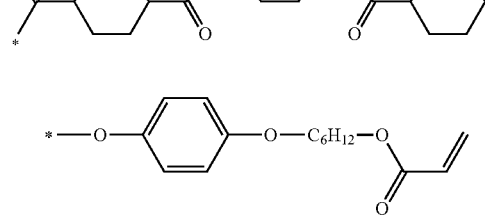
(A56-2)
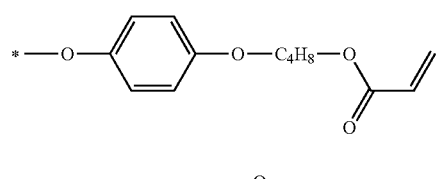
(A56-3)
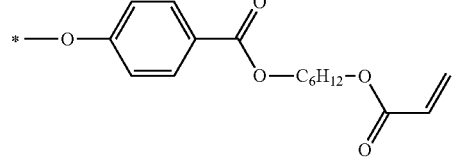
(A56-4)
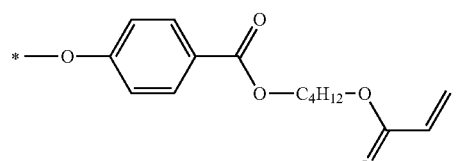
(A56-5)
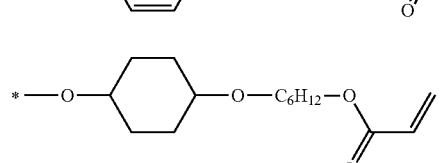
(A56-6)
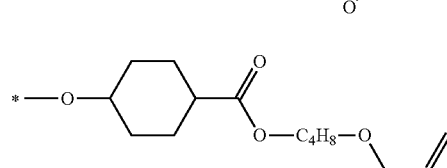
(A56-7)
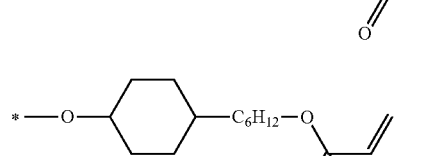
(A56-8)
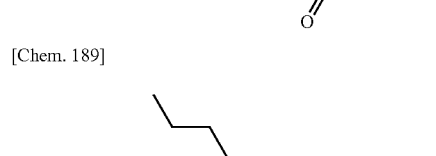
[Chem. 189]
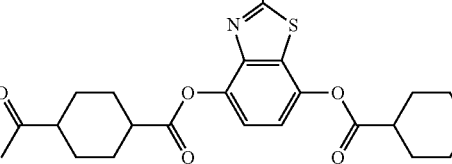

(A57-1)
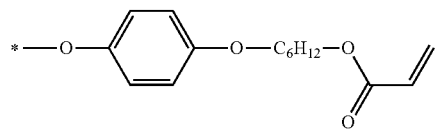
(A57-2)
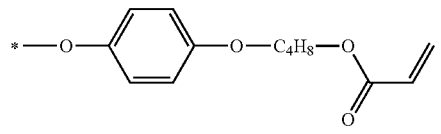
(A57-3)
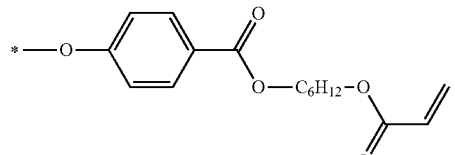
(A57-4)
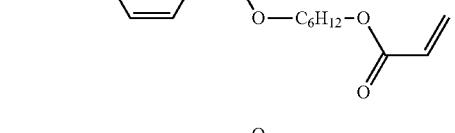
(A57-5)
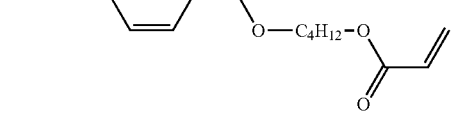
(A57-6)
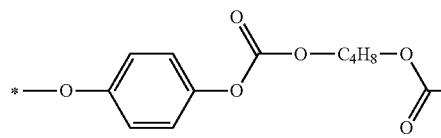
(A57-7)
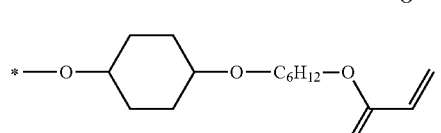
(A57-8)
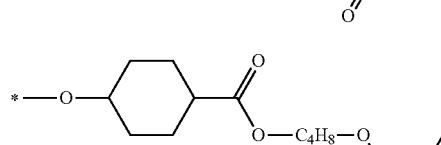
[Chem. 190]
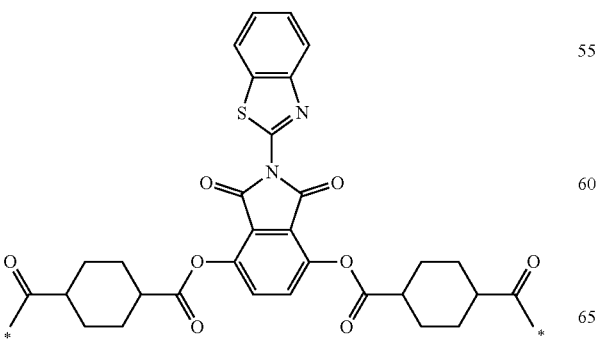
(A58-1)
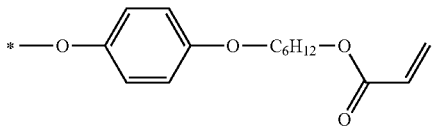
(A58-2)
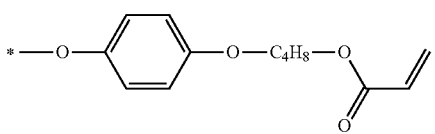
(A58-3)
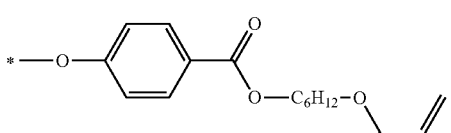
(A58-4)
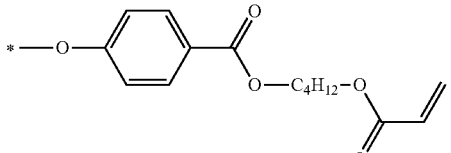
(A58-5)
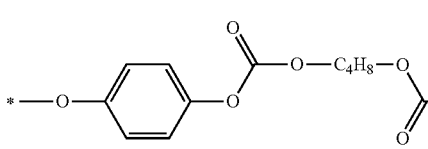
(A58-6)
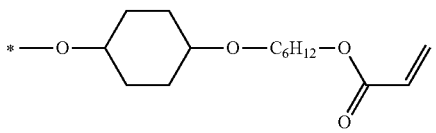
(A58-7)
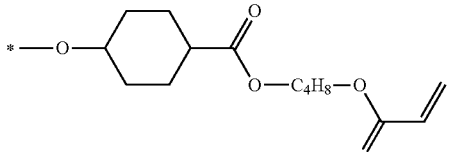
(A58-8)
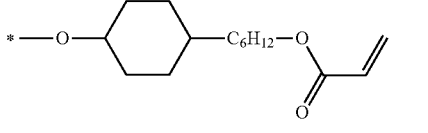
[Chem. 191]

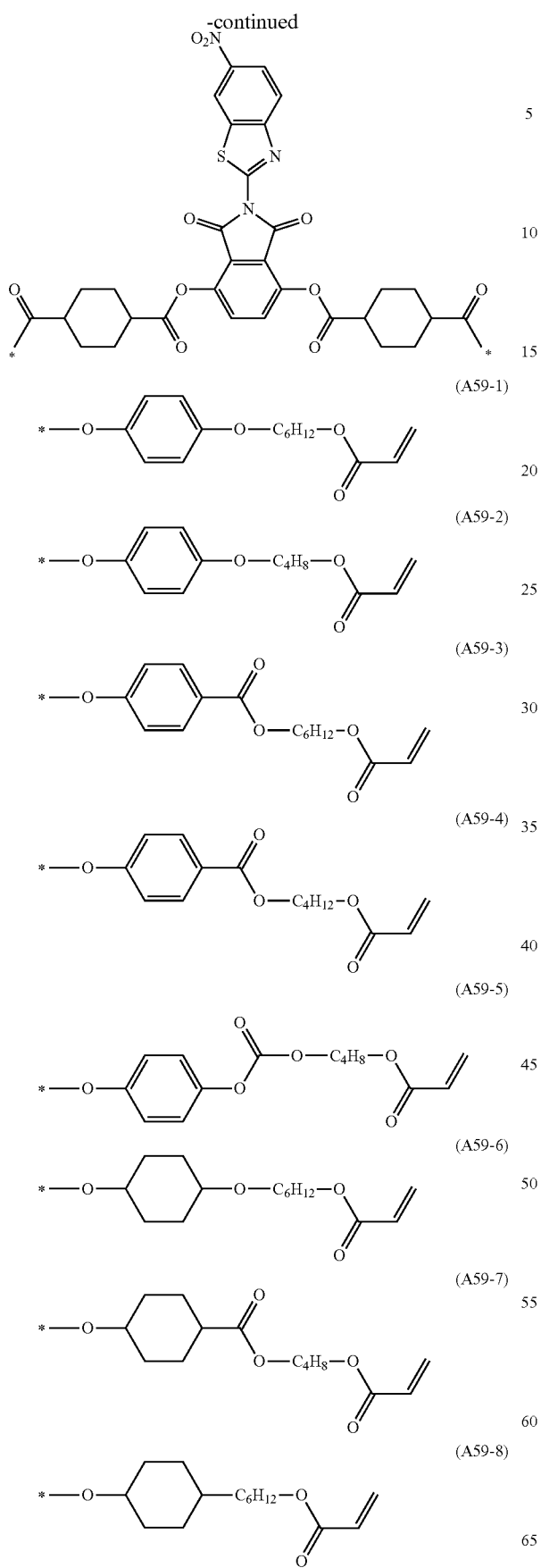
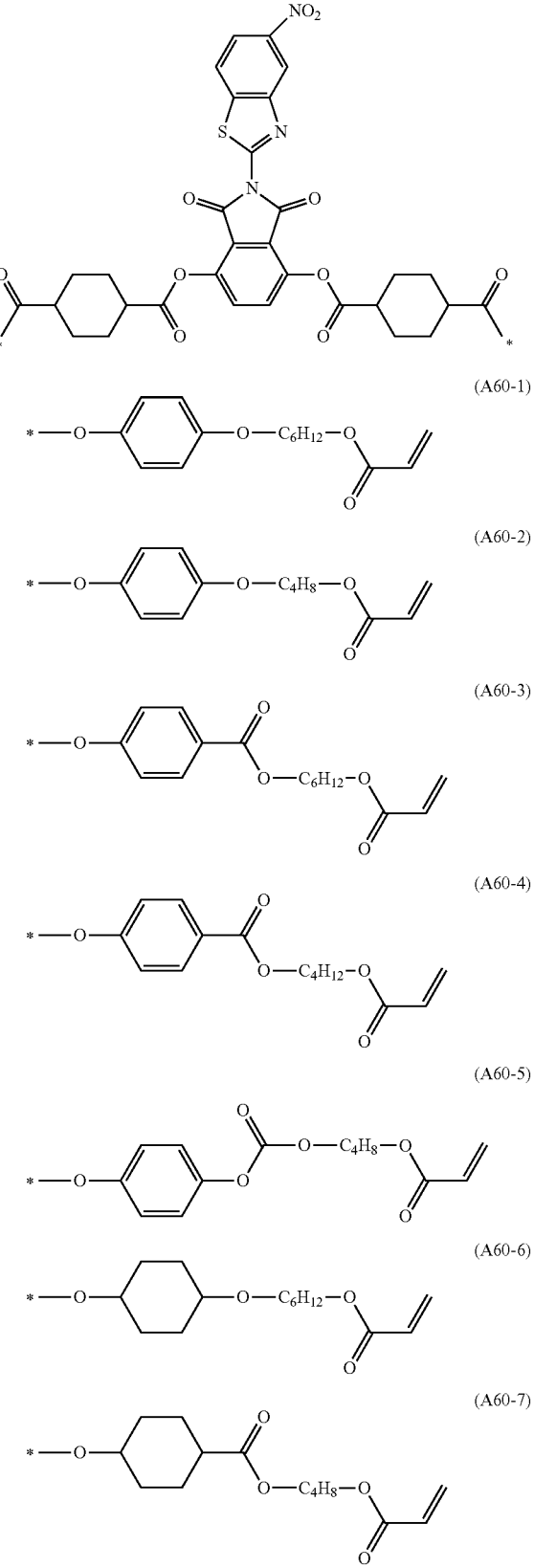

(A60-8) 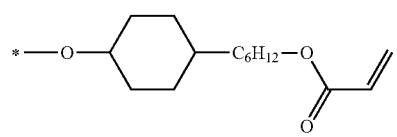
[Chem. 193]
(A61-1) 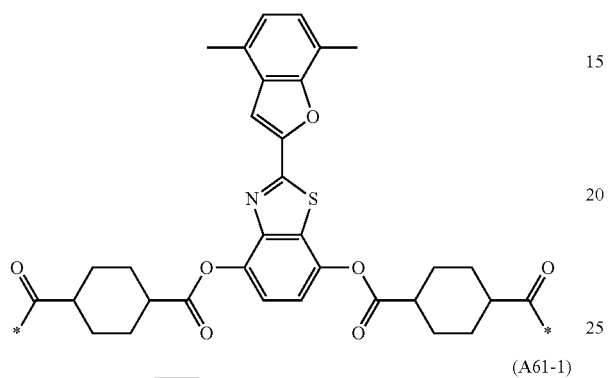
(A61-2) 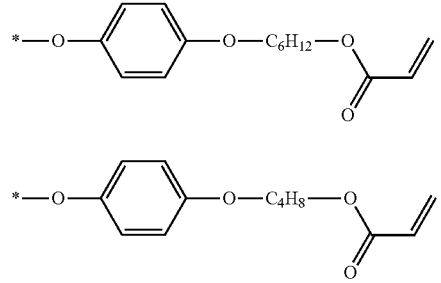
(A61-3)
(A61-4)
(A61-5)
(A61-6) 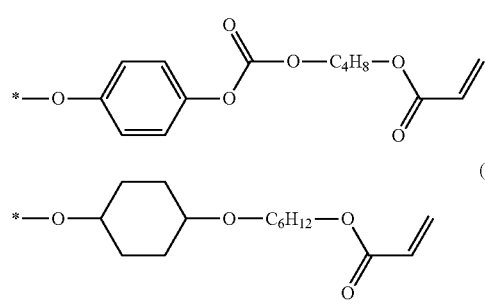
(A61-7) 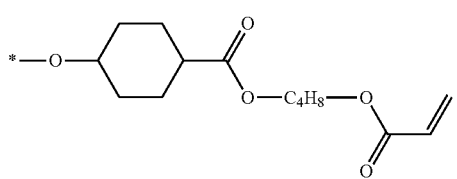
(A61-8) 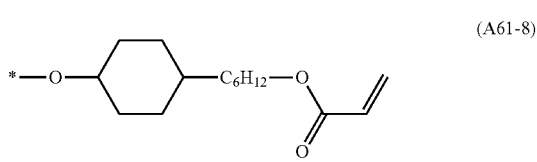
[Chem. 194]
(A62-1) 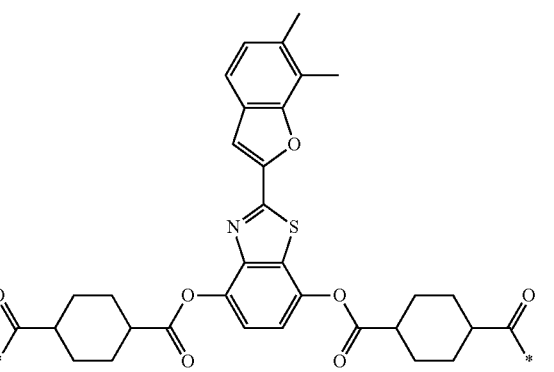
(A62-2)
(A62-3)
(A62-4)
(A62-5) 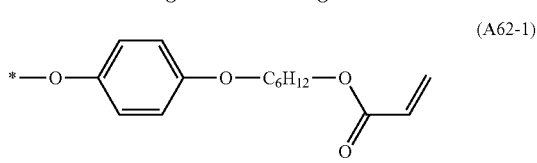

-continued
(A62-6)
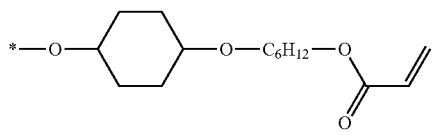
(A62-7)
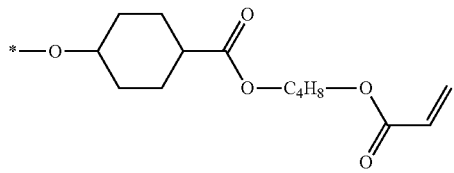
(A62-8)
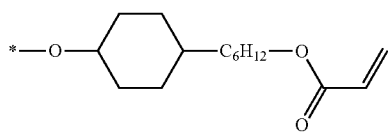
[Chem. 195]
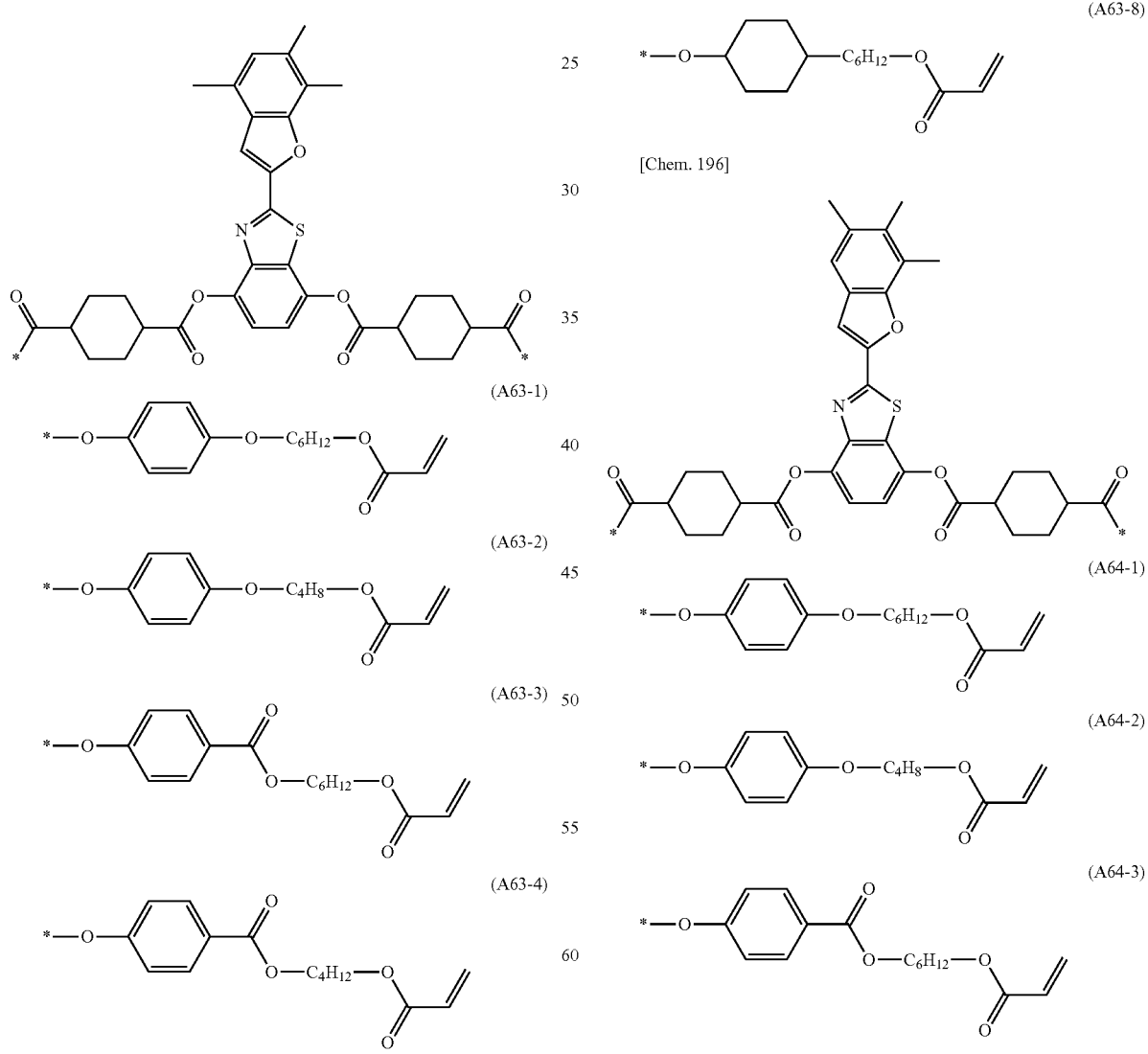
(A63-1)
(A63-2)
(A63-3)
(A63-4)
-continued
(A63-5)
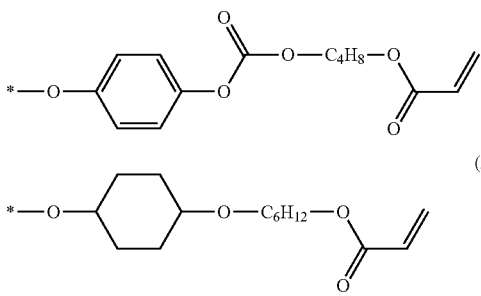
(A63-6)
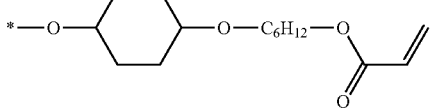
(A63-7)
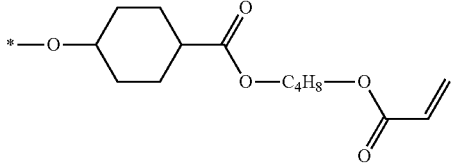
(A63-8)
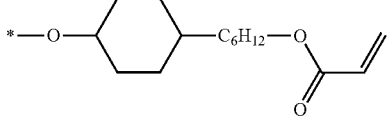
[Chem. 196]
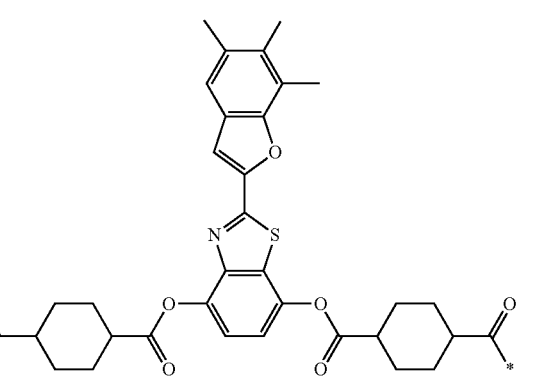
(A64-1)
(A64-2)
(A64-3)

(A64-4)
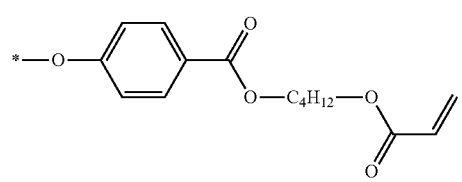
(A64-5)
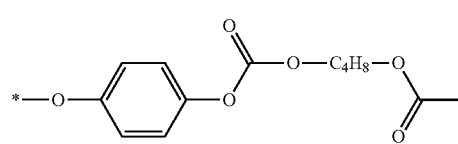
(A64-6)
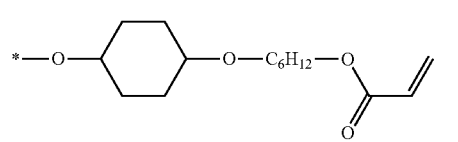
(A64-7)
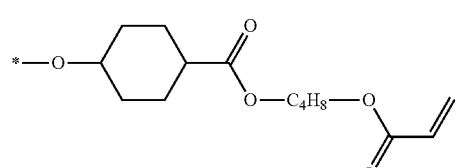
(A64-8)
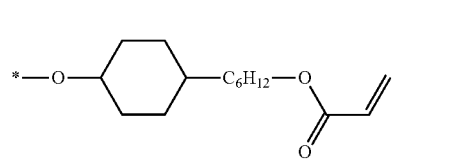
[Chem. 197]
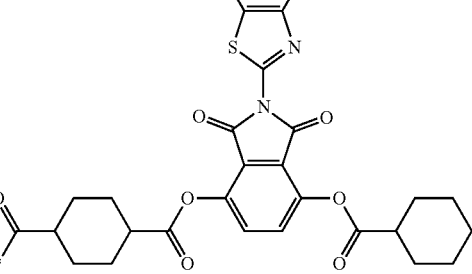
(A66-1)
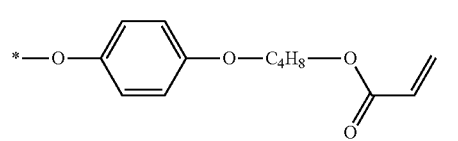
(A66-2)
(A66-3)
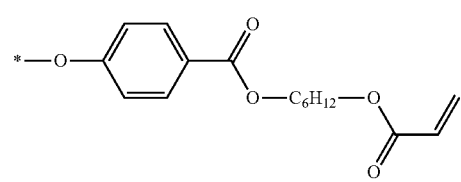
(A66-4)
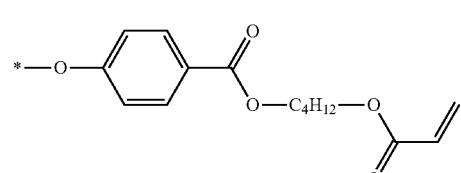
(A66-5)
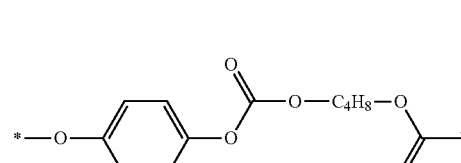
(A66-6)
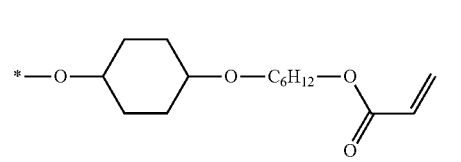
(A66-7)
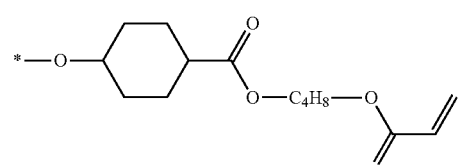
(A66-8)
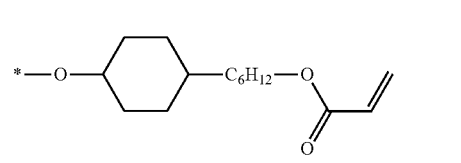
[Chem. 198]
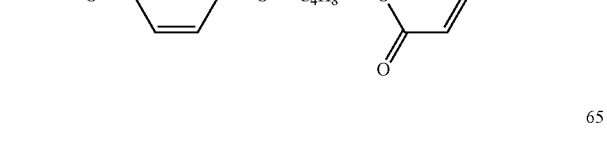
(A67-1)

(A67-2) 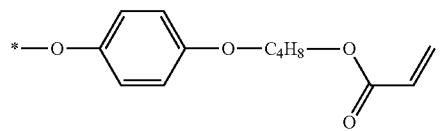
(A67-3) 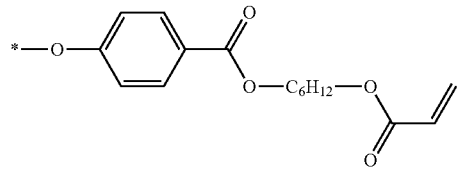
(A67-4) 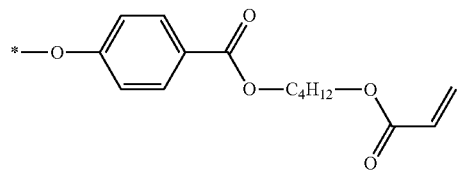
(A67-5) 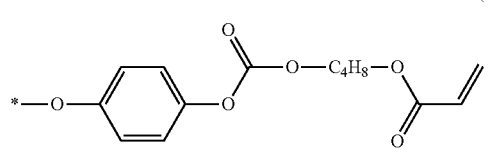
(A67-6) 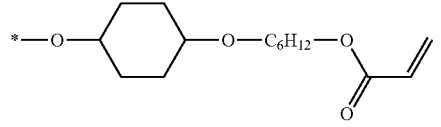
(A67-7) 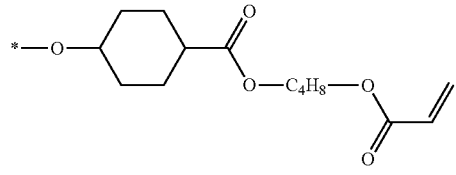
(A67-8) 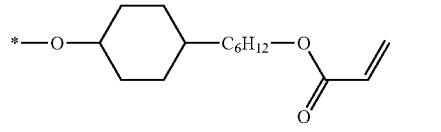
[Chem. 199]
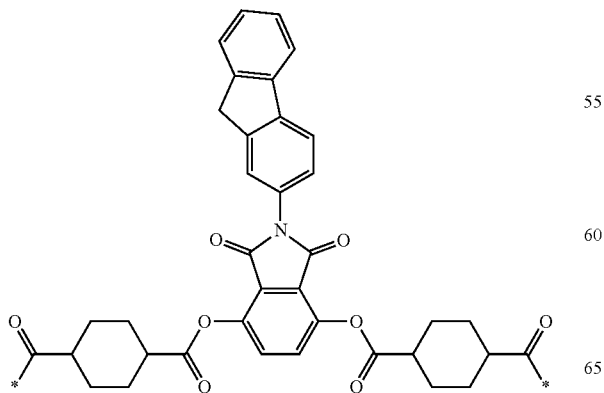
(A68-1) 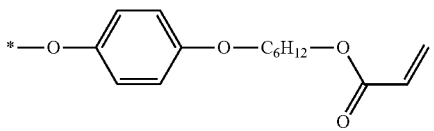
(A68-2) 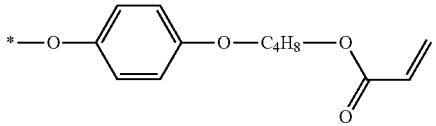
(A68-3) 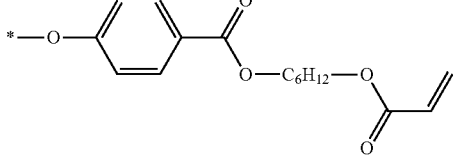
(A68-4) 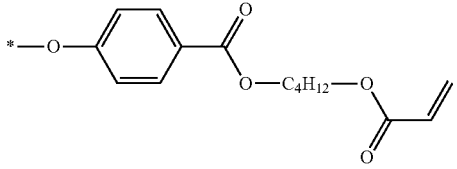
(A68-5) 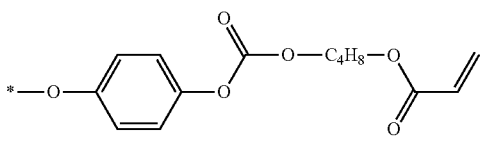
(A68-6) 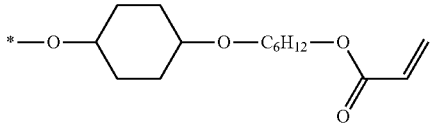
(A68-7) 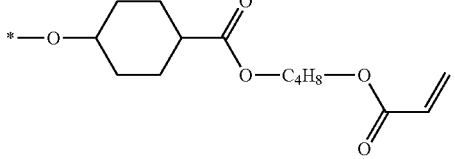
(A68-8) 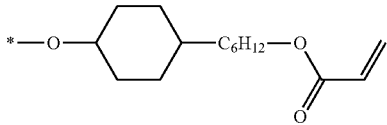
[Chem. 200]

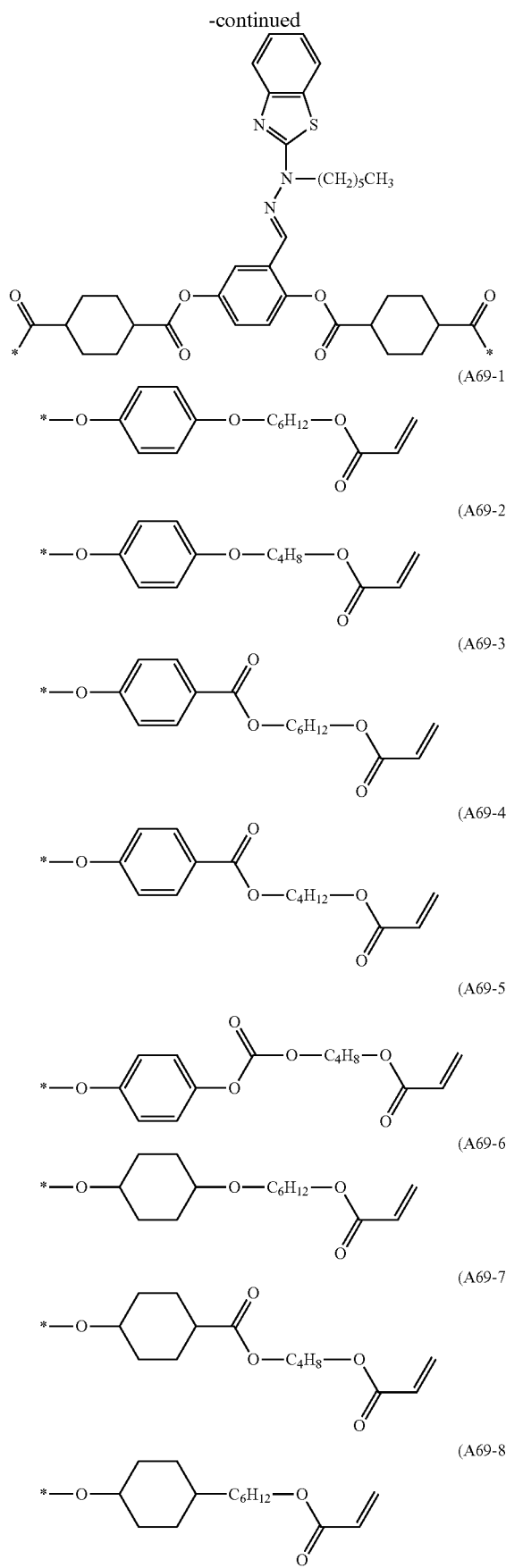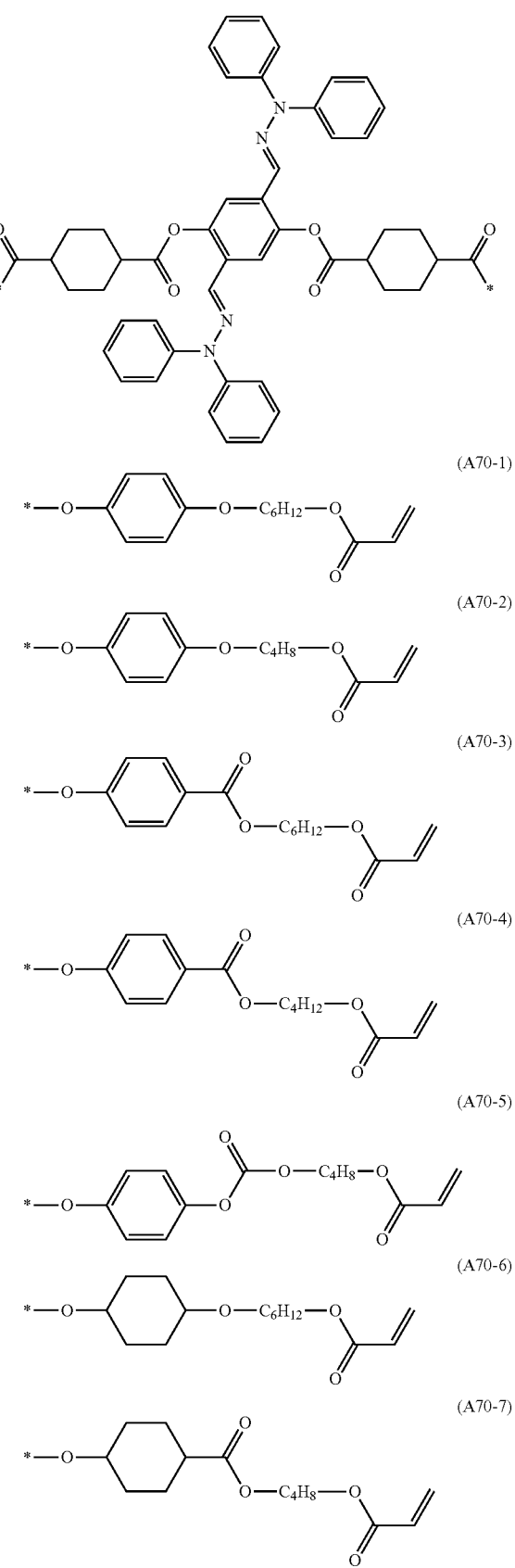

(A70-8)
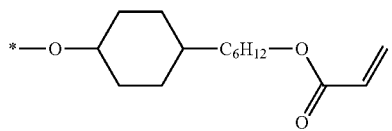

[Chem. 202]
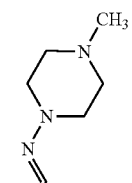
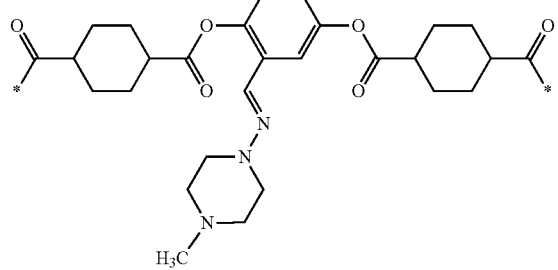

(A71-1)
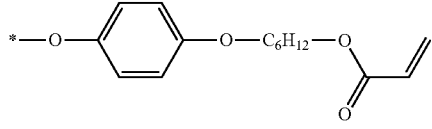

(A71-2)
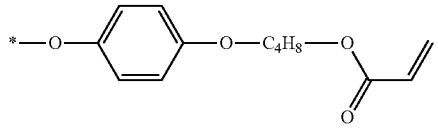

(A71-3)
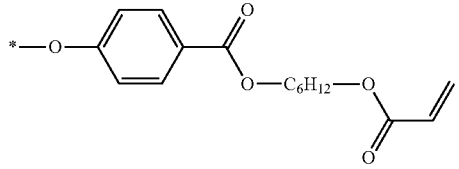

(A71-4)
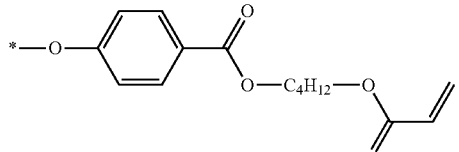

(A71-5)
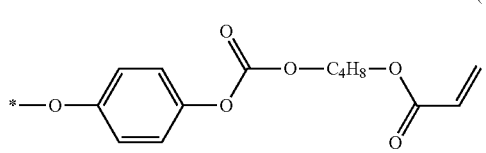

(A71-6)
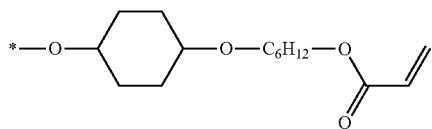

(A71-7)
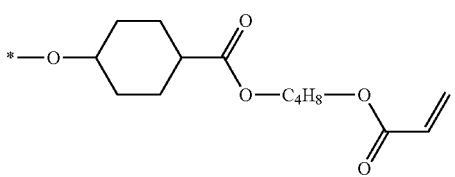

(A71-8)
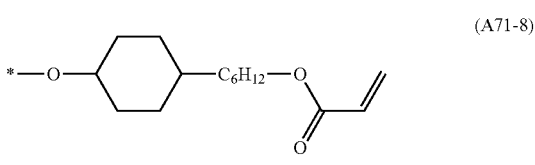

The optical film obtained by orienting the liquid crystal compound (2) preferably exhibits a positive wavelength dispersion characteristic. When it exhibits, the wavelength dispersion of the optical film containing the polymer of the liquid crystal composition can be controlled by changing the ratio of liquid crystal compound (2) to liquid crystal compound (1) in the liquid crystal composition, which is preferable.

Examples of the liquid crystal compound (2) include the following compounds.

[Chem. 203]
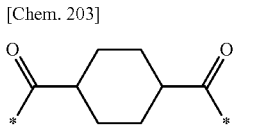

(B1-1)
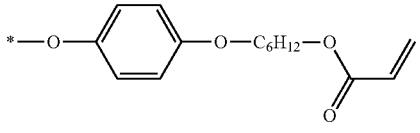

(B1-2)
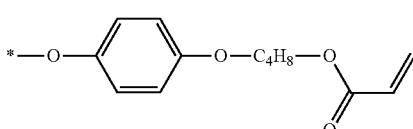

(B1-3)
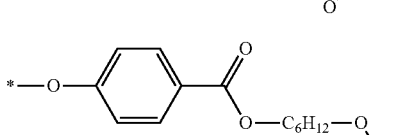

(B1-4)
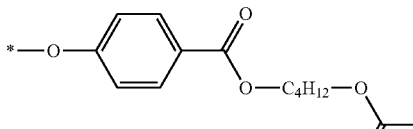

(B1-5)
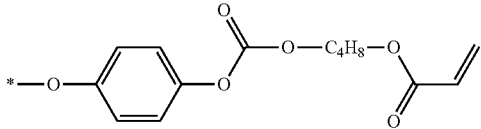

-continued

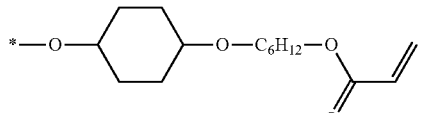
(B1-6)

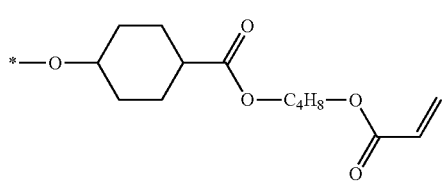
(B1-7)

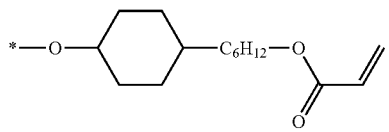
(B1-8)

When the optical film obtained by orienting liquid crystal compound (1) exhibits a reverse wavelength dispersion characteristic and the optical film obtained by orienting liquid crystal compound (2) exhibits a positive wavelength dispersion characteristic, it is possible to arbitrarily control the optical characteristics of the optical film produced using the liquid crystal composition of the present invention, that is, the optical film containing a polymer of the liquid crystal composition of the present invention, by adjusting the contents of liquid crystal compounds (1) and (2) in the liquid crystal composition.

The content of the liquid crystal compound (2) in the liquid crystal composition of the present invention is in the range of preferably 0.1 to 70 parts by mass, more preferably 1 to 50 parts by mass, and even more preferably 5 to 30 parts by mass, relative to 100 parts by mass of the liquid crystal compound (1). Further, the content of the liquid crystal compound (2) can be 8 parts by mass or more, further 12 parts by mass or more, and furthermore 17 parts by mass or more. The content of the liquid crystal compound (2) in the liquid crystal composition of the present invention is in the range of preferably 0.1 to 70% by mass, more preferably 1 to 50% by mass, and even more preferably 5 to 30% by mass, relative to 100 parts by mass of the liquid crystal compound (1) at ratio of mass.

When the content of the liquid crystal compound (2) in the liquid crystal composition is not less than the lower limit, it is easy to adjust the wavelength dispersion characteristic of the optical film, which is preferable. When the content thereof is not more than the upper limit, it is possible to exhibit the wavelength dispersion characteristic of the optical film, which is preferable.

The optical film obtained by orienting the liquid crystal composition of the present invention has a degree of wavelength dispersion Re(450 nm)/Re(550 nm) of preferably 0.65 or more and less than 1, more preferably 0.75 or more and 0.95 or less, and even more preferably 0.80 or more and 0.90 or less. When the degree of wavelength dispersion Re(450 nm)/Re(550 nm) is not less than the lower limit, conversion of circularly polarized light is possible in a short wavelength region around 450 nm. When the degree is not more than the upper limit, the resulting optical film exhibits a reverse wavelength dispersion characteristic, which is preferable.

The liquid crystal composition of the present invention containing the liquid crystal compounds (1) and (2) can be produced by a method including, for example, the following steps:

step (a) of allowing an alcohol compound (3) represented by formula (3):

[Chem. 204]

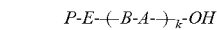
(3)

and a dicarboxylic acid compound (4) represented by formula (4):

[Chem. 205]

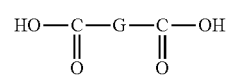
(4)

to react each other to thereby obtain a mixture containing a carboxylic acid compound (5) represented by formula (5):

[Chem. 206]

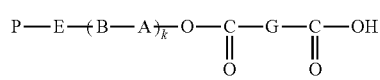
(5)

and the liquid crystal compound (2); and step (b) of allowing the mixture containing the carboxylic acid compound (5) and the liquid crystal compound (2) to react with an alcohol compound (6) represented by formula (6):

[Chem. 207]

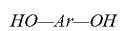
(6)

to thereby obtain a liquid crystal composition containing liquid crystal compounds (1) and (2). Here, the carboxylic acid compound (5) is a precursor of the liquid crystal compound (1). A, B, P, E, G and Ar in formulae (3) to (6) are the same as those defined above.

Specific examples of the alcohol compound (3) include compounds represented by the following formulae (3-1-1) to (3-36-e).

[Chem. 208]

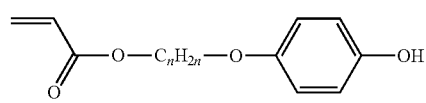
(3-1)

(3-1-a) n = 4
(3-1-b) n = 6
(3-1-c) n = 8
(3-1-d) n = 11
(3-1-e) n = 12

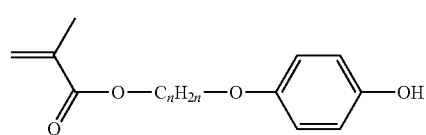
(3-2)

(3-2-a) n = 4
(3-2-b) n = 6
(3-2-c) n = 8
(3-2-d) n = 11
(3-2-e) n = 12

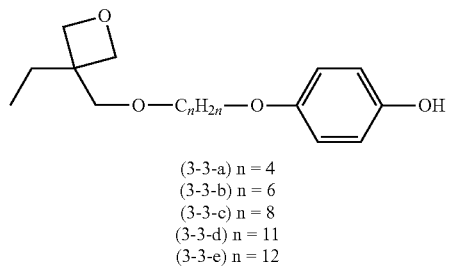
(3-3)
(3-3-a) n = 4
(3-3-b) n = 6
(3-3-c) n = 8
(3-3-d) n = 11
(3-3-e) n = 12
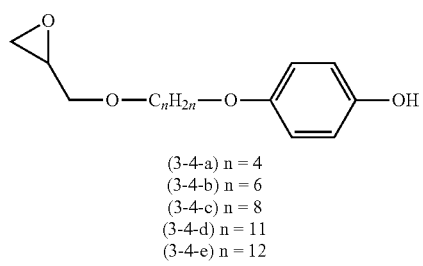
(3-4)
(3-4-a) n = 4
(3-4-b) n = 6
(3-4-c) n = 8
(3-4-d) n = 11
(3-4-e) n = 12
[Chem. 209]
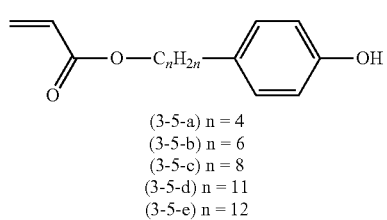
(3-5)
(3-5-a) n = 4
(3-5-b) n = 6
(3-5-c) n = 8
(3-5-d) n = 11
(3-5-e) n = 12
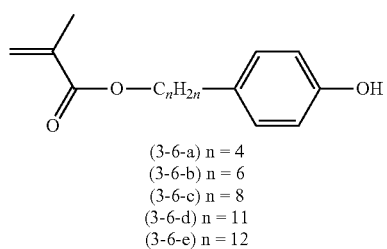
(3-6)
(3-6-a) n = 4
(3-6-b) n = 6
(3-6-c) n = 8
(3-6-d) n = 11
(3-6-e) n = 12
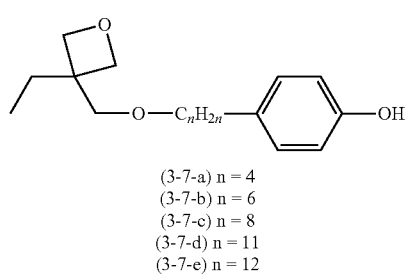
(3-7)
(3-7-a) n = 4
(3-7-b) n = 6
(3-7-c) n = 8
(3-7-d) n = 11
(3-7-e) n = 12
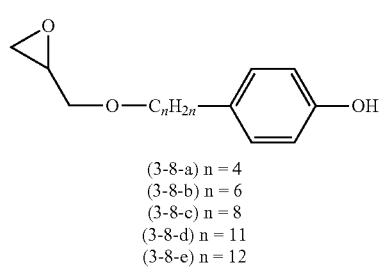
(3-8)
(3-8-a) n = 4
(3-8-b) n = 6
(3-8-c) n = 8
(3-8-d) n = 11
(3-8-e) n = 12
[Chem. 210]
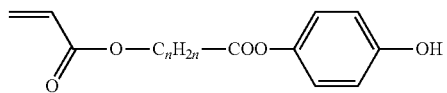
(3-9)
(3-9-a) n = 3
(3-9-b) n = 5
(3-9-c) n = 7
(3-9-d) n = 10
(3-9-e) n = 11
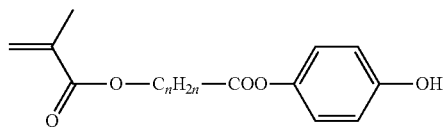
(3-10)
(3-10-a) n = 3
(3-10-b) n = 5
(3-10-c) n = 7
(3-10-d) n = 10
(3-10-e) n = 11
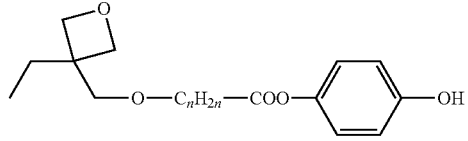
(3-11)
(3-11-a) n = 3
(3-11-b) n = 5
(3-11-c) n = 7
(3-11-d) n = 10
(3-11-e) n = 11
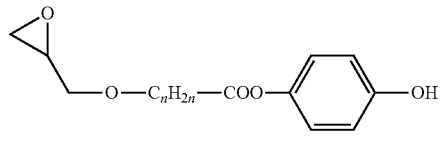
(3-12)
(3-12-a) n = 3
(3-12-b) n = 5
(3-12-c) n = 7
(3-12-d) n = 10
(3-12-e) n = 11
[Chem. 211]
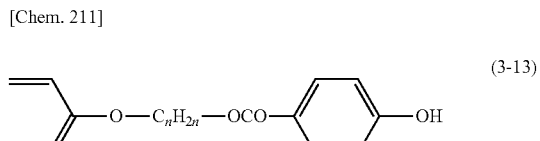
(3-13)
(3-13-a) n = 3
(3-13-b) n = 5
(3-13-c) n = 7
(3-13-d) n = 10
(3-13-e) n = 11
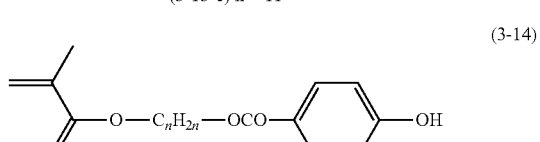
(3-14)
(3-14-a) n = 3
(3-14-b) n = 5
(3-14-c) n = 7
(3-14-d) n = 10
(3-14-e) n = 11

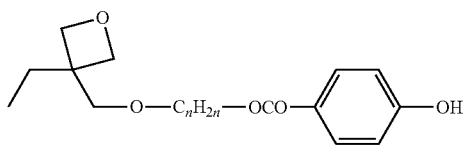
(3-15)
(3-15-a) n = 3
(3-15-b) n = 5
(3-15-c) n = 7
(3-15-d) n = 10
(3-15-e) n = 11
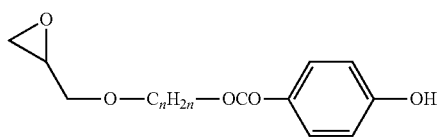
(3-16)
(3-16-a) n = 3
(3-16-b) n = 5
(3-16-c) n = 7
(3-16-d) n = 10
(3-16-e) n = 11
[Chem. 212]
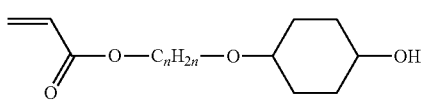
(3-17)
(3-17-a) n = 4
(3-17-b) n = 6
(3-17-c) n = 8
(3-17-d) n = 11
(3-17-e) n = 12
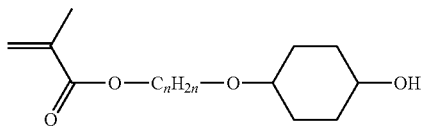
(3-18)
(3-18-a) n = 4
(3-18-b) n = 6
(3-18-c) n = 8
(3-18-d) n = 11
(3-18-e) n = 12
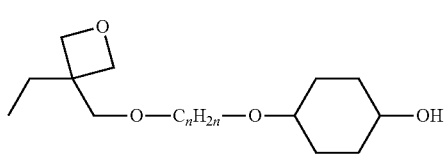
(3-19)
(3-19-a) n = 4
(3-19-b) n = 6
(3-19-c) n = 8
(3-19-d) n = 11
(3-19-e) n = 12
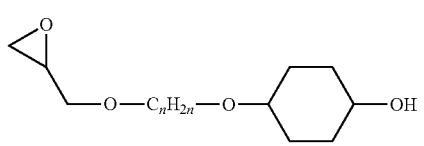
(3-20)
(3-20-a) n = 4
(3-20-b) n = 6
(3-20-c) n = 8
(3-20-d) n = 11
(3-20-e) n = 12
[Chem. 213]
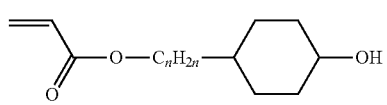
(3-21)
(3-21-a) n = 4
(3-21-b) n = 6
(3-21-c) n = 8
(3-21-d) n = 11
(3-21-e) n = 12
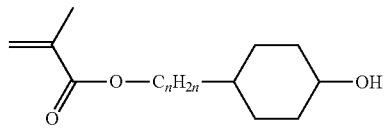
(3-22)
(3-22-a) n = 4
(3-22-b) n = 6
(3-22-c) n = 8
(3-22-d) n = 11
(3-22-e) n = 12
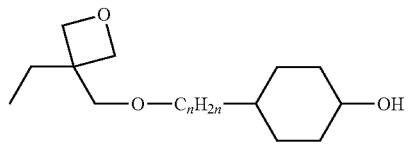
(3-23)
(3-23-a) n = 4
(3-23-b) n = 6
(3-23-c) n = 8
(3-23-d) n = 11
(3-23-e) n = 12
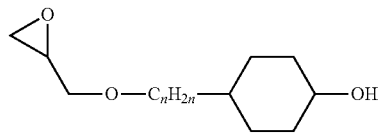
(3-24)
(3-24-a) n = 4
(3-24-b) n = 6
(3-24-c) n = 8
(3-24-d) n = 11
(3-24-e) n = 12
[Chem. 214]
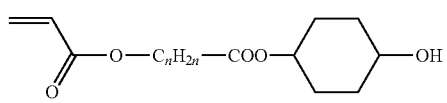
(3-25)
(3-25-a) n = 3
(3-25-b) n = 5
(3-25-c) n = 7
(3-25-d) n = 10
(3-25-e) n = 11
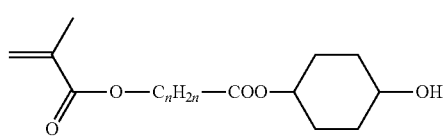
(3-26)
(3-26-a) n = 3
(3-26-b) n = 5
(3-26-c) n = 7
(3-26-d) n = 10
(3-26-e) n = 11

(3-27)

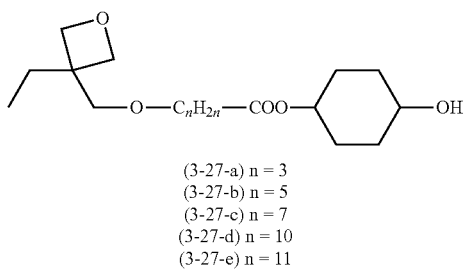

(3-27-a) n = 3
(3-27-b) n = 5
(3-27-c) n = 7
(3-27-d) n = 10
(3-27-e) n = 11

(3-28)

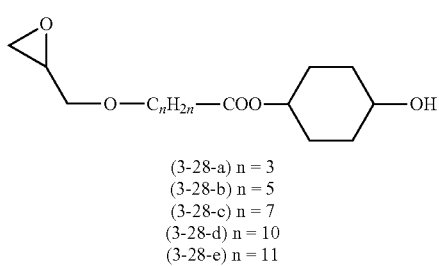

(3-28-a) n = 3
(3-28-b) n = 5
(3-28-c) n = 7
(3-28-d) n = 10
(3-28-e) n = 11

[Chem. 215]

(3-29)

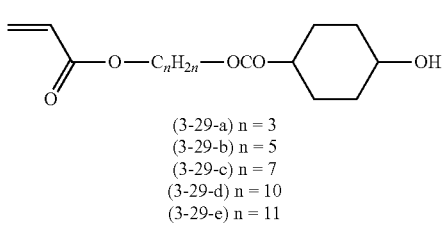

(3-29-a) n = 3
(3-29-b) n = 5
(3-29-c) n = 7
(3-29-d) n = 10
(3-29-e) n = 11

(3-30)

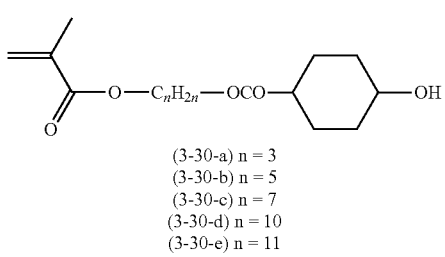

(3-30-a) n = 3
(3-30-b) n = 5
(3-30-c) n = 7
(3-30-d) n = 10
(3-30-e) n = 11

(3-31)

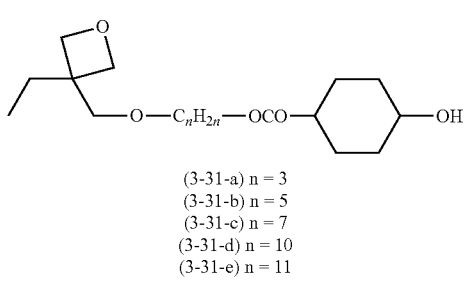

(3-31-a) n = 3
(3-31-b) n = 5
(3-31-c) n = 7
(3-31-d) n = 10
(3-31-e) n = 11

(3-32)

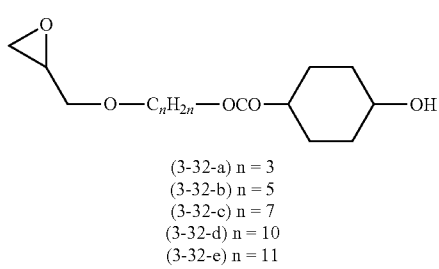

(3-32-a) n = 3
(3-32-b) n = 5
(3-32-c) n = 7
(3-32-d) n = 10
(3-32-e) n = 11

[Chem. 216]

(3-33)

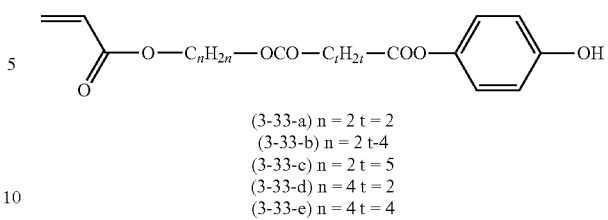

(3-33-a) n = 2 t = 2
(3-33-b) n = 2 t-4
(3-33-c) n = 2 t = 5
(3-33-d) n = 4 t = 2
(3-33-e) n = 4 t = 4

(3-34)

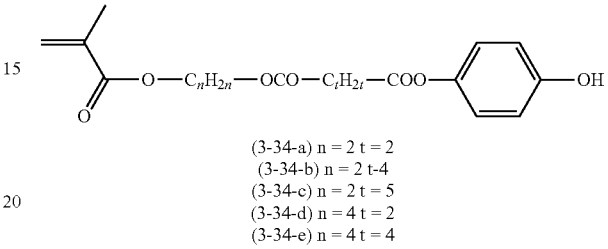

(3-34-a) n = 2 t = 2
(3-34-b) n = 2 t-4
(3-34-c) n = 2 t = 5
(3-34-d) n = 4 t = 2
(3-34-e) n = 4 t = 4

(3-35)

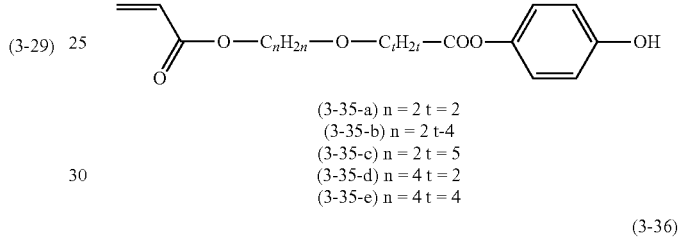

(3-35-a) n = 2 t = 2
(3-35-b) n = 2 t-4
(3-35-c) n = 2 t = 5
(3-35-d) n = 4 t = 2
(3-35-e) n = 4 t = 4

(3-36)

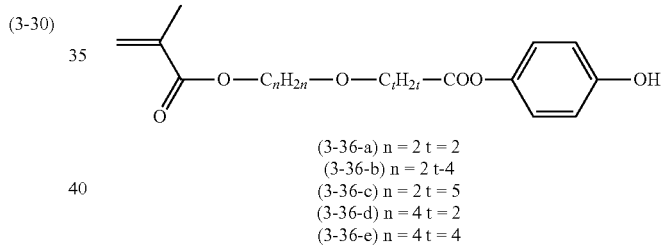

(3-36-a) n = 2 t = 2
(3-36-b) n = 2 t-4
(3-36-c) n = 2 t = 5
(3-36-d) n = 4 t = 2
(3-36-e) n = 4 t = 4

Examples of the dicarboxylic acid compound (4) include compound (4-1) represented by the following formula (4-1).

[Chem. 218]

(4-1)

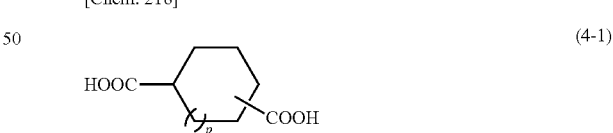

[wherein the hydrogen atom contained in the alicyclic hydrocarbon group is optionally substituted with a halogen atom, an alkyl group having 1 to 4 carbon atoms that is optionally substituted with a halogen atom, an alkoxy group having 1 to 4 carbon atoms that is optionally substituted with a halogen atom, a cyano group, or a nitro group. —$CH_2$— contained in the alicyclic hydrocarbon group is optionally replaced by —O—, —S—, or —N($_R{}^{12}$)—, and the carbon atom of a methylene group or a methine group contained in the alicyclic hydrocarbon group may be a nitrogen atom. $R^{12}$ represents a hydrogen atom or an alkyl group having 1 to 4 carbon atoms.

p represents 0 or 1.]

Dicarboxylic acid compound (4) is preferably a compound (4-2) represented by formula (4-2), and more preferably a compound (4-3) represented by formula (4-3).

[Chem. 219]

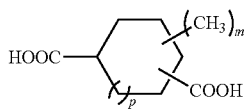
(4-2)

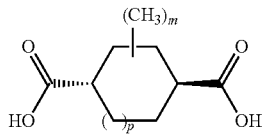
(4-3)

[wherein m represents an integer of 0 to 3; and p represents 0 or 1.]

Specific examples of the dicarboxylic acid compound (4) include 1,2-cyclopentanedicarboxylic acid, 1,3-cyclopentanedicarboxylic acid, 1,2-cyclohexanedicarboxylic acid, 1,3-cyclohexanedicarboxylic acid, 1,4-cyclohexanedicarboxylic acid, 3-methyl-1,2-cyclopentanedicarboxylic acid, 2-methyl-1,3-cyclopentanedicarboxylic acid, 3,4-dimethyl-1,2-cyclohexanedicarboxylic acid, 2-methyl-1,4-cyclohexanedicarboxylic acid, 2,5-dimethyl-1,4-cyclohexanedicarboxylic acid, 2,6-dimethyl-1,4-cyclohexanedicarboxylic acid, 1,3-adamantanedicarboxylic acid, 1,1'-cyclobutanedicarboxylic acid, 1,1'-cyclopropanedicarboxylic acid, epoxysuccinic acid, and 4-cyclohexene-1,2-dicarboxylic acid. Of these, 1,4-cyclohexanedicarboxylic acid is preferable, and trans-1,4-cyclohexanedicarboxylic acid is more preferable.

Alcohol compound (6) may be a compound in which two hydroxyl groups are bonded to an aromatic group of Ar. The aromatic group of Ar is the same as defined above, and examples thereof include compounds in which two * portions each refer to a hydroxyl group in the above formulae (Ar-1) to (Ar-14).

<Step (a)>

In step (a), the alcohol compound (3) and the dicarboxylic acid compound (4) are subjected to esterification reaction. The esterification reaction is conducted in the presence of a condensing agent. The esterification reaction in the presence of a condensing agent can realize efficient and prompt esterification reaction.

Examples of the condensing agent include carbodiimide compounds such as 1-cyclohexyl-3-(2-morpholinoethyl)carbodiimide metho-p-toluenesulfonate, dicyclohexylcarbodiimide, diisopropylcarbodiimide, 1-ethyl-3-(3-dimethylaminopropyl)carbodiimide, 1-ethyl-3-(3-dimethylaminopropyl)carbodiimide hydrochloric acid salt (water-soluble carbodiimide: commercially available as WSC), bis(2,6-diisopropylphenyl)carbodiimide and bis(trimethylsilyl)carbodiimide; 2-methyl-6-nitrobenzoic anhydride, 2,2'-carbonylbis-1H-imidazole, 1,1'-oxalyldimidazole, diphenylphosphoryl azide, 1(4-nitrobenzenesulfonyl)-1H-1,2,4-triazole, 1H-benzotriazol-1-yloxytripyrrolidinophosphpnium hexafluorophosphate, 1H-benzotriazol-1-yloxytris(dimethylamino)phosphonium hexafluorophosphate, N,N,N',N'-tetramethyl-O—(N-succinimidyfluronium tetrafluoroborate, N-(1,2,2,2-tetrachloroethoxycarbonyloxy)succinimide, N-carbobenzoxysuccinimide, O-(6-chlorobenzotriazol-1-yl)-N,N,N',N'-tetramethyluronium tetrafluoroborate, O-(6-chlorobenzotriazol-1-yl)-N,N,N',N'-tetramethyluronium hexafluorophosphate, 2-bromo-1-ethylpyridinium tetrafluoroborate, 2-chloro-1,3-dimethylimidazolinium chloride, 2-chloro-1,3-dimethylimidazolinium hexafluorophosphate, 2-chloro-1-methylpyridinium iodide, 2-chloro-1-methylpyridinium p-toluenesulfonate, 2-fluoro-1-methylpyridinium p-toluenesulfonate and pentachlorophenyl trichloroacetate.

Of these, preferable are carbodiimide compounds, 2,2'-carbonylbis-1H-imidazole, 1,1'-oxalyldimidazole, diphenylphosphoryl azide, 1H-benzotriazol-1-yloxytripyrrolidinophosphpnium hexafluorophosphate, 1H-benzotriazol-1-yloxytris(dimethylamino)phosphonium hexafluorophosphate, N,N,N',N'-tetramethyl-O—(N-succinimidyl)uronium tetrafluoroborate, N-(1,2,2,2-tetrachloroethoxycarbonyloxy)succinimide, O-(6-chlorobenzotriazol-1-yl)-N,N,N',N'-tetramethyluronium tetrafluoroborate, 2-chloro-1,3-dimethylimidazolinium chloride, 2-chloro-1,3-dimethylimidazolinium hexafluorophosphate, 2-chloro-1-methylpyridinium iodide, and 2-chloro-1-methylpyridinium p-toluenesulfonate.

More preferable are carbodiimide compounds, 2,2'-carbonylbis-1H-imidazole, 1H-benzotriazol-1-yloxytripyrrolidinophosphpnium hexafluorophosphate, 1H-benzotriazol-1-yloxytris(dimethylamino)phosphonium hexafluorophosphate, N,N,N',N'-tetramethyl-O—(N-succinimidyl)uronium tetrafluoroborate, O-(6-chlorobenzotriazol-1-yl)-N,N,N',N'-tetramethyluronium tetrafluoroborate, 2-chloro-1,3-dimethylimidazolinium chloride, and 2-chloro-1-methylpyridinium iodide; and even more preferable are carbodiimide compounds from the viewpoint of economic advantages.

Of the carbodiimide compounds, preferable are dicyclohexylcarbodiimide, diisopropylcarbodiimide, 1-ethyl-3-(3-dimethylaminopropyl)carbodiimide, 1-ethyl-3-(3-dimethylaminopropyl)carbodiimide hydrochloric acid salt (water-soluble carbodiimide: commercially available as WSC), and bis(2,6-diisopropylphenyl)carbodiimide.

The amount of the condensing agent used is usually from 1 to 3 moles relative to 1 mole of alcohol compound (3).

In the esterification reaction, further, N-hydroxysuccinimide, benzotrlazole, p-nitrophenol, 3,5-dibutyl-4-hydroxytoluene, or the like may be added as an additive and then mixed. The amount of the additive used is preferably from 0.03 to 1.2 moles relative to 1 mole of the condensing agent.

The esterification reaction may be conducted in the presence of a catalyst. Examples of the catalyst include N,N-dimethylaminopyridine, N,N-dimethylaniline, and dimethylammonium pentafluorobenzenesulfonate. Of these, N,N-dimethylaminopyridine and N,N-dimethylaniline are preferable, and N,N-dimethylaminopyridine is more preferable. The amount of the catalyst used is preferably from 0.01 to 0.5 moles relative to 1 mole of alcohol compound (3).

The esterification reaction is usually conducted in a solvent. Examples of the solvent include ketone solvents such as acetone, methyl ethyl ketone, cyclopentanone, cyclohexanone, methyl amyl ketone, and methyl isobutyl ketone; aliphatic hydrocarbon solvents such as pentane, hexane, and heptane; aromatic hydrocarbon solvents such as toluene, xylene, benzene, and chlorobenzene; nitrile solvents such as acetonitrile; ether solvents such as tetrahydrofuran, and dimethoxyethane; ester solvents such as ethyl lactate; halogenated hydrocarbon solvents such as chloroform and chlorobenzene; nonprotic polar solvents such as dimethyl sulfoxide, N-methyl-2-pyrrolidone, N,N-dimethylformamide, N,N-dimethylacetamide, and hexamethylphosphoric triamide. These organic solvents may be used alone or in combination.

Of these, the solvent is preferably a hydrophilic organic solvent such as acetone, acetonitrile, tetrahydrofuran, dimethoxyethane, ethyl lactate, dimethyl sulfoxide, N-methyl-2-pyrrolidone, N, N-dimethylformamide, N,N-dimethylacetamide, or hexamethylphosphoric triamide; and more preferably a nonprotic polar solvents such as dimethyl sulfoxide, N-methyl-2-pyrrolidone, N,N-dimethylformamide, N,N-dimethylacetamide, or hexamethylphosphoric triamide.

The amount of dicarboxylic acid compound (4) used is preferably from 1 to 50 moles, more preferably from 3 to 50 moles, even more preferably from 4 to 40 moles, and especially preferably from 5 to 20 moles, relative to 1 mole of alcohol compound (3). When the amount of dicarboxylic acid compound (4) used is not less than the lower limit, the yield of liquid crystal compound (1) is good. When the amount thereof is not more than the upper limit, the post treatment work for removing unreacted dicarboxylic acid compound (4) can be easily performed, so that productivity tends to be enhanced.

The amount of the solvent used is preferably from 0.5 to 50 parts by mass, more preferably from 1 to 20 parts by mass, and even more preferably from 2 to 10 parts by mass, relative to 1 part by mass of the total amount of alcohol compound (3) and dicarboxylic acid compound (4).

In step (a), the esterification reaction temperature is preferably from −20 to 120° C., more preferably from 20 to 80° C., and even more preferably from 30 to 60° C. The esterification reaction time is preferably from 1 minute to 72 hours, more preferably from 1 to 48 hours, and even more preferably from 1 to 24 hours. There is a tendency that the reaction yield is improved and the productivity is further enhanced by performing the esterification reaction in the above-mentioned temperature and time ranges.

After the esterification reaction, an unreacted dicarboxylic acid compound (4) can be removed as required. As the method of removing the unreacted dicarboxylic acid compound (4), the following method may be used. The reaction mixture obtained in step (a), a basic compound, and water are mixed to prepare a suspension. In the suspension, the unreacted dicarboxylic acid compound (4) is ionized and then dissolved therein, so that unreacted dicarboxylic acid compound (4) can be removed, and a mixture containing carboxylic acid compound (5) and liquid crystal compound (2) can be precipitated.

The basic compound may be a compound capable of undergoing an acid-base reaction with dicarboxylic acid compound (4). Preferable is a basic compound having alkali metal or alkaline-earth metal such as hydride of alkali metal, hydride of alkaline earth metal, hydroxide of alkali metal, hydroxide of alkaline earth metal, alkoxide of alkali metal, and alkoxide of alkaline-earth metal. A basic compound having alkali metal or alkaline-earth metal such as hydride of alkali metal, hydride of alkaline earth metal, hydroxide of alkali metal, and hydroxide of alkaline earth metal is more preferable. Specific examples thereof include lithium hydride, sodium hydride, potassium hydride, lithium hydroxide, sodium hydroxide, potassium hydroxide, calcium hydroxide, t-butoxysodium, and t-butoxypotassium.

The amount of the basic compound used is preferably from 0.05 to 50 moles, more preferably from 0.1 to 10 moles, and even more preferably from 0.2 to 2 moles, relative to 1 mole of dicarboxylic acid compound (4). When the amount of the basic compound used is not less than the lower limit, dicarboxylic acid compound (4) is easily dissolved, so that it tends to be easily removed. When the amount thereof is not more than the upper limit, it is possible to reduce the amount of carboxylic acid compound (5) that generates salts and to conveniently operate the subsequent treatment, so that productivity can be enhanced.

The amount of water used is preferably from 20 to 10000 parts by mass, more preferably from 50 to 5000 parts by mass, or even more preferably from 100 to 1000 parts by mass, relative to 100 parts by mass of the reaction mixture. By mixing the basic compound and water in the above-mentioned amount ranges, it becomes easier to dissolve the substances such as unreacted dicarboxylic acid compound (4) in water and to precipitate the mixture containing carboxylic acid compound (5) and liquid crystal compound (2), which is preferable.

As a method of obtaining solids containing carboxylic acid compound (5) and liquid crystal compound (2) from the resulting suspension, filtration, decantation, or the like may be used. Filtration is preferably used.

According to such method, solids containing carboxylic acid compound (5) and liquid crystal compound (2) can be obtained. Relative to 1 part by mass of the solids obtained in step (a), the content of dicarboxylic acid compound (4) in the solids is preferably 0.01 parts by mass or less, more preferably 0.005 parts by mass or less, and even more preferably 0.001 parts by mass or less.

<Step (b)>

In step (b), the mixture containing carboxylic acid compound (5) and liquid crystal compound (2) obtained in step (a) is allowed to react with alcohol compound (6). In this reaction, an esterification reaction of carboxylic acid compound (5) and alcohol compound (6) occurs. The esterification reaction is preferably conducted in the presence of a condensing agent. Further, it is possible to conduct the esterification reaction in step (b) in the presence of a catalyst. Usually, such esterification reaction is conducted in a solvent. As the condensing agent, catalyst and solvent, for example, those used in step (a) may be used. The esterification reaction in step (b) can be conducted in the same manner as in step (a).

The amount of alcohol compound (6) used is preferably from 0.2 to 0.7 moles, more preferably from 0.3 to 0.6 moles, even more preferably from 0.4 to 0.5 moles and especially preferably from 0.42 to 0.45 moles, relative to 1 mole of carboxylic acid compound (5). When the amount of the alcohol compound (6) used is not less than the lower limit, the amount of unreacted carboxylic acid compound is reduced, which facilitates purification. When the amount thereof is not more than the upper limit, a shortage of carboxylic acid compounds is suppressed and the yield can be improved.

The amount of the solvent used is preferably from 0.5 to 50 parts by mass, more preferably from 1 to 20 parts by mass, and even more preferably from 2 to 10 parts by mass, relative to 1 part by mass of the total amount of carboxylic acid compound (5), liquid crystal compound (2) and alcohol compound (6).

In step (b), the esterification reaction temperature is preferably from −20 to 100° C., more preferably from −10 to 50° C., and even more preferably from 0 to 30° C. The esterification reaction time is preferably from 1 minute to 72 hours, more preferably from 1 to 48 hours, and even more preferably from 1 to 24 hours. There is a tendency that the reaction yield is improved and the productivity is further enhanced by performing the esterification reaction in the above-mentioned temperature and time ranges.

As a result of the reaction described above, a liquid crystal composition containing liquid crystal compounds (1) and (2) can be obtained. The liquid crystal composition can be purified by filtration, decantation, or the like.

It is preferable that the liquid crystal composition of the present invention further contains a polymerization initiator. Examples of the polymerization initiator include a photo-polymerization initiator and a thermal polymerization initiator. In the present invention, a photo-polymerization initiator is preferable as the polymerization initiator.

Examples of the photo-polymerization initiator include benzoins, benzophenones, benzyl ketals, α-hydroxyketones, α-aminoketones, iodonium salts and sulfonium salts. More specific examples thereof include Irgacure 907, 184, 651, 819, 250 and 369 (hereinabove all manufactured by Ciba Japan K. K.); Seikuol BZ, Z, BEE (hereinabove all manufactured by Seiko Chemical Co., Ltd.); Kayacure BP100 (manufactured by Nippon Kayaku Co., Ltd.); Cyracure UVI-6992 (manufactured by the Dow Chemical Company); and Adeka Optomer SP-152 or SP-170 (hereinabove all manufactured by Adeka Corporation).

The content of the polymerization initiator is, for example, from 0.1 to 30 parts by mass, and preferably from 0.5 to 10 parts by mass, relative to 100 part by mass of the total amount of liquid crystal compounds (1) and (2). When the content thereof is within the above range, liquid crystal compounds (1) and (2) can be polymerized without disturbing the orientation of the liquid crystal compounds.

In the present invention, an optical film refers to a film which is capable of transmitting light and has an optical function. The optical function means refraction, birefringence, or the like. A retardation film, which is a type of optical film, is used for converting linearly polarized light into circularly polarized light or ellipticallypolarized light, and vice versa. The optical film of the present invention contains a polymer of the liquid crystal composition of the present invention. That is, the optical film of the present invention contains a polymer composed of a structural unit derived from liquid crystal compound (1) and a structural unit derived from liquid crystal compound (2).

The wavelength dispersion characteristic of the optical film according to the present invention can be arbitrarily controlled by adjusting the content of the structural unit derived from liquid crystal compound (1) and the structural unit derived from liquid crystal compound (2) in the above-mentioned polymer which composes the optical film. When the content of the structural unit derived from liquid crystal compound (1) among the structural units in the polymer which composes the optical film is increased, the optical film exhibits a flatter wavelength dispersion characteristic and reverse wavelength dispersion characteristic. For example, when the content of the structural unit derived from liquid crystal compound (1) among them is increased, it is possible to lower the numerical value of Re(450 nm)/Re(550 nm), and when the content of the structural unit derived from liquid crystal compound (2) is increased, it is possible to increase the numerical value of Re(450 nm)/Re(550 nm).

The content of the structural units derived from liquid crystal compounds (1) and (2) in the above-mentioned polymer which composes the optical film can be adjusted by selecting the contents of the liquid crystal compounds, and the following method is preferably used.

In the production method of the present invention, it is possible to adjust the content of liquid crystal compounds (1) and (2) in the formed liquid crystal composition by selecting the amounts of the alcohol compound (3) and the dicarboxylic acid compound (4) used as rawmaterials. By adjusting the content thereof, the wavelength dispersion characteristic of the optical film obtained from the liquid crystal composition can be selected. Specifically, the following method is used. First, two or more kinds of liquid crystal compositions each having different content of the structural units derived from liquid crystal compounds (1) and (2) are prepared, and with these liquid crystal compositions, optical films each having the same film thickness are produced as described later. Next, the retardation values of the optical films thus produced are calculated, and the correlation between the content of the structural units derived from liquid crystal compounds (1) and (2) and the retardation value of the optical film is obtained from the results. Then, from the obtained correlation, the content of the structural units derived from liquid crystal compound (1) and (2) which are necessary to impart a desired wavelength dispersion characteristic to the optical film having the above-mentioned film thickness is determined. Further, in order to obtain the determined content of the structural units derived from liquid crystal compounds (1) and (2), the amounts of the above alcohol compound (3) and the above dicarboxylic acid compound (4) used are selected, so that an optical film having a desired wavelength dispersion characteristic can be conveniently produced. According to the production method of the present invention, it is not necessary to independently produce the liquid crystal compounds, and without conducting a complicated operation such as a terminal capping step, it is possible to simultaneously produce the liquid crystal compounds in one pot, which enables the production step to be significantly shortened. Therefore, the production method of the present invention is highly economically advantageous.

<Production Method of Optical Film>

The production method of the optical film of the present invention will be described below.

First, an additive such as an organic solvent, the polymerization initiator mentioned above, a polymerization inhibitor, a photosensitizer or a leveling agent is added to the liquid crystal composition containing liquid crystal compounds (1) and (2) as required, to prepare a mixing solution. In particular, the mixing solution preferably contains an organic solvent because it facilitates formation of layers at the time, and a polymerization initiator because it serves to cure the resulting optical film.

[Polymerization Inhibitor]

A polymerization inhibitor may be used for preparing the optical film of the present invention. Examples of the polymerization inhibitor include hydroquinone or hydroquinones having a substituent such as alkyl ether; catechols having a substituent including alkyl ether such as butyl catechol; pyrogallols; a radical scavenger such as 2,2,6,6-tetramethyl-1-piperidinyloxy radical; thiophenols; β-naphthylamines and β-naphthols.

The use of the polymerization inhibitor allows the polymerization of liquid crystal compounds (1) and (2) to be controlled, so that the stability of the resulting optical film can be improved. The amount of the polymerization inhibitor used is, for example, from 0.1 to 30 parts by mass, and preferably from 0.5 to 10 parts by mass, relative to 100 parts by mass of the total amount of liquid crystal compounds (1) and (2). When the amount thereof is within the above range, liquid crystal compounds (1) and (2) can be polymerized without disturbing the orientation of the liquid crystal compounds.

[Photosensitizer]

A photosensitizer may also be used for preparing the optical film of the present invention. Examples of the photosensitizer include xanthones such as xanthone and thioxanthone; anthracene or anthracenes having a substituent such as alkyl ether; phenothiazine; and rubrene.

The use of the photosensitizer can make the polymerization of liquid crystal compounds (1) and (2) highly sensitive. The amount of the photosensitizer used is, for example, from 0.1 to 30 parts by mass, and preferably from 0.5 to 10 parts by mass, relative to 100 parts by mass of the total amount of liquid crystal compounds (1) and (2). When the amount thereof is within the above range, liquid crystal compounds (1) and (2) can be polymerized without disturbing the orientation of the liquid crystal compounds.

[Leveling Agent]

A leveling agent may further be used for preparing the optical film of the present invention. Examples of the leveling agent include additives for radiation-curable coating (manufactured by BYK Japan KK: BYK-352, BYK-353 and BYK-361N), coating additives (manufactured by Dow Corning Toray Co., Ltd.: SH28PA, DC11PA and ST80PA), coating additives (manufactured by Shin-Etsu Chemical Co., Ltd.: KP321, KP323, X22-161AandKF6001), and fluorine-based additives (manufactured by DIC Co., F-445, F-470 and F-479).

The use of the leveling agent allows the optical film to be smoothed. Further, by using the leveling agent, in the step of producing the optical film, it is possible to control the fluidity of the mixing solution containing liquid crystal compounds and to adjust the crosslinkage density of the optical film which is obtained by polymerizing liquid crystal compounds (1) and (2). The specific numerical value of the amount of the leveling agent used is, for example, from 0.1 to 30 parts by mass, and preferably from 0.5 to 10 parts by mass, relative to 100 parts by mass of the total amount of liquid crystal compounds (1) and (2). When the amount thereof is within the above range, liquid crystal compounds (1) and (2) can be polymerized without disturbing the orientation of the liquid crystal compounds.

[Organic Solvent]

An organic solvent to be used for preparation of the mixing solution containing the liquid crystal composition of the present invention is capable of dissolving liquid crystal compounds (1), (2) or the like and may be inert to polymerization reaction. Examples of the organic solvent include alcohols such as methanol, ethanol, ethylene glycol, isopropyl alcohol, propylene glycol, methyl cellosolve, butyl cellosolve, and propylene glycol monomethyl ether; ester solvents such as ethyl acetate, butyl acetate, ethylene glycol methyl ether acetate, y-butyrolactone, propylene glycol methyl ether acetate and ethyl lactate; ketone solvents such as acetone, methyl ethyl ketone, cyclopentanone, cyclohexanone, methyl amyl ketone and methyl isobutyl ketone; non-chlorinated aliphatic hydrocarbon solvents such as pentane, hexane and heptane; non-chlorinated aromatic hydrocarbon solvents such as toluene, xylene and phenol; nitrile solvents such as acetonitrile; ether solvents such as tetrahydrofuran and dimethoxyethane; and chlorinated hydrocarbon solvents such as chloroform and chlorobenzene. These organic solvents may be used alone or in combination. Since the liquid crystal composition of the present invention has excellent compatibility and can also be dissolved in alcohols, ester solvents, ketone solvents, non-chlorinated aliphatic hydrocarbon solvents, and non-chlorinated aromatic hydrocarbon solvents, it can be dissolved for coating without using chlorinated hydrocarbon solvents such as chloroform.

It is preferable that the viscosity of the mixing solution containing the liquid crystal composition of the present invention is adjusted, for example, to 10 Pa·s or less, and preferably to 0.1 to 7 Pa·s or so for ease of coating.

The concentration of the solids in the mixing solution is, for example, from 5 to 50% by mass. When the concentration of the solids is not less than 5%, there is a tendency that the optical film does not become excessively thin and the birefringence index required for optical compensation for liquid crystal panels is given thereto. When the concentration thereof is not more than 50%, there is a tendency that unevenness does not easily occur in the thickness of the optical film because of the low viscosity of the mixing solution.

The mixing solution containing the liquid crystal composition is then applied onto a supporting substrate and dried to form a liquid crystal layer. When the liquid crystal layer exhibits a liquid crystal phase such as a nematic phase, the obtained optical film has a birefringence characteristic due to monodomain orientation. Since the liquid crystal layer is oriented at a low temperature of 0 to 120° C. or so, and preferably 25 to 80° C., a supporting substrate which is not always satisfactory in the heat resistance as exemplified above can be used as an orientation layer. In addition, even when the liquid crystal layer is further cooled to 30 to 10° C. or so after the orientation, it is not crystalized, so that the liquid crystal layer is easily handled.

By appropriately adjusting the coating amount and the concentration of the mixing solution, the thickness of the layer can be adjusted so as to provide a desired retardation. In the case of the mixing solution having a constant amount of liquid crystal compounds (1) and (2), the retardation value (retardation value $Re(\lambda)$) of the obtained optical film is determined as formula (I). Therefore, in order to obtain a desired $Re(\lambda)$, a film thickness d may be adjusted.

$$Re(\lambda)=d\times\Delta n(\lambda) \qquad (I)$$

(wherein $Re(\lambda)$ represents a retardation value at a wavelength of $\lambda$ nm; d represents a film thickness; and $\Delta n(\lambda)$ represents a birefringence index at a wavelength of $\lambda$ nm.)

Examples of a method for applying the mixing solution to the supporting substrate include an extrusion coating method, a direct gravure coating method, a reverse gravure coating method, a CAP coating method, and a die coating method. Examples thereof also include a method for coating by using a coater such as a dip coater, a bar coater or a spin coater.

Examples of the above-mentioned supporting substrate include glass, plastic sheets, plastic films, or translucent films. Examples of the translucent film include polyolefin films such as polyethylene, polypropylene and norbornene-based polymers; polyvinyl alcohol films; polyethylene terephthalate films; polymethacrylate films; polyacrylate films; cellulose ester films; polyethylene naphthalate films; polycarbonate films; polysulfone films; polyethersulfone films; polyetherketone films; polyphenylenesulfide films; and polyphenylene oxide films.

By using the supporting substrate, the optical film of the present invention can be easily handled without breakage, even in the steps requiring strength of the optical film, such as a bonding step, a conveying step, and a storing step of the optical film.

It is preferable that the orientation layer is formed on the supporting substrate and the mixing solution containing the liquid crystal composition of the present invention is applied onto the orientation layer. It is preferable that the orientation layer has solvent resistance so as not to be dissolved in the mixing solution containing the liquid crystal composition of the present invention when the mixing solution is applied thereonto; has heat resistance at the time of removal of the solvent or of heat-treatment of the liquid crystal orientation; and does not generate peeling due to friction at the time of rubbing. It is also preferable that the orientation layer is composed of a polymer or a composition containing a polymer.

Examples of the above-mentioned polymer include polyamides and gelatins having amide bonds in the molecule, polyimides having imide bonds in the molecule and polyamic acids which are the hydrolysate thereof, polyvinyl alcohol, alkyl-modified polyvinyl alcohols, polyacrylamide, polyoxazoles, polyethylene imine, polystyrene, polyvinylpyrrolidone, polyacrylic acid, and polyacrylic acid esters. These polymers may be used alone, in combination of two or more kinds, or copolymerized. These polymers can be easily obtained by a polycondensation based on dehydration, deamination or the like, a chain polymerization such as radical polymerization, anion polymerization or cation polymerization, coordination polymerization, ring-opening polymerization or some other polymerization.

These polymers can also be dissolved in a solvent and then applied. The solvent is not particularly limited, and specific examples thereof include water; alcohol solvents such as methanol, ethanol, ethylene glycol, isopropyl alcohol, propylene glycol, methylcellosolve, butylcellosolve and propylene glycol monomethyl ether; ester solvents such as ethyl acetate, butyl acetate, ethylene glycol methyl ether acetate, y-butyrolactone, propylene glycol methyl ether acetate and ethyl lactate; ketone solvents such as acetone, methyl ethyl ketone, cyclopentanone, cyclohexanone, methyl amyl ketone and methyl isobutyl ketone; non-chlorinated aliphatic hydrocarbon solvents such as pentane, hexane and heptane; non-chlorinated aromatic hydrocarbon solvents such as toluene and xylene; nitrile solvents such as acetonitrile; ether solvents such as tetrahydrofuran and dimethoxyethane; and chlorinated hydrocarbon solvents such as chloroform and chlorobenzene. These organic solvents may be used alone or in combination.

In order to form the orientation layer, a commercially available material for orientation layers may be used as it is. Examples of the commercially available material for orientation layers include SUNEVER (registered trademark, manufactured by Nissan Chemical Industries ltd.) and OPTMER (registered trademark, manufactured by JSR Corporation).

The use of such orientation layer can eliminate the need of controlling refractive index by drawing, so that in-plane dispersion of birefringence can be reduced. For this reason, there is exhibited an effect that a large optical film which can meet the requirements of upsizing of a flat panel display device (FPD) can be provided on a supporting substrate.

As a method for forming the orientation layer on the supporting substrate, for example, a commercially available material for orientation layers or a compound serving as an orientation layer material is converted into a solution, the resulting solution is applied thereonto, followed by annealing, to thereby form an orientation layer on the supporting substrate.

The thickness of the orientation layer thus obtained is, for example, from 10 nm to 10000 nm, and preferably from 10 nm to 1000 nm. When the thickness thereof is within the above range, liquid crystal compounds (1) and (2) or the like can be oriented to a desired angle on the orientation layer.

Further, these orientation layers can be subjected to rubbing or polarized UV irradiation as required. By forming the orientation layer, liquid crystal compounds (1) and (2) or the like can be oriented to a desired direction.

As a method for rubbing the orientation layer, for example, a method in which a rotating rubbing roll wrapped with a rubbing cloth is brought into contact with the orientation layer which is being conveyed on a stage may be used.

As described above, in the step of preparing the liquid crystal layer, a liquid crystal layer may be laminated on the orientation layer which is laminated on any supporting substrate. In such case, production cost can be reduced as compared with a method in which a liquid crystal cell is produced and a liquid crystal composition is injected into the liquid crystal cell. Further, it is possible to produce a film in the form of a roll film.

The solvent may be dried as the polymerization proceeds. Most of the solvent is, however, preferably dried before the polymerization from the viewpoint of layer formability.

Examples of a method for drying the solvent include natural drying, air drying, and vacuum drying. The specific heating temperature is preferably from 10 to 120° C., and more preferably from 25 to 80° C. The heating time is preferably from 10 seconds to 60 minutes, and more preferably from 30 seconds to 30 minutes. When the heating temperature and the heating time are within the above ranges, a supporting substrate which is not always satisfactory in the heat resistance can be used as the above-mentioned supporting substrate.

Next, the liquid crystal layer obtained above is polymerized and then cured. This produces a film in which the orientation of liquid crystal compounds (1) and (2) is fixed, that is, a film (an optical film) containing a polymer of the liquid crystal composition of the present invention. Accordingly, an optical film in which a change in refractive index is small in a film-plane direction and is large in a film normal line direction can be produced.

The method for polymerizing the liquid crystal layer is determined depending on the type of liquid crystal compounds (1) and (2). The above-mentioned liquid crystal layer can be polymerized by photo polymerization when the polymerizable group contained in liquid crystal compounds (1) and (2) is photo-polymerizable or by thermal polymerization when the polymerizable group is thermally polymerizable. In the present invention, it is preferable that the liquid crystal layer is polymerized, in particular, by photo-polymerization. According to the photo polymerization, it is possible to polymerize the liquid crystal layer at low temperature, so that a selection range for heat resistance of the supporting substrate is enhanced. In addition, photo polymerization makes the production industrially easier. From the viewpoint of layer formability, photo polymerization is preferable. Photo polymerization is performed by irradiating the liquid crystal layer with visible light, ultraviolet light or laser light. From the viewpoint of handleability, irradiation of ultraviolet light which is especially preferable, may be performed with warming at a temperature at which liquid crystal compounds (1) and (2) are in liquid crystal phase. At this time, the optical film can be patterned by masking or the like.

Further, the optical film of the present invention is a thin layer as compared with a drawn film in which a polymer is drawn to cause retardation.

The method for producing the optical film of the present invention may further include a step of separating the supporting substrate. From such structure, the resulting laminated body becomes a film composed of an orientation layer and an optical film. In addition to the above-mentioned step of separating the supporting substrate, a step of separating the orientation layer may further be included. From such structure, an optical film can be produced.

The optical film thus produced is excellent in transparency and can be used as various display films. The thickness of the optical film varies depending on the retardation values and desired thickness of the produced optical film as described above. In the present invention, the thickness thereof is preferably from 0.1 to 10 µm, and more preferably from 0.5 to 3 µm in view of reducing photoelasticity.

When the optical film has birefringence using the orientation layer, the retardation value is, for example, from 50 to 500 nm or so, and preferably from 100 to 300 nm.

The film, which is of a thin layer and is capable of uniform conversion of polarized light over a wider wavelength band, can be used as an optical compensation film in all the FPDs including crystal liquid panels and organic ELs.

In order to use the optical film of the present invention as a wide band λ/4 plate or λ/2 plate, the content of the structural unit derived from liquid crystal compound (1) and the structural unit derived from liquid crystal compound (2) in the polymer which composes the optical film of the present invention is appropriately selected. When the optical film of the present invention is used as a λ/4 plate, the content of the structural units derived from liquid crystal compounds (1) and (2) in the above-mentioned polymer and the film thickness may be adjusted so that the retardation value (Re(550)) at a wavelength of 550 nm of the resulting optical film is preferably from 113 to 163 nm, more preferably from 135 to 140 nm, and especially preferably from about 137.5 nm. When the optical film is used as a λ/2 plate, such content and the film thickness may be adjusted so that Re(550) of the resulting optical film is preferably from 250 to 300 nm, more preferably from 273 to 277 nm, and especially preferably from about 275 nm. According to the present invention, Re(550) can be controlled by adjusting the content of the structural units derived from liquid crystal compounds (1) and (2) in the above-mentioned polymer alone. Therefore, it is possible to select a desired film thickness.

In order to use the optical film of the present invention as an optical film of VA (vertical alignment) mode, the content of the structural units derived from liquid crystal compounds (1) and (2) is appropriately selected. The content of the structural units derived from liquid crystal compounds (1) and (2) in the above-mentioned polymer and the film thickness may be adjusted so that Re(550) is preferably from about 40 to 100 nm and more preferably from about 60 to 80 nm.

In order to adjust the content of the structural units derived from liquid crystal compounds (1) and (2) in the above-mentioned polymer which composes the optical film of the present invention, the content of liquid crystal compounds (1) and (2) in the liquid crystal composition of the present invention maybe adjusted. To do so, the amounts of alcohol compound (3) and dicarboxylic acid compound (4) used may be adjusted.

The wavelength dispersion characteristic of the optical film can be varied by selecting the contents of liquid crystal compounds (1) and (2) in the liquid crystal composition which is used when the optical film is produced, that is, the amounts of alcohol compound (3) and dicarboxylic acid compound (4) used. Therefore, the wavelength dispersion characteristic thereof can be controlled to a desired one by a convenient method.

The optical film of the present invention can be used as an antireflective film such as an antireflection (AR) film, a polarizing film, a retardation film, an elliptically polarizing film, a viewing angle expansion film or an optical compensation film for viewing angle compensation of a translucent liquid crystal display. Even one sheet of the optical film of the present invention exhibits excellent optical characteristics, but two or more sheets thereof may be laminated.

The optical film may also be combined with another film. Specifically, an elliptically polarizing plate and a circularly polarizing plate containing the optical film and the polarizing film of the present invention are provided in the present invention. In these plates, the optical film of the present invention is bonded to the polarizing film. Further, in the present invention, it is possible to provide a wide-band circularly polarizing plate in which the optical film of the present invention is bonded to the elliptically polarizing plate or the circularly polarizing plate as a wide-band λ/4 plate.

The optical film of the present invention can be used for a retardation plate of a reflective liquid crystal display and an organic electro-luminescence (EL) display, and for an FPD having the retardation plate and the optical film. The above FPD is not particularly limited, and examples thereof include a liquid crystal display (LCD) device and an organic EL display device.

In the present invention, the flat panel display device has the optical film of the present invention, and examples thereof include a liquid crystal display device having a bonded product obtained by bonding the polarizing film of the present invention and a liquid crystal panel to each other, and an organic EL display device having an organic EL panel in which the polarizing film of the present invention and a light emitting layer are bonded to each other.

[Organic EL Display Device]

In the present invention, an organic electro-luminescence (EL) display device including an organic EL panel containing the circularly polarizing plate of the present invention is also provided. The organic EL display device comprises an organic EL panel, and the organic EL panel is formed by bonding the optical film of the present invention and a light emitting layer through an adhesive layer as required. In the organic EL panel, the optical film serves as a circularly polarizing plate. The light emitting layer is of at least one layer made of a conductive organic compound.

EXAMPLES

The present invention will, hereinafter, be illustrated using Examples further in detail. The units, "%" and "part (s)", presented in the examples are % by mass and part(s) by mass, unless otherwise specified therein.

The liquid chromatography (LC) analysis conditions are indicated below.

<LC Analysis Conditions>

Measuring apparatus: LC-10AT (manufactured by Shimadzu Corp.)

Column: Kinetex (registered trademark) ODS(5 µm, 4.6 mmφ×15 cm)

Column temperature: 40° C.

Mobile phase: A: 0.1% trifluoroacetic acid aqueous solution

B: 0.1% trifluoroacetic acid-containing acetonitrile solution

Gradient: 0 min B=2%

30 min B=100%

35 min B=100%

35.1 min B=2%

45 min STOP Total analysis time 45 min

Flow rate: 1.0 mL/min

Detection: UV absorption (wavelength: 220 nm)

Example 1

A mixture of liquid crystal compound (1) having a reverse wavelength dispersion characteristic represented by formula (1) and liquid crystal compound (2) having a positive wavelength dispersion characteristic represented by formula (2) was synthesized according to the following scheme.

the mixture, 6.9 g (55 mmol) of diisopropylcarbodiimide was added dropwise in over 1 hour, and the added mixture was then subjected to esterification reaction by stirring for 15 hours.

On the other hand, 2.1 g (53 mmol) of sodium hydroxide and 145 g of water were mixed. The resulting mixture was added dropwise to the above-mentioned reaction mixture and the added mixture was stirred for 2 hours to obtain a suspension. The suspension thus obtained was filtered to

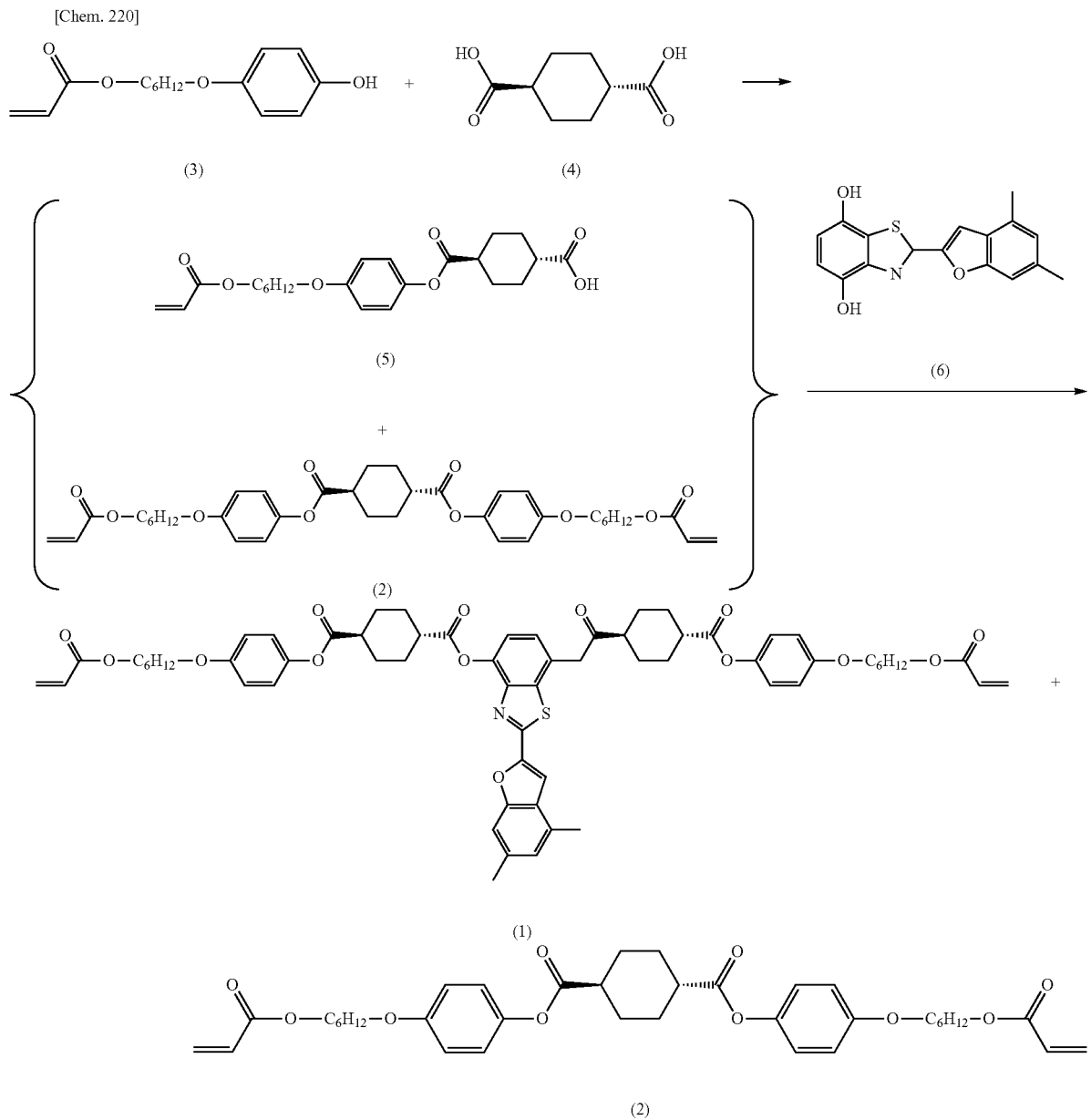

Mixed were 36 g (210 mmol) of the trans-cyclohexanedicarboxylic acid represented by the above formula (4) and 72 g of N-methyl-2-pyrrolidone, to obtain a solution. To the solution thus obtained, 9.9 g (42 mmol) of monoalcohol compound represented by the above formula (3), 0.7 g (2.9 mmol) of 3,5-dibutyl-4-hydroxytoluene, and 0.055 g (0.4 mmol) of N,N-dimethylaminopyridine were added, and the temperature of the resulting mixture was kept at 45° C. To give solids. The solids were washed 6 times with a mixed solvent of methanol and water (mass ratio 1:1), further followed by drying under reduced pressure, to thereby obtain 12.6 g of white solids.

Added were 12.6 g of the white solids, 4.25 g (14 mmol) of the alcohol compound represented by the above formula (6), 0.033 g (0.3 mmol) of N,N-dimethylaminopyridine, and 60 g of chloroform, and the temperature of the mixture was kept at 0° C. To the resulting mixture, 4.3 g(34 mmol) of diisopropylcarbodiimide was added dropwise in over 1 hour, and the added mixture was then subjected to esterification reaction by stirring for 15 hours. The reaction mixture thus obtained was filtered to remove insoluble fractions, the filtrate was added dropwise to heptane, and precipitated solids were filtered. The solids thus obtained were washed 3 times with heptane, further followed by drying under reduced pressure, to thereby obtain 16. 4 g of mixture A of liquid crystal compound (1) having a reverse wavelength dispersion characteristic represented by formula (1) and liquid crystal compound (2) having a positive wavelength dispersion characteristic represented by formula (2).

Mixture A was analyzed using the LC analysis conditions described above. The mixture A contained 7 parts by mass of liquid crystal compound (2) relative to 100 parts by mass of liquid crystal compound (1). Thus, the content of the liquid crystal compound (2) is 7% by mass relative to 100% by mass of liquid crystal compound (1). The measurement with spectrophotometer (chloroform solution) indicated that the maximum absorption wavelength ($A_{max}$) of liquid crystal compound (1) was 350 nm.

[Preparation of Composition for Forming Photo-Orientation Layer]

The following components were mixed, and the resulting mixture was stirred at 80° C. for 1 hour to obtain a composition for forming a photo-orientation layer. The following photo-orientation materials were synthesized by the method disclosed in JP-A-2013-33248.

Photo-orientation material (5 parts)

[Chem. 221]

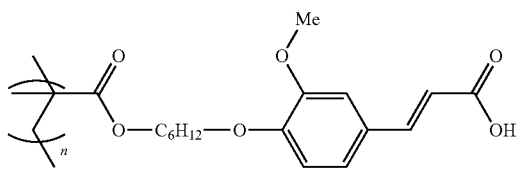

Solvent (95 parts): Cyclopentanone

[Production of Optical Film]

The optical film obtained by polymerizing the above mixture A was produced as follows:

A polyethylene terephthalate film (PET) (DIAFOIL T140E25 manufactured by Mitsubishi Plastics, Inc.) was treated once using a Corona generator (AGF-B10, manufactured by Kasuga Denki Inc.) under the conditions of an output of 0.3 kW and a treatment rate of 3 m/min. The composition for forming a photo-orientation layer was applied to the corona-treated surface using a bar coater, and dried at 80° C. for 1 minute, followed by exposure to polarized UV radiation using a polarized UV irradiation device (SPOT CURE SP-7; manufactured by Ushio Inc.) at an integrated light intensity of 100 mJ/cm². The thickness of the obtained orientation layer was measured using an ellipsometer. The result was 122 nm. Subsequently, a coating solution composed of 1.0 g of mixture A, 0.060 g of Irg369, and 10.7 g of N-methylpyrrolidone was applied onto the orientation layer using a bar coater, and then dried at 120° C. for 1 minute, followed by exposure to ultraviolet radiation (in a nitrogen atmosphere, wavelength: 365 nm, integrated light intensity at a wavelength of 365 nm: 1000 mJ/cm²) using a high-pressure mercury lamp (UNICURE VB-15201 BY-A, manufactured by Ushio Inc.). Thus, an optical film was produced. A pressure-sensitive adhesive was applied to the optical film thus produced, and the optical film was bonded to a Cyclo-olefin Polymer (COP) (ZF-14, manufactured by Zeon Corporation) which was treated once using a Corona generator (AGF-B10, manufactured by Kasuga Denki Inc.) under the conditions of an output of 0.3 kW and a treatment rate of 3 m/min. Thereafter, the PET film as a substrate was separated therefrom to produce optical film (1).

The optical film thus produced had a thickness of 2.0 μm, a retardation value (Re(550)) of 140 nm, and a degree of wavelength dispersion Re(450 nm)/Re(550 nm) of 0.84.

Examples 2 to 4

Optical films (2) to (4) were each produced in the same manner as in Example 1, except that before mixture A was applied onto a polarizing layer, the liquid crystal compound having a positive wavelength dispersion characteristic represented by formula (2), which was synthesized according to the method disclosed in JP-B-05451176, was added to mixture A and then mixed so as to obtain the concentration of the liquid crystal compound (2) shown in Table 1. The degrees of wavelength dispersion Re(450 nm)/Re(550 nm) of the optical films (2) to (4) thus produced were measured. The results were shown in Table 1.

Reference Example 1

An optical film (5) was produced in the same manner as in Example 1, except that liquid crystal compound (1) represented by formula (1), which was synthesized according to the method disclosed in JP-A-2009-173893, was used alone instead of using mixture A. The degree of wavelength dispersion Re(450 nm)/Re(550 nm) of the optical film (5) thus produced was measured. The results were shown in Table 1.

Example 5

An optical film (6) was produced in the same manner as in Example 1, except that liquid crystal compound (1) represented by formula (1), which was synthesized according to the method disclosed in JP-A-2009-173893, and liquid crystal compound (2) (content of liquid crystal compound (2) to liquid crystal compound (1): 7.0 parts by mass) represented by formula (2), which was synthesized according to the method disclosed in JP-B-05451176, were used. The degree of wavelength dispersion Re(450 nm)/Re(550 nm) of the optical film (6) thus produced was measured. The results were shown in Table 1.

TABLE 1

| Example No. | Content of Compound (2) Relative to 100 Parts by Mass of Compound (1) [pts. mass] | Degree of Wavelength Dispersion Re (450 nm/550 nm) |
| --- | --- | --- |
| Example 1 | 7 | 0.84 |
| Example 2 | 10 | 0.85 |
| Example 3 | 15 | 0.86 |
| Example 4 | 20 | 0.87 |
| Example 5 | 7 | 0.84 |
| Reference Example 1 | 0 | 0.82 |

Example 6

A mixture B of a liquid crystal compound (1) having a reverse wavelength dispersion characteristic represented by formula (1) and a liquid crystal compound (2) having a positive wavelength dispersion characteristic represented by formula (2) was obtained in the same manner as in Example 1, except that the amount of trans-cyclohexanedicarboxylic acid used was changed to 21.6 g (126 mmol) and the amount of sodium hydroxide used was changed to 1.1 g (28 mmol).

Next, an optical film (7) was produced in the same manner as in Example 1, except that mixture B was used instead of mixture A. Because of high content of liquid crystal compound (2), the optical film (7) showed higher degree of wavelength dispersion than the optical film (1).

Example 7

A mixture C of a liquid crystal compound (1) having a reverse wavelength dispersion characteristic represented by formula (1) and a liquid crystal compound (2) having a positive wavelength dispersion characteristic represented by formula (2) was obtained in the same manner as in Example 1, except that the amount of trans-cyclohexanedicarboxylic acid used was changed to 50.4 g (294 mmol) and the amount of sodium hydroxide used was changed to 4.2 g (105 mmol).

Next, an optical film (8) was produced in the same manner as in Example 1, except that mixture C was used instead of mixture A. Because of low content of liquid crystal compound (2), the optical film (8) showed lower degree of wavelength dispersion than the optical film (1).

In view of these results, according to the present invention, it is possible to easily produce an optical film having a desired wavelength dispersion characteristic by selecting the contents of liquid crystal compounds (1) and (2). Further, according to the production method of the present invention, since the wavelength dispersion characteristic of the optical film finally produced can be controlled by selecting the amounts of alcohol compound (3) and dicarboxylic acid compound (4) used, a desired wavelength dispersion characteristic can be very conveniently produced.

What is claimed is:

1. A method for producing a liquid crystal composition comprising a first liquid crystal compound represented by formula (1):

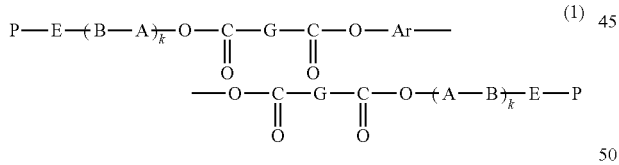

and a second liquid crystal compound represented by formula (2):

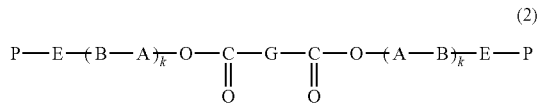

wherein the content of the liquid crystal compound represented by formula (2) in the liquid crystal composition is in the range of 1 to 50 parts by mass relative to 100 parts by mass of the liquid crystal compound represented by formula (1), the method comprising a step of allowing a first alcohol compound represented by formula (3):

and a dicarboxylic acid compound represented by formula (4):

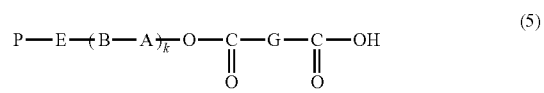

to react with each other to thereby obtain a mixture containing a carboxylic acid compound represented by formula (5):

and the second liquid crystal compound, and a step of allowing the mixture containing the carboxylic acid compound and the second liquid crystal compound to react with a second alcohol compound (6) represented by formula (6):

$$HO-Ar-OH \qquad (6)$$

to thereby obtain a liquid crystal composition containing the first and second liquid crystal compounds, wherein:

G represents a divalent alicyclic hydrocarbon group, where a hydrogen atom contained in the alicyclic hydrocarbon group is optionally substituted with a halogen atom, an alkyl group having 1 to 4 carbon atoms, a fluoro alkyl group having 1 to 4 carbon atoms, an alkoxy group having 1 to 4 carbon atoms, a cyano group or a nitro group, and —$CH_2$— contained in the alicyclic hydrocarbon group is optionally substituted with —O—, —S— or —NH—, B represents a single bond or a divalent linking group, A represents a divalent alicyclic hydrocarbon group having 3 to 20 carbon atoms or a divalent aromatic hydrocarbon group having 6 to 20 carbon atoms, the hydrogen atom contained in the alicyclic hydrocarbon group and the aromatic hydrocarbon group is optionally substituted with an alkyl group having 1 to 4 carbon atoms optionally substituted with a halogen atom, an alkoxy group having 1 to 4 carbon atoms optionally substituted with a fluorine atom, a cyano group or a nitro group, —CH2— contained in the alicyclic hydrocarbon group is optionally substituted with —O—,—S—, or —$N^1$—, and —CH(—)— contained in the alicyclic hydrocarbon group is optionally substituted with —N(—)—, $R^1$ represents a hydrogen atom or an alkyl group having 1 to 4 carbon atoms, k represents an integer of 0 to 3, where when k is an integer of 2 or more, a plurality of As and Bs may be the same or different from each other, E represents an alkanediyl group having 1 to 17 carbon atoms, where the hydrogen atom contained in an alkanediyl group is optionally substituted with a halogen atom, and —$CH_2$— contained in the alkanediyl group is optionally substituted with —O— or —CO—, P represents a polymerizable group, and Ar is selected from the group consisting of formula (Ar-1) to formula (Ar-22):

(Ar-1) 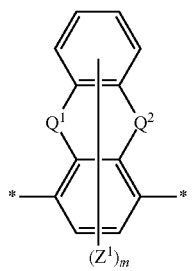
(Ar-2) 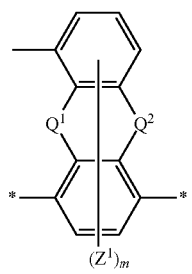
(Ar-3) 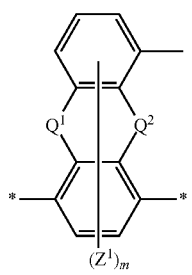
(Ar-4) 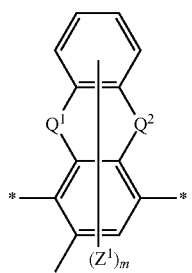
(Ar-5) 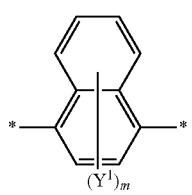
(Ar-6) 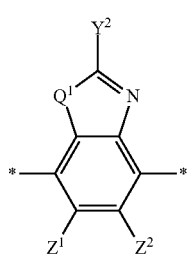
-continued
(Ar-7) 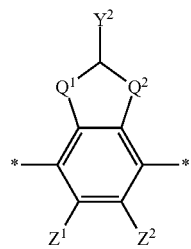
(Ar-8) 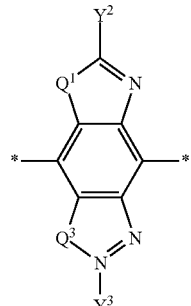
(Ar-9) 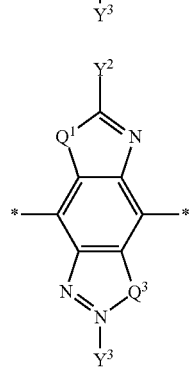
(Ar-10) 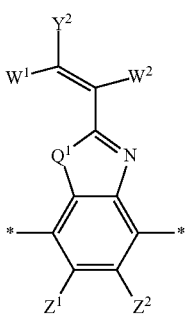
(Ar-11) 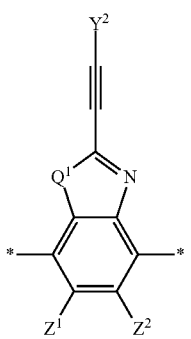

-continued
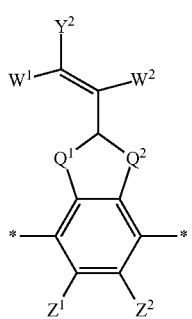
(Ar-12)
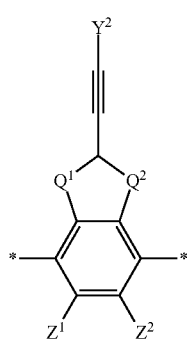
(Ar-13)
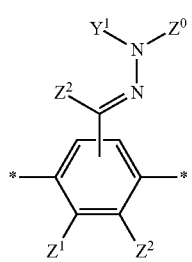
(Ar-14)
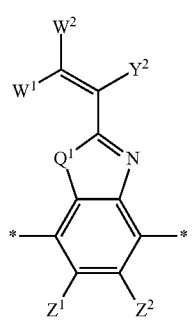
(Ar-15)
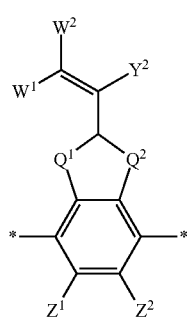
(Ar-16)
-continued
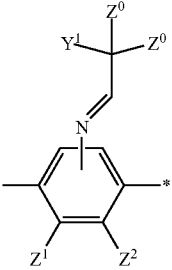
(Ar-17)
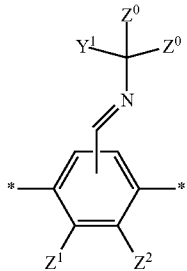
(Ar-18)
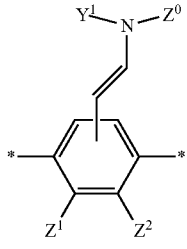
(Ar-19)
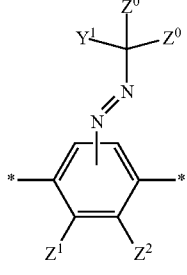
(Ar-20)
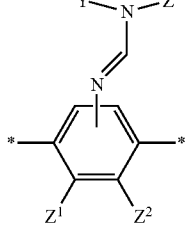
(Ar-21)
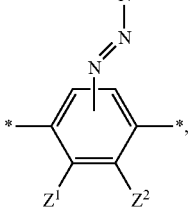
(Ar-22)
wherein:
* represents a linking unit, $Z^0$, $Z^1$, and $Z^2$ each independently represent a hydrogen atom, a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a carboxyl group, a fluoroalkyl group having 1 to 6 carbon atoms, an alkoxy group having 1 to 6 carbon atoms, a fluoroalkyl group having 1 to 6 carbon atoms, an alkoxy group having 1 to 6 carbon atoms, an alkylthio group having 1 to 6 carbon atoms, an N-alkylamino group having 1 to 6 carbon atoms, an N,N-dialkylamino group having 2 to 12 carbon atoms, an N-alkylsulfamoyl group having 1 to 6 carbon atoms, or an N,N-dialkylsulfamoyl group having 2 to 12 carbon atoms, $O^1$, $O^2$, and $O^3$ each independently represent —$CR^2R^3$—, —S—, —$NR^2$—, —CO—, or —O—, $R^2$ and $R^3$ each independently represent a hydrogen atom or an alkyl group having 1 to 4 carbon atoms, $Y^1$, $Y^2$, and $Y^3$ each independently represent an aromatic hydrocarbon group or an aromatic heterocyclic group, which is optionally substituted, $W^1$ and $W^2$ each independently represent a hydrogen atom, a cyano group, a methyl group, or a halogen atom, and m represents an integer of 0 to 6.

2. The method according to claim 1, wherein an amount of the dicarboxylic acid compound used is from 1 to 50 moles, relative to 1 mole of the first alcohol compound.

3. The method according to claim 1, wherein a reaction of the first alcohol compound and the dicarboxylic acid compound, and/or a reaction of the mixture containing the carboxylic acid compound and the second liquid crystal compound with the second alcohol compound is/are conducted in the presence of a condensing agent.

* * * * *